(12) United States Patent
Bailey et al.

(10) Patent No.: US 7,141,586 B2
(45) Date of Patent: *Nov. 28, 2006

(54) NICOTINAMIDE DERIVATIVES USEFUL AS PDE4 INHIBITORS

(75) Inventors: Simon Bailey, San Diego, CA (US); Christopher Gordon Barber, Sandwich (GB); Paul Alan Glossop, Sandwich (GB); Donald Stuart Middleton, Sandwich (GB)

(73) Assignee: Pfizer Inc., New York, NY (US)

( * ) Notice: Subject to any disclaimer, the term of this patent is extended or adjusted under 35 U.S.C. 154(b) by 8 days.

This patent is subject to a terminal disclaimer.

(21) Appl. No.: 10/896,315

(22) Filed: Jul. 20, 2004

(65) Prior Publication Data

US 2005/0032838 A1   Feb. 10, 2005

Related U.S. Application Data

(60) Provisional application No. 60/497,090, filed on Aug. 22, 2003.

(30) Foreign Application Priority Data

Jul. 25, 2003   (GB) ................................ 0317516.3

(51) Int. Cl.
C07D 213/02   (2006.01)
A61K 31/44   (2006.01)

(52) U.S. Cl. ................... 514/336; 514/350; 546/268.1; 546/298

(58) Field of Classification Search ................ 514/336, 514/350; 546/268.1, 298
See application file for complete search history.

(56) References Cited

U.S. PATENT DOCUMENTS

| | | | |
|---|---|---|---|
| 6,380,218 B1 | 4/2002 | Marfat et al. ................ | 514/326 |
| 6,559,168 B1 | 5/2003 | Marfat et al. ................ | 514/338 |
| 6,649,633 B1 | 11/2003 | Chambers et al. .......... | 514/337 |
| 6,740,655 B1 | 5/2004 | Magee et al. .......... | 514/255.05 |
| 2002/0111495 A1 | 8/2002 | Magee et al. ................ | 546/291 |

FOREIGN PATENT DOCUMENTS

| | | |
|---|---|---|
| WO | WO 9845268 | 10/1998 |
| WO | WO 0157025 | 8/2001 |
| WO | WO 0157036 | 8/2001 |
| WO | WO 0260896 | 8/2002 |
| WO | WO 0368235 | 8/2003 |

OTHER PUBLICATIONS

Torphy et al., "Phosphodieterase IV Inhibitors as Therapy for Eosinophil-induced Lung Injury in Asthma", Environmental Health Perspectives, 1994, 102 Suppl. 10, p. 79-84.
Duplantier et al., "Biarylcarboxylic Acids and -amides: Inhibition of Phospodiesterase Type IV verses [$^3$H]Rolipram Binding Activity and Their Relationship to Emetic Behavior in the Ferret", J. Med. Chem., 1996, 39, p. 120-125.
Schneider et al., "Discriminative Stimulus Properties of the Stereoisomers of the Phosphodiesterase Inhibitor Rolipram", Pharmacology Biochemistry Behavior, 1995, 50, p. 211-217.
Banner and Page, "Acute versus chronic administration of phosphodiesterase inhibitors on allergen-induced pulmonary cell influx in sensitized guinea-pigs", British Journal of Pharmacology, 1995, 114, p. 93-98.
Barnette et al., "The ability of phosphodiesterase IV inhibitors to suppress superoxide production in guinea pig eosinophils is correlated with inhibition of phosphodiesterase IV catalytic activity", J. Pharmacol. Exp. Ther., 1995, 273, p. 674-679.
Wright et al., "Differential in vivo and in vitro bronchorelaxant activities of CP-80,633, a selective phosphodiesterase 4 inhibitor", Can. J. Physiol. Pharmacol., 1997, 75, p. 1001-1008.
Manabe et al., "Anti-inflammatory and bronchodilator properties of KF19514, a phosphodiesterase 4 and 1 inhibitor", European Journal of Pharmacology, 1997, 332, p. 97-107.
Ukita et al., "Novel Potent, and Selective Phosphodiesterase-4 Inhibitors as Antiasthmatic Agents: Synthesis and Biological Activities of a Series of 1-Pyridylnaphthalene Derivatives", J. of Med. Chem., 1999, 42, p. 1088-1099.

*Primary Examiner*—Zinna N. Davis
(74) *Attorney, Agent, or Firm*—Charles W. Ashbrook; Rosanne Goodman

(57) ABSTRACT

This invention relates to nicotinamide derivatives of formula (I) and to processes for the preparation of, intermediates used in the preparation of, pharmaceutical compositions containing, and the uses of such derivatives:

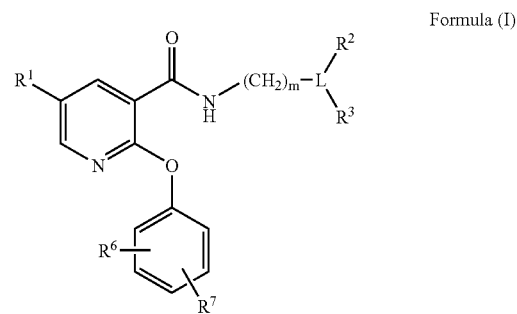

Formula (I)

wherein each substituent is defined herein.

13 Claims, No Drawings

NICOTINAMIDE DERIVATIVES USEFUL AS PDE4 INHIBITORS

This invention relates to nicotinamide derivatives of general formula:

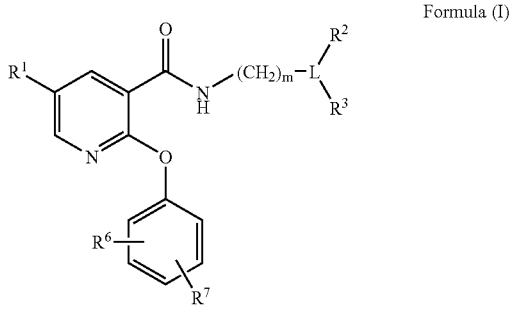

Formula (I)

in which $R^1$, $R^2$, $R^3$, $R^6$, $R^7$ and L have the meanings indicated below, and to processes for the preparation of, intermediates used in the preparation of, compositions containing and the uses of such derivatives.

The 3',5'-cyclic nucleotide phosphodiesterases (PDEs) comprise a large class of enzymes divided into at least eleven different families which are structurally, biochemically and pharmacologically distinct from one another. The enzymes within each family are commonly referred to as isoenzymes, or isozymes. A total of more than fifteen gene products is included within this class, and further diversity results from differential splicing and post-translational processing of those gene products. The present invention is primarily concerned with the four gene products of the fourth family of PDEs, i.e., PDE4A, PDE4B, PDE4C, and PDE4D. These enzymes are collectively referred to as being isoforms or subtypes of the PDE4 isozyme family.

The PDE4s are characterized by selective, high affinity hydrolytic degradation of the second messenger cyclic nucleotide, adenosine 3',5'-cyclic monophosphate (cAMP), and by sensitivity to inhibition by rolipram. A number of selective inhibitors of the PDE4s have been discovered in recent years, and beneficial pharmacological effects resulting from that inhibition have been shown in a variety of disease models (see, e.g., Torphy et al., *Environ. Health Perspect.*, 1994, 102 Suppl. 10, p. 79–84; Duplantier et al., *J. Med. Chem.*, 1996, 39, p. 120–125; Schneider et al., *Pharmacol. Biochem. Behav.*, 1995, 50, p. 211–217; Banner and Page, *Br. J. Pharmacol.*, 1995, 114, p. 93–98; Barnette et al., *J. Pharmacol. Exp. Ther.*, 1995, 273, p. 674–679; Wright et al., *Can. J. Physiol. Pharmacol.*, 1997, 75, p. 1001–1008; Manabe et al., *Eur. J. Pharmacol.*, 1997, 332, p. 97–107 and Ukita et al., *J. Med. Chem.*, 1999, 42, p. 1088–1099). Accordingly, there continues to be considerable interest in the art with regard to the discovery of further selective inhibitors of PDE4s.

Successful results have already been obtained in the art with the discovery and development of selective PDE4 inhibitors. In vivo, PDE4 inhibitors reduce the influx of eosinophils to the lungs of allergen-challenged animals while also reducing the bronchoconstriction and elevated bronchial responsiveness occurring after allergen challenge. PDE4 inhibitors also suppress the activity of immune cells (including CD4+ T-lymphocytes, monocytes, mast cells, and basophils), reduce pulmonary edema, inhibit excitatory nonadrenergic noncholinergic neurotransmission (eNANC), potentiate inhibitory nonadrenergic noncholinergic neurotransmission (iNANC), reduce airway smooth muscle mitogenesis, and induce bronchodilation. PDE4 inhibitors also suppress the activity of a number of inflammatory cells associated with the pathophysiology of COPD, including monocytes/macrophages, CD4+ T-lymphocytes, eosinophils and neutrophils. PDE4 inhibitors also reduce vascular smooth muscle mitogenesis and potentially interfere with the ability of airway epithelial cells to generate pro-inflammatory mediators. Through the release of neutral proteases and acid hydrolases from their granules, and the generation of reactive oxygen species, neutrophils contribute to the tissue destruction associated with chronic inflammation, and are further implicated in the pathology of conditions such as emphysema. Therefore, PDE4 inhibitors are particularly useful for the treatment of a great number of inflammatory, respiratory and allergic diseases, disorders or conditions and for wounds and some of them are in clinical development mainly for treatment of asthma, COPD, bronchitis and emphysema.

The effects of PDE4 inhibitors on various inflammatory cell responses can be used as a basis for profiling and selecting inhibitors for further study. These effects include elevation of cAMP and inhibition of superoxide production, degranulation, chemotaxis, and tumor necrosis factor alpha (TNFa) release in eosinophils, neutrophils and monocytes.

Some nicotinamide derivatives having a PDE4 inhibitory activity have already been synthetized. For example, the patent application WO 98/45268 discloses nicotinamide derivatives having activity as selective inhibitors of PDE4D isozyme.

The patent applications WO 01/57036 and PCT/IB03/00439 also disclose nicotinamide derivatives which are PDE4 inhibitors useful in the treatment of various inflammatory allergic and respiratory diseases and conditions.

However, there is still a huge need for additional PDE4 inhibitors showing improved therapeutic index with possibly less adverse effects such as for example emesis.

Thus, the present invention concerns new nicotinamide derivatives of general formula (I):

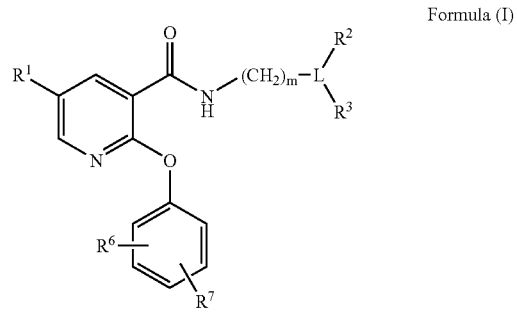

Formula (I)

wherein $R^1$ is selected from the group consisting of hydrogen, methyl or halo;

$R^7$ is attached to the 3- or 4-position of the phenyl ring and is $S(O)_pR^8$, $R^8$ is $(C_1-C_4)$alkyl optionally substituted by $(C_3-C_6)$cycloalkyl; p is 0, 1 or 2;

$R^6$ is selected from the group consisting of hydrogen, halo, $(C_1-C_3)$alkyl and $(C_1-C_3)$alkoxy;

m is 0 or 1;

L is a $(C_3-C_8)$carbocyclic non-aromatic ring;

$R^2$ is hydrogen, hydroxy, $(C_1–C_3)$alkoxy, $(C_1–C_3)$alkyl (optionally substituted by hydroxy or by $(C_1–C_3)$alkoxy), $CO_2R^9$, $NR^{10}R^{11}$ or $CONR^{10}R^{11}$;

$R^3$ is hydrogen or $(C_1–C_3)$alkyl;

$R^9$ is hydrogen or $(C_1–C_3)$alkyl;

$R^{10}$ and $R^{11}$ are each independently hydrogen, or are selected from the group consisting of:
 $(C_1–C_6)$alkyl optionally substituted by phenyl or a 5- or 6-membered heterocyclic ring incorporating 1 to 3 heteroatom(s) independently selected from N, O and S, which phenyl is optionally substituted by one or more subsituents selected from hydroxy, halo, $(C_1–C_3)$alkyl or $(C_1–C_3)$alkoxy and which heterocyclic ring is optionally substituted by one or more subsituents selected from hydroxy, halo, $(C_1–C_3)$alkyl, $(C_1–C_3)$alkoxy or oxo;
 $(C_3–C_8)$cycloalkyl;
 $CO((C_1–C_6)$alkyl) optionally substituted by hydroxy, halo, $(C_3–C_8)$cycloalkyl, $(C_1–C_3)$alkoxy, phenyl or a 5- or 6-membered heterocyclic ring incorporating 1 to 3 heteroatom(s) independently selected from N, O and S, which phenyl is optionally substituted by one or more subsituents selected from hydroxy, halo, $(C_1–C_3)$alkyl or $(C_1–C_3)$alkoxy and which heterocyclic ring is optionally substituted by one or more subsituents selected from hydroxy, halo, $(C_1–C_3)$alkyl, $(C_1–C_3)$alkoxy or oxo;
 $CO(R^{12})$, wherein $R^{12}$ is $(C_3–C_8)$cycloalkyl optionally substituted by $(C_1–C_3)$alkyl or $R^{12}$ is phenyl or a 5- or 6-membered heterocyclic ring incorporating 1 to 3 heteroatom(s) independently selected from N, O and S, which phenyl is optionally substituted by one or more subsituents selected from hydroxy, halo, $(C_1–C_3)$alkyl or $(C_1–C_3)$alkoxy and which heterocyclic ring is optionally substituted by one or more subsituents selected from hydroxy, halo, $(C_1–C_3)$alkyl, $(C_1–C_3)$alkoxy or oxo; and
 $CO_2(C_1–C_3)$alkyl);
 or $R^{10}$ and $R^{11}$ are taken together with the N atom to which they are attached to form a 5- or 6-membered lactam;

and the pharmaceutically acceptable salts and solvates (including hydrates) thereof.

As a preferred aspect, the invention relates to nicotinamide derivatives of general formula (Ia):

Formula (Ia)

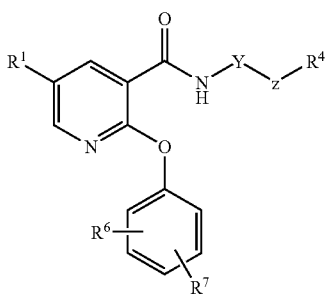

wherein $R^1$ is selected from the group consisting of hydrogen, methyl or halo;

$R^7$ is attached to the 3- or 4-position of the phenyl ring and is $(C_1–C_4)$alkylthio, $R^6$ is selected from the group consisting of hydrogen, halo, $(C_1–C_3)$alkyl and $(C_1–C_3)$alkoxy;

Y is a group selected from:

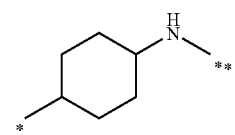
(1.5)

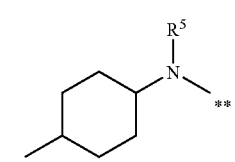
(1.8)

where the symbol "*" indicates the point of attachment of each partial formula to the remaining portions —NH— of formula (Ia) and "**" indicates the point of attachment of each partial formula to the remaining portions Z of formula (Ia), and wherein $R^5$ is a member selected from the groups consisting of $(C_1–C_4)$alkyl and phenyl$(C_1–C_4)$alkyl, where said phenyl group is optionally substituted by halo, $(C_1–C_3)$alkyl, $(C_1–C_3)$alkoxy or hydroxy;

Z is —C(=O)—; and $R^4$ is selected from the group consisting of:
 a $(C_3–C_8)$cycloalkyl optionally substituted by $(C_1–C_3)$alkyl;
 a phenyl or a 5- or 6-membered heterocyclic ring incorporating 1 to 3 heteroatom(s) independently selected from N, O and S, which phenyl and heterocyclic ring are each optionally substituted by one or more substituents selected from the group consisting of hydroxy, halo, $(C_1–C_3)$alkyl and $(C_1–C_3)$alkoxy; and
 a $(C_1–C_6)$alkyl optionally substituted with a hydroxy, or with a phenyl or a 5- or 6-membered heterocyclic ring incorporating 1 to 3 heteroatom(s) independently selected from N, O and S, which phenyl and heterocyclic ring are each optionally substituted by one or more substituents selected from the group consisting of hydroxy, halo, $(C_1–C_3)$alkyl and $(C_1–C_3)$alkoxy;

and the pharmaceutically acceptable salts and solvates (including hydrates) thereof.

According to a further preferred aspect, the invention relates to nicotinamide derivatives of the formulae (I) and (Ia) in which Y is a group of formula:

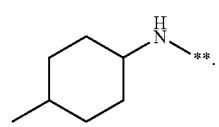
(1.5)

More particularly preferred are the nicotinamide derivatives of the formulae (I) and (Ia) in which $R^7$ is a $(C_1–C_4)$alkylthio in the 3-position of the phenyl ring.

More particularly preferred are the nicotinamide derivatives of the formulae (I) and (Ia) in which $R^4$ is benzyl, phenyl or a 5- or 6-membered heterocyclic ring incorporating 1 to 3 heteroatom(s) independently selected from N, O and S, which benzyl, phenyl and heterocyclic ring are each optionally substituted by one or more substituents selected from the group consisting of hydroxy, halo, (C$_1$–C$_3$)alkyl and (C$_1$–C$_3$)alkoxy.

More particularly preferred are the nicotinamide derivatives of the formula (Ib):

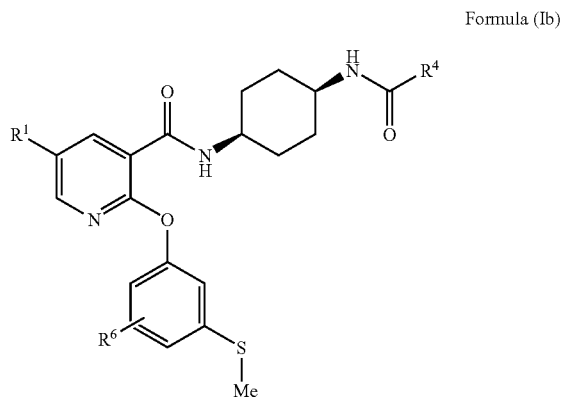

Formula (Ib)

in which R$^1$ is selected from hydrogen, halo and methyl;
R$^4$ is benzyl, phenyl or a 5- or 6-membered heterocyclic ring incorporating 1 to 3 heteroatom(s) independently selected from N, O and S, which benzyl, phenyl and heterocyclic ring are each optionally substituted by hydroxy, halo, (C$_1$–C$_3$)alkyl or (C$_1$–C$_3$)alkoxy; and
R$^6$ is in the 4- or 5- position and is selected from the group consisting of hydrogen, fluoro, chloro or (C$_1$–C$_3$)alkyl.

More particularly preferred are the nicotinamide derivatives of the formulae (I), (Ia) or (Ib) in which R$^4$ is selected from the group consisting of benzyl, phenyl, pyridine, pyrimidine, pyrazine, imidazole, pyrazole, pyridazine and triazole, which are each optionally substituted by one or more substituents selected from the group consisting of hydroxy, halo, (C$_1$–C$_3$)alkyl and (C$_1$–C$_3$)alkoxy.

Even more particularly preferred are the nicotinamide derivatives of the formulae (I), (Ia) or (Ib) in which R$^1$ is fluoro.

Particularly preferred examples of the nicotinamide derivatives of the formulae (I), (Ia) and (Ib) are as described in the Examples section hereafter.

Most preferred are the nicotinamide derivatives of the formula (I), (Ia) and (Ib) selected from:
Syn-5-fluoro-N-{4-[(1H-imidazole-5-carbonyl)-amino]-cyclohexyl}-2-(3-methylsulfanyl-phenoxy)-nicotinamide;
Syn-5-fluoro-N-[4-(2-hydroxy-4-methyl-benzoylamino)-cyclohexyl]-2-(3-methylsulfanyl-phenoxy)-nicotinamide;
Syn-5-fluoro-N-[4-(2-hydroxy-benzoylamino)-cyclohexyl]-2-(3-methylsulfanyl-phenoxy)-nicotinamide;
Syn-5-fluoro-N-[4-(2-hydroxy-5-methyl-benzoylamino)-cyclohexyl]-2-(3-methylsulfanyl-phenoxy)-nicotinamide;
Syn-5-fluoro-2-(3-methylsulfanyl-phenoxy)-N-{4-[(2,3-dimethyl-1H-pyrazole-5-carbonyl)-amino]-cyclohexyl}-nicotinamide;
Syn-5-fluoro-N-{4-[(4-methyl-1H-imidazole-2-carbonyl)-amino]-cyclohexyl}-2-(3-methylsulfanyl-phenoxy)-nicotinamide;
Syn-5-fluoro-N-[4-(4-hydroxy-2-methoxy-benzoylamino)-cyclohexyl]-2-(3-methylsulfanyl-phenoxy)-nicotinamide; and
Syn-5-fluoro-N-[4-(5-chloro-2-hydroxy-benzoylamino)-cyclohexyl]-2-(3-methylsulfanyl-phenoxy)-nicotinamide;

and the pharmaceutically acceptable salts and solvates thereof.

It has been found that these nicotinamide derivatives are inhibitors of PDE4 isoenzymes, particularly useful for the treatment of inflammatory, respiratory and allergic diseases and conditions or for wounds by showing excellent therapeutic utility and therapeutic index.

In the here above general formulae (I), (Ia) and (Ib), halo denotes a halogen atom selected from the group consisting of fluoro, chloro, bromo and iodo in particular fluoro or chloro.

(C$_1$–C$_3$)alkyl, (C$_1$–C$_4$)alkyl or (C$_1$–C$_6$)alkyl radicals denote a straight-chain or branched group containing respectively 1 to 3, 1 to 4 and 1 to 6 carbon atoms. This also applies if they carry substituents or occur as substituents of other radicals, for example in (C$_1$–C$_3$)alkoxy radicals, (C$_1$–C$_4$) alkylthio radicals, etc. . . . Examples of suitable (C$_1$–C$_3$) alkyl, (C$_1$–C$_4$)alkyl and (C$_1$–C$_6$)alkyl radicals are methyl, ethyl, n-propyl, iso-propyl, n-butyl, iso-butyl, sec-butyl, tert-butyl, pentyl and hexyl. Examples of suitable (C$_1$–C$_3$) alkoxy radicals are methoxy, ethoxy, n-propyloxy and iso-propyloxy. Examples of suitable (C$_1$–C$_4$)alkylthio radicals are methylthio, ethylthio, n-propylthio, iso-propylthio, n-butylthio, iso-butylthio, sec-butylthio and tert-butylthio.

(C$_3$–C$_8$)cycloalkyl radicals represent 3-membered to 8-membered saturated monocyclic rings. Examples of suitable (C$_3$–C$_8$)cycloalkyl radicals are in particular cyclopropyl, cyclobutyl, cyclopentyl, cyclohexyl, cycloheptyl and cyclooctyl. These radical can be optionally substituted as indicated in the definition of R$_3$. Examples of substituted (C$_3$–C$_8$)cycloalkyl radicals are for example 2-methylcyclohexyl, 3-methylcyclohexyl, 4-methylcyclohexyl, 5-methylcyclohexyl, 6-methylcyclohexyl, 2-hydroxycyclohexyl, 3-hydroxycyclohexyl, 4-hydroxycyclohexyl, 5-hydroxycyclohexyl, 6-hydroxycyclohexyl, 2-fluorocyclohexyl, 3-fluorocyclohexyl, 4-fluorocyclohexyl, 5-fluorocyclohexyl, 6-fluorocyclohexyl 2-methyl-3-hydroxycyclohexyl, 2-methyl-4-hydroxycyclohexyl, 2-hydroxy-4-methylcyclohexyl, etc.

In the hereabove general formulae (I), (Ia) and (Ib), a heterocyclic ring is a 5 or 6 membered ring incorporating 1, 2 or 3 hetero ring atoms independently selected from N, O and S, which ring is optionally substituted by hydroxy, halo, (C$_1$–C$_3$)alkyl, (C$_1$–C$_3$)alkoxy or oxo, unless stated otherwise If several heteroatoms are contained, these can be identical or different. Preferred heterocyclic rings are pyridine, pyrimidine, pyrazine, imidazole, pyrazole, pyridazine and triazole. Nitrogen heteroaryl radicals can also be present as N-oxides or as quaternary salts.

In the general formulae (I), (Ia) and (Ib) according to the present invention, when a radical is mono- or poly-substituted, said substituent(s) can be located at any desired position(s). Also, when a radical is polysubstituted, said substituents can be identical or different, unless otherwise stated.

The nicotinamide derivatives of the formulae (I), (Ia) and (Ib) can be prepared using conventional procedures such as by the following illustrative methods in which R$^1$, R$^2$, R$^3$, R$^4$, R$^6$, R$^7$ and L, Y and Z are as previously defined for the nicotinamide derivatives of the formulae (I) and (Ia) unless otherwise stated. Other methods may be used in accordance with the skilled person's knowledge.

Unless otherwise provided herein:
PyBOP® means Benzotriazol-1-yloxytris(pyrrolidino) phosphonium hexafluorophosphate;
PyBrOP® means bromo-tris-pyrrolidino-phosphonium hexafluorophosphate;

CDI means N,N'-carbonyldiimidazole;
WSCDI means 1-(3-dimethylaminopropyl)-3-ethylcarbodiimide hydrochloride;
Mukaiyama's reagent means 2-chloro-1-methylpyridinium iodide;
HATU means O-(7-Azabenzotriazol-1-yl)-N,N,N'N'-tetramethyluronium hexafluorophosphate;
HBTU means O-Benzotriazol-1-yl-N,N,N'N'-tetramethyluronium hexafluorophosphate;
DCC means N,N'-dicyclohexylcarbodiimide;
HOAT means 1-hydroxy-7-azabenzotriazole;
HOBT means 1-hydroxybenzotriazole hydrate;
Hünig's base means N-ethyldiisopropylamine;
Et$_3$N means triethylamine;
NMM means N-methylmorpholine;
NMP means 1-methyl-2-pyrrolidinone;
DMAP means 4-dimethylaminopyridine;
Boc means tert-butoxycarbonyl;
CBz means benzyloxycarbonyl;
MeOH means methanol, EtOH means, ethanol, and EtOAc means ethyl acetate;
THF means tetrahydrofuran, DMSO means dimethyl sulphoxide, and DCM means dichloromethane; DMF means N,N-dimethylformamide; AcOH means acetic acid, TFA means trifluoroacetic acid; rt means room temperature; 3° means tertiary; eq means equivalents; Me means methyl, Et means ethyl, Bn means benzyl; other abbreviations are used in accordance with standard synthetic chemistry practice.

Method A

Compounds of formula (I) may be prepared by reaction of the corresponding nicotinic acid (XIV) with a compound of formula NH$_2$—(CH$_2$)$_m$-LR$^2$R$^3$:

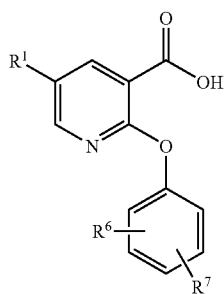

Formula (XIV)

suitably in the presence of an acid/amine, or peptide, coupling agent. The reaction may suitably be carried by reaction of the acid with carbonyldiimidazole in a suitable inert solvent such as dichloromethane, followed by addition of the compound NH$_2$—(CH$_2$)$_m$-LR$^2$R$^3$, suitably in the presence of a base such as 4-dimethylaminopyridine, as exemplified below.

An alternative method starting from acids (XIV) is to use a suitable diimide such as 1-(3-dimethylaminopropyl)-3-ethylcarbodiimide in conjunction with an agent such as 1-hydroxybenzotriazole. The acid (XIV) may be added to the mixture in an inert solvent such as dichloromethane, followed by addition of the amine NH$_2$—(CH$_2$)$_m$-LR$^2$R$^3$. This reaction type, reagents, conditions, solvents and variations thereof are exemplified below.

Other suitable regimes for the transformation of compounds of formula (XIV) to compounds of formula (I) may be found in "Comprehensive Organic Transformations" by R C Larock, VCH Publishered Inc. (1989), pp 972–976.

The nicotinic acids of formula (XIV) and amines of formula NH$_2$—(CH$_2$)$_m$-LR$^2$R$^3$ may be commercially available, or can be made using the methods described herein, including in the Preparations below, the art mentioned herein, or routine adaptation thereof.

Method B

Alternatively, compounds of formula (I) may be prepared by a coupling reaction of a chloro-compound of formula (XV) with a phenol of formula (XVI).

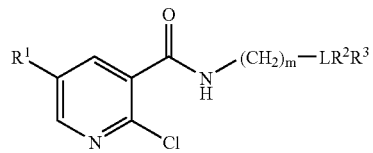

Formula (XV)

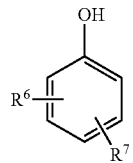

Formula (XVI)

Suitably the phenol (XVI) and chloro-compound (XV) are mixed with caesium carbonate in an inert solvent such as toluene:N-methylpyrrolidine at ambient temperature, followed by addition of copper (I) iodide and then heating to a suitable temperature such as 110° C.

The chloro-compounds (XV) and the phenols (XVI) may be commercially available, or can be made using the methods described herein, including in the Preparations below, the art mentioned herein, or routine adaptation thereof.

Certain compounds of formula (I) can be prepared following the route outlined in Scheme 1 below, and suitable variation thereof, where the acid portion of a 2-halonicotinic acid derivative can be protected With one of a range of standard protecting groups well known to those skilled in the art. See 'Protective Groups in Organic Synthesis', T. W. Greene (Wiley) or 'Protecting Groups', P. J. Kocienski (Thieme) for examples. In particular, esters may be used, especially those derived from simple alcohols. This protection may take place under acidic (eg saturated HCl in low mw alcohol) or basic conditions (eg caesium carbonate, methyl iodide). An alternative strategy to the direct protection of the carboxylic acid would be to leave a group that could be readily converted into a carboxylic acid, for example, through oxidation of a primary alcohol or a methyl group.

Step 2 of Scheme 1—the displacement of the leaving group at the 2-position, typically a halo group with a suitable phenol—may be undertaken under basic conditions. Suitable bases included inorganic bases such as potassium, sodium, or caesium carbonate, and suitable solvents include dioxan, DMSO or DMF or a mixture of toluene and N-methylpyrrolidinone and the reaction may be heated, preferably under anhydrous conditions, preferably 80–120° C. In certain cases additives such as copper (I) iodide may be employed (JACS, 1997, 10539).

Step 3 of Scheme 1—the deprotection of the acid group may be performed under well-known conditions—see for examples 'Protective Groups in Organic Synthesis', T. W.

Greene (Wiley) or 'Protecting Groups', P. J. Kocienski (Thieme). If simple alcohol esters were formed, then these may be suitably hydrolysed to the nicotinic acid derivative under basic conditions using an alkali metal carbonates or hydroxides in a solvent system such as aqueous methanol, ethanol, THF at ambient temperature.

Alternatively, the direct displacement of the 2-leaving group with a suitable phenol in the presence of the free 3-carboxylic acid may be undertaken, negating the need for protection and deprotection of the carboxylic acid. Similar conditions to those described for step 2 may be used.

The preparation of the nicotinamide from the nicotinic acid of step 3 may be undertaken under one of the many well-reported amide coupling preparations. For example, between an acid chloride and an amine. Typically, the acid chloride is treated with the amine (one or more equivalents), preferably with an excess of 3° amine such as Et₃N, Hünigs base or N-methyl morpholine, in DCM or THF, rt for 1 to 24 hrs. Alternatively, the acid may activated by a suitable agent, optionally in the presence of a catalyst, optionally with an excess of acid acceptor in a suitable solvent. Typically, the acid is treated with 1-(3-dimethylaminopropyl)-3-ethylcarbodiimide hydrochloride or N,N'-dicyclohexylcarbodiimide and 1-hydroxybenzotriazole hydrate or 1-hydroxy-7-azabenzotriazole, together with the amine, and an excess of N-methyl morpholine, or Et₃N, or Hünigs base in THF, DCM or EtOAc, at rt for 4 to 48 hrs. Alternatively, the acid may be treated with, benzotriazol-1-yloxytris(pyrrolidino)phosphonium hexafluorophosphate or bromo-tris-pyrrolidino-phosphonium hexafluorophosphate or Mukaiyama's reagent (2-chloro-1-methylpyridinium iodide), together with the amine, in the presence of an excess of N-methyl morpholine, Et₃N, or Hünigs base in THF, DCM or EtOAc, at rt for 4 to 24 hrs.

An alternative route is outlined in Scheme 2 whereby the nicotinic acid amide coupling is undertaken under conditions such as those described for Step 4 of Scheme 1 above, followed by displacement of the leaving group at the 2-position (typically a halogen) with a suitable phenoxy group using conditions such as those described for Step 3 of Scheme 1. This again circumvents the need for protection of the carboxylic acid.

Further modification of the assembled molecules may be undertaken as shown in Schemes 3 and 4. In the former scheme, a suitably protected amine may be released to afford an amine which may then be further functionalised. Suitable protecting groups and deprotection conditions will be known by those skilled in the art (see for example, 'Protective Groups in Organic Synthesis', T. W. Greene (Wiley) or 'Protecting Groups', P. J. Kocienski (Thieme) and could include Boc or Cbz protecting groups. Subsequent functionalisation could include acylation to form an amide (see the conditions of Step 4 of Scheme 1 for example). Alternatively a carbamate could be formed through reaction of the amine with a suitable haloformate. Typical conditions would be a chloroformate in the presence of an acid scavenger—either inorganic (such as an alkali metal carbonate or bicarbonate) or organic (such as a tertiary amine eg triethylamine, Hunig's base or N-methyl morpholine).

Acylation could be followed by alkylation of the resultant amide—such as the intramolecular reaction depicted in Scheme 5. Typical conditions for this alkyation would be the use of an alkali metal hydride in an aprotic solvent, such as DMF or N-methylpyrrolidine, at room temperature, or optionally heated.

Scheme 4 shows the deprotection of a carboxylic acid, and subsequent amide formation using the conditions described above for Scheme 1.

Further elaboration of the substituents of the phenoxide may be possible either before, or after the formation of the nicotinamide bond. Scheme 6 shows oxidation of the thioether to either the sulphoxide or to the sulphone when the amide bond is in place. This oxidation may be undertaken using one of the many well-known procedures. A peracid such as meta-chloroperbenzoic acid may be used, or alternatively oxone™ may be used in a suitable solvent or solvent mixture, preferably at room temperature. An example of such a suitable solvent mixture is one comprising of isopropyl alcohol, water and THF.

Where chiral centres are present, the compounds may be prepared as mixtures of all possible stereochemistries, or as diastereomeric pairs—such as cis or trans isomers, or as individual homochiral entities. The latter may be prepared through the use of homochiral fragments, or by chiral separation of the final compounds through standard techniques such as chiral HPLC.

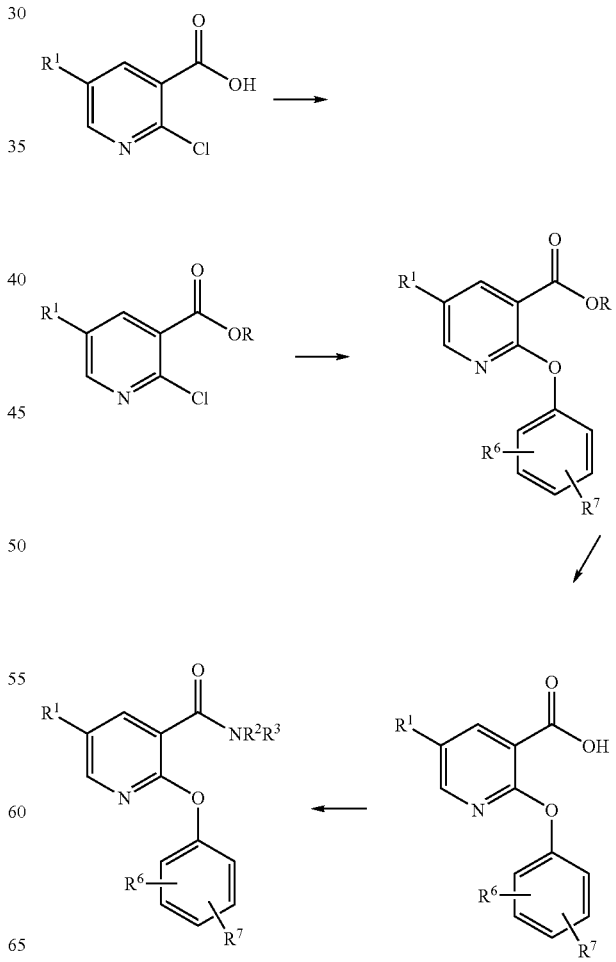

Scheme 1

In the scheme above, $R^1$, $R^2$, $R^3$, $R^6$ and $R^7$ are as previously defined and R is a carboxylic acid protecting group.
Scheme 2
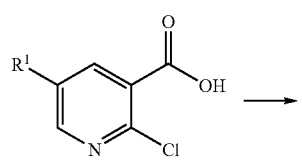
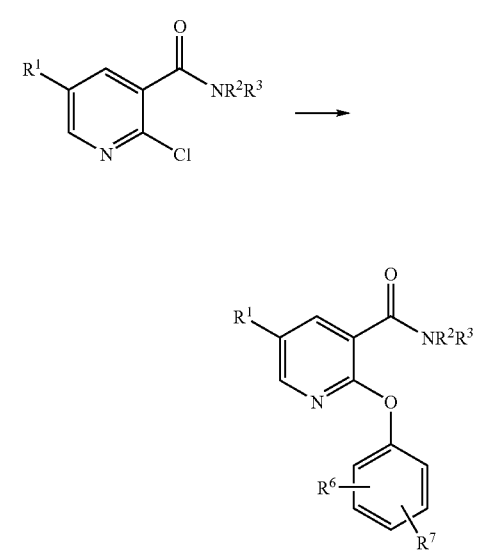
Scheme 3
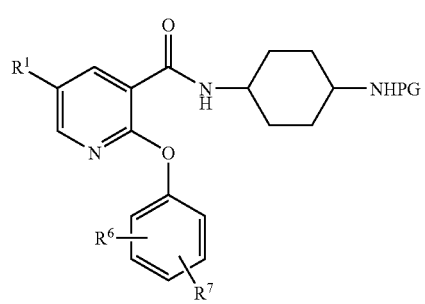
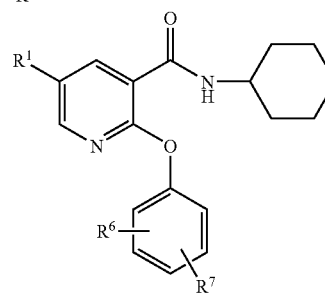
-continued
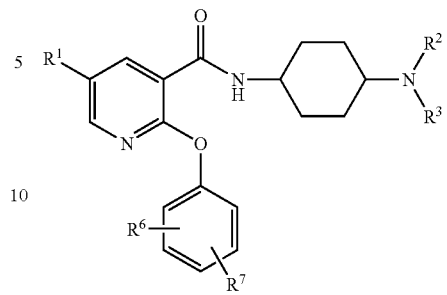
In the scheme above, PG is a suitable amine protecting group.
Scheme 4
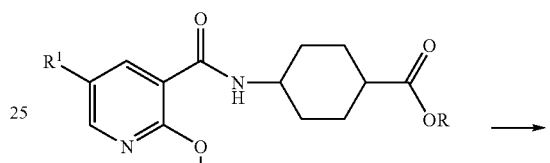
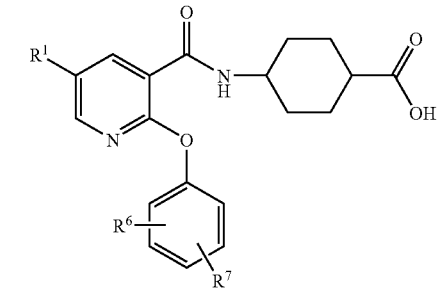
In the scheme above, R is a suitable carboxylic acid protecting group.

Scheme 5
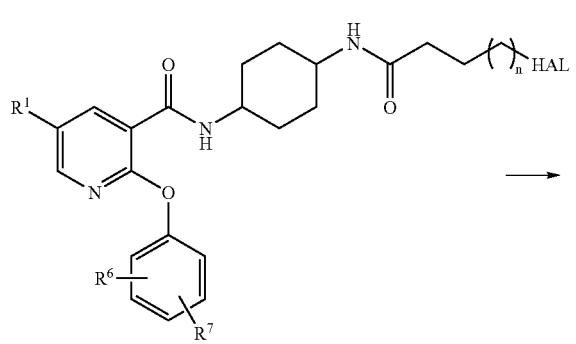
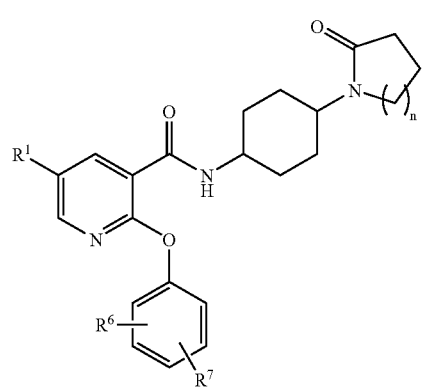
In the scheme above, n is 1 or 2.
Scheme 6
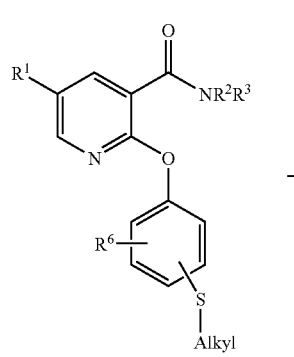
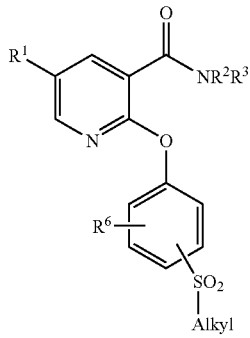
Compounds of formula (Ia) may be prepared by the following route:
Route A
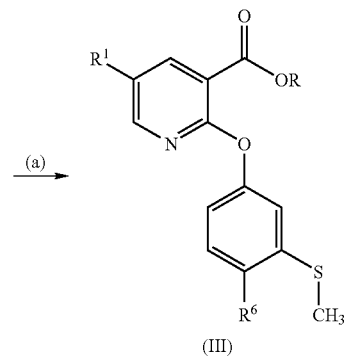
(II)
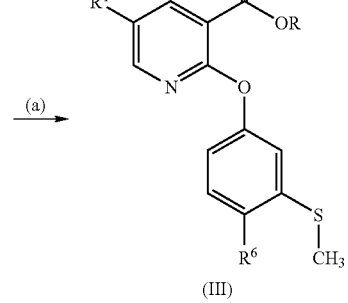
(III)
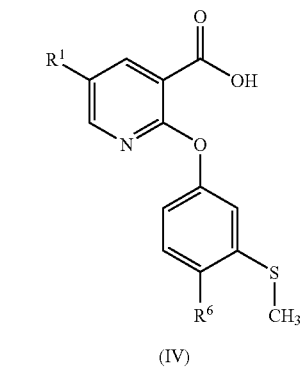
(IV)

-continued

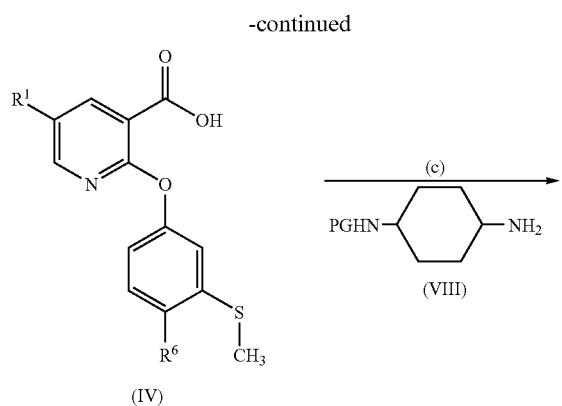
(IV)

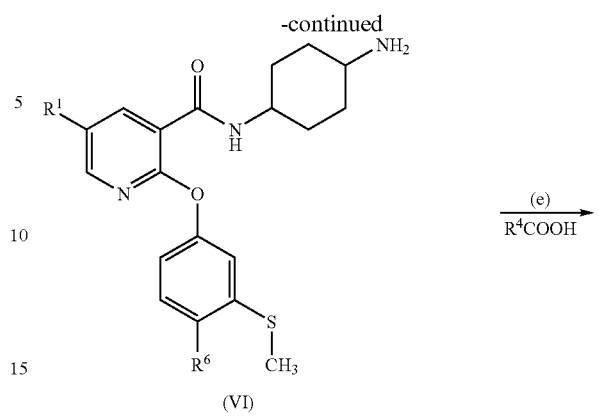
(VI)

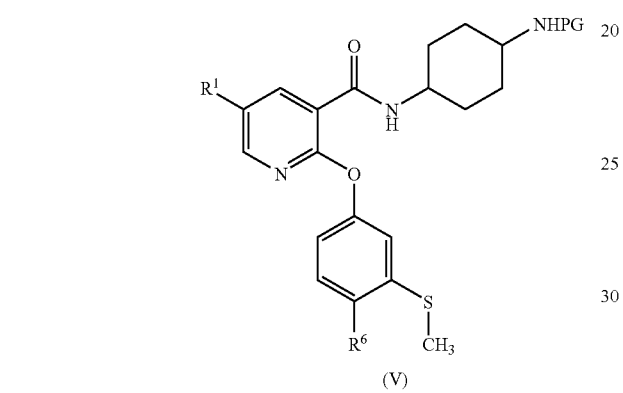
(V)

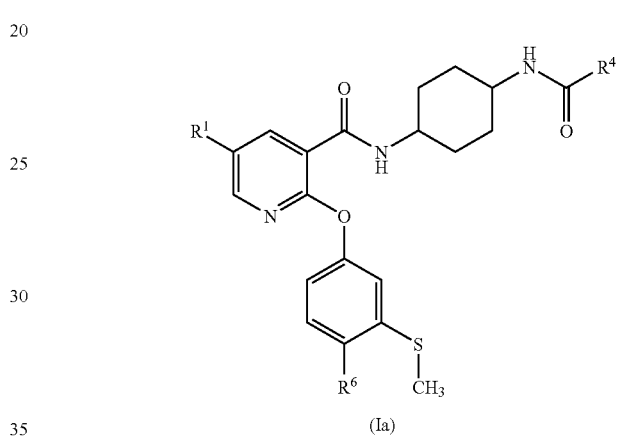
(Ia)

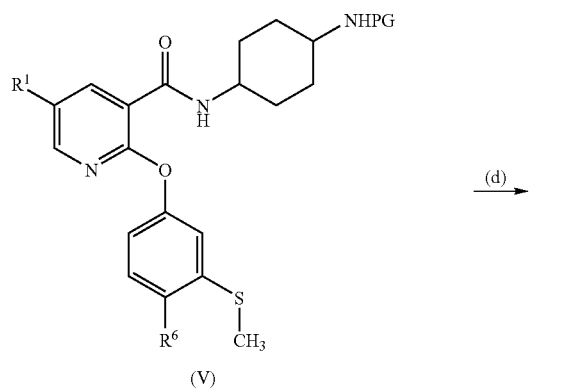
(V)

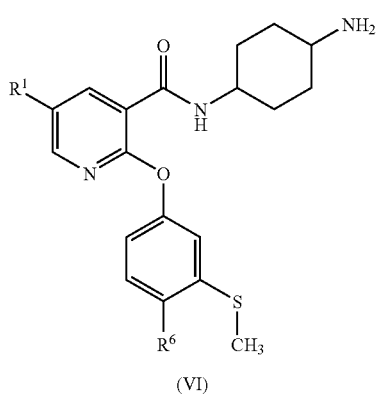
(VI)

Compounds of the formula (II) are either available commercially or may be obtained from the compounds of formula (XII), using standard esterification conditions. Nicotinic acids of formula (XII) are either available commercially or may be obtained by analogy with the methods of Haylor et. al. (EP 0634413) or Marzi et. al. (*Eur. J. Org. Chem.*, 2001, (7), 1371–1376). The protected amines of formula (VIII) are either available commercially or may be prepared by analogy with the method of Oku et al (WO 99/54284).

In the scheme above, $R^1$, $R^4$ and $R^6$ are as previously defined, wherein $R^6$ may be in the 4- or 5-position. R is a carboxylic acid protecting group, typically lower alkyl or Benzyl, and preferably ethyl, PG is a suitable amine protecting group, typically Boc, CBz or Bn, and preferably Boc, and LG is a suitable leaving group, typically halo, and preferably Cl.

Step (a)—Ether Formation

The compound of formula (II) is treated with an excess of the appropriate 3-methylsulfanyl-phenol to give compound (III) in the presence of a suitable alkali metal base (e.g. $Cs_2CO_3$, $K_2CO_3$, NaOH), in a suitable solvent (e.g. MeCN, dioxan, toluene, NMP), optionally in the presence of a catalyst (e.g. CuI) to provide the ether (III).

The preferred conditions are: chloride (II), 1.5–2.5 eq 3-methylsulfanyl-phenol, in the presence of an excess of Cs$_2$CO$_3$, optionally in the presence of CuI, in either dioxan or a toluene:NMP (4:1 by volume) mixture, at 100–110° C. for 18–48 hours.

Step (b)—Ester Hydrolysis

Hydrolysis of the ester (III) may be achieved in the presence of acid or base, in a suitable solvent, optionally at elevated temperature to afford the acid (IV). Typically, when R represents lower alkyl, the ester (III) is treated with a suitable base (e.g. LiOH, NaOH, K$_2$CO$_3$, Cs$_2$CO$_3$) in an appropriate aqueous solvent (THF, EtOH, MeOH) at room temperature, to give the acid of formula (IV).

The preferred conditions are: ester (III) in THF with a 1M aqueous solution of LiOH at rt for 2–3 hours.

Step (c)—Acid-Amine Coupling

This coupling may be undertaken by using either:

(i) an acyl chloride derivative of acid (IV)+amine (VIII), with an excess of acid acceptor in a suitable solvent; or (ii) the acid (IV) with a conventional coupling agent+amine (VIII), optionally in the presence of a catalyst, with an excess of acid acceptor in a suitable solvent.

Typically the conditions are as follows:

(i) acid chloride of acid (IV) (generated in-situ), an excess of amine (VIII), optionally with an excess of 3° amine such as Et$_3$N, Hünig's base or NMM, in DCM or THF, without heating for 1 to 24 hrs; or (ii) acid (IV), WSCDI/DCC/CDI, optionally in the presence of HOBT or HOAT, an excess of amine (VIII), with an excess of NMM, Et$_3$N or Hünig's base in THF, DCM or EtOAc, at rt for 4 to 48 hrs; or acid (IV), PYBOP®/PyBrOP®/Mukaiyama's reagent, an excess of amine (VIII), with an excess of NMM, Et$_3$N or Hünig's base in THF, DCM or EtOAc, at rt for 4 to 24 hrs.

The preferred conditions are: acid chloride of acid (IV) (generated in-situ), about 1.1 eq amine (VIII), in either DCM or THF, and optionally Hünig's base, at rt for 18–48 hours.

Step (d)—Removal of Amine Protecting Group

Deprotection of the N-protecting group (PG) from (V) to give amine (VI) is undertaken using standard methodology, as described in "Protective Groups in Organic Synthesis" by T. W. Greene, and P. Wutz.

When PG is Boc, the preferred conditions are: hydrochloric acid in dioxan or dichloromethane at rt for about 3–5 hours.

Step (e)—Reaction of Amino Group with R$^4$—COOH

Compounds of the formula (Ia) may be prepared by reaction of the amine of formula (VI) with R$^4$—CO$_2$H according to the general methods described previously for step (c).

The preferred conditions are: WSCDI, HOBT, amine (VI), R$^4$—CO$_2$H, an excess of 3° amine base (Et$_3$N or NMM) in dichloromethane or DMF, at rt. for 18–48 hrs.

Optionally, R$^4$ may contain one or more hydroxyl functions which require protecting. In this instance, compounds of formula (Ia) may be prepared from compounds of formula (VI) by the following route:

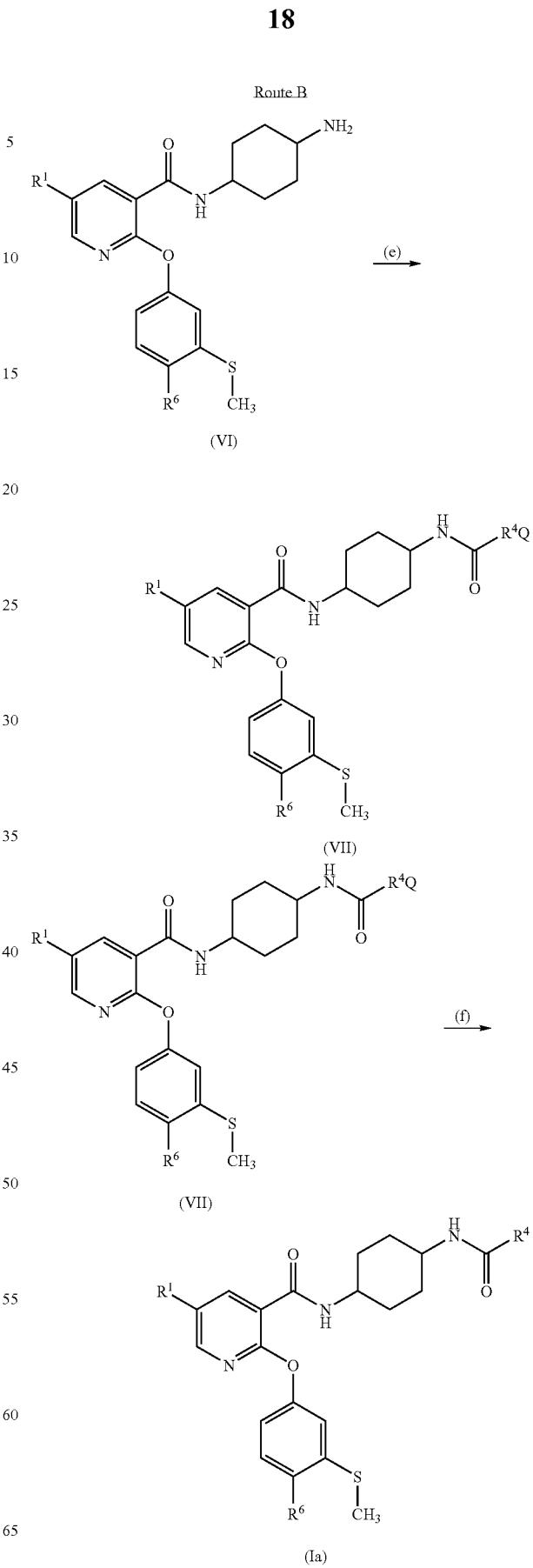

Q represents an alcohol protecting group, suitably THP, phenyl, preferably phenyl.

Step (e)—Reaction of Amino Group with QR⁴—COOH

Compounds of formula (VII) may be prepared by reaction of amine (VI) with a suitable acid, QR⁴COOH, as described in step (e) of Route A.

The preferred conditions are: QR⁴COOH, oxalyl chloride and DMF, in DCM at rt for 40 minutes (to give the acid chloride), then amine (VI), Et₃N in DCM at rt for 3 hours.

Step (f)—Removal of Hydroxyl Protecting Group

Deprotection of the HO-protecting group (Q) from (VII) to give a compound of formula (I) is undertaken using standard methodology, as described in "Protective Groups in Organic Synthesis" by T. W. Greene and P. Wutz.

When Q represents phenyl, the preferred conditions are: compound of formula (VII), BBr₃ in DCM at 0° C. for 30 minutes.

Alternatively, compounds of formula (Ia) may be prepared by the following route:

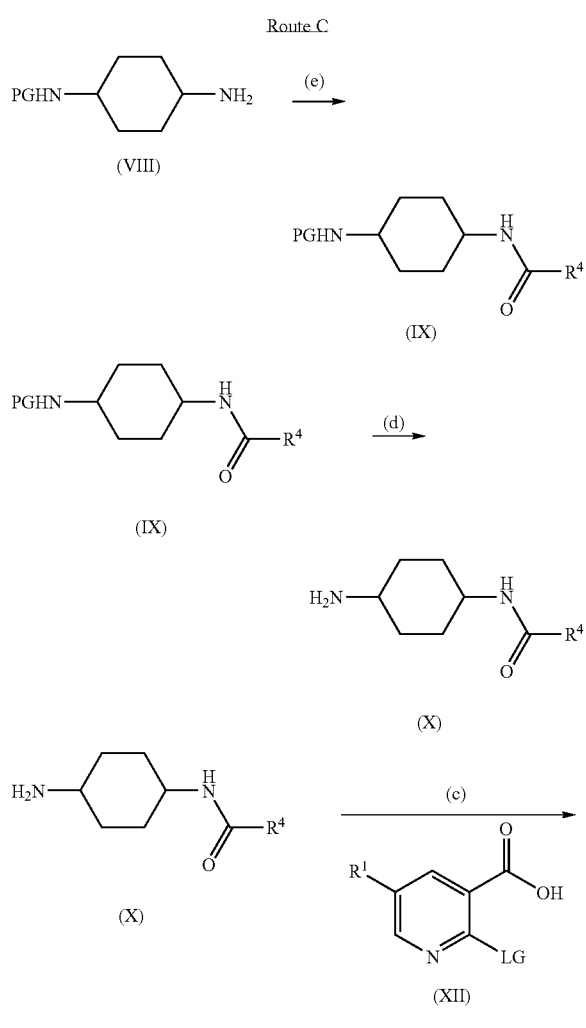

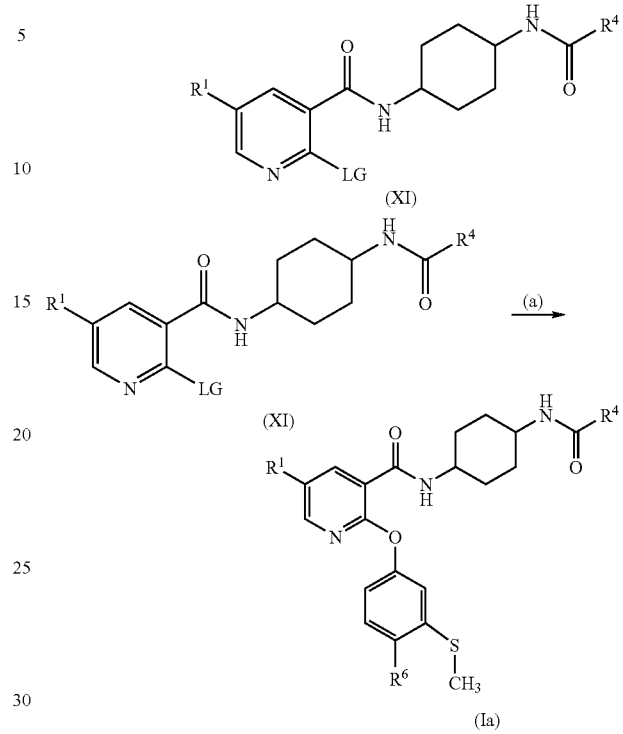

Step (e)—Reaction of Amino Group with R⁴—COOH

The compound of formula (IX) may be prepared from the amine of formula (VIII) by reaction with a carboxylic acid of formula R⁴COOH according to the methods described previously in step (e) of Route A.

Step (d)—Removal of Amine Protecting Group

The compound of formula (X) may be prepared by deprotection of the compound of formula (IX) according to the methods described previously in step (d) of Route A.

Step (c)—Acid-Amine Coupling

Compounds of formula (XI) may be prepared by reaction of the amine of formula (X) with the acid of formula (XII) according to the methods described previously in step (c) of Route A.

Step (a)—Ether Formation

Compounds of formula (Ia) may be prepared by reaction of compounds of formula (XI) with the appropriate 3-methylsulfanyl-phenol, as described previously in step (a) of Route A.

Alternatively, compounds of formula (V) may be prepared from compounds of formula (XII) according to the following route:

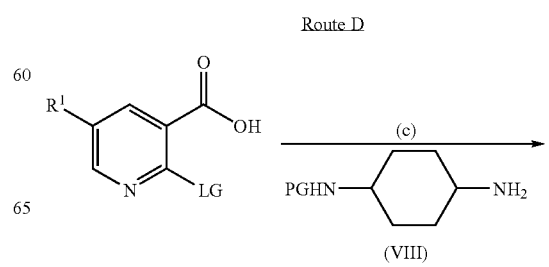

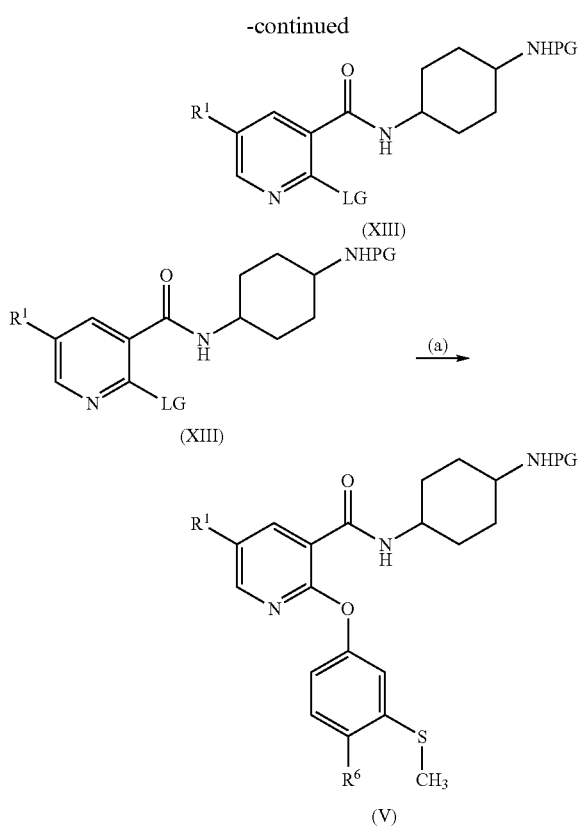

Step (c)—Acid-Amine Coupling

The compound of formula (XIII) may be prepared by the reaction of the nicotinic acid of formula (XII) with the amine of formula (VIII) according to the methods described previously in step (c) of Route A.

Step (a)—Ether Formation

The compound of formula (V) may be prepared from the compound of formula (XIII) by analogy with the methods described previously in step (a) of Route A.

Compounds of formula (V) may be transformed to compounds of formula (Ia) according to the methods described previously in steps (d) and (e) of Route A.

Further Routes

Certain $R^4$ groups may undergo further functional group interconversions (FGIs) and transformations, such as alkylation of a phenol hydroxy group, using a suitable alkylbromide, in the presence of a suitable alkali metal base (such as $K_2CO_3$), optionally in the presence of a catalyst (eg KI) in a suitable solvent such as acetonitrile and/or N,N-dimethylformamide at elevated temperature (see examples 25 and 26), or demethylation of a methoxy group by treatment with lithium iodide in pyridine or collidine, or by treatment with $BBr_3$ in dichloromethane.

For some of the steps of the here above described processes of preparation of the nicotinamide derivatives of formulae (I) and (Ia), it can be necessary to protect the potential reactive functions that are not wished to react. In such a case, any compatible protecting radical can be used. In particular methods such as those described by T. W. GREENE (*Protective Groups in Organic Synthesis*, A. Wiley-Interscience Publication, 1981) or by McOMIE (*Protective Groups in Organic Chemistry*, Plenum Press, 1973), can be used. For example, a hydroxyl group may be protected using a tetrahydropyran group, and deprotection may be achieved by treatment with a solution of acetic acid:water:tetrahydrofuran (4:1:2 by volume) at rt for up to 18 hours. Further, a benzyloxy group may be used and deprotected to give the corresponding hydroxyl compound, for example by using a reduction (e.g. with palladium black in acid).

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the examples and preparations hereto.

Also, the nicotinamide derivatives of formulae (I) and (Ia) as well as intermediates for the preparation thereof can be purified according to various well-known methods, such as for example crystallization or chromatography.

The nicotinamide derivatives of formulae (I), (Ia) and (Ib) may also be optionally transformed in pharmaceutically acceptable salts. In particular, these pharmaceutically acceptable salts of the nicotinamide derivatives of the formulae (I), (Ia) and (Ib) include the acid addition and the base salts (including disalts) thereof.

Suitable acid addition salts are formed from acids which form non-toxic salts. Examples include the acetate, aspartate, benzoate, besylate, bicarbonate/carbonate, bisulphate, camsylate, citrate, edisylate, esylate, fumarate, gluceptate, gluconate, glucuronate, hibenzate, hydrochloride/chloride, hydrobromide/bromide, hydroiodide/iodie, hydrogen phosphate, isethionate, D- and L-lactate, malate, maleate, malonate, mesylate, methylsulphate, 2-napsylate, nicotinate, nitrate, orotate, palmoate, phosphate, saccharate, stearate, succinate sulphate, D- and L-tartrate, 1-hydroxy-2-naphtoate, 3-hydroxy-2-naphthoate and tosylate saltes.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see Stahl and Wermuth, Handbook of Pharmaceutical Salts: Properties, Selection and Use, Wiley-VCH, Weinheim, Germany (2002).

A pharmaceutically acceptable salt of a nicotinamide derivative of the formulae (I), (Ia) and (Ib) may be readily prepared by mixing together solutions of the nicotinamide derivative of formulae (I), (Ia) and (Ib) and the desired acid or base, as appropriate. The salt may precipitate from solution and be collected by filtration or may be recovered by evaporation of the solvent.

Pharmaceutically acceptable solvates in accordance with the invention include hydrates and solvates wherein the solvent of crystallization may be isotopically substituted, e.g. D2O, $d_6$-acetone, $d_6$-DMSO.

Also within the scope of the invention are clathrates, drug-host inclusion complexes wherein, in contrast to the aforementioned solvates, the drug and host are are present in non-stoichiometric amounts. For a review of such complexes, see J Pharm Sci, 64 (8), 1269–1288 by Haleblian (August 1975).

Hereinafter all references to nicotinamide derivatives of formulae (I), (Ia) and (Ib) include references to salts thereof and to solvates and clathrates of compounds of formulae (I), (Ia) and (Ib) and salts thereof.

The invention includes all polymorphs of the nicotinamide derivatives of formulae (I), (Ia) and (Ib).

Also within the scope of the invention are so-called "prodrugs" of the nicotinamide derivatives of formulae (I), (Ia) and (Ib). Thus certain derivatives of nicotinamide derivatives of formulae (I), (Ia) and (Ib) which have little or no pharmacological activity themselves can, when metabolised upon administration into or onto the body, give rise to nicotinamide derivatives of formulae (I), (Ia) and (Ib) having the desired activity. Such derivatives are referred to as "prodrugs".

Prodrugs in accordance with the invention can, for example, be produced by replacing appropriate functionalities present in the nicotinamide derivatives of formulae (I), (Ia) and (Ib) with certain moieties known to those skilled in the art as "pro-moieties" as described, for example, in "Design of Prodrugs" by H Bundgaard (Elsevier, 1985).

Finally, certain nicotinamide derivatives of formulae (I), (Ia) and (Ib) may themselves act as prodrugs of other nicotinamide derivatives of formulae (I), (Ia) and (Ib).

Nicotinamide derivatives of formulae (I), (Ia) and (Ib) containing one or more asymmetric carbon atoms can exist as two or more optical isomers. Where a nicotinamide derivative of formulae (I), (Ia) and (Ib) contains an alkenyl or alkenylene group, geometric cis/trans (or Z/E) isomers are possible, and where the nicotinamide derivative contains, for example, a keto or oxime group, tautomeric isomerism ('tautomerism') may occur. It follows that a single nicotinamide derivative may exhibit more than one type of isomerism.

Included within the scope of the present invention are all optical isomers, geometric isomers and tautomeric forms of the nicotinamide derivatives of formulae (I), (Ia) and (Ib), including compounds exhibiting more than one type of isomerism, and mixtures of one or more thereof.

Cis/trans isomers may be separated by conventional techniques well known to those skilled in the art, for example, fractional crystallisation and chromatography.

Conventional techniques for the preparation/isolation of individual stereoisomers include the conversion of a suitable optically pure precursor, resolution of the racemate (or the racemate of a salt or derivative) using, for example, chiral HPLC, or fractional crystallisation of diastereoisomeric salts formed by reaction of the racemate with a suitable optically active acid or base, for example, tartaric acid.

The present invention also includes all pharmaceutically acceptable isotopic variations of a nicotinamide derivative of formulae (I), (Ia) and (Ib). An isotopic variation is defined as one in which at least one atom is replaced by an atom having the same atomic number, but an atomic mass different from the atomic mass usually found in nature.

Examples of isotopes suitable for inclusion in the nicotinamide derivatives of the invention include isotopes of hydrogen, such as $^2H$ and $^3H$, carbon, such as $^{13}C$ and $^{14}C$, nitrogen, such as $^{15}N$, oxygen, such as $^{17}O$ and $^{18}O$, phosphorus, such as $^{32}P$, sulphur, such as $^{35}S$, fluorine, such as $^{18}F$, and chlorine, such as $^{36}Cl$.

Substitution of the nicotinamide derivative of formulae (I), (Ia) and (Ib) isotopes such as deuterium, i.e. $^2H$, may afford certain therapeutic advantages resulting from greater metabolic stability, for example, increased in vivo half-life or reduced dosage requirements, and hence may be preferred in some circumstances.

Certain isotopic variations of the nicotinamide derivatives of formulae (I), (Ia) and (Ib), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Isotopic variations of the nicotinamide derivatives of formulae (I), (Ia) and (Ib) can generally be prepared by conventional techniques known to those skilled in the art or by processes analogous to those described in the accompanying Examples and Preparations using appropriate isotopic variations of suitable reagents.

According to a further aspect, the present invention concerns mixtures of nicotinamide derivatives of the formulae (I), (Ia) and (Ib), as well as mixtures with or of their pharmaceutically acceptable salts, solvates, polymorphs, isomeric forms and/or isotope forms.

According to the present invention, all the here above mentioned forms of the nicotinamide derivatives of formulae (I), (Ia) and (Ib) except the pharmaceutically acceptable salts (i.e. said solvates, polymorphs, isomeric forms and isotope forms), are defined as "derived forms" of the nicotinamide derivatives of formulae (I), (Ia) and (Ib) in what follows.

The nicotinamide derivatives of formulae (I), (Ia) and (Ib), their pharmaceutically acceptable salts and/or derived forms, are valuable pharmaceutical active compounds, which are suitable for the therapy and prophylaxis of numerous disorders in which the PDE4 enzymes are involved, in particular the inflammatory disorders, allergic disorders, respiratory diseases and wounds.

The nicotinamide derivatives of formulae (I), (Ia) and (Ib) and their pharmaceutically acceptable salts and derived forms as mentioned above can be administered according to the invention to animals, preferably to mammals, and in particular to humans, as pharmaceuticals for therapy or prophylaxis. They can be administered per se, in mixtures with one another or in combination with other drugs, or in the form of pharmaceutical preparations which permit enteral (gastric) or parenteral (non-gastric) administration and which as active constituent contain an efficacious dose of at least one nicotinamide derivative of the formulae (I), (Ia) and (Ib), its pharmaceutically acceptable salts and/or derived forms, in addition to customary pharmaceutically innocuous excipients and/or additives. The term "excipient" is used herein to describe any ingredient other than the compound of the invention. The choice of excipient will to a large extent depend on the particular mode of administration.

The nicotinamide derivatives of formulae (I), (Ia) and (Ib), their pharmaceutically acceptable salts and/or derived forms may be freeze-dried, spray-dried, or evaporatively dried to provide a solid plug, powder, or film of crystalline or amorphous material. Microwave or radio frequency drying may be used for this purpose.

Oral Administration

The nicotinamide derivatives of formulae (I), (Ia) and (Ib) their pharmaceutically acceptable salts and/or derived forms of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, propylene glycol, methylcellulose, or a suitable oil, and one or more emulsifying agents and/or suspending agents. Liquid formulations may also be prepared by the reconstitution of a solid, for example, from a sachet.

The nicotinamide derivatives of formulae (I), (Ia) and (Ib), their pharmaceutically acceptable salts and/or derived forms of the invention may also be used in fast-dissolving, fast-disintegrating dosage forms such as those described in Expert Opinion in Therapeutic Patents, 11 (6), 981–986 by Liang and Chen (2001).

The composition of a typical tablet in accordance with the invention may comprise:

| Ingredient | % w/w |
|---|---|
| Nicotinamide derivative of formula (1) | 10.00* |
| Microcrystalline cellulose | 64.12 |
| Lactose | 21.38 |
| Croscarmellose sodium | 3.00 |
| Magnesium stearate | 1.50 |

*Quantity adjusted in accordance with drug activity.

A typical tablet may be prepared using standard processes known to a formulation chemist, for example, by direct compression, granulation (dry, wet, or melt), melt congealing, or extrusion. The tablet formulation may comprise one or more layers and may be coated or uncoated.

Examples of excipients suitable for oral administration include carriers, for example, cellulose, calcium carbonate, dibasic calcium phosphate, mannitol and sodium citrate, granulation binders, for example, polyvinylpyrrolidine, hydroxypropylcellulose, hydroxypropylmethylcellulose and gelatin, disintegrants, for example, sodium starch glycolate and silicates, lubricating agents, for example, magnesium stearate and stearic acid, wetting agents, for example, sodium lauryl sulphate, preservatives, anti-oxidants, flavours and colourants.

Solid formulations for oral administration may be formulated to be immediate and/or modified release. Modified release formulations include delayed-, sustained-, pulsed-, controlled dual-, targeted and programmed release. Details of suitable modified release technologies such as high energy dispersions, osmotic and coated particles are to be found in Verma et al, Pharmaceutical Technology On-line, 25(2), 1–14 (2001). Other modified release formulations are described in U.S. Pat. No. 6,106,864.

Parenteral Administration

The nicotinamide derivatives of formulae (I), (Ia) and (Ib), their pharmaceutically acceptable salts and/or derived forms of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of nicotinamide derivatives of formulae (I), (Ia) and (Ib) used in the preparation of parenteral solutions may be increased by suitable processing, for example, the use of high energy spray-dried dispersions (see WO 01/47495) and/or by the use of appropriate formulation techniques, such as the use of solubility-enhancing agents.

Formulations for parenteral administration may be formulated to be immediate and/or modified release. Modified release formulations include delayed-, sustained-, pulsed-, controlled dual-, targeted and programmed release.

Topical Administration

The nicotinamide derivatives of the invention may also be administered topically to the skin or mucosa, either dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin and propylene glycol. Penetration enhancers may be incorporated—see, for example, J Pharm Sci, 88 (10), 955–958 by Finnin and Morgan (October 1999).

Other means of topical administration include delivery by iontophoresis, electroporation, phonophoresis, sonophoresis and needle-free or microneedle injection.

Formulations for topical administration may be formulated to be immediate and/or modified release. Modified release formulations include delayed-, sustained-, pulsed-, controlled dual-, targeted and programmed release. Thus nicotinamide derivatives of formulae (I), (Ia) and (Ib) may be formulated in a more solid form for administration as an implanted depot providing long-term release of the active compound.

Inhaled/Intranasal Administration

The nicotinamide derivatives of formulae (I), (Ia) and (Ib) can also be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurised container, pump, spray, atomiser (preferably an atomiser using electrohydrodynamics to produce a fine mist), or nebuliser, with or without the use of a suitable propellant, such as dichlorofluoromethane.

The pressurised container, pump, spray, atomizer, or nebuliser contains a solution or suspension of the active compound comprising, for example, ethanol (optionally, aqueous ethanol) or a suitable alternative agent for dispersing, solubilising, or extending release of the active, the propellant(s) as solvent and an optional surfactant, such as sorbitan trioleate or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

A suitable solution formulation for use in an atomiser using electrohydrodynamics to produce a fine mist may contain from 1 µg to 20 mg of the nicotinamide derivative of formulae (I), (Ia) and (Ib) per actuation and the actuation volume may vary from 1 µl to 100 µl. A typical formulation may comprise a nicotinamide derivative of formulae (I), (Ia) and (Ib), propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the nicotinamide derivative of formulae (I), (Ia) and (Ib), a suitable powder base such as lactose or starch and a performance modifier such as I-leucine, mannitol, or magnesium stearate.

In the case of dry powder inhalers and aerosols, the dosage unit is determined by means of a valve which delivers a metered amount. Units in accordance with the invention are typically arranged to administer a metered dose or "puff" containing from 1 µg to 4000 µg of the nicotinamide derivative of formulae (I), (Ia) and (Ib). The overall daily dose will typically be in the range 1 µg to 20 mg which may be administered in a single dose or, more usually, as divided doses throughout the day.

Formulations for inhaled/intranasal administration may be formulated to be immediate and/or modified release. Modified release formulations include delayed-, sustained-, pulsed-, controlled dual-, targeted and programmed release. Sustained or controlled release can be obtained by using for example poly(D,L-lactic-co-glycolic acid).

Flavouring agents, such as methol and levomethol and/or sweeteners such as saccharing or saccharin sodium can be added to the formulation.

Rectal/Intravaginal Administration

The nicotinamide derivatives of formulae (I), (Ia) and (Ib) may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled dual-, targeted and programmed release.

Ocular/Andial Administration

The nicotinamide derivatives of formulae (I), (Ia) and (Ib) may also be administered directly to the eye or ear, typically in the form of drops of a micronised suspension or solution in isotonic, pH-adjusted, sterile saline. Other formulations suitable for ocular and andial administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/andial administration may be formulated to be immediate and/or modified release. Modified release formulations include delayed-, sustained-, pulsed-, controlled dual-, targeted, or programmed release.

Enabling Technologies

The nicotinamide derivatives of formulae (I), (Ia) and (Ib) may be combined with soluble macromolecular entities such as cyclodextrin or polyethylene glycol-containing polymers to improve their solubility, dissolution rate, taste-masking, bioavailability and/or stability.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

For administration to human patients, the total daily dose of the nicotinamide derivatives of formulae (I), (Ia) and (Ib) is typically in the range 0.001 mg/kg to 100 mg/kg depending, of course, on the mode of administration. The total daily dose may be administered in single or divided doses. The physician will readily be able to determine doses for subjects depending on age, weight, health state and sex or the patient as well as the severity of the disease.

According to another embodiment of the present invention, the nicotinamide derivatives of the formulae (I), (Ia) and (Ib), their pharmaceutically acceptable salts and/or their derived forms, can also be used as a combination with one or more additional therapeutic agents to be co-administered to a patient to obtain some particularly desired therapeutic end result. The second and more additional therapeutic agents may also be a nicotinamide derivatives of the formulae (I), (Ia) and (Ib), their pharmaceutically acceptable salts and/or their derived forms, or one or more PDE4 inhibitors known in the art. More typically, the second and more therapeutic agents will be selected from a different class of therapeutic agents.

As used herein, the terms "co-administration", "co-administered" and "in combination with", referring to the nicotinamide derivatives of formulae (I), (Ia) and (Ib) and one or more other therapeutic agents, is intended to mean, and does refer to and include the following:

simultaneous administration of such combination of nicotinamide derivative(s) and therapeutic agent(s) to a patient in need of treatment, when such components are formulated together into a single dosage form which releases said components at substantially the same time to said patient, substantially simultaneous administration of such combination of nicotinamide derivative(s) and therapeutic agent(s) to a patient in need of treatment, when such components are formulated apart from each other into separate dosage forms which are taken at substantially the same time by said patient, whereupon said components are released at substantially the same time to said patient, sequential administration of such combination of nicotinamide derivative(s) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of nicotinamide derivative(s) and therapeutic agent(s) to a patient in need of treatment, when such components are formulated together into a single dosage form which releases said components in a controlled manner whereupon they are concurrently, consecutively, and/or overlappingly administered at the same and/or different times by said patient.

Suitable examples of other therapeutic agents which may be used in combination with the nicotinamide derivatives of the formulae (I), (Ia) and (Ib), their pharmaceutically acceptable salts and/or their derived forms include, but are by no mean limited to:

(a) 5-Lipoxygenase (5-LO) inhibitors or 5-lipoxygenase activating protein (FLAP) antagonists,
(b) Leukotriene antagonists (LTRAs) including antagonists of LTB4, LTC4, LTD4, and LTE4,
(c) Histaminic receptor antagonists including H1, H3 and H4 antagonists,
(d) α1- and α2-adrenoceptor agonist vasoconstrictor sympathomimetic agents for decongestant use,
(e) Muscarinic M3 receptor antagonists or anticholinergic agents,
(f) β2-adrenoceptor agonists,
(g) Theophylline,
(h) Sodium cromoglycate,
(i) COX-1 inhibitors (NSAIDs) and COX-2 selective inhibitors,
(j) Oral or inhaled Glucocorticosteroids,
(k) Monoclonal antibodies active against endogenous inflammatory entities,
(l) Anti-tumor necrosis factor (anti-TNF-a) agents,
(m) Adhesion molecule inhibitors including VLA-4 antagonists,
(n) Kinin-B1- and B2-receptor antagonists,
  (o) Immunosuppressive agents,
  (p) Inhibitors of matrix metalloproteases (MMPs),
  (q) Tachykinin NK1, NK2 and NK3 receptor antagonists,
  (r) Elastase inhibitors,
  (s) Adenosine A2a receptor agonists,
  (t) Inhibitors of urokinase,
  (u) Compounds that act on dopamine receptors, e.g. D2 agonists,
  (v) Modulators of the NFkb pathway, e.g. IKK inhibitors,
  (w) Agents that can be classed as mucolytics or anti-tussive,
  (x) antibiotics, and
  (y) p38 MAP kinase inhibitors According to the present invention, combination of the nicotinamide derivatives of formulae (I), (Ia) and (Ib) with:

muscarinic M3 receptor agonists or anticholinergic agents including in particular ipratropium salts, namely bromide, tiotropium salts, namely bromide, oxitropium salts, namely bromide, perenzepine, and telenzepine, β2-adrenoceptor agonists including albutarol, salbutamol, formoterol and salmeterol, glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, and mometasone furoate, or adenosine A2a receptor agonists, are preferred.

It is to be appreciated that all references herein to treatment include curative, palliative and prophylactic treatment. The description which follows concerns the therapeutic applications to which the nicotinamide derivatives of formulae (I), (Ia) and (Ib) may be put.

The nicotinamide derivatives of formulae (I), (Ia) and (Ib) inhibit the PDE4 isozyme and thereby have a wide range of therapeutic applications, as described further below, because of the essential role, which the PDE4 family of isozymes plays in the physiology of all mammals. The enzymatic role performed by the PDE4 isozymes is the intracellular hydrolysis of adenosine 3',5'-monophosphate (cAMP) within pro-inflammatory leukocytes. cAMP, in turn, is responsible for mediating the effects of numerous hormones in the body, and as a consequence, PDE4 inhibition plays a significant role in a variety of physiological processes. There is extensive literature in the art describing the effects of PDE inhibitors on various inflammatory cell responses, which in addition to cAMP increase, include inhibition of superoxide production, degranulation, chemotaxis and tumor necrosis factor (TNF) release in eosinophils, neutrophils and monocytes.

Therefore, a further aspect of the present invention relates to the use of the nicotinamide derivatives of formulae (I), (Ia) and (Ib), their pharmaceutically acceptable salts and/or derived forms, in the treatment of diseases, disorders, and conditions in which the PDE4 isozymes are involved. More specifically, the present invention also concerns the use of the nicotinamide derivatives of formulae (I), (Ia) and (Ib), their pharmaceutically acceptable salts and/or derived forms, in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma and wheezy infant syndrome, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated therewith, COPD that is characterized by irreversible, progressive airways obstruction, adult respiratory distress syndrome (ARDS) and exacerbation of airways hyperreactivity consequent to other drug therapy pneumoconiosis of whatever type, etiology, or pathogenesis, in particular pneumoconiosis that is a member selected from the group consisting of aluminosis or bauxite workers' disease, anthracosis or miners' asthma, asbestosis or steam-fitters' asthma, chalicosis or flint disease, ptilosis caused by inhaling the dust from ostrich feathers, siderosis caused by the inhalation of iron particles, silicosis or grinders' disease, byssinosis or cotton-dust asthma and talc pneumoconiosis;

bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis, seasonal allergic rhinitis or perennial allergic rhinitis or sinusitis of whatever type, etiology, or pathogenesis, in particular sinusitis that is a member selected from the group consisting of purulent or nonpurulent sinusitis, acute or chronic sinusitis and ethmoid, frontal, maxillary, or sphenoid sinusitis, rheumatoid arthritis of whatever type, etiology, or pathogenesis, in particular rheumatoid arthritis that is a member selected from the group consisting of acute arthritis, acute gouty arthritis, chronic inflammatory arthritis, degenerative arthritis, infectious arthritis, Lyme arthritis, proliferative arthritis, psoriatic arthritis and vertebral arthritis, gout, and fever and pain associated with inflammation, an eosinophil-related disorder of whatever type, etiology, or pathogenesis, in particular an eosinophil-related disorder that is a member selected from the group consisting of eosinophilia, pulmonary infiltration eosinophilia, Loffler's syndrome, chronic eosinophilic pneumonia, tropical pulmonary eosinophilia, bronchopneumonic aspergillosis, aspergilloma, granulomas containing eosinophils, allergic granulomatous angiitis or Churg-Strauss syndrome, polyarteritis nodosa (PAN) and systemic necrotizing vasculitis, atopic dermatitis, allergic dermatitis, contact dermatitis, or allergic or atopic eczema, urticaria of whatever type, etiology, or pathogenesis, in particular urticaria that is a member selected from the group consisting of immune-mediated urticaria, complement-mediated urticaria, urticariogenic material-induced urticaria, physical agent-induced urticaria, stress-induced urticaria, idiopathic urticaria, acute urticaria, chronic urticaria, angioedema, cholinergic urticaria, cold urticaria in the autosomal dominant form or in the acquired form, contact urticaria, giant urticaria and papular urticaria, conjunctivitis of whatever type, etiology, or pathogenesis, in particular conjunctivitis that is a member selected from the group consisting of actinic conjunctivitis, acute catarrhal conjunctivitis, acute contagious conjunctivitis, allergic conjunctivitis, atopic conjunctivitis, chronic catarrhal conjunctivitis, purulent conjunctivitis and vernal conjunctivitis, uveitis of whatever type, etiology, or pathogenesis, in particular uveitis that is a member selected from the group consisting of inflammation of all or part of the uvea, anterior uveitis, iritis, cyclitis, iridocyclitis, granulomatous uveitis, nongranulomatous uveitis, phacoantigenic uveitis, posterior uveitis, choroiditis; and chorioretinitis, psoriasis;

multiple sclerosis of whatever type, etiology, or pathogenesis, in particular multiple sclerosis that is a member selected from the group consisting of primary progressive multiple sclerosis and relapsing remitting multiple sclerosis, autoimmune/inflammatory diseases of whatever type, etiology, or pathogenesis, in particular an autoimmune/inflammatory disease that is a member selected from the group consisting of autoimmune hematological disorders, hemolytic anemia, aplastic anemia, pure red cell anemia, idiopathic thrombocytopenic purpura, systemic lupus erythematosus, polychondritis, scleroderma, Wegner's granulomatosis, dermatomyositis, chronic active hepatitis, myasthenia gravis, Stevens-Johnson syndrome, idiopathic sprue, autoimmune inflammatory bowel diseases, ulcerative colitis, endocrin opthamopathy, Grave's disease, sarcoidosis, alveolitis, chronic hypersensitivity pneumonitis, primary biliary cirrhosis, juvenile diabetes or diabetes mellitus type I, keratoconjunctivitis sicca, epidemic keratoconjunctivitis, diffuse interstitial pulmonary fibrosis or interstitial lung fibrosis, idiopathic pulmonary fibrosis, cystic fibrosis, glomerulonephritis with and without nephrotic syndrome, acute glomerulonephritis, idiopathic nephrotic syndrome, minimal change nephropathy, inflammatory/hyperproliferative skin diseases, benign familial pemphigus, pemphigus erythematosus, pemphigus foliaceus, and pemphigus vulgaris, prevention of allogeneic graft rejection following organ transplantation, inflammatory bowel disease (IBD) of whatever type, etiology, or pathogenesis, in particular inflammatory bowel disease that is a member selected from the group consisting of collagenous colitis, colitis polyposa, transmural colitis, ulcerative colitis and Crohn's disease (CD), septic shock of whatever type, etiology, or pathogenesis, in particular septic shock that is a member selected from the group consisting of renal failure, acute renal failure, cachexia, malarial cachexia, hypophysial cachexia, uremic cachexia, cardiac cachexia, cachexia suprarenalis or Addison's disease, cancerous cachexia and cachexia as a consequence of infection by the human immunodeficiency virus (HIV), liver injury, pulmonary hypertension of whatever type, etiology or pathogenesis including primary pulmonary hypertension/essential hypertension, pulmonary hypertension secondary to congestive heart failure, pulmonary hypertension secondary to chronic obstructive pulmonary disease, pulmonary venous hypertension, pulmonary arterial hypertension and hypoxia-induced pulmonary hypertension, bone loss diseases, primary osteoporosis and secondary osteoporosis, central nervous system disorders of whatever type, etiology, or pathogenesis, in particular a central nervous system disorder that is a member selected from the group consisting of depression, Alzheimers disease, Parkinson's disease, learning and memory impairment, tardive dyskinesia, drug dependence, arteriosclerotic dementia and dementias that accompany Huntington's chorea, Wilson's disease, paralysis agitans, and thalamic atrophies, infection, especially infection by viruses wherein such viruses increase the production of TNF-α in their host, or wherein such viruses are sensitive to upregulation of TNF-α in their host so that their replication or other vital activities are adversely impacted, including a virus which is a member selected from the group consisting of HIV-1, HIV-2, HIV-3, cytomegalovirus (CMV), influenza, adenoviruses and *Herpes* viruses including *Herpes zoster* and *Herpes simplex*, yeast and fungus infections wherein said yeast and fungi are sensitive to upregulation by TNF-α or elicit TNF-α production in their host, e.g., fungal meningitis, particularly when administered in conjunction with other drugs of choice for the treatment of systemic yeast and fungus infections, including but are not limited to, polymixins, e.g. Polymycin B, imidazoles, e.g. clotrimazole, econazole, miconazole, and ketoconazole, triazoles, e.g. fluconazole and itranazole as well as amphotericins, e.g. Amphotericin B and liposomal Amphotericin B, ischemia-reperfusion injury, ischemic heart disease, autoimmune diabetes, retinal autoimmunity, chronic lymphocytic leukemia, HIV infections, lupus erythematosus, kidney and ureter disease, urogenital and gastrointestinal disorders and prostate diseases, reduction of scar formation in the human or animal body, such as scar formation in the healing of acute wounds, and psoriasis, other dermatological and cosmetic uses, including antiphlogistic, skin-softening, skin elasticity and moisture-increasing activities.

According to one aspect the present invention relates in particular to the treatment of a respiratory disease, such as adult respiratory distress syndrome (ARDS), bronchitis, chronic bronchitis, chronic obstructive pulmonary disease, cystic fibrosis, asthma, emphysema, bronchiectasis, chronic sinusitis and rhinitis.

According to another aspect the present invention relates in particular to the treatment of gastrointestinal (GI) disorders, in particular inflammatory bowel diseases (IBD) such as Crohn's disease, ileitis, collagenous colitis, colitis polyposa, transmural colitis and ulcerative colitis.

A still further aspect of the present invention also relates to the use of the nicotinamide derivatives of formulae (I), (Ia) and (Ib), their pharmaceutically acceptable salts and/or derived forms, for the manufacture of a drug having a PDE4 inhibitory activity. In particular, the present inventions concerns the use of the nicotinamide derivatives of formulae (I), (Ia) and (Ib), their pharmaceutically acceptable salts and/or derived forms, for the manufacture of a drug for the treatment of inflammatory, respiratory, allergic and scar-forming diseases, disorders, and conditions, and more precisely for the treatment of diseases, disorders, and conditions that are listed above.

As a consequence, the present invention provides a particularly interesting method of treatment of a mammal, including a human being, with a PDE4 inhibitor including treating said mammal with an effective amount of a nicotinamide derivative of formulae (I), (Ia) and (Ib), its pharmaceutically acceptable salts and/or derived forms. More precisely, the present invention provides a particularly interesting method of treatment of a mammal, including a human being, to treat an inflammatory, respiratory, allergic and scar-forming disease, disorder or condition, including treating said mammal with an effective amount of a nicotinamide derivative of formulae (I), (Ia) and (Ib), its pharmaceutically acceptable salts and/or derived forms.

The following examples illustrate the preparation of the nicotinamide derivatives of the formulae (I), (Ia) and (Ib):

Preparation 1

2-Chloro-5-fluoro Nicotinic Acid

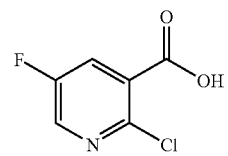

Ethyl-2-chloro-5-fluoro-nicotinoate (50.4 g, 0.247 mol) (J. Med. Chem., 1993, 36(18), 2676–88) was dissolved in tetrahydrofuran (350 mL) and a 2M aqueous solution of lithium hydroxide (247 mL, 0.495 mol) added. The reaction mixture was stirred at room temperature for 3 days. The pH of the solution was reduced to pH1 by addition of 6M hydrochloric acid and then extracted with dichloromethane (x3). The combined extracts were dried over magnesium sulphate and the solvent concentrated in vacuo to give a solid which was triturated with diethyl ether and then dried to give the title compound as a white solid, 40.56 g.

$^1$HNMR(DMSO-D$_6$, 400 MHz): δ=8.20 (s, 1H), 8.62 (s, 1H) ppm MS ES+ m/z 174 [MH]$^+$ Preparation 2

Syn-tert-Butyl 4-aminocyclohexylcarbamate

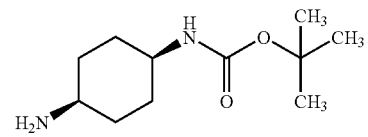

5% Palladium on charcoal (5.0 g) was mixed with toluene (10 mL) and was added to Syn-(4-azido-cyclohexyl)-carbamic acid tert-butyl ester (170 g, 0.71 mol) (WO 99/54284, pg 80, prep 77(1)) in methanol (400 mL). The mixture was hydrogenated (80 atmospheres) at room temperature for 18 hours and then filtered. The solvent was evaporated in-vacuo and the residue was triturated with ethyl acetate (50 mL) and then with hexane (200 mL). The solid obtained was isolated by filtration, dissolved in ethyl acetate (600 mL) and filtered through Celite®. The filtrate was concentrated in-vacuo to give a slush that was diluted with hexane (300 mL). The solid obtained was isolated by filtration and was washed with ethyl acetate in hexane (20:80). The mother liquors were combined and evaporated in-vacuo, the residue was purified by chromatography on silica gel using ethyl acetate and then methanol as eluant. The material obtained was crystallised from ethyl acetate and hexane and combined with the first crop to give the title compound as a white solid, 76.0 g. Mpt 88–90° C.

$^1$HNMR(CDCl$_3$, 400 MHz): δ=1.41(s, 9H), 1.52–1.77(m, 8H), 1.82(m, 1H), 1.97(m, 1H), 2.61(m, 1H), 3.62(m, 1H), 4.59(m, 1H) ppm. MS ES+ m/z 215 [MH]$^+$.

Preparation 3

1-Fluoro-4-methoxy-2-methylsulfanyl-benzene

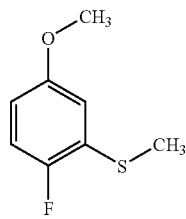

1,2-Difluoro-4-methoxy-benzene (100 mg, 0.69 mmol) and sodium methanethiolate (148 mg, 2.08 mmol) were dissolved in N,N-dimethylformamide (2 mL) and the reaction mixture stirred at 60° C. for 18 hours. Additional sodium methanethiolate (99 mg, 139 mmol) was added and the reaction mixture heated to 100° C. for 18 hours. The reaction mixture was diluted with water and extracted with ether (x2). The ether extracts were washed with water (x2), dried over magnesium sulphate and concentrated in vacuo. The residue was taken up in pentane:ether 1:1 mixture (2 mL) and filtered through a plug of silica in a pipette, washing through with pentane:ether 1:1 mixture (5 mL). The solution was concentrated in vacuo to yield the title product as a colourless oil, 135 mg.

$^1$HNMR(CDCl$_3$, 300 MHz): δ=2.45(s, 3H), 3.80(s, 3H), 6.65(dd, 1H), 6.80(dd, 1H), 6.95(t, 1H) ppm.

Preparation 4

4-Fluoro-3-methylsulfanyl-phenol

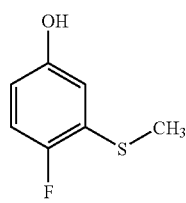

Boron tribromide (2.5 mL, 2.5 mmol) was added to a solution of the ether of preparation 3 (118.3 mg, 0.69 mmol) in dichloromethane (10 mL) at 0° C. under nitrogen and the reaction mixture was stirred at 0° C. for 4 hours. The reaction mixture was then stirred for a further 18 hours at room temperature. The reaction mixture was quenched with sodium carbonate solution (10 mL) and stirred for 1 hour. The mixture was then acidified with 2M hydrochloric acid, the layers separated and the organic phase concentrated in vacuo. The crude product was taken up in a mixture of ether:pentane 1:1 (2 mL) and the solution filtered through a plug of silica in a pipette. The residue was washed with additional ether:pentane 1:1 (5 mL) and concentrated in vacuo to yield the title product as a yellow oil, 110 mg.

$^1$HNMR(CDCl$_3$, 400 MHz): δ=2.45 (s, 3H), 6.57 (m, 1H), 6.72 (m, 1H), 6.90 (t, 1H) ppm. MS ES– m/z 157 [M–H]$^-$.

Preparation 5

5-Fluoro-2-(3-methylsulfanyl-phenoxy)-nicotinic acid ethyl ester

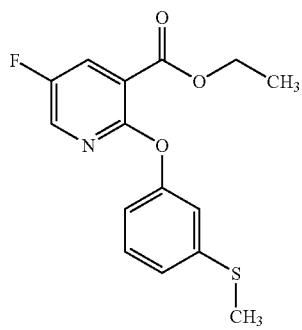

A solution of ethyl-2-chloro-5-fluoro-nicotinoate (J. Med. Chem., 1993, 36(18), 2676–88) (29 g, 0.143 mol) and 3-methylsulphanyl-phenol (WO 98/45268, pg. 68, preparation 61) (20 g, 0.143 mol) in dioxane (300 mL) was treated with caesium carbonate (46.5 g, 0.143 mol) at room temperature. The reaction mixture was heated to 100° C. and stirred for 48 hours. The reaction mixture was concentrated in vacuo and the residue taken up in water (600 mL) and extracted with ethyl acetate (3×250 mL). The organics were combined, washed with brine (200 mL), dried over magnesium sulphate and concentrated in vacuo. The residue was purified by column chromatography on silica gel eluting with dichloromethane:toluene (99.75:0.25 to 99.5:0.5) to yield the title product as a yellow oil, 27.1 g.

$^1$HNMR(CDCl$_3$, 400 MHz): δ=1.37(t, 3H), 2.23(s, 3H), 4.40(q, 2H), 6.84(m, 1H), 7.01(m, 1H) 7.08(m, 1H), 7.26(m, 1H), 7.98(m, 1H), 8.13(m, 1H) ppm. MS APCI+ m/z 308 [MH]$^+$.

Preparation 6

5-Fluoro-2-(3-methylsulfanyl-phenoxy)-nicotinic acid

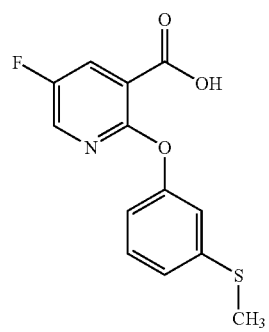

The ester of preparation 5 (27.1 g, 88.2 mmol) was dissolved in tetrahydrofuran (300 mL) and the solution treated with a 1M aqueous solution of lithium hydroxide (220 mL, 220 mmol). The reaction mixture was stirred at room temperature for 2 hours. The reaction mixture was concentrated in vacuo to remove the tetrahydrofuran and the aqueous was cooled to 0° C. before being acidified to pH 1 with hydrochloric acid. The resulting pink precipitate was removed by filtration and washed with iced water. The solid was dissolved in dichloromethane (800 mL) and washed with acidified brine solution (200 mL). The organic layer was separated, dried over magnesium sulphate and concentrated in vacuo. The residue was triturated with toluene to yield the title product as a white solid, 22.13 g.

$^1$HNMR(CD$_3$OD, 400 MHz): δ=2.43(s, 3H), 6.83(m, 1H), 7.01(m, 1H), 7.06(m, 1H), 7.25(m, 1H), 8.03(m, 2H) ppm. MS APCI+ m/z 280 [MH]$^+$.

Preparation 7

Syn-(4-{[5-Fluoro-2-(3-methylsulfanyl-phenoxy)-pyridine-3-carbonyl]-amino}-cyclohexyl)-carbamic acid tert-butyl ester

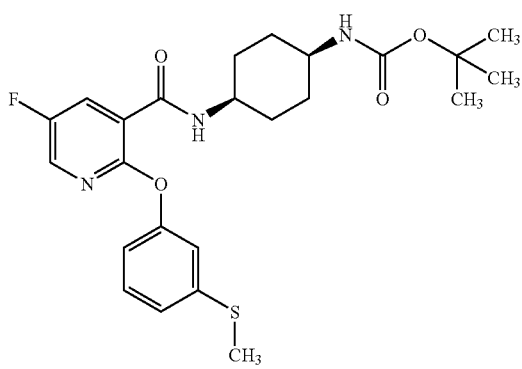

The acid of preparation 6 (5 g, 17.9 mmol) and N,N-dimethylformamide (5 drops) were dissolved in dichloromethane (100 mL) and the reaction mixture cooled to 0° C. The reaction mixture was treated dropwise with oxalyl chloride (3.1 mL, 35.8 mmol) over 15 minutes and then stirred at room temperature for 2 hours. The reaction mixture was concentrated in vacuo and the residue taken up in dichloromethane (100 mL). The solution was cooled to 0° C. and treated with triethylamine (7.5 mL, 54 mmol) and the amine of preparation 2 (4.2 g, 19.6 mmol). The reaction mixture was allowed to warm to room temperature and was stirred at room temperature for 48 hours. The reaction mixture was diluted with dichloromethane (100 mL) and washed with water (70 mL), 10% citric acid solution (2×70 mL), saturated sodium hydrogencarbonate solution (2×70 mL) and water (70 mL). The organic layer was dried over magnesium sulphate and concentrated in vacuo to yield the title product, 8.0 g.

$^1$HNMR(CDCl$_3$, 400 MHz): δ=1.40(s, 9H), 1.53(m, 2H), 1.68(m, 2H), 1.77(m, 4H), 2.46(s, 3H), 3.60(m, 1H), 4.18(m, 1H), 4.37(m, 1H), 6.88(m, 1H), 7.02(m, 1H), 7.17(m, 1H), 7.37(m, 1H), 7.93(m, 1H), 8.06(m, 1H), 8.36(m, 1H) ppm. MS ES+ m/z 476 [MH]$^+$.

Preparation 8

Syn-N-(4-Amino-cyclohexyl)-5-fluoro-2-(3-methyl-sulfanyl-phenoxy)-nicotinamide hydrochloride

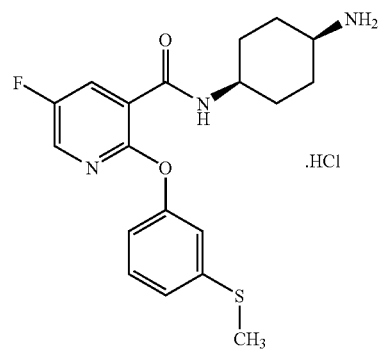

The Boc protected amine of preparation 7 (8.0 g, 16.8 mmol) was dissolved in dioxane (50 mL) and the solution treated with a 4M solution of hydrochloric acid in dioxane (25 mL). The reaction mixture was stirred at room temperature for 5 hours before being concentrated in vacuo and azeotroped with ethyl acetate and dichloromethane to yield the title product, 5.0 g.

$^1$HNMR(CD$_3$OD, 400 MHz): δ=1.67(m, 2H), 1.80–2.01 (m, 6H), 2.45(s, 3H), 3.24(m, 1H), 4.14(m, 1H), 6.92(m, 1H), 7.09(m, 1H), 7.17(m, 1H), 7.35(t, 1H), 8.08(m, 2H) ppm.

MS ES+ m/z 376 [MH]$^+$.

Preparation 9

2-(3-Methylsulfanyl-phenoxy)-nicotinic acid methyl ester

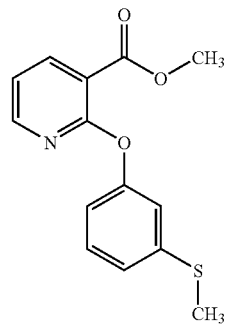

2-Chloronicotinic acid methyl ester (WO 02/085358, pg. 21, example 1) (8.00 g, 47 mmol), caesium carbonate (21.30 g, 65 mmol) and copper iodide (890 mg, 4.7 mmol) were dissolved in a toluene:1-methyl-2-pyrrolidinone 4:1 mixture (155 mL) and the reaction mixture treated with 3-methyl-sulphanyl-phenol (6.21 g, 44 mmol) (WO 98/45268, pg. 68, preparation 61). The reaction mixture was heated td 110° C. for 18 hours. The reaction mixture was diluted with water (250 mL), and ethyl acetate (250 mL) and filtered through Arbocel®. The organic layer was separated and the aqueous extracted with ethyl acetate (2×250 mL). The organics were combined, washed with water and brine and dried over magnesium sulphate. The organics were concentrated in vacuo and the residue purified by column chromatography on silica gel eluting with toluene:ethyl acetate 100:0 to 98:2. The crude product was triturated with hexane:ether 66:33 to yield the title product, 4.90 g.

¹HNMR(CDCl₃, 400 MHz): δ=2.45(s, 3H), 3.62(s, 3H), 6.91(d, 1H), 7.07(m, 1H), 7.22(m, 2H), 7.37(t, 1H), 8.35(m, 1H), 8.52(d, 1H) ppm.

Preparation 10

2-(3-Methylsulfanyl-phenoxy)-nicotinic acid

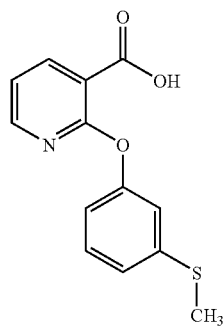

The ester of preparation 9 (4.80 g, 17.0 mmol) was dissolved in tetrahydrofuran (87 mL) and the solution treated with an aqueous solution of lithium hydroxide (43.6 mL, 44.0 mmol) and stirred for 3 hours at room temperature. The reaction mixture was concentrated in vacuo and the residue taken up in 10M hydrochloric acid (3 mL). The mixture was diluted with dichloromethane (100 mL) and the organic layer separated and washed with brine. The organics were dried over magnesium sulphate and concentrated in vacuo to yield the title product as a white solid, 3.58 g.

¹HNMR(CDCl₃, 400 MHz): δ=2.45(s, 3H), 6.91(d, 1H), 7.07(m, 1H), 7.22(m, 2H), 7.37(t, 1H), 8.35(m, 1H), 8.52(d, 1H) ppm. MS ES- m/z 260 [M-H]⁻.

Preparation 11

Syn-(4-{[2-(3-Methylsulfanyl-phenoxy)-pyridine-3-carbonyl]-amino}-cyclohexyl)-carbamic acid tert-butyl ester

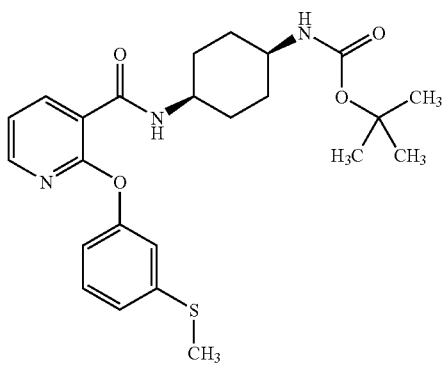

The acid of preparation 10 (2.00 g, 7.67 mmol) was dissolved in dichloromethane (25 mL) and the solution treated with N,N-dimethylformamide (3 drops) and oxalyl chloride (800 µL, 9.20 mmol). The reaction mixture was stirred for 2 hours at room temperature and then diluted with tetrahydrofuran (15 mL), the reaction mixture was then stirred for a further 1 hour at room temperature. The reaction mixture was concentrated in vacuo, the residue dissolved in dichloromethane (50 mL) and the solution treated with a solution of the amine of preparation 2 (3.30 g, 15.35 mmol) in tetrahydrofuran (20 mL). The reaction mixture was stirred at room temperature for 18 hours, diluted with dichloromethane (50 mL) and washed with 10% citric acid solution, saturated sodium hydrogencarbonate solution, water and brine. The solution was then dried over magnesium sulphate and concentrated in vacuo. The residue was purified by column chromatography on silica gel eluting with pentane:ethyl acetate 90:10 to 30:70 to yield the title product, 900 mg.

¹HNMR(CDCl₃, 400 MHz): δ=1.42(s, 9H), 1.62–1.85(m, 10H), 2.48(s, 3H), 4.20(m, 1H), 4.42(m, 1H), 6.93(m, 1H), 7.05(m, 1H), 7.19(m, 2H), 7.39(t, 1H), 7.97(m, 1H), 8.23(m, 1H) ppm. MS ES+ m/z 458 [MH]⁺.

Preparation 12

Syn-N-(4-Amino-cyclohexyl)-2-(3-methylsulfanyl-phenoxy)-nicotinamide hydrochloride

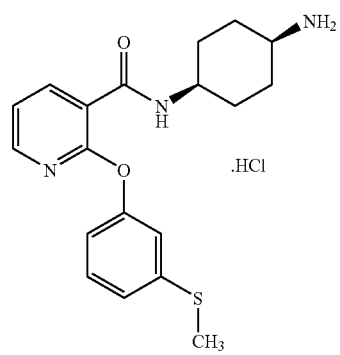

The product of preparation 11 (890 mg, 1.94 mmol) was dissolved in dichloromethane (5 mL) and the solution treated with a 4M solution of hydrochloric acid in dioxan (20 mL). The reaction mixture was stirred at room temperature for 3 hours and concentrated in vacuo to yield the title product as a white solid, 820 mg.

¹HNMR(CD₃OD, 400 MHz): δ=1.63–1.98(m, 8H), 2.44 (s, 3H), 3.59(m, 1H), 3.68(m, 1H), 6.95(m, 1H), 7.09(m, 1H), 7.17(m, 1H), 7.24(m, 1H), 7.37(t, 1H), 8.199 m, 1H), 8.27(m, 1H) ppm. MS ES+ m/z 358 [MH]⁺.

Preparation 13

Syn-[4-(2-Hydroxy-4-methyl-benzoylamino)-cyclohexyl]-carbamic acid tert-butyl ester

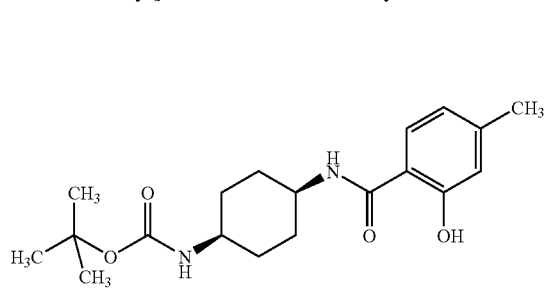

The amine of preparation 2 (17.14 g, 80.0 mmol) was dissolved in dichloromethane (180 mL) and the solution treated with N-ethyldiisopropylamine (20.9 mL, 120 mmol), 1-hydroxybenzotriazole hydrate (12.97 g, 96 mmol), 1-(3-dimethylaminopropyl)-3-ethylcarbodiimide hydrochloride (19.94 g, 104 mmol) and 4-methyl-salicylic acid (10.96 g, 72 mmol). The reaction mixture was stirred at room temperature for 48 hours and then diluted with dichloromethane (300 mL) and water (450 mL). The aqueous layer was acidified to pH 3 by dropwise addition of 2M hydrochloric acid and the organic layer washed with water (2×300 mL), dried over magnesium sulphate and concentrated in vacuo. The residue was triturated from ethyl acetate to yield the title product as a white solid, 17.59 g.

$^1$HNMR(CDCl$_3$, 400 MHz): δ=1.46(s, 9H), 1.87(m, 10H), 2.33(s, 3H), 3.67(m, 1H), 4.10(m, 1H), 6.09(m, 1H), 6.80(m, 1H), 7.12(m, 1H) ppm.

MS ES+ m/z 349 [MH]$^+$.

Preparation 14

Syn-N-(4-Amino-cyclohexyl)-2-hydroxy-4-methyl-benzamide hydrochloride

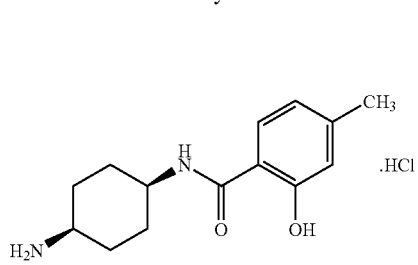

The protected amine of preparation 13 (20.00 g, 57 mmol) was dissolved in dichloromethane (300 mL) and hydrogen chloride gas bubbled through the solution at 0° C. for 2 hours. The reaction mixture was then stirred for a further 90 minutes, then concentrated in vacuo and the residue azeotroped from dichloromethane (×2) to yield the title product as a white solid, 16.21 g.

$^1$HNMR(CD$_3$OD, 400 MHz): δ=1.76(m, 4H), 1.82(m, 4H), 2.29(s, 3H), 3.34(m, 1H), 4.10(m, 1H), 6.75(m, 2H), 7.75(d, 1H) ppm.

MS ES+ m/z 249 [MH]$^+$.

Preparation 15

Syn-2-Chloro-5-fluoro-N-[4-(2-hydroxy-4-methyl-benzoylamino)-cyclohexyl]-nicotinamide

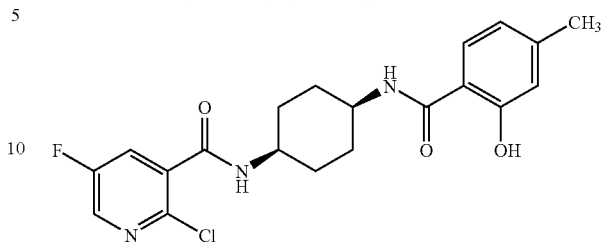

The amine of preparation 14 (14.195 g, 50.0 mmol), the acid of preparation 1 (7.29 g, 41.6 mmol), N-ethyldiisopropylamine (32.62 mL, 187 mmol), 1-hydroxybenzotriazole hydrate (6.76 g, 50.0 mmol) and finally 1-(3-dimethylaminopropyl)-3-ethylcarbodiimide hydrochloride (11.96 g, 62.4 mmol) were dissolved in dichloromethane (260 mL) and the reaction mixture stirred at room temperature for 18 hours. Additional 1-(3-dimethylaminopropyl)-3-ethylcarbodiimide hydrochloride (3.80 g, 20.0 mmol) was added and the reaction mixture was stirred for a further 3 hours. The reaction mixture was diluted with dichloromethane and hydrochloric acid and the aqueous layer washed with dichloromethane. The organics were combined, and washed with water, saturated sodium hydrogencarbonate solution and brine and then dried over magnesium sulphate and concentrated in vacuo. The residue was triturated with isopropyl acetate to yield the title product, 8.89 g.

$^1$HNMR(CD$_3$OD, 400 MHz): δ=1.85(m, 8H), 2.30(s, 3H), 4.06(m, 2H), 6.73(m, 2H), 7.71(d, 1H), 7.78(m, 1H), 8.39(m, 1H) ppm.

MS ES+ m/z 406 [MH]$^+$.

Preparation 16

Syn-N-[4-(3,5-Diphenoxy-benzoylamino)-cyclohexyl]-5-fluoro-2-(3-methylsulfanyl-phenoxy)-nicotinamide

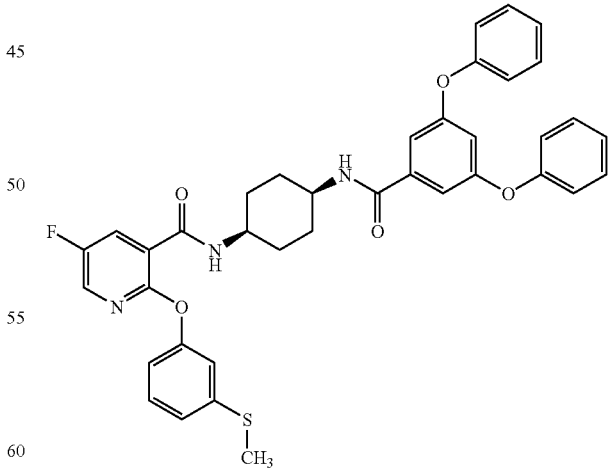

3,5-Diphenoxy-benzoic acid (791 mg, 2.37 mmol) was dissolved in dichloromethane (20 mL) and the solution treated with 2 drops of N,N-dimethylformamide and oxalyl chloride (635 mg, 5 mmol). The mixture was stirred at room temperature for 40 minutes and was then concentrated in vacuo. The residue was dissolved in dichloromethane (5 mL) and the solution added dropwise to a solution of the amine of preparation 8 (975 mmol, 2.37 mmol) and triethylamine (606 mg, 6.0 mmol) in dichloromethane (15 mL). The reaction mixture was then stirred at room temperature for 3 hours. The reaction mixture was poured into an aqueous solution of sodium hydrogencarbonate and then extracted with dichloromethane (3×30 mL). The organics were combined, dried over magnesium sulphate and concentrated in vacuo. The residue was purified by column chromatography on silica gel eluting with dichloromethane:methanol 100:0 to 96:4 to yield the title product as a white solid, 1.55 g (95%).

$^1$HNMR(CDCl$_3$, 400 MHz): δ=1.50(m, 2H), 1.87(m, 6H), 2.36(s, 3H), 4.06(m, 1H), 4.24(m, 1H), 5.06(s, 4H), 5.78(d, 1H), 6.73(s, 1H), 6.90(m, 3H), 7.00(s, 1H), 7.02(d, 1H), 7.29–7.44(brm, 11H), 8.07(m, 2H), 8.35(dd, 1H) ppm.

MS APCI+ m/z 692 [MH]$^+$.

Preparation 17

1-Methoxy-3-methylsulfanyl-benzene

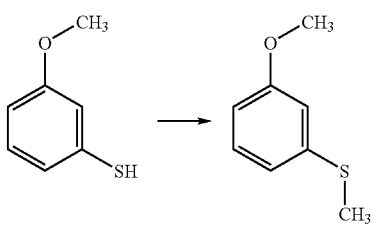

Methyl iodide (14.67 ml, 0.235 mol) was added dropwise to a solution of 3-methoxy-benzenethiol (30 g, 0.214 mol) and potassium carbonate (29.6 g, 0.214 mol) in acetone (400 ml) under nitrogen at 3° C. The reaction was allowed to warm to room temperature and the solvent was removed under reduced pressure. The residue was diluted with water (300 ml) and the aqueous layer was extracted with diethylether (3×200 ml). The combined organic extracts were dried over MgSO$_4$ and the solvent was removed under reduced pressure to give 1-Methoxy-3-methylsulfanyl-benzene (32.87 g) as a pale yellow liquid.

$^1$H NMR (400 MHz, CDCl$_3$): δ=7.17–7.21 (1H, t), 6.83–6.86 (1H, d), 6.81 (1H, s), 6.65–6.69 (1H, m), 3.80 (3H, s), 2.46 (3H, s) ppm.

Preparation 18

3-Methylsulfanyl-phenol

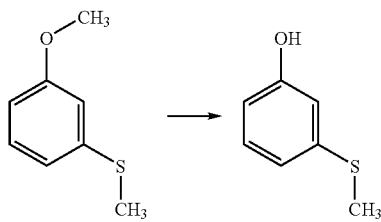

1-Methoxy-3-methylsulfanyl-benzene (32.87 g, 0.213 mol) was dissolved in a mixture of 30% hydrogen bromide in acetic acid (96 ml) and 48% aqueous hydrobromic acid (24 ml). The reaction was heated to reflux, and stirred at this temperature under nitrogen for 5.5 h. After cooling to room temperature the reaction mixture was poured into water (600 ml) and extracted with diethylether (3×300 ml). The combined organic extracts were washed with water (2×150 ml), brine (100 ml), dried over MgSO$_4$ and the solvent was removed under reduced pressure. The residue was purified by flash column chromatography on silica gel eluting with a solvent gradient of ethyl acetate:pentane (1:19 changing to 3:37 then 1:9, by volume) and the product was azeotroped with toluene (2×100 ml) to give 3-Methylsulfanyl-phenol (19.3 g) as a crimson oil.

$^1$H NMR (400 MHz, CDCl$_3$): δ=7.10–7.20 (1H, t), 6.77–6.84 (1H, d), 6.74 (1H, s), 6.55–6.63 (1H, d), 4.65–4.83 (1H, brs), 2.43 (3H, s) ppm.

Preparation 19

2-Amino-1-methyl cyclohexanol hydrochloride

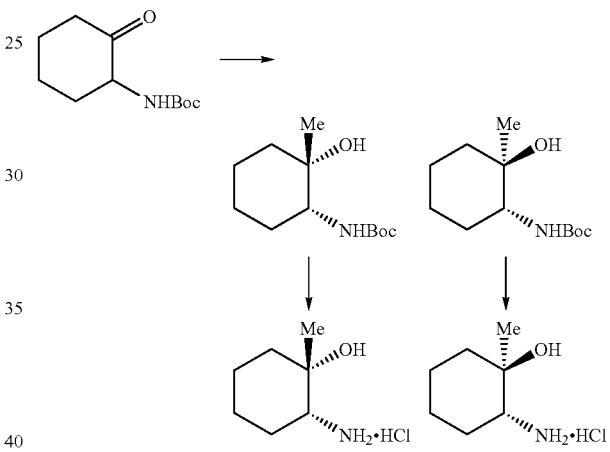

A solution of methyl magnesium chloride (3M in tetrahydrofuran, 19 ml, 57 mmol) was added to a solution of tert-butyl 2-oxocyclohexylcarbamate (4.0 g, 18.8 mmol) (Synth. Commun. (1992), 22(20), 3003–12) in tetrahydrofuran (80 ml) at −78° C. The mixture was allowed to warm to ambient temperature and was stirred for 3 h. The mixture was quenched by the addition of saturated ammonium chloride solution (20 ml) and was partitioned between water and diethyl diethyl ether. The organic phase was washed with water, brine, dried over MgSO$_4$, and the solvent removed under reduced pressure to give a white solid which was purified by flash column chromatography using ethyl acetate:cyclohexane (98:2 to 70:30) as eluant to give the less polar diastereoisomer of tert-butyl 2-hydroxy-2-methylcyclohexylcarbamate (940 mg) as a white solid.

$^1$H NMR (400 MHz, CDCl$_3$): δ=4.40–4.56 (1H, br s), 3.40–3.58 (1H, m), 1.76–1.88 (2H, m), 1.18–1.75(15H, m+s), 1.15 (3H, s) ppm. LRMS (electrospray): m/z [M+H]$^+$ 230 Anal. Found C, 63.17; H, 10.12; N, 5.91. C$_{12}$H$_{23}$NO$_3$ requires C, 62.85; H, 10.11; N, 6.11%.

Further elution gave the more polar diastereoisomer of tert-butyl 2-hydroxy-2-methylcyclohexylcarbamate (1.64 g) as a white solid.

$^1$H NMR (400 MHz, CDCl$_3$): δ=4.75–4.85 (1H, br s), 3.32–3.42 (1H, m), 1.68–1.80 (3H, m), 1.26–1.57 (14H, m+s), 1.25 (3H, s) ppm. LRMS (electrospray): m/z [M+H]$^+$ 230. Anal. Found C, 62.84; H, 10.05; N, 6.11. $C_{12}H_{23}NO_3$ requires C, 62.85; H, 10.11; N, 6.11%.

4M Hydrochloric acid in dioxan (40 ml, 160 mmol) was added to a solution of the less polar diastereoisomer of tert-butyl 2-hydroxy-2-methylcyclohexylcarbamate (875 mg, 3.82 mmol) in dioxan (5 ml). The mixture was stirred for 4 h then the solvent was removed under reduced pressure and the residue dried in vacuo to afford a single diastereoisomer of 2-amino-1-methylcyclohexanol hydrochloride (656 mg) as a white solid.

$^1$H NMR (400 MHz, CD$_3$OD): δ=2.90–2.98 (1H, dd), 1.60–1.92 (3H, m), 1.30–1.57 (5H, m), 1.18 (3H, s) ppm. LRMS (electrospray): m/z [M+H]$^+$ 130. Anal. Found C, 50.28; H, 9.51; N, 8.04. $C_7H_{15}$NO. HCl. 0.1H$_2$O requires C, 50.21; H, 9.75; N, 8.36%.

4M Hydrochloric acid in dioxan (40 ml, 160 mmol) was added to a solution of the more polar disatereoisomer of tert-butyl 2-hydroxy-2-methylcyclohexylcarbamate (1.52 g, 6.63 mmol) in dioxan (5 ml). The mixture was stirred for 4 h then the solvent was removed under reduced pressure and the residue dried in vacuo to afford a single diastereoisomer of 2-amino-1-methylcyclohexanol hydrochloride (1.05 g) as a white solid.

$^1$H NMR (400 MHz, CD$_3$OD): δ=2.94–3.03 (1H, dd), 1.57–1.85 (5H, m), 1.30–1.58 (3H, m), 1.30 (3H, s) ppm. LRMS (electrospray): m/z [M+H]$^+$ 130. Anal. Found C, 50.24; H, 9.52; N, 8.14. $C_7H_{15}$NO. HCl. 0.1H$_2$O requires C, 50.21; H, 9.75; N, 8.36%.

Preparation 20

4-Amino-1-methylcyclohexanol hydrochloride

Racemic, Single Distereoisomers, Unknown Relative Stereochemistry

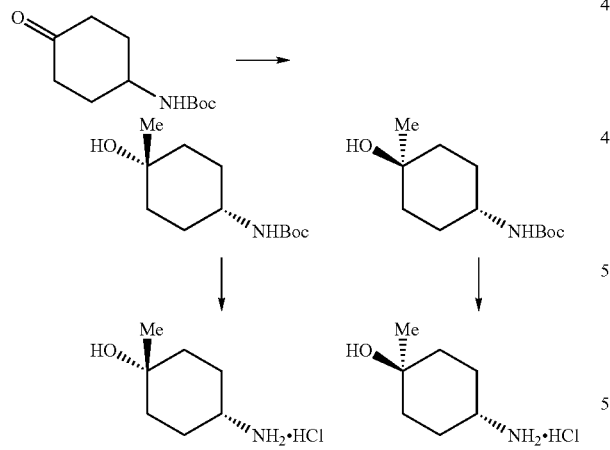

A solution of methyl magnesium chloride (3M in tetrahydrofuran, 57 ml, 171 mmol) was added to a solution of tert-butyl 4-oxocyclohexylcarbamate (12 g, 56 mmol) (WO9613262) in tetrahydrofuran (240 ml) at −78° C. The mixture was allowed to warm to ambient temperature and was stirred for 18 h. The mixture was quenched by the addition of saturated ammonium chloride solution (100 ml) and the volatile solvents were removed under reduced pressure. The residue was taken up in water (200 ml) and dichloromethane (400 ml) and solid citric acid was added until the layers separated. The organic phase was washed with saturated sodium bicarbonate solution, water, brine, dried over MgSO$_4$, and the solvent removed under reduced pressure to give a gum which was purified by flash column chromatography using ethyl acetate:cyclohexane (20:80 to 80:20) as eluant to give the less polar diastereoisomer of tert-butyl 4-hydroxy-4-methylcyclohexylcarbamate (680 mg) as a white solid.

$^1$H NMR (400 MHz, CDCl$_3$): δ=4.28–4.44 (1H, br s), 3.28–3.45 (1H, m), 1.75–1.84 (4H, m), 1.26–1.53 (13H, m+s), 1.21 (3H, s) ppm. LRMS (electrospray): m/z [M+H]$^+$ 230. Anal. Found C, 62.67; H, 9.92; N, 6.18. $C_{12}H_{23}NO_3$ requires C, 62.85; H, 10.11; N, 6.11%.

Further elution gave the more polar diastereoisomer of tert-butyl 4-hydroxy-4-methylcyclohexylcarbamate (450 mg) as a white solid.

$^1$H NMR (400 MHz, CDCl$_3$): δ=4.36–4.54 (1H, br s), 3.48–3.60 (1H, m), 1.87–1.20 (2H, m), 1.30–1.90 (15H, m+s), 1.26 (3H, s) ppm. LRMS (electrospray): m/z [M+H]$^+$ 230. Anal. Found C, 62.72; H, 9.93; N, 5.99. $C_{12}H_{23}NO_3$ requires C, 62.85; H, 10.11; N, 6.11%.

4M Hydrochloric acid in dioxan (20 ml, 80 mmol) was added to a solution of the less polar diastereoisomer of tert-butyl 4-hydroxy-4-methylcyclohexylcarbamate (610 mg, 2.66 mmol) in dioxan (5 ml). The mixture was stirred for 3 h then the solvent was removed under reduced pressure and the residue dried in vacuo to afford a single diastereoisomer of 4-amino-1-methylcyclohexanol hydrochloride (625 mg) as a gum.

$^1$H NMR (400 MHz, CD$_3$OD): δ=2.96–3.20 (1H, m), 1.64–2.18 (6H, m), 1.44–1.56 (2H, m), 1.24 (3H, s) ppm. LRMS (electrospray): m/z [M+H]$^+$ 130.

4M Hydrochloric acid in dioxan (40 ml, 160 mmol) was added to a solution of the more polar diastereoisomer of tert-butyl 4-hydroxy-4-methylcyclohexylcarbamate (405 g, 1.77 mmol) in dioxan (5 ml). The mixture was stirred for 3 h then the solvent was removed under reduced pressure and the residue dried in vacuo to afford a single diastereoisomer of 4-amino-1-methylcyclohexanol hydrochloride (305 mg) as a white solid.

$^1$H NMR (400 MHz, CD$_3$OD): δ=3.10–3.26 (1H, m), 1.92–2.08 (2H, m), 1.45–1.80 (6H, m), 1.28 (3H, s) ppm. LRMS (electrospray): m/z [M+H]$^+$ 130. Anal. Found C, 50.06; H, 9.50; N, 8.04. $C_7H_{15}$NO. HCl. 0.15H$_2$O requires C, 49.94; H, 9.76; N, 8.32%.

Preparation 21

6-(allyloxy)-1,3-benzoxathiol-2-one

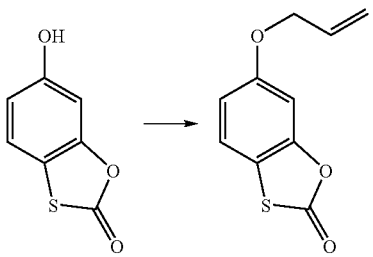

Allyl bromide (28.3 ml, 0.327 mol) was added to a mixture of tioxolone (50 g, 0.297 mol) and potassium carbonate (82 g, 0.595 mol) in acetone (300 ml), and the resultant suspension stirred at RT overnight. After removal of the solvent in vacuo, the residue was partioned between EtOAc (700 ml) and water (500 ml). The aqueous phase was removed, extracted with further EtOAc (2×300 ml), and the combined organics dried over MgSO₄ and concentrated to an off-white solid (66.6 g). Purification by flash column chromatography on silica eluting with EtOAc:pentane (1:39 to 1:9) gave the title compound as a white solid (48.3 g, 0.23 mol).

¹H NMR (400 MHz, CDCl₃): δ 7.25 (1H, d), 6.88 (1H, s), 6.85 (1H, dd), 6.1–5.95 (1H, m), 5.41 (1H, d), 5.30 (1H, d), 4.55 (2H, d) ppm. LRMS (thermospray): m/z [M+NH4]⁺ 226.

Preparation 22

5-(allyloxy)-2-sulfanylphenol

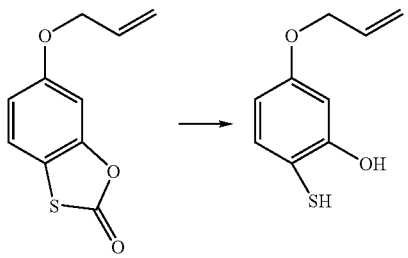

6-(Allyloxy)-1,3-benzoxathiol-2-one (48.3 g, 0.232 mol) was dissolved in aq. NaOH solution (2M, 300 ml) and THF (300 ml) to give a yellow solution which stirred at RT for 2 h. The THF was removed in vacuo, a small amount of precipitated starting material removed by filtration, and further starting material was removed by extraction of the aqueous phase into diethyl ether (3×300 ml). The aqueous phase was then acidified to pH 1 with cHCl (~150 ml) with ice-cooling. Gas evolution was observed, and after 15 min, the title compound was obtained following extraction into diethyl ether (3×300 ml), drying over MgSO₄ and concentration to a yellow oil (37.84 g, 0.18 mol).

¹H NMR (400 MHz, CDCl₃): δ=6.53 (1H, d), 6.41 (1H, dd), 6.35 (1H, s), 6.1–5.95 (1H, m), 5.38 (1H, d), 5.25 (1H, d), 4.47 (2H, d) ppm.

Preparation 23

4-(allyloxy)-2-methoxy-1-(methylsulfanyl)benzene

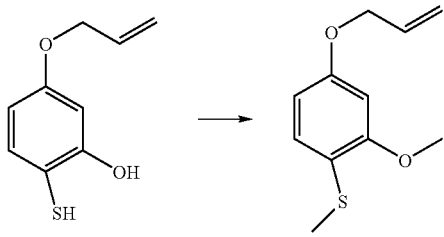

5-(Allyloxy)-2-sulfanylphenol (37.84 g, 0.21 mol) and potassium carbonate (43 g, 0.31 mol) in acetone (450 ml) was cooled to 5° C. and treated with methyl iodide (32.32 ml, 0.52 mol) dropwise and stirred for 1 h at RT. After removal of the solvent in vacuo, the residue was partioned between diethyl ether (300 ml) and water (400 ml). The aqueous phase was separated and extracted with further diethyl ether (2×150 ml) and the combined organics were dried over MgSO₄ and evaporated to a clear oil (26 g, 0.12 mol).

¹H NMR (400 MHz, CDCl₃): δ=7.19 (1H, d), 6.51 (1H, s), 6.50 (1H, d), 6.1–6.0 (1H, m), 5.42 (1H, d), 5.30 (1H, d), 4.53 (2H, d), 3.88 (3H, s), 2.40 (3H, s) ppm. LRMS (thermospray): m/z [M+H]⁺ 211.

Preparation 24

3-methoxy-4-(methylsulfanyl)phenol

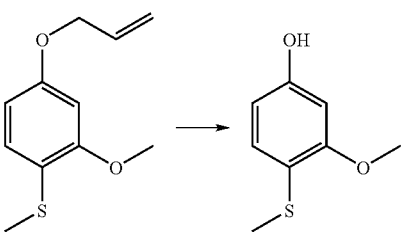

Sodium borohydride (18.92 g, 0.5 mol) was added portionwise to a solution of 4-(allyloxy)-2-methoxy-1-(methylsulfanyl)benzene (26.0 g, 0.124 mol), and tetrakis(triphenylphosphine)palladium (0) (7.14 g, 6.18 mol) in THF (600 ml) at 5° C. The resultant solution was allowed to warm to RT and then heated to 45° C. for 14 h whilst protected under an atmosphere of nitrogen. After cooling in an ice-bath, the reaction mixture was acidified to pH5 with HCl (2M, 200 ml). Water (200 ml) and EtOAc (300 ml) were added, and the aqueous phase separated and extracted with EtOAc (2×200 ml). The combined organics were dried over MgSO4 and concentrated to a black solid (40 g) which was purified by flash column chromatography on silica gel eluting with EtOAc:pentane (1:9 to 3:7) to afford the title compound as a white solid (11.85 g, 0.07 mol).

¹H NMR (400 MHz, CDCl₃): δ=7.10 (1H, d), 6.39 (1H, s), 6.38 (1H, d), 4.75 (1H, s, OH), 3.85 (3H, s), 2:35 (3H, s) ppm.

Preparation 25

4-chloro-3-(methylsulfanyl)phenol

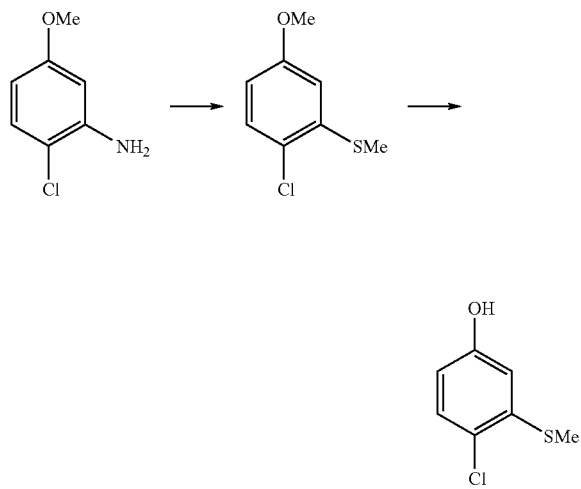

A solution of 2-chloro-5-methoxyaniline (5.0 g, 32 mmol) in 2N hydrochloric acid (60 ml) was heated at 50° C. for 30 min then cooled to 0° C. A solution of sodium nitrite (2.41 g, 35 mmol) in water (30 ml) was added dropwise and the mixture was stirred at 0° C. for 45 min then added slowly to a solution of sodium methane thiolate (4.45 g, 63 mmol) in water (120 ml). The mixture was allowed to warm to room temperature and stirred for 18 h, then extracted with diethyl diethyl ether (2×250 ml). The organic phase was washed with 2N sodium hydroxide solution, dried over MgSO$_4$ and the solvent removed under reduced pressure. The residue was purified by flash column chromatography using ethyl acetate:cyclohexane (5:95 to 10:90) as eluant to give 1-chloro-4-methoxy-2-(methylsulfanyl)benzene (2.88 g) as a brown oil.

Boron tribromide (1M in dichloromethane, 31 ml, 31 mmol) was added dropwise to a solution of 1-chloro-4-methoxy-2-(methylsulfanyl)benzene (2.88 g, 15 mmol) in dichloromethane (80 ml) at 0° C. The mixture was allowed to warm to room temperature, stirred for 72 h then cooled to 0° C. A solution of diethanolamine (10 ml) in dichloromethane (20 ml) was added dropwise (Caution—strong exotherm!) and the mixture was stirred at ambient temperature for 15 min once addition was complete, then partitioned between dichloromethane and 2N hydrochloric acid. The organic phase was washed with water, dried over MgSO$_4$ and the solvent removed under reduced pressure. The residue was purified by flash column chromatography using ethyl acetate:cyclohexane (10:90 to 85:15) as eluant to give 4-chloro-3-(methylsulfanyl)phenol (2.12 g) as a brown oil.

$^1$H NMR (400 MHz, CDCl$_3$): δ=7.10–7.18 (1H, d), 6.62 (1H, s), 6.48–6.54 (1H, d), 4.97 (1H, s), 2.42 (3H, s) ppm. LRMS (electrospray): m/z [M−H]$^+$ 173.

Preparation 26

(4-Amino-cyclohexyl)-carbamic acid tert-butyl ester

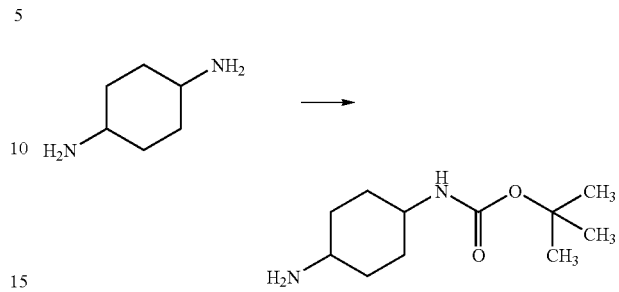

1,4-Diaminocyclohexane (80:20 cis:trans, 25.7 g, 0.229 mol) was dissolved in dichloromethane (300 ml) under nitrogen and cooled to 0° C. A solution of ditertbutyl dicarbonate (10 g, 45.8 mmol) in dichloromethane (100 ml) was then added dropwise over 4 h and the reaction was allowed to warm to room temperature and stirred for 18 h. The solvent was removed under reduced pressure and the residue was partitioned between 10% citric acid (200 ml) and diethylether (100 ml). The aqueous phase was extracted with diethylether (100 ml) and basified to pH 10 with concentrated aqueous ammonia. It was then extracted with dichloromethane (300 ml+4×100 ml) and the combined dichloromethane extracts were washed with brine (100 ml), dried over MgSO$_4$ and the solvent was removed under reduced pressure to give (4-Amino-cyclohexyl)-carbamic acid tert-butyl ester (9.29 g) as a crystalline solid.

$^1$H NMR (400 MHz, CDCl$_3$): δ=4.53–4.68 (0.8H, brs), 4.25–4.37 (0.2H, brs), 3.53–3.71 (0.8H, brs), 3.32–3.42 (0.2H, brs), 2.81–2.90 (0.8H, m), 2.57–2.66 (0.2H, m), 1.96–2.02 (0.4H, d), 1.83–1.89 (0.4H, d), 1.55–1.73 (3.2H, m), 1.10–1.55 (13H, 2×m+s) ppm. LRMS (thermospray): m/z [M+H]$^+$ 215.

Preparation 27

{cis-4-[(2-Chloro-5-fluoro-pyridine-3-carbonyl)-amino]-cyclohexyl}-carbamic acid tert-butyl ester

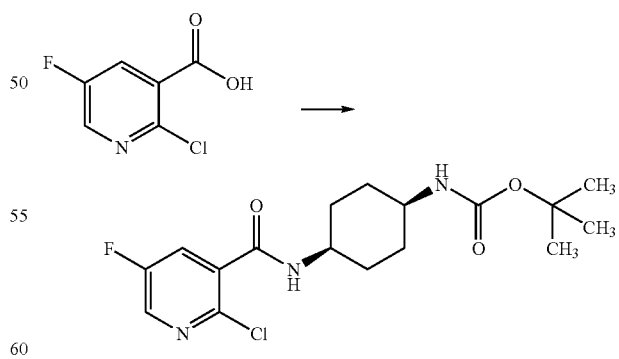

(4-Amino-cyclohexyl)-carbamic acid tert-butyl ester (80:20 syn:anti, 4.49 g, 20.9 mmol) was dissolved in dimethylformamide (100 ml) and triethylamine (8.34 ml, 59.8 mmol) was added followed by 5-fluoro-2-chloronicotinic acid (3.5 g, 19.9 mmol), 1-(3-dimethylaminopropyl)-3-ethylcarbodiimide hydrochloride (4.2 g, 21.9 mmol) and 1-hydroxybenzotriazole (2.96 g, 21.9 mmol). The reaction was stirred under nitrogen at room temperature for 18 h and the solvent was removed under reduced pressure. The residue was partitioned between sat. sodium bicarbonate solution (50 ml) and ethyl acetate (100 ml) and the aqueous phase was extracted with dichloromethane (2×50 ml). The combined organic extracts were concentrated under reduced pressure, re-dissolved in dichloromethane (100 ml), washed with water (50 ml), dried over MgSO$_4$ and the solvent was removed under reduced pressure. The residue was purified by flash column chromatography on silica gel eluting with a solvent gradient of ethyl acetate:pentane (2:3 changing to 1:1, by volume) to give {cis-4-[(2-Chloro-5-fluoro-pyridine-3-carbonyl)-amino]-cyclohexyl}-carbamic acid tert-butyl ester (5.44 g) as a white foam.

$^1$H NMR (400 MHz, CDCl$_3$): δ=8.33–8.38 (1H, d), 7.92–7.97 (1H, dd), 6.60–6.69 (1H, brs), 4.66–4.74 (1H, brs), 4.10–4.20 (1H, brs), 3.56–3.68 (1H, brs), 1.79–1.90 (4H, m), 1.48–1.60 (2H, m, partially masked by solvent), 1.43 (9H, s) ppm. LRMS (thermospray): m/z [M-Boc+H]$^+$ 272, [M+H]$^+$ 372, [M+NH$_4$]$^+$ 389.

Preparation 28

(cis-4-{[-5-fluoro-2-(3-methylsulfanyl-phenoxy)-pyridine-3-carbonyl]-amino}-cyclohexyl)-carbamic acid tert-butyl ester

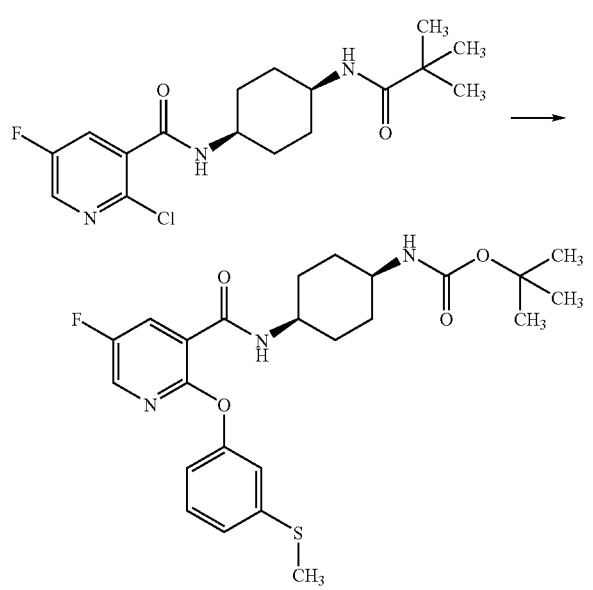

{cis-4-[(2-Chloro-5-fluoro-pyridine-3-carbonyl)-amino]-cyclohexyl}-carbamic acid tert-butyl ester (5.44 g, 14.6 mmol), 3-methylsulfanylphenol (2.05 g, 14.6 mmol) and caesium carbonate (7.15 g, 21.9 mmol) were suspended in dimethylformamide (100 ml) and the reaction was heated to 65° C. and stirred at this temperature under nitrogen for 18 h, then at room temperature for 48 h. The reaction was cooled to room temperature, concentrated under reduced pressure and the residue was diluted with water (75 ml). It was then extracted with ethyl acetate (3×100 ml) and the combined organic extracts were washed with water (2×30 ml), brine (30 ml), dried over MgSO$_4$ and the solvent removed under reduced pressure. The residue was purified by flash column chromatography on silica gel eluting with pentane:ether (50:50 changing to 45:55 then 40:60, by volume) to give (cis-4-{[-5-fluoro-2-(3-methylsulfanyl-phenoxy)-pyridine-3-carbonyl]-amino}-cyclohexyl)-carbamic acid tert-butyl ester (3.69 g) as a white solid.

$^1$H NMR (400 MHz, CDCl$_3$): δ=8.33–8.38 (1H, m), 8.06–8.09 (1H, m), 7.92–7.99 (1H, d), 7.34–7.39 (1H, t), 7.15–7.19 (1H, d), 7.03 (1H, d), 6.86–6.92 (1H, d), 4.34–4.43 (1H, brs), 4.12–4.21 (1H, brs), 3.53–3.64 (1H, brs), 2.48 (3H, s), 1.75–1.87 (4H, m), 1.64–1.74 (2H, m), 1.39–1.50 (11H, m+s) ppm. LRMS (thermospray): m/z [M-Boc+H]$^+$ 376, [M+H]$^+$ 476.

Preparation 29 cis-4-[(2-Chloro-5-fluoro-pyridine-3-carbonyl)-amino]-cyclohexanecarboxylic acid benzyl ester

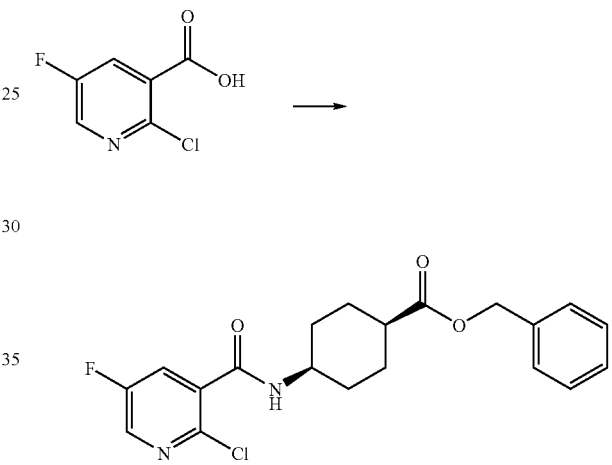

cis-4-Amino-cyclohexanecarboxylic acid benzyl ester mesylate (5.34 g, 13.2 mmol) was dissolved in dimethylformamide (75 ml) and triethylamine (5.5 ml, 39.5 mmol) was added followed by 5-fluoro-2-chloronicotinic acid (2.31 g, 13.2 mmol), 1-(3-dimethylaminopropyl)-3-ethylcarbodiimide hydrochloride (2.77 g, 14.5 mmol) and 1-hydroxybenzotriazole (1.96 g, 14.5 mmol). The reaction was stirred under nitrogen at room temperature for 18 h and the solvent was removed under reduced pressure. The residue was partitioned between sat. sodium bicarbonate solution (50 ml) and ethyl acetate (75 ml) and the aqueous phase was extracted with ethyl acetate (2×75 ml). The combined organic extracts were washed with water (2×20 ml), brine (20 ml), dried over MgSO$_4$ and the solvent was removed under reduced pressure. The residue was purified by flash column chromatography on silica gel eluting with ethyl acetate:pentane (1:1, by volume) to give cis-4-[(2-Chloro-5-fluoro-pyridine-3-carbonyl)-amino]-cyclohexanecarboxylic acid benzyl ester (2.14 g) as a white solid.

$^1$H NMR (400 MHz, CDCl$_3$): δ=8.30–8.32 (1H, d), 7.86–7.91 (1H, dd), 7.28–7.39 (5H, m), 6.52–6.59 (1H, brs), 5.13 (2H, s), 4.11–4.21 (1H, m), 2.55–2.62 (1H, m), 1.88–2.00 (2H, m), 1.77–1.87 (4H, m), 1.66–1.77 (2H, m) ppm. LRMS (thermospray): m/z [M+H]$^+$ 391, [M+NH$_4$]$^+$ 408.

Preparation 30 cis-4-{[5-Fluoro-2-(3-methylsulfanyl-phenoxy)-pyridine-3-carbonyl]-amino}-cyclohexanecarboxylic acid benzyl ester

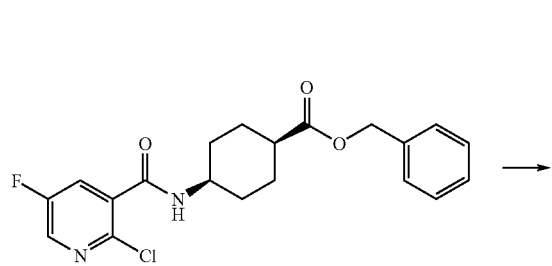

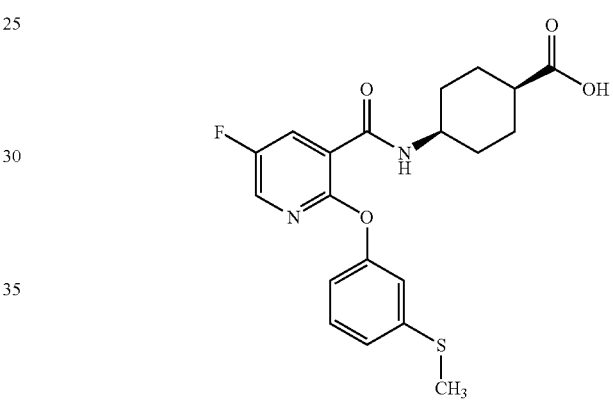

cis-4-[(2-Chloro-5-fluoro-pyridine-3-carbonyl)-amino]-cyclohexanecarboxylic acid benzyl ester (2.14 g, 5.5 mmol), 3-methylsulfanylphenol (844 mg, 6.02 mmol) and caesium carbonate (2.67 g, 8.21 mmol) were suspended in dimethylformamide (50 ml) and the reaction was heated to 65° C. and stirred at this temperature under nitrogen for 18 h. The reaction was cooled to room temperature, concentrated under reduced pressure and the residue was diluted with water (50 ml). It was then extracted with ethyl acetate (3×40 ml) and the combined organic extracts were washed with water (2×10 ml), brine (10 ml), dried over MgSO$_4$ and the solvent removed under reduced pressure. The residue was purified by flash column chromatography on silica gel eluting with a solvent gradient of pentane:ethyl acetate (2:8 changing to 1:3 then 3:7, by volume) to give cis-4-{[5-Fluoro-2-(3-methylsulfanyl-phenoxy)-pyridine-3-carbonyl]-amino}-cyclohexanecarboxylic acid benzyl ester (2.0 g) as a pale yellow oil.

$^1$H NMR (400 MHz, CDCl$_3$): δ=8.32–8.36 (1H, dd), 8.04–8.06 (1H, d), 7.92–7.98 (1H, d), 7.28–7.35 (6H, m), 7.14–7.18 (1H, d), 7.03 (1H, s), 6.85–6.90 (1H, m), 5.09 (2H, s), 4.15–4.22 (1H, m), 2.50–2.58 (1H, m), 2.47 (3H, s), 1.83–1.93 (2H, m), 1.76–1.83 (4H, m), 1.68–1.76 (2H, m) ppm. LRMS (thermospray): m/z [M+H]$^+$ 495, [M+NH$_4$]$^+$ 512.

Preparation 31 cis-4-{[5-Fluoro-2-(3-methylsulfanyl-phenoxy)-pyridine-3-carbonyl]-amino}-cyclohexanecarboxylic acid

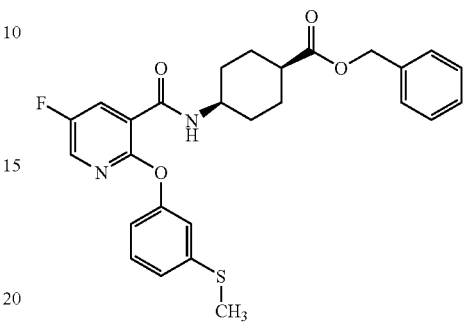

cis-4-{[5-Fluoro-2-(3-methylsulfanyl-phenoxy)-pyridine-3-carbonyl]-amino}-cyclohexanecarboxylic acid benzyl ester (1.75 g, 3.54 mmol) was dissolved in a solution of 4.4% formic acid in methanol (40 ml) and this was added dropwise to a suspension of palladium black (2 g) in 4.4% formic acid in methanol (120 ml) at room temperature under nitrogen. The mixture was stirred for 2 h, then filtered through arbocel washing with methanol (5×50 ml). The filtrates were concentrated under reduced pressure and basified to pH10 with 1M sodium hydroxide solution (50 ml). The aqueous phase was extracted with diethylether (3×50 ml) then acidified to pH1 with concentrated hydrochloric acid. After extraction with diethylether (3×50 ml) the combined organic extracts were washed with water (10 ml), dried over MgSO$_4$ and the solvent removed under reduced pressure to give cis-4-{[5-Fluoro-2-(3-methylsulfanyl-phenoxy)-pyridine-3-carbonyl]-amino}-cyclohexanecarboxylic acid (691 mg) as a white solid.

$^1$H NMR (400 MHz, CDCl$_3$): δ=8.32–8.38 (1H, dd), 8.03–8.09 (1H, dd), 7.93–8.03 (1H, m), 7.29–7.38 (1H, t), 7.08–7.16 (1H, m), 7.02 (1H, s), 6.86–6.93 (1H, d), 4.15–4.24 (1H, m), 2.49–2.58 (1H, m), 2.45 (3H, s), 1.60–1.95 (8H, m) ppm. LRMS (thermospray): m/z [M+H]$^+$ 405.

Preparation 32

2-Chloro-nicotinic acid methyl ester

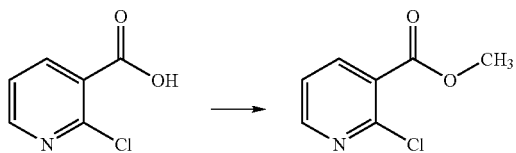

Oxalyl chloride (13.28 ml, 0.15 mmol) was added dropwise to a solution of 2-chloronicotinic acid (24 g, 0.153 mmol) in dichloromethane (250 ml) containing dimethylformamide (10 drops) under nitrogen at room temperature. The reaction was stirred at room temperature for 1.5 h and was then cooled to 0° C. Triethylamine (63.7 ml, 0.457 mmol) was added slowly followed by methanol (60 ml). After stirring at 0° C. for 30 min, the solvent was removed under reduced pressure and the residue was dissolved in sat. sodium bicarbonate solution (200 ml). This was extracted with diethylether (5×100 ml) and the combined organic extracts were dried over MgSO$_4$ and the solvent was removed under reduced pressure. The residue was purified by flash column chromatography on silica gel eluting with diethylether to give 2-chloronicotinic acid methyl ester (20.7 g) as a pale yellow oil.

$^1$H NMR (400 MHz, CDCl$_3$): δ=8.46–8.52 (1H, m), 8.12–8.17 (1H, m), 7.28–7.32 (1H, m), 3.92 (3H, s) ppm.

Preparation 33

2-(4-Methylsulfanyl-phenoxy)-nicotinic acid methyl ester

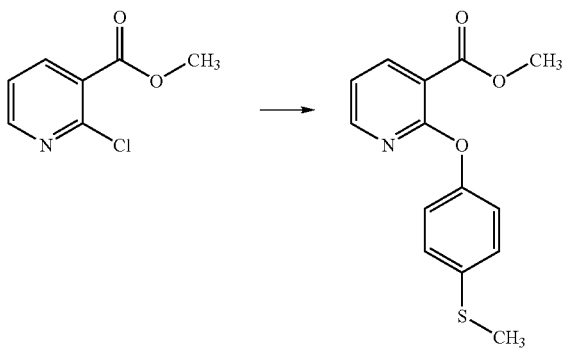

2-Chloronicotinic acid methyl ester (12 g, 69.9 mmol), 4-methylsulfanylphenol (9.80 g, 69.9 mmol) and potassium carbonate (14.5 g, 0.105 mol) were suspended in dimethylformamide (300 ml) and the reaction was heated to 65° C. and stirred at this temperature under nitrogen for 10 h. It was then heated to 90° C. and stirred at this temperature for 7 h, and then progressed to 100° C. and stirred for 16 h. The reaction was cooled to room temperature, concentrated under reduced pressure and the residue was diluted with water (300 ml). It was then extracted with diether (3×250 ml) and the combined organic extracts were washed with water (2×100 ml), dried over MgSO$_4$ and the solvent removed under reduced pressure. The residue was purified by flash column chromatography on silica gel eluting with dichloromethane:methanol:concentrated aqueous ammonia (99.5:0.5:0.05, by volume) to give 2-(4-methylsulfanyl-phenoxy)-nicotinic acid methyl ester (8.0 g) as a white solid.

$^1$H NMR (400 MHz, CDCl$_3$): δ=8.20–8.24 (2H, m), 7.25–7.30 (2H, d), 6.98–7.08 (3H, m), 3.89 (3H, s), 2.44 (3H, s) ppm. LRMS (thermospray): m/z [M+H]$^+$ 276.

Preparation 34

2-(4-Methylsulfanyl-phenoxy)-nicotinic acid

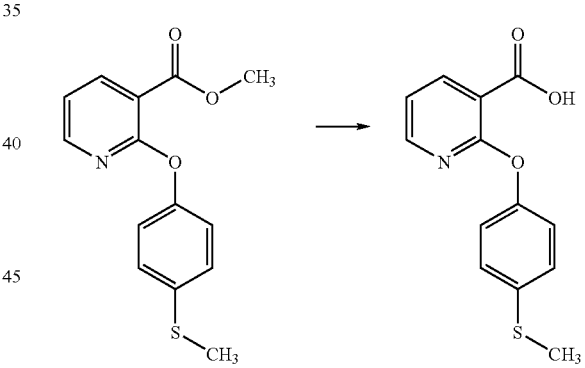

2-(4-methylsulfanyl-phenoxy)-nicotinic acid methyl ester (10.36 g, 37.6 mmol) was dissolved in tetrahydrofuran (140 ml) and 1M aqueous lithium hydroxide solution (94 ml, 94 mmol) was added. The reaction was stirred at room temperature for 18 h and the tetrahydrofuran was removed under reduced pressure. The residue was acidified to pH1 with concentrated hydrochloric acid and the resulting precipitate was filtered, washed with water (2×10 ml), diethyether (3×10 ml) and dried in vacuo to give 2-(4-methylsulfanyl-phenoxy)-nicotinic acid (9.3 g) as a white solid.

$^1$H NMR (400 MHz, CDCl$_3$): δ=8.16–8.20 (1H, m), 8.12–8.16 (1H, d), 7.24–7.30 (2H, d), 7.15–7.19 (2H, m), 7.00–7.06 (2H, d), 2.47 (3H, s) ppm. LRMS (thermospray): m/z [M+H]$^+$ 262.

Preparation 35 cis-4-{[2-(4-methylsulfanyl-phenoxy)-pyridine-3-carbonyl]-amino}-cyclohexanecarboxylic acid benzyl ester

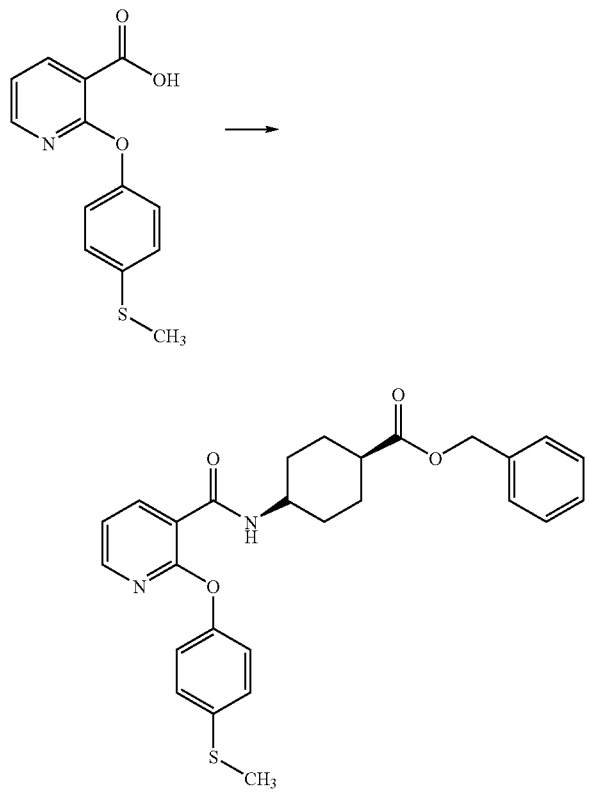

2-(4-methylsulfanyl-phenoxy)-nicotinic acid (3.0 g, 11.5 mmol) was dissolved in dimethylformamide (60 ml) and triethylamine (4.8 ml, 34.4 mmol) was added followed by cis-4-Amino-cyclohexanecarboxylic acid benzyl ester mesylate (4.66 g, 11.5 mmol), 1-(3-dimethylaminopropyl)-3-ethylcarbodiimide hydrochloride (2.42 g, 12.6 mmol) and 1-hydroxybenzotriazole (1.71 g, 12.6 mmol). The reaction was stirred under nitrogen at room temperature for 18 h and the solvent was removed under reduced pressure. The residue was partitioned between sat. sodium bicarbonate solution (50 ml) and ethyl acetate (50 ml) and the aqueous phase was extracted with ethyl acetate (3×100 ml). The combined organic extracts were washed with water (25 ml), brine (25 ml), dried over MgSO₄ and the solvent was removed under reduced pressure. The residue was purified by flash column chromatography on silica gel eluting with ethyl acetate: pentane (1:1, by volume) to give cis-4-{[2-(4-methylsulfanyl-phenoxy)-pyridine-3-carbonyl]-amino}-cyclohexanecarboxylic acid benzyl ester (4.75 g) as a white solid.

$^1$H NMR (400 MHz, CDCl$_3$): δ=8.57–8.60 (1H, d), 8.17–8.20 (1H, m), 7.90–7.97 (1H, d), 7.23–7.30 (7H, m), 7.07–7.13 (1H, m), 7.04–7.07 (2H, d), 5.04 (2H, s), 4.15–4.23 (1H, m), 2.46–2.54 (1H, m), 2.45 (3H, s), 1.63–1.90 (8H, m) ppm. LRMS (thermospray): m/z [M+H]⁺ 477.

Preparation 36 cis-4-{[2-(4-methylsulfanyl-phenoxy)-pyridine-3-carbonyl]-amino}-cyclohexanecarboxylic acid

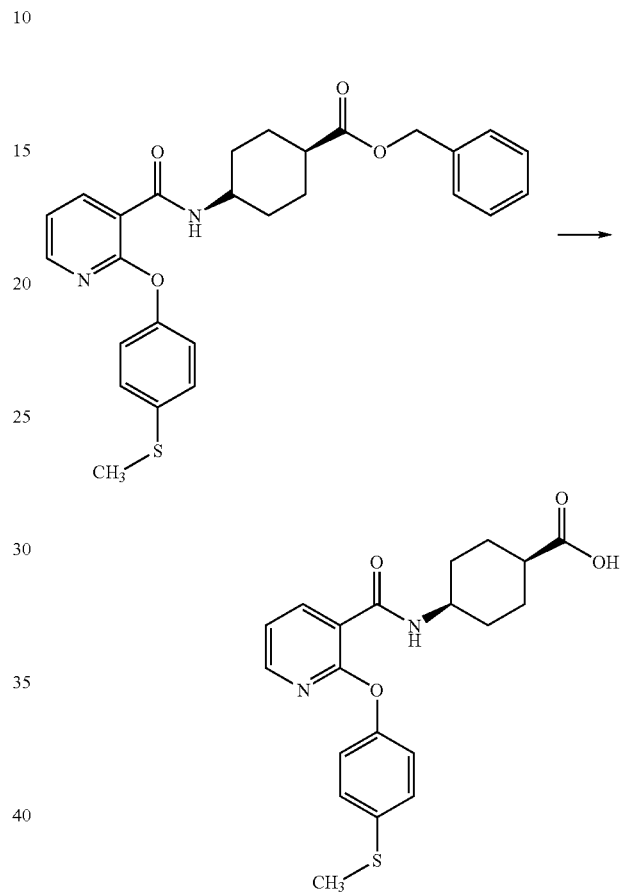

cis-4-{[2-(4-methylsulfanyl-phenoxy)-pyridine-3-carbonyl]-amino}-cyclohexanecarboxylic acid benzyl ester (4.35 g, 9.13 mmol) was dissolved in a solution of 4.4% formic acid in methanol (100 ml) and dimethylformamide (25 ml) and this was added to a suspension of palladium black (5 g) in 4.4% formic acid in methanol (300 ml) at room temperature under nitrogen. The mixture was stirred for 2.5 h, then filtered through arbocel washing with methanol (4×200 ml). The filtrates were concentrated under reduced pressure and the residue was azeotroped with toluene (2×50 ml). The residue was then diluted with water (50 ml) and basified to pH10 with 1M sodium hydroxide pellets. The aqueous phase was extracted with diethylether (2×50 ml) then acidified to pH1 with concentrated hydrochloric acid. After extraction with diethylether (5×50 ml) the combined organic extracts were washed with water (20 ml), dried over MgSO₄ and the solvent removed under reduced pressure to give cis-4-{[2-(4-methylsulfanyl-phenoxy)-pyridine-3-carbonyl]-amino}-cyclohexanecarboxylic acid (2.7 g) as a white solid.

$^1$H NMR (400 MHz, DMSO): δ=12.00–12.10 (1H, brs), 8.20–8.26 (1H, d), 8.12–8.19 (1H, d), 7.98–8.04 (1H, d), 7.25–7.32 (2H, d), 7.15–7.20 (1H, dd), 7.10–7.15 (2H, d), 3.87–3.97 (1H, m), 2.47 (3H, s), 2.32–2.39 (1H, m), 1.74–1.88 (2H, m), 1.54–1.73 (6H, m) ppm. LRMS (thermospray): m/z [M+H]$^+$ 387.

Preparation 37

3-(Ethylsulfanyl)phenol

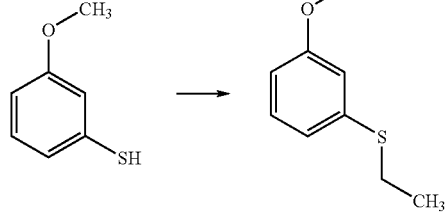

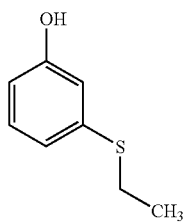

Solid potassium hydroxide (2.2 g, 39 mmol) and ethyl iodide (3.14 ml, 39 mmol) were added to a solution of 3-methoxybenzenethiol (5.0 g, 35 mmol) in ethanol (35 ml) (Caution—exotherm). The mixture was stirred for 72 h, then partitioned between water and ethyl acetate. The organic phase was dried over MgSO$_4$ and the solvent removed under reduced pressure to give 1-(ethylsulfanyl)-3-methoxybenzene (5.9 g) as a yellow liquid.

Boron tribromide (1M in dichloromethane, 70 ml, 70 mmol) was added dropwise to a solution of 1-(ethylsulfanyl)-3-methoxybenzene (5.9 g, 35 mmol) in dichloromethane (150 ml) at 0° C. The mixture was allowed to warm to room temperature, stirred for 18 h then cooled to 0° C. A solution of diethanolamine (20 ml) in dichloromethane (40 ml) was added dropwise (Caution—strong exotherm!) and the mixture was stirred at ambient temperature for 15 min once addition was complete, then poured onto ice water. The mixture was extracted with dichloromethane and the organic phase was washed with 2N hydrochloric acid, water, dried over MgSO$_4$ and the solvent removed under reduced pressure. The residue was purified by flash column chromatography using ethyl acetate:cyclohexane (20:80 to 30:70) as eluant to give 3-(ethylsulfanyl)phenol (4.53 g) as a colourless oil.

$^1$H NMR (400 MHz, CDCl$_3$): δ=7.10–7.18 (1H, t), 6.85–6.90 (1H, dd), 6.80 (1H, d), 6.60–6.66 (1H, dd), 5.15–5.27 (1H, br s), 2.88–2.97 (2H, q), 1.28–1.36 (3H, t) ppm.

Preparation 38

Ethyl 2-[3-(ethylsulfanyl)phenoxy]-5-fluoronicotinate

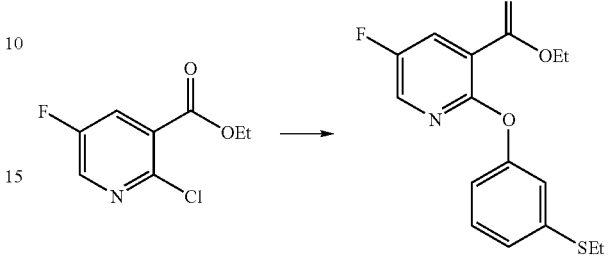

Ethyl 2-chloro-5-fluoro-nicotinate (J. Med. Chem. 1993, 36, 2676, M. Winn et. al.) (5.0 g, 24 mmol), 3-ethylsulfanylphenol (3.8 g, 24 mmol) and caesium carbonate (7.98 g, 24 mmol) were suspended in dioxan (50 ml) and the reaction was heated to 100° C. and stirred at this temperature under nitrogen for 8 h. The reaction was cooled to room temperature, filtered and the solid washed with ethyl acetate (50 ml). The filtrate was concentrated under reduced pressure, and the residue was purified by flash column chromatography on silica gel eluting with cyclohexane:ethyl acetate (95:5) to give 5-fluoro-2-(3-ethylsulfanyl-phenoxy)-nicotinic acid ethyl ester (1.16 g).

$^1$H NMR (400 MHz, CDCl$_3$): δ=8.12–8.15 (1H, d), 7.98–8.04 (1H, dd), 7.28–7.33 (1H, t), 7.14–7.20 (1H, m), 7.06–7.08 (1H, m), 6.90–6.94 (1H, dd), 4.37–4.44 (2H, quart) 2.92–3.00 (2H, quart), 1.37–1.40 (3H, t), 1.30–1.35 (3H, t) ppm. LRMS (electrospray): m/z [M+NH$_4$]$^+$ 344.

Preparation 39

2-[3-(Ethylsulfanyl)phenoxy]-5-fluoronicotinic acid

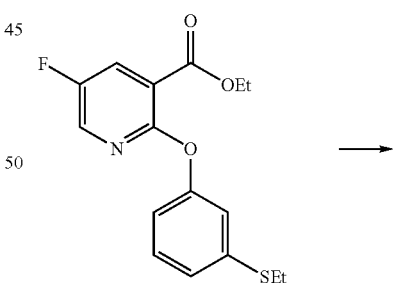

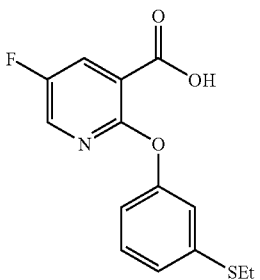

Lithium hydroxide hydrate (1.37 g, 33 mmol) was added to a solution of ethyl 2-[3-(ethylsulfanyl)phenoxy]-5-fluoronicotinate (4.21 g, 13 mmol) in tetrahydrofuran (50 ml) and water (30 ml). The mixture was stirred for 4 h, then the volatile solvent was removed under reduced pressure and the residue partitioned between diethyl ether and 2N hydrochloric acid. The organic phase was washed with water, dried over $MgSO_4$ and the solvent removed under reduced pressure. The residue was purified by flash column chromatography using dichloromethane:methanol:acetic acid (95:5:0.5) as eluant to give 2-[3-(ethylsulfanyl)phenoxy]-5-fluoronicotinic acid (3.45 g) as a white solid.

$^1$H NMR (400 MHz, $CDCl_3$): δ=8.16–8.24 (2H, m), 7.25–7.38 (1H, t), 7.19–7.23 (1H, d), 7.08–7.10 (1H, m), 6.92–6.96 (1H, dd), 2.94–3.00 (2H, quart), 1.34–1.38 (3H, t) ppm. LRMS (electrospray): m/z [M–H]$^+$ 292.

Preparation 40

2-Chloro-5-fluoro-N-(trans-4-hydroxy-cyclohexyl)-nicotinamide

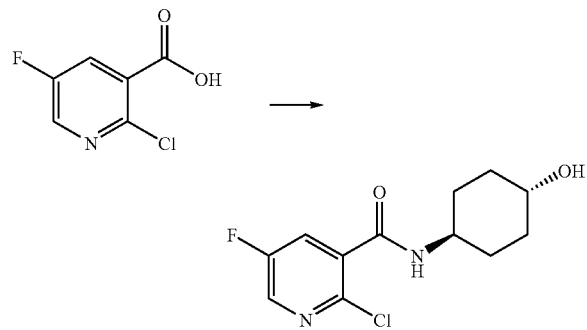

Oxalyl chloride (6 ml, 68.4 mmol) was added dropwise to a solution of 2-chloronicotinic acid (4 g, 22.8 mmol) in dichloromethane (500 ml) containing dimethylformamide (1 drop) under nitrogen at room temperature. The reaction was stirred at room temperature for 2 h and the solvent was removed under reduced pressure. The residue was suspended in dichloromethane (200 ml) and triethylamine (9.5 ml, 68.4 mmol) was added slowly followed by trans-4-aminocyclohexanol. After stirring at room temperature for 18 h, the reaction mixture was washed with water (100 ml), brine (100 ml, dried over $MgSO_4$ and the solvent was removed under reduced pressure. The residue was purified by flash column chromatography on silica gel eluting with dichloromethane:methanol:concentrated aqueous ammonia (99:1:0.1 changing to 97.5:2.5:0.25, by volume) to give 2-chloro-5-fluoro-N-(trans-4-hydroxy-cyclohexyl)-nicotinamide (2.22 g) as a white solid.

mp 197–200° C. $^1$H NMR (400 MHz, $CDCl_3$): δ=8.45–8.47 (1H, d), 8.38–8.45 (1H, d), 7.85–7.90 (1H, dd), 4:46–4.50 (1H, d), 3.53–3.65 (1H, m), 3.30–3.40 (1H, m), 1.74–1.88 (4H, m), 1.12–1.28 (4H, m) ppm. LRMS (electrospray): m/z [M–H]$^+$ 271. Anal. Found C, 52.46; H, 5.17; N, 10.02. $C_{12}H_{14}FN_2O_2S$. 0.1 mol $H_2O$ requires C, 52.51; H, 5.21; N, 10.02%.

Preparation 41

5-Fluoro-2-(4-methylsulfanyl-phenoxy)-nicotinic acid ethyl ester

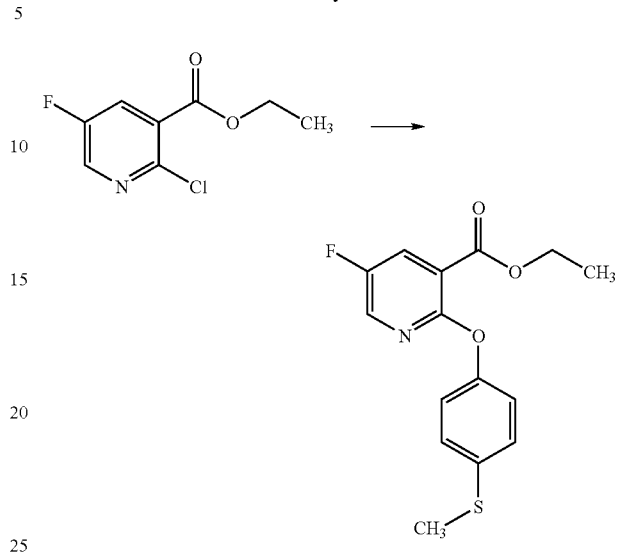

To a suspension of ethyl-2-chloro-5-fluoro-nicotinate (2.00 g, 9.82 mmol) and caesium carbonate (4.48 g, 13.8 mmol) in toluene/N-methylpyrrolidine (4:1, 50 ml) was added 4-methylsulfanylphenol (1.51 g, 10.8 mmol) at room temperature under nitrogen. Copper iodide (94 mg, 0.49 mmol) and the reaction was heated to 100° C. and stirred at this temperature for 17 h. The reaction was cooled to room temperature, partitioned between water (100 ml) and ethyl acetate (200 ml) and filtered. The filtrate was separated and the organic phase washed with brine (50 ml), dried over $MgSO_4$ and concentrated under reduced pressure. The residue was purified by flash column chromatography on silica gel eluting with toluene:ethyl acetate (95:5, by volume) and the product was triturated with pentane (10 ml) to give 5-fluoro-2-(4-methylsulfanyl-phenoxy)-nicotinic acid ethyl ester (2.09 g) as a yellow oil.

$^1$H NMR (400 MHz, $CDCl_3$): δ=8.10–8.13 (1H, d), 7.95–8.00 (1H, dd), 7.26–7.32 (2H, d), 7.02–7.06 (2H, d), 4.37–4.43 (2H, quart), 2.47 (3H, s), 1.33–1.41 (3H, t) ppm.

Preparation 42

2-Chloro-5-fluoro-N-(1-hydroxymethyl-cyclopentyl)-nicotinamide

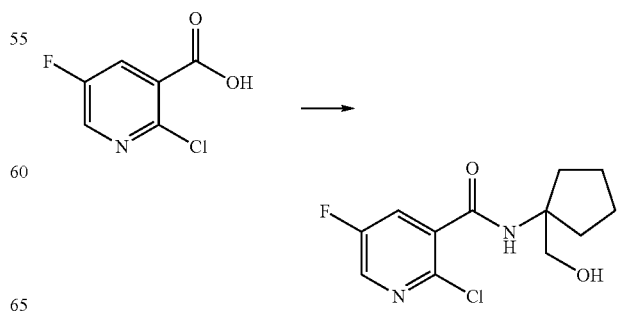

Carbonyldiimidazole (254 mg, 1.57 mmol) was added to a suspension of 2-chloro-5-fluoro-nicotinic acid (250 mg, 1.42 mmol) in dichloromethane (10 ml) under nitrogen at room temperature. The resulting solution was stirred for 15 min after which a solution of (1-amino-cyclopentyl)-methanol (197 mg, 1.71 mmol) and 4-dimethylaminopyridine (9 mg, 0.07 mmol) in dichloromethane (5 ml) was added. The reaction was stirred at room temperature for 18 h then diluted with dichloromethane (20 mls) and washed with sat. ammonium chloride solution (20 ml). The organic phase was dried over MgSO$_4$ and the solvent was removed under reduced pressure. The residue was triturated with dichloromethane (5 ml) to give 2-Chloro-5-fluoro-N-(1-hydroxymethyl-cyclopentyl)-nicotinamide (100 mg) as white solid.

$^1$H NMR (400 MHz, CDCl$_3$): δ=8.28–8.32 (1H, d), 7.80–7.84 (1H, dd), 6.64–6.77 (1H, brs), 3.77 (2H, s), 3.67 (1H, s), 1.60–1.99 (8H, 3×m) ppm. LRMS (electrospray): m/z [M+Na]$^+$ 295, [M−H]$^+$ 271.

Preparation 43

Preparation 44

(1R,2S-2-Hydroxy-cyclohexyl)-carbamic acid benzyl ester

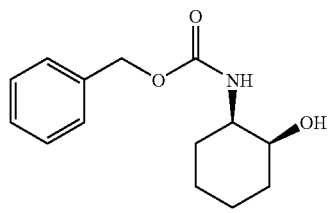

(1S,2R-2-Hydroxy-cyclohexyl)-carbamic acid benzyl ester

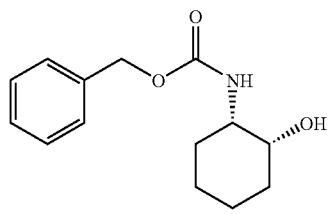

cis-Aminocyclohexan-1-ol hydrochloride (10.25 g, 67.6 mmol) was dissolved in water (275 ml) at room temperature and sodium bicarbonate (11.36 g, 135 mmol) was added followed by carbonic acid benzyl ester 2,5-dioxo-pyrrolidine-1-yl ester (16.8 g, 67.6 mmol), and the reaction was stirred at room temperature for 6 h. The suspension was filtered and the solid was dissolved in dioxan (250 ml) and combined with the filtrate. The solution was stirred at room temperature for 6 h and the dioxan was removed under reduced pressure. The residual slurry was filtered and the solid was dissolved in dichloromethane (250 ml), dried over MgSO$_4$ and concentrated under reduced pressure. The residue was purified by preparative chiral HPLC resulting in two major products.

Chiral HPLC conditions: Chiralpak AD250 eluting with 80% hexane, 20% IPA gave product 1 with a retention time of 4.75 min and product 2 with a rentention time of 6.5 min.

Product 1:(1R,2S-2-Hydroxy-cyclohexyl)-carbamic acid benzyl ester (6.6 g), white solid.

$^1$H NMR (400 MHz, CDCl$_3$): δ=7.18–7.27 (5H, m), 4.92–5.06 (3H, m+s), 3.82–3.87 (1H, brs), 3.48–3.60 (1H, brs), 1.38–1.68 (6H, m), 1.20–1.38 (2H, m), 1.09–1.15 (1H, d) ppm. [α$_D$] (2 mg/ml, MeOH, 589 nm)−32.8°.

Product 2:(1S,2R-2-Hydroxy-cyclohexyl)-carbamic acid benzyl ester (6.6g), white solid.

$^1$H NMR (400 MHz, CDCl$_3$): δ=7.23–7.36 (5H, m), 4.98–5.11 (3H, m+s), 3.91–3.96 (1H, m), 3.52–3.63 (1H, brs), 1.40–1.72 (6H, m), 1.22–1.40 (2H, m), 1.14–1.18 (1H, d) ppm. [α$_D$] (2.4 mg/ml, MeOH, 589 nm)+33.1°.

Preparation 45 tert-Butyl 4-[(3-hydroxy-2,2-dimethylpropanoyl) amino]cyclohexylcarbamate

Mixture of Cis (Major) and Trans (Minor)

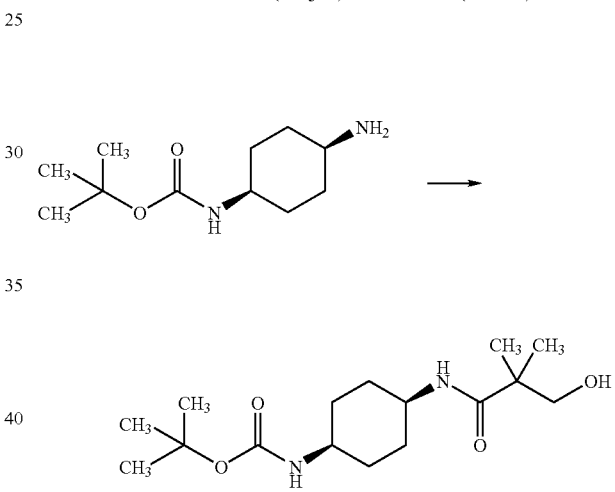

tert-Butyl 4-aminocyclohexylcarbamate (4:1 cis:trans mix of isomers, 1.00 g, 4.67 mmol), 3-hydroxy-2,2-dimethylpropanoic acid (0.60 g, 5.13 mmol) and triethylamine (1.30 ml, 9.33 mmol) were dissolved in dimethylformamide (20 ml) and 1-(3-dimethylaminopropyl)-3-ethylcarbodiimide hydrochloride (984 mg, 5.13 mmol) and 1-hydroxybenzotriazole (694 mg, 5.13 mmol) were added. The reaction was stirred under nitrogen at room temperature for 18 h then partitioned between water and ethyl acetate. The organic phase was washed with water, dried over MgSO$_4$ and the solvent was removed under reduced pressure. The residue was purified by flash column chromatography on silica gel eluting using dichloromethane:methanol:0.880ammonia (95:5:0.5) as eluant to give tert-butyl 4-[(3-hydroxy-2,2-dimethylpropanoyl)amino]cyclohexylcarbamate (840 mg) as a white foam as a ca. 4:1 mixture of diastereoisomers.

$^1$H NMR (400 MHz, CDCl$_3$): (peaks relating to major diastereoisomer) δ=6.08–6.18 (1H, m), 4.48–4.59 (1H, m), 3.84–3.94 (1H, m), 3.56 (3H, s), 1.46–1.82 (8H, m), 1.44 (9H, s), 1.16 (6H, s) ppm. LRMS (electrospray): m/z [M+Na]$^+$ 337.

Preparation 46

N-(4-Aminocyclohexyl)-3-hydroxy-2,2-dimethyl-propanamide hydrochloride (Mixture of Cis (Major) and Trans (Minor))

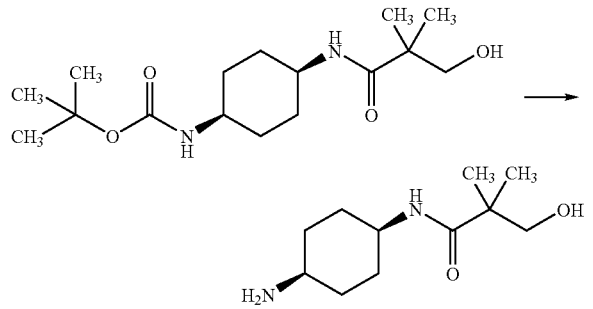

4M Hydrochloric acid in dioxan (13 ml, 52 mmol) was added to a solution of the more polar diastereoisomer of tert-butyl 4-[(3-hydroxy-2,2-dimethylpropanoyl)amino]cyclohexylcarbamate (840 g, 2.67 mmol) in dioxan (5 ml). The mixture was stirred for 2 h then the solvent was removed under reduced pressure and the residue dried in vacuo to give tert-butyl 4-[(3-hydroxy-2,2-dimethylpropanoyl)amino]cyclohexylcarbamate hydrochloride (305 mg) as a hygroscopic foam, as a ca. 4:1 mixture of diastereoisomers.

$^1$H NMR (400 MHz, CD$_3$OD): δ=(peaks relating to major diastereoisomer) 3.86–3.96 (1H, br s), 3.44–3.57 (3H, m+s), 3.18–3.28 (1H, m), 1.57–1.95 (8H, m), 1.12 (6H, s) ppm. LRMS (electrospray): m/z [M+H]$^+$ 214.

Preparation 47

2-Chloro-5-fluoro-N-{cis-4-[(methoxyacetyl)amino]cyclohexyl}nicotinamide

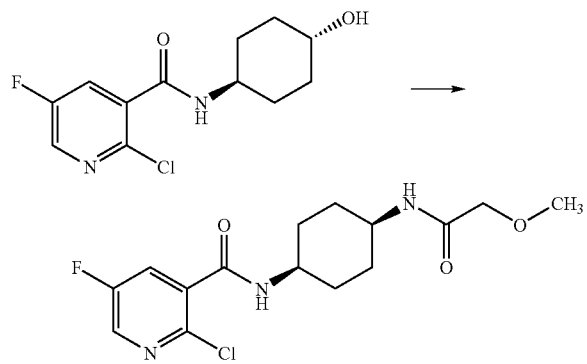

N-(cis-4-Aminocyclohexyl)-2-chloro-5-fluoronicotinamide (837 mg, 2.72 mmol) and triethylamine (1.14 ml, 8.15 mmol) were dissolved in dimethylformamide (20 ml) and 2-methoxy acetic acid (208 µl, 2.72 mmol), 1-(3-dimethylaminopropyl)-3-ethylcarbodiimide hydrochloride (573 mg, 2.99 mmol) and 1-hydroxybenzotriazole (404 mg, 2.99 mmol) were added. The reaction was stirred under nitrogen at room temperature for 18 h then partitioned between water and ethyl acetate. The organic phase was dried over MgSO$_4$ and the solvent was removed under reduced pressure. The residue was purified by flash column chromatography on silica gel eluting using dichloromethane:methanol (96:4 to 91:9) as eluant to give 2-chloro-5-fluoro-N-{cis-4-[(methoxyacetyl)amino]cyclohexyl}nicotinamide (550 mg).

$^1$H NMR (400 MHz, CDCl$_3$): δ=8.30–8.37 (1H, m), 7.89–7.96 (1H, dd), 6.62–6.68 (1H, br s), 6.45–6.39 (1H, br s), 4.16–4.25 (1H, m), 3.94–4.05 (1H, m), 3.88 (2H, s), 3.42 (3H, s), 1.70–1.96 (6H, m), 1.54–1.69 (2H, s) ppm. LRMS (electrospray): m/z [M+H]$^+$ 344.

Preparation 48

(1S,2R)-2-Amino-cyclohexan-1-ol formate

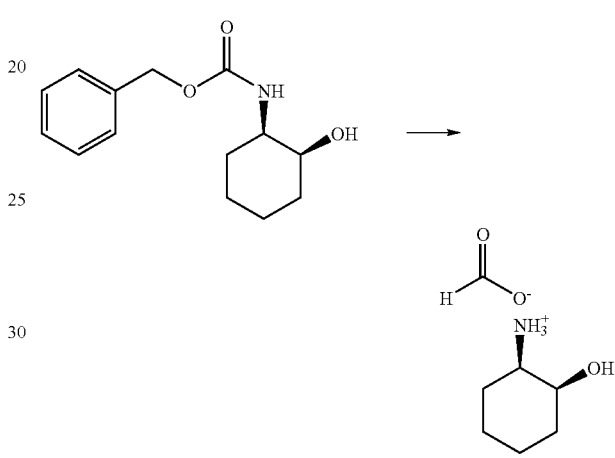

(1R,2S-2-Hydroxy-cyclohexyl)-carbamic acid benzyl ester (4.57 g, 18.3 mmol), ammonium formate (7 g, 0.111 mol) and 10% palladium on carbon (50 mg) were mixed together in ethanol (50 ml) and tetrahydrofuran (50 ml). The reaction was heated to 50° C. for 2 h, cooled and, filtered through glass filter paper. The filtrate was concentrated under reduced pressure and the residue was dried in vacuo to give (1S,2R)-2-amino-cyclohexan-1-ol formate (2.94 g) as a white solid.

$^1$H NMR (400 MHz, CD$_3$OD): δ 8.54 (1H, s), 3.95–3.99 (1H, m), 3.12–3.19 (1H, m), 1.55–1.84 (6H, m), 1.34–1.49 (2H, m) ppm. LRMS (electrospray): m/z [M+Na]$^+$ 148. Anal. Found C, 51.44; H, 9.42; N, 8.80. C$_6$H$_{12}$NO. 1 mol H$_2$CO$_2$ requires C, 51.58; H, 9.40; N, 8.59%. [α$_D$] (1.5 mg/ml, MeOH, 589 nm)−22.1°.

Preparation 49

(1R,2S)-2-Amino-cyclohexan-1-ol formate

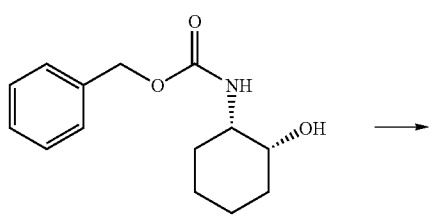

-continued

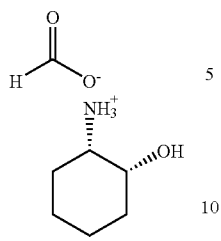

(1S,2R-2-Hydroxy-cyclohexyl)-carbamic acid benzyl ester (5.85 g, 23.4 mmol), ammonium formate (8.9 g, 0.141 mol) and 10% palladium on carbon (60 mg) were mixed together in ethanol (60 ml) and tetrahydrofuran (60 ml). The reaction was heated to 50° C. for 3 h, cooled and filtered through glass filter paper. The filtrate was concentrated under reduced pressure and the residue was dried in vacuo to give (1S,2R)-2-amino-cyclohexan-1-ol formate (3.4 g) as a white solid.

$^1$H NMR (400 MHz, CD$_3$OD): δ 8.56 (1H, s), 3.96–4.00 (1H, m), 3.96–4.00 (1H, m) 3.14–3.19 (1H, m), 1.52–1.82 (6H, m), 1.36–1.50 (2H, m) ppm. Anal. Found C, 50.79; H, 9.38; N, 8.80. C$_6$H$_{12}$NO. 1 mol H$_2$CO$_2$. 0.25 mol H$_2$O requires C, 50.74; H, 9.43; N, 8.45%. [α$_D$] (1.2 mg/ml, MeOH, 589 nm)+28.3°.

Preparation 50 cis-Methyl 2-aminocyclohexanecarboxylate

cis-2-Amino-1-cyclohexane carboxylic acid (2500 mg, 17.5 mmol) was suspended in methanol (30 ml) at 0° C. Gaseous hydrochloric acid was bubbled through the suspension for 10 minutes. The reaction was allowed to reach room temperature then stirred under nitrogen for 1 h and the solvent removed under reduced pressure. The residue was azeotroped with diethyl ether (2×20 ml) and dried to give the title compound as a solid.

$^1$H NMR (400 MHz, CDCl$_3$): δ=3.76 (3H, s), 3.44–3.54 (1H, m), 3.04–3.10 (1H, q), 2.08–2.18 (1H, m), 1.82–1.92 (2H, m), 1.68–1.80 (1H, m), 1.36–1.60 (3H, m) ppm. LRMS (thermospray): m/z [M+H]$^+$ 158.

EXAMPLE 1

Syn-5-Fluoro N-[4-(2-hydroxy-5-methyl-benzoylamino)-cyclohexyl]-2-(3-methylsulfanyl-phenoxy)-nicotinamide

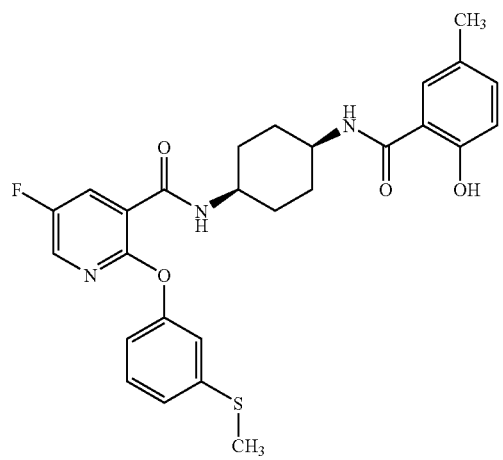

The amine of preparation 8 (250 mg, 0.60 mmol), 2-hydroxy-5-methyl-benzoic acid (84 mg, 0.55 mmol), 1-(3-dimethylaminopropyl)-3-ethylcarbodiimide hydrochloride (124 mg, 0.65 mmol), 1-hydroxybenzotriazole hydrate (80 mg, 0.60 mmol) and 4-methylmorpholine (205 μL, 1.88 mmol) were dissolved in dichloromethane (10 mL). The reaction mixture was stirred at room temperature for 18 hours before being diluted with dichloromethane (20 mL). The reaction mixture was washed with 10% citric acid solution, saturated sodium hydrogencarbonate solution and brine, dried over magnesium sulphate and concentrated in vacuo. The crude product was purified by column chromatography on silica gel eluting with pentane:ethyl acetate 90:10 to 80:20 to yield the title product, 120 mg (39%).

$^1$HNMR(CD$_3$OD, 400 MHz): δ=1.74(m, 2H), 1.86(m, 6H), 2.27(s, 3H), 2.43(s, 3H), 4.00(m, 1H), 4.12(m, 1H), 6.77(s, 1H), 6.93(m, 1H), 7.09(m, 1H), 7.13(m, 1H), 7.33(m, 1H), 7.59(m, 2H), 8.05(m, 1H), 8.12(s, 1H) ppm. Microanalysis: Observed—C=62.53%, H=5.64%, N=8.10%. C$_{27}$H$_{28}$FN$_3$O$_4$S Calculated—C=62.61%, H=5.68%, N=7.31%.

The following compounds, of the general formula shown below, were prepared by a method similar to that described for example 1 using the amine of preparation 8 and the appropriate carboxylic acid, R$^4$COOH.

| No. | R⁴ | Data |
|---|---|---|
| 2 | (3-methyl-2-hydroxyphenyl) | ¹HNMR(CDCl₃, 400 MHz): δ = 1.53(m,2H), 1.86(m,4H), 1.96(m,2H), 2.25(s,3H), 2.47(s,3H), 4.07(m,1H), 4.27(m,1H), 5.97(m,1H), 6.73(m,1H), 6.91(m,1H), 7.05(m,2H), 7.18(m,1H), 7.26(m,1H), 7.37(m,1H), 8.08(m,2H), 8.37(m,1H), 12.42(brm, 1H) ppm. Microanalysis: Observed - C = 63.20%, H = 5.60%, N = 8.19% C₂₇H₂₈FN₃O₄S Calculated - C = 63.19%, H = 5.58%, N = 8.26% |
| 3 | (1,5-dimethyl-1H-pyrazol-3-yl) | ¹HNMR(DMSO-D₆, 400 MHz): δ = 1.65(m,8H), 2.23(s,3H), 1.96(m,2H), 2.25(s,3H), 2.47(s,3H), 4.07(m,1H), 4.27(m,1H), 6.92(d,1H), 7.06(m,2H), 7.14(d,1H), 7.31(t,1H), 8.00(dd,1H), 8.22(m,2H) ppm. MS ES+ m/z 520 [MNa]⁺ Microanalysis: Observed - C = 60.14%, H = 5.72%, N = 13.92% C₂₅H₂₈FN₅O₃S Calculated - C = 60.35%, H = 5.67%, H = 5.67%, N = 14.07% |
| 4 | (4-methyl-1H-imidazol-2-yl) | ¹HNMR(CD₃OD, 400 MHz): δ= 1.57–1.79(m,8H), 2.18(m,3H), 2.46(s,3H), 3.83(m,1H), 4.97(m,1H), 6.94(m,1H), 7.07(m,2H), 7.53(m,1H), 8.02(m,1H), 8.25(m,2H) ppm. MS ES⁻ m/z 482 [M-H]⁻ Microanalysis: Observed - C = 59.37%, H = 5.51%, N = 14.10% C₂₄H₂₆FN₅O₃S Calculated - C = 59.61%, H = 5.42%, N = 14.48% |
| 5 | (5-chloro-2-hydroxyphenyl) | ¹HNMR(CD₃OD, 400 MHz): δ= 1.48(m,2H), 1.92(m,6H), 2.43(s,3H), 4.05(m,1H), 4.28(m,1H), 5.86(m,1H), 6.92(m,2H), 7.03(m,1H), 7.16(m,2H), 7.32(m,1H), 7.40(m,1H), 8.10(m,2H), 8.37(m,1H) ppm. MS APCI+ m/z 530 [MH]⁺ Microanalysis: Observed - C = 58.84%, H = 4.77%, N = 8.02% C₂₆H₂₅FN₃O₄S Calculated - C = 58.32%, H = 4.75%, N = 7.93% |
| 6 | (3,5-dimethyl-4-hydroxyphenyl) | ¹HNMR(CDCl₃, 400 MHz): δ= 1.50(m,2H), 1.91(m,6H), 2.27(s,6H), 2.44(s,3H), 4.06(m,1H), 4.26(m,1H), 5.05(m,1H), 5.72(m,1H), 6.92(m,1H), 7.04(m,1H), 7.15(m,1H), 7.32(m,2H), 7.35(m,1H), 8.05(m,1H), 8.08(m,1H), 8.35(m,1H) ppm. MS APCI+ m/z 524 [MH]⁺ Microanalysis: Observed - C = 64.05%, H = 5.77%, N = 8.03% C₂₈H₃₀FN₃O₄S Calculated - C = 64.23%, H = 5.77%, N = 8.02% |
| 7 | (2-hydroxy-3-methylphenyl) | ¹HNMR(CDCl₃, 400 MHz): δ= 1.51(m, 2H), 1.84(m,4H), 1.92(m,2H), 2.26(s,3H), 2.44(s,3H), 4.06(m,1H), 4.25(m,1H), 5.77(d,1H), 6.79(d,1H), 6.92(dd,1H), 7.04(s,1H), 7.13(d,1H), 7.35(m,2H), 7.47(s,1H), 8.08(m,2H), 8.35(dd,1H) ppm. MS APCI+ m/z 510 [MH]⁺ Microanalysis: Observed - C = 63.24%, H = 5.58%, N = 8.20% C₂₇H₂₈FN₃O₄S Calculated - C = 63.64%, H = 5.54%, N = 8.25% |
| 8 | (2-hydroxy-3-chlorophenyl) | ¹HNMR(CDCl₃, 400 MHz): δ = 1.50(m,2H), 1.86(m,4H), 1.96(m,2H), 2.47(s,3H), 4.05(m,1H), 4.27(m,1H), 5.68(d,1H), 6.05(s,1H), 6.91(dd,1H), 7.04(m,2H), 7.16(dd,1H), 7.37(t,1H), 7.47(dd,1H),7.71(s,1H), 8.08(m,2H), 8.35(dd,1H) ppm. MS APCI+m/z 530 [MH]⁺ Microanalysis: Observed - C = 58.11%, H = 4.70%, N = 7.74% C₂₆H₂₅FN₃O₄S Calculated - C = 58.42%, H = 4.81%, N = 7.86% |

Examples 3,4,5 and 6 were prepared using N-ethyldiisopropylamine in the place of 4-methylmorpholine
Example 4: 4-Methylimidazole-2-carboxylic acid used (J. Org. Chem., 44(16), 1979, 2902–2906)

EXAMPLE 9

Syn-5-Fluoro-N-{4-[2-(2-hydroxy-phenyl)-acetylamino]-cyclohexyl}-2-(3-methylsulfanyl-phenoxy)-nicotinamide

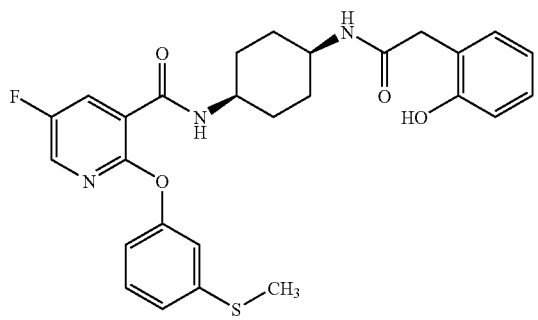

The amine of preparation 8 (250 mg, 0.60 mmol), (2-hydroxy-phenyl)-acetic acid (91 mg, 0.60 mmol), 1-hydroxybenzotriazole hydrate (88 mg, 0.66 mmol) and triethylamine (333 μL, 0.66 mmol) were dissolved in N,N-dimethylformamide (5 mL) and the mixture treated with 1-(3-dimethylaminopropyl)-3-ethylcarbodiimide hydrochloride (172 mg, 0.9 mmol). The reaction mixture was then stirred at room temperature for 18 hours. The reaction mixture was concentrated in vacuo and the residue partitioned between ethyl acetate (15 mL) and 2M hydrochloric acid solution (10 mL). The aqueous was extracted with ethyl acetate (3×10 mL). The organics were combined and then washed with brine, dried over magnesium sulphate and concentrated in vacuo. The crude product was purified by column chromatography on silica gel eluting with dichloromethane:methanol 99:1 to 92:8 to yield the title product, 100 mg.

$^1$HNMR (CDCl$_3$, 400 MHz): δ=1.60–2.00 (m, 8H), 2.42 (s, 3H), 3.21(m, 2H), 3.68 (m, 2H), 4.18 (m, 2H), 6.46 (d, 1H), 6.60 (m, 1H), 6.92 (m, 1H), 7.02 (s, 1H), 7.12 (d, 1H), 7.34 (t,1H), 7.94–8.08 (m, 4H), 8.34 (m,1H) ppm.

MS ES+ m/z 548 [MNa]$^+$. Microanalysis: Observed —C=62.56%, H=5.56%, N=8.17%. C$_{28}$H$_{28}$FN$_3$O$_4$S Calculated —C=62.53%, H=5.64%, N=8.10%.

The following compounds, of the general formula below, were prepared by a method similar to that described for example 9 using the appropriate amine and carboxylic acid, R$^4$COOH.

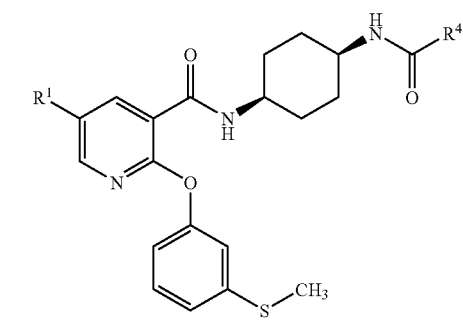

| No. | R$^1$ | R$^4$ | Data |
|---|---|---|---|
| 10 | F | ![CH3/OH phenyl] | $^1$HNMR(CD$_3$OD, 400 MHz): δ = 1.63–1.92(m,8H), 2.29(s,3H), 2.42(s,3H), 3.99(m,1H), 4.17(m,1H), 6.69(s,2H), 6.91(d,2H), 7.09(m,2H), 7.32(t,1H), 7.60(d,1H), 8.10(m,2H) ppm. MS ES+ m/z 510 [MH]$^+$ Microanalysis: Observed - C = 62.97%, H = 5.60%, N = 8.16% C$_{27}$H$_{28}$FN$_3$O$_4$S Calculated - C = 63.07%, H =5.53%, N =8.12% |
| 11 | F | ![OH phenyl] | $^1$HNMR(CD$_3$OD, 400 MHz): δ = 1.68–1.90(m,8H), 2.43(s,3H), 4.02(m,1H), 4.16(m,1H), 6.84(m,2H), 6.92(m,1H), 7.12(m,2H), 7.34(m,2H), 7.76(d,1H), 8.08(m,1H), 8.11(m,1H) ppm. MS ES+ m/z 518 [MNa]$^+$ |
| 12 | F | ![OCH3/OH phenyl] | $^1$HNMR(CD$_3$OD, 400 MHz): δ = 1.63–1.92(m,8H), 2.43(s,3H), 3.79(s,3H), 3.98(m,1H), 4.14(m,1H), 6.39(m,1H), 6.43(m,1H), 6.94(m,1H), 7.08(m,1H), 7.13(m,1H), 7.33(t,1H), 7.64(d,1H), 7.80(s,0.5H), 8.11(m,2H) ppm. MS ES+ m/z 548 [MNa]$^+$ |

-continued

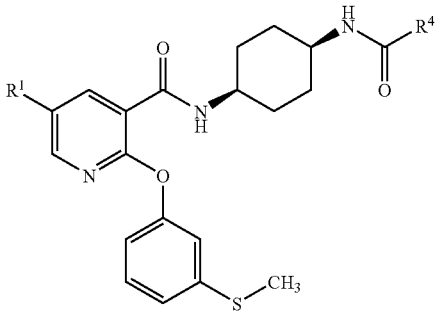

| No. | R¹ | R⁴ | Data |
|---|---|---|---|
| 13 | H | 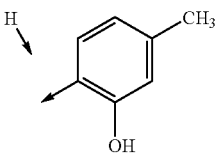 | ¹HNMR(CD₃OD, 400 MHz): δ = 1.68–1.89(m,8H), 2.29(s,3H), 2.44(s,3H), 4.00(m,1H), 4.14(m,1H), 6.70(m,2H), 6.94(m,1H), 7.13(m,2H), 7.24(m,1H), 7.34(m,1H), 7.63(d,2H), 8.18(m,1H), 8.28(m,1H) ppm. MS ES+m/z 514 [MNa]⁺ |
| 14 | H | 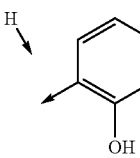 | ¹HNMR(CD₃OD, 400 MHz): δ = 1.63–1.92(m,8H), 2.43(s,3H), 3.78(s,3H), 3.98(m,1H), 4.16(m,1H), 6.39(m,1H), 6.42(m,1H), 6.94(m,1H), 7.12(m,2H), 7.24(m,1H), 7.36(t,1H), 7.67(d,1H), 8.18(m,1H), 8.25(m,1H) ppm. |

EXAMPLE 15

Syn-5-Fluoro-2-(3-methylsulfanyl-phenoxy)-N-{4-[(pyridine-2-carbonyl)-amino]-cyclohexyl}-nicotinamide

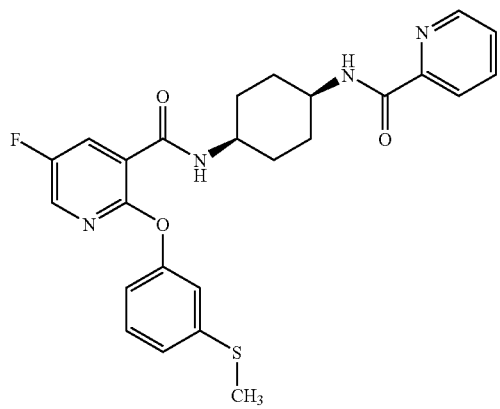

The amine of preparation 8 (245 mg, 595 mmol) was dissolved in N,N-dimethylformamide (5 mL) and the solution treated with triethylamine (250 μL, 1.78 mmol), pyridine-2-carboxylic acid (81 mg, 654 mmol), 1-hydroxybenzotriazole hydrate (88 mg, 654 mmol) and finally 1-(3-dimethylaminopropyl)-3-ethylcarbodiimide hydrochloride (125 mg, 654 mmol). The reaction mixture was stirred at room temperature for 48 hours. The reaction mixture was concentrated in vacuo and the residue basified with saturated sodium hydrogencarbonate solution (5 mL) and extracted with ethyl acetate (3×10 mL). The organics were combined and washed with water (5 mL) and brine (5 mL), dried over magnesium sulphate and concentrated in vacuo. The residue was triturated with ether to yield the title product, 300 mg.

¹HNMR(CD₃OD, 400 MHz): δ=1.63(m, 2H), 1.77(m, 2H), 1.89(m, 4H), 2.42(s, 3H), 4.15(m, 1H), 4.269 m, 1H), 6.91(m, 1H), 7.02(m, 1H), 7.18(m, 1H), 7.37(m, 1H), 7.42 (m, 1H), 7.83(m, 1H), 8.03(m, 2H), 8.36(m, 1H), 8.40(m, 1H) ppm. MS APCI+ m/z 481 [MH]⁺.

The following compounds, of the general formula below, were prepared by a method similar to that described for example 15 using the appropriate amine and carboxylic acid, R⁴COOH.

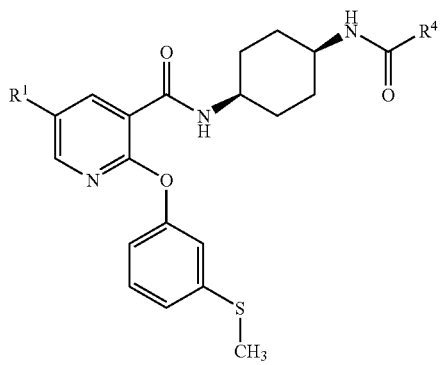

| No. | R¹ | R⁴ | Data |
|---|---|---|---|
| 16 | F | pyrimidin-5-yl | ¹HNMR(CDCl₃, 400 MHz): δ = 1.50(m,2H), 1.90(m,4H), 1.98(m,2H), 2.48(s,3H), 4.11(m,1H), 4.29(m,1H), 5.78(m,1H), 6.90(dd,1H), 7.03(s,1H), 7.16(d,1H), 7.38(t,1H), 8.06(m,1H), 8.09(d,1H), 8.38(dd,1H), 8.99(s,2H), 9.33(s,1H) ppm. MS ES+ m/z 482 [MH]⁺ |
| 17 | F | pyrazin-2-yl | ¹HNMR(CDCl₃, 400 MHz): δ = 1.65(m,2H), 1.80(m,2H), 1.92(m,4H), 2.47(s,3H), 4.14(m,1H), 4.25(m,1H), 6.92(dd,1H), 7.03(s,1H), 7.18(d,1H), 7.38(t,1H), 7.69(m,1H), 8.00(m,1H), 8.05(d,1H), 8.38(dd,1H), 8.50(s,1H), 8.77(s,1H), 9.39(m,1H) ppm. MS ES+ m/z 482 [MH]⁺ |
| 18 | F | 1H-imidazol-4-yl | ¹HNMR(CDCl₃, 400 MHz): δ = 1.65(m,2H), 1.79(m,2H), 6.93(dd,1H), 7.02(m,1H), 7.08(m,1H), 7.18(m,1H), 7.38(t,1H), 7.59(s,1H), 7.62(s,1H), 7.95(m,1H), 8.07(d,1H), 8.38(m,1H) ppm. MS ES+ m/z 470 [MH]⁺ |
| 19 | F | 1H-pyrazol-4-yl | ¹HNMR(CDCl₃, 400 MHz): δ = 1.48(m,2H), 1.83(m,4H), 1.92(m,2H), 2.48(s,3H), 4.06(m,1H), 4.28(m,1H), 5.46(m,1H), 6.93(m,1H), 7.06(s,1H), 7.18(d,1H), 7.38(t,1H), 7.85(s,2H), 8.05(m,1H), 8.08(d,1H), 8.38(m,1H) ppm. MS ES+ m/z 470 [MH]⁺ |
| 20 | H | pyridin-2-yl | ¹HNMR(CDCl₃, 400 MHz): δ = 1.62–1.95(m,8H), 2.43(s,3H), 4.14(m,1H), 4.24(m,1H), 6.96(m,1H), 7.08(m,1H), 7.18(m,2H), 7.36(t,1H), 7.45(d,1H), 7.88(m,2H), 8.22(m,3H), 8.58(m,2H) ppm. MS APCI+ m/z 463 [MH]⁺ |
| 21 | H | 2-hydroxyphenyl | ¹HNMR(CDCl₃, 400 MHz): δ = 1.51(m,2H), 1.85(m,6H), 2.44(s,3H), 4.06(m,1H), 4.27(m,1H), 5.93(m,1H), 6.91(m,1H), 6.97(d,2H), 7.16(t,3H), 7.45–7.73(m,3H), 7.97(m,1H), 8.21(s,1H), 8.59(m,1H) ppm. MS ES- m/z 476 [M-H]⁻ |
| 22 | F | 4-hydroxy-2-methoxyphenyl | ¹HNMR(CDCl₃, 400 MHz): δ = 1.60–2.00(m,8H), 2.42(s,3H), 3.68(s,3H), 4.18(m,2H), 6.46(d,1H), 6.60(m,1H), 6.92(m,1H), 7.02(s,1H), 7.12(d,1H), 7.34(t,1H), 7.94–8.08(m,4H), 8.34(m,1H) ppm. MS ES+ m/z 548 [MNa]⁺ |

Example 16—Pyrimidine-5-carboxylic acid used (WO 93/18028, pg. 15, description 4).

Example 18—The crude product was purified by column chromatography on silica gel eluting with dichloromethane:methanol 95:5 before trituaration with ether.

Example 22—4-hydroxy-2-methoxybenzoic acid used (WO 97/25992, pg. 24, step 4).

EXAMPLE 23

Syn-5-Fluoro-2-(4-fluoro-3-methylsulfanyl-phenoxy)-N-[4-(2-hydroxy-4-methyl-benzoylamino)-cyclohexyl]-nicotinamide

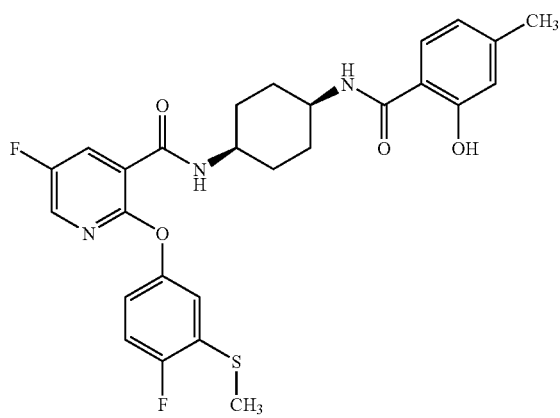

The chloro compound of preparation 15 (170 mg, 0.42 mmol), 4-fluoro-3-methylsulfanyl-phenol (99 mg, 0.63 mmol) and caesium carbonate (409 mg, 1.26 mmol) were dissolved in acetonitrile (5 mL) and the reaction mixture refluxed for 18 hours. N,N-Dimethylformamide (5 mL) was added and the reaction mixture heated to 80° C. for 18 hours. The reaction mixture was concentrated in vacuo and the residue taken up in dichloromethane and water. The layers were separated and the aqueous extracted with dichloromethane. The organics were combined, dried over magnesium sulphate and concentrated in vacuo. The crude product was purified by column chromatography on silica gel eluting with pentane:ethyl acetate 75:25 to yield the title product as a brown oil, 74 mg.

$^1$HNMR(DMSO-D$_6$, 400 MHz): δ=1.62–1.80 (m, 8H), 2.23 (s, 3H), 2.41 (s, 3H), 3.84 (m, 1H), 3.95 (m, 1H), 6.68 (m, 2H), 7.02 (m, 1H), 7.19 (m, 1H), 7.21 (d, 1H) 7.75 (d, 2H), 7.99 (m, 1H), 8.22 (d, 1H), 8.34 (m, 1H), 12.27 (s, 1H) ppm. MS ES+ m/z 550 [MH]$^+$.

EXAMPLE 24

Syn-N-[4-(3,5-Dihydroxy-benzoylamino)-cyclohexyl]-5-fluoro-2-(3-methylsulfanyl-phenoxy)-nicotinamide

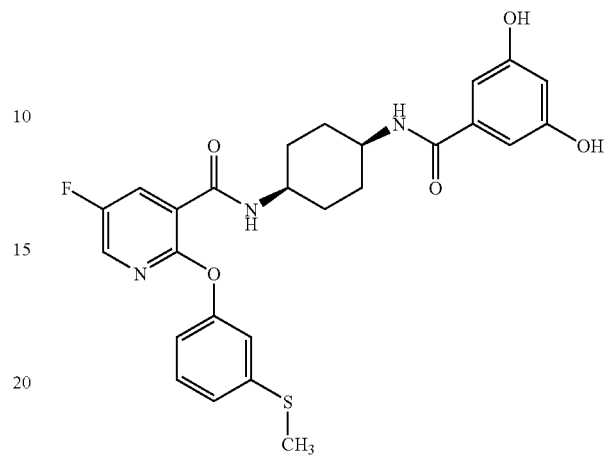

The product of preparation 16 (287 mg, 0.42 mmol) was dissolved in dichloromethane (10 mL) under nitrogen and cooled in an ice bath to 0° C. The solution was treated dropwise with boron tribromide (2.1 mL, 2.10 mmol) over 2 minutes and the reaction mixture stirred at 0° C. for 30 minutes. The reaction mixture was quenched with a saturated solution of sodium hydrogencarbonate and stirred for 10 minutes. The mixture was acidified with 1M citric acid and then extracted with dichloromethane (3×40 mL). The organics were combined, dried over magnesium sulphate and concentrated in vacuo. The residue was purified by column chromatography on silica gel eluting with dichloromethane:methanol 100:0 to 95:5 to yield the title product as a white solid, 142 mg (66%).

$^1$HNMR(CDCl$_3$, 400 MHz): δ=1.41(m, 2H), 1.74(m, 6H), 2.36(s, 3H), 3.91(m, 1H), 4.10(m, 1H), 6.18(m, 1H), 6.43(m, 1H), 6.60(s, 1H), 6.83(d, 1H), 6.97(s, 1H), 7.03(d, 1H), 7.08(d, 1H), 7.35(t, 1H), 7.77(s, 1H), 8.00(d, 1H), 8.09(d, 1H), 8.24(dd, 1H) ppm. MS APCI+ m/z 512 [MH]$^+$.

EXAMPLE 25 AND 26

Syn-N-[4-(3,5-Dimethoxy-benzoylamino)-cyclohexyl]-5-fluoro-2-(3-methylsulfanyl-phenoxy)-nicotinamide

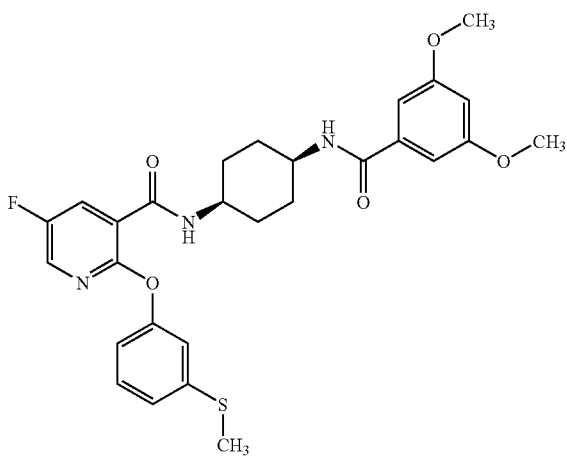

Example 24 (840 mg, 1.64 mmol) was dissolved in N,N-dimethylformamide (10 mL) and the solution treated with sodium hydride (66 mg, 1.64 mmol). The mixture was stirred for 10 minutes and was then treated with iodomethane (233 mg, 1.64 mmol). The reaction mixture was stirred at room temperature for 18 hours, diluted with ethyl acetate and washed with 0.1M citric acid, water and brine, dried over magnesium sulphate and concentrated in vacuo. The residue was purified by column chromatography on silica gel eluting with dichloromethane:methanol 100:0 to 95:5. The crude product was crystallised from diethyl ester to yield the title product, 217 mg.

$^1$HNMR(CDCl$_3$, 400 MHz): δ=1.50(m, 2H), 1.87(m, 6H), 2.44(s, 3H), 3.82(s, 6H), 4.07(s, 1H), 4.24(s, 1H), 5.79(d, 1H), 6.57(d, 1H), 6.79(d, 2H), 6.91(d, 1H), 7.02(s, 1H), 7.13(d, 1H), 7.36(t, 1H), 8.04(d, 1H), 8.08(d, 1H), 8.36(dd, 1H) ppm. MS APCI+ m/z 540 [MH]+.

Further elution of the column gave the following compound:

EXAMPLE 26

Syn-5-Fluoro-N-[4-(3-hydroxy-5-methoxy-benzoylamino)-cyclohexyl]-2-(3-methylsulfanyl-phenoxy)-nicotinamide

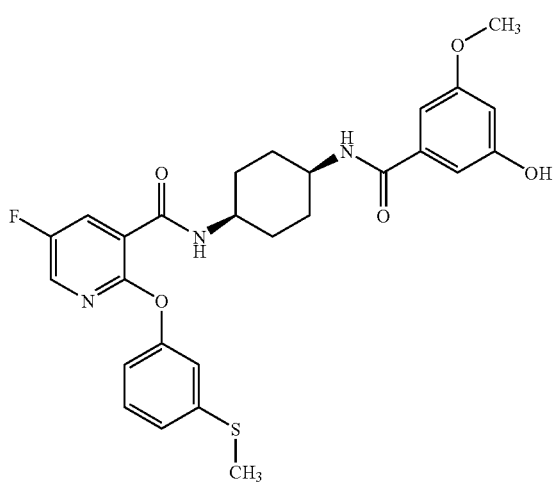

$^1$HNMR(CDCl$_3$, 400 MHz): δ=1.48(m, 2H), 1.83(m, 4H), 1.92(m, 2H), 2.46(s, 3H), 3.79(s, 3H), 4.04(m, 1H), 4.25(m, 1H), 5.82(d, 1H), 6.54(s, 1H), 6.71 (s, 1H), 6.85(s, 1H), 6.91(d, 1H), 7.04(s, 1H), 7.14(d, 1H), 7.36(t, 1H), 8.08(m, 2H), 8.35(dd, 1H) ppm. MS APCI+ m/z 526 [MH]+.

EXAMPLE 27

Syn-N-{4-[(1,5-Dimethyl-1H-pyrazole-3-carbonyl)-amino]-cyclohexyl}-2-(3-methylsulfanyl-phenoxy)-nicotinamide

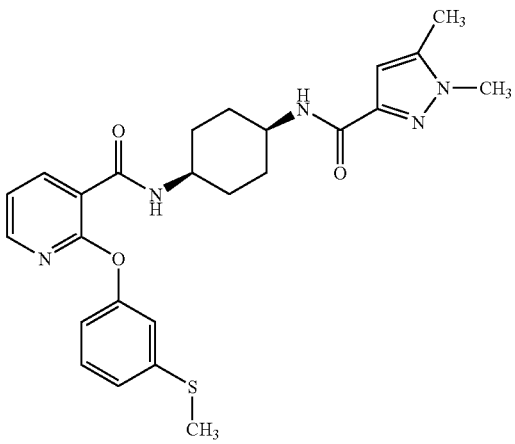

The amine of preparation 12 (450 mg, 1.14 mmol) was taken up in a mixture of dichloromethane and sodium hydroxide solution and the organic layer was separated and concentrated in vacuo. The residue was taken up in N,N-dimethylformamide (5 mL) and the solution treated with 1-hydroxybenzotriazole hydrate (154 mg, 1.14 mmol), 1-(3-dimethylaminopropyl)-3-ethylcarbodiimide hydrochloride (328 mg, 1.71 mmol), N-ethyldiisopropylamine (796 μL, 4.57 mmol) and 1,5-dimethyl-1H-pyrazole-3-carboxylic acid (144 mg, 1.03 mmol) and the reaction mixture stirred at room temperature for 18 hours. The reaction mixture was partitioned between ethyl acetate and 2M hydrochloric acid, the organic layer washed with 2M hydrochloric acid, saturated sodium hydrogencarbonate solution, water and brine. The organic layer was then dried over magnesium sulphate and concentrated in vacuo. The residue was purified by column chromatography on silica gel eluting with pentane:ethyl acetate 50:50 to 30:70 to 0:100 to yield the title product as a glossy solid, 57 mg.

$^1$HNMR(CDCl$_3$, 400 MHz): δ=1.57–1.92(m, 8H), 2.23(s, 3H), 2.42(s, 3H), 3.7(s, 3H), 4.04(m, 1H), 4.21 (m, 1H), 6.78(m, 1H), 6.91 (d, 1H), 7.07(m, 1H), 7.17(m, 2H), 7.37(t, 1H), 7.93(m, 1H), 8.20(m, 1H), 8.60(m, 1H) ppm. MS ES– m/z 487 [M–H]−.

EXAMPLE 28

N-Cyclohexyl-2-[3-(methylsulfanyl)phenoxy]nicotinamide

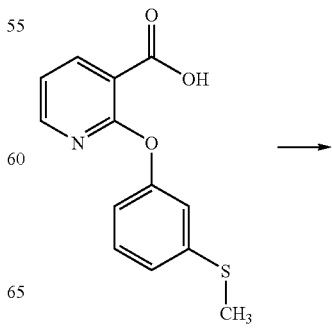

-continued

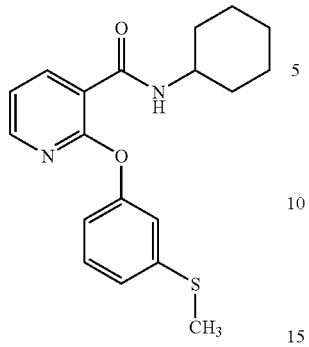

2-[3-(Methylsulfanyl)phenoxy]nicotinic acid (200 mg, 0.77 mmol) was dissolved in dimethylformamide (5 ml) and triethylamine (427 ul, 3.07 mmol) was added followed by cyclohexylamine hydrochloride (88 ug, 0.77 mmol), 1-(3-dimethylaminopropyl)-3-ethylcarbodiimide hydrochloride (294 mg, 1.53 mmol) and 1-hydroxybenzotriazole (114 mg, 0.84 mmol). The reaction was stirred under nitrogen at room temperature for 18 h and the solvent was removed under reduced pressure. The residue was partitioned between water (50 ml) and diethyl diethyl ether (50 ml). The organic phase was washed with brine, dried over MgSO₄ and the solvent was removed under reduced pressure. The residue was purified by flash column chromatography using ethyl acetate:cyclohexane (20:80 to 35:65) as eluant to give a white solid which was recrystallised from diethyl diethyl ether/pentane to give N-cyclohexyl-2-[3-(methylsulfanyl) phenoxy]nicotinamide (134 mg) as a white solid.

¹H NMR (400 MHz, CDCl3): δ=8.60–8.64 (1H, d), 8.18–8.24 (1H, m), 7.35–7.40(1H, t), 7.12–7.20 (1H, m), 7.04–7.08 (1H, m), 6.90–6.96 (1H, dd), 3.99–4.12 (1H, m), 2.50 (3H, s), 1.94–2.08 (2H, m), 1.64–1.78 (2H, m), 1.18–1.52 (4H, m) ppm. LRMS (thermospray): m/z [M+H]⁺ 343. Anal. Found C, 66.59; H, 6.42; N, 8.16. $C_{19}H_{22}N_2O_2S$ requires C, 66.64; H, 6.48; N, 8.18%.

EXAMPLE 29

N-[(1R,2S)-2-Hydroxycyclohexyl]-2-[3-(methylsulfanyl)phenoxy]nicotinamide

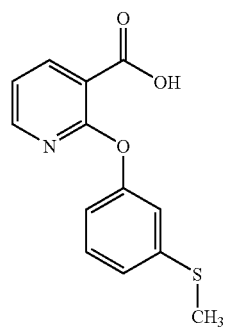

-continued

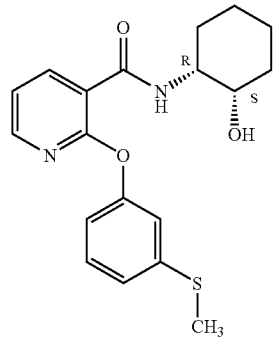

1-(3-Dimethylaminopropyl)-3-ethylcarbodiimide hydrochloride (294 mg, 1.53 mmol) was added to a solution of 2-(3-methylsulfanyl-phenoxy)-nicotinic acid (200 mg, 0.765 mmol), (1S,2R)-2-aminocyclohexanol hydroformate [8151/194/1] (128 mg, 0.765 mmol), 1-hydroxybenzotriazole (114 mg, 0.842 mmol) and triethylamine (430 µl, 3.10 mmol) in dimethylformamide (5 ml) under nitrogen at room temperature. The reaction was stirred for 18 h and partitioned between diethyl ether (25 ml) and water (25 ml). The organic phase was washed with brine (30 ml), dried over MgSO₄ and the solvent was removed under reduced pressure. The residue was purified by flash column chromatography on silica gel eluting with a solvent gradient of ethyl acetate: cyclohexane (35:65 to 50:50) to give an off-white solid which was purified by flash column chromatography using ethyl acetate:cyclohexane (50:50 as eluant) to give N-[(1R,2S)-2-hydroxycyclohexyl]-2-[3-(methylsulfanyl) phenoxy]nicotinamide (133 mg) as a gum.

¹H NMR (400 MHz, CDCl₃): δ=8.58–8.62 (1H, d), 8.20–8.30 (2H, m), 7.34–7.40(1H, t), 7.12–7.20 (1H, m), 7.06–7.10 (1H, m), 6.90–6.96 (1H, dd), 4.20–4.30 (1H, m), 4.00–4.08 (1H, m), 2.54 (3H, s), 1.64–1.82 (2H, m), 1.36–1.50 (6H, m) ppm. LRMS (electrospray): m/z [M+H]⁺ 359, [M+Na]⁺ 359.

EXAMPLE 30

N-[(1S,2R)-2-Hydroxycyclohexyl]-2-[3-(methylsulfanyl)phenoxy]nicotinamide

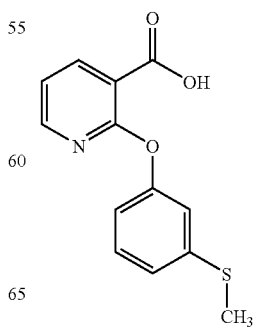

-continued

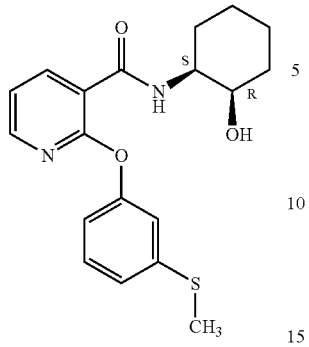

1-(3-Dimethylaminopropyl)-3-ethylcarbodiimide hydrochloride (293 mg, 1.53 mmol) was added to a solution of 2-(3-methylsulfanyl-phenoxy)-nicotinic acid (200 mg, 0.765 mmol), (1R,2S)-2-aminocyclohexanol hydroformate [8151/195/2] (123 mg, 0.765 mmol), 1-hydroxybenzotriazole (114 mg, 0.842 mmol) and triethylamine (430□l, 3.10 mmol) in dimethylformamide (5 ml) under nitrogen at room temperature. The reaction was stirred for 18 h and partitioned between diethyl ether (25 ml) and water (25 ml). The organic phase was washed with brine (30 ml), dried over MgSO$_4$ and the solvent was removed under reduced pressure. The residue was purified by flash column chromatography using ethyl acetate:cyclohexane (50:50 as eluant) to give N-[(1 S,2R)-2-hydroxycyclohexyl]-2-[3-(methylsulfanyl)phenoxy]nicotinamide (133 mg) as a gum.

$^1$H NMR (400 MHz, CDCl$_3$): δ=8.58–8.62 (1H, d), 8.20–8.30 (2H, m), 7.34–7.40 (1H, t), 7.12–7.20 (1H, m), 7.06–7.10 (1H, m), 6.90–6.96 (1H, dd), 4.20–4.30 (1H, m), 4.00–4.08 (1H, m), 2.54 (3H, s), 1.64–1.82 (2H, m), 1.36–1.50 (6H, m) ppm. LRMS (electrospray): m/z [M+H]$^+$ 377, [M+Na]$^+$ 399, [M−H]$^−$ 375.

EXAMPLE 31

5-Fluoro-N-[cis-2-hydroxy-cyclohexyl]-2-(3-methylsulfanyl-phenoxy)-nicotinamide

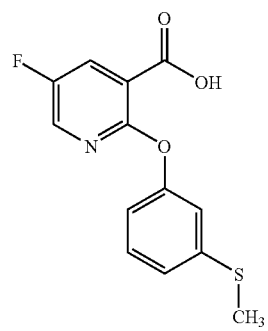

-continued

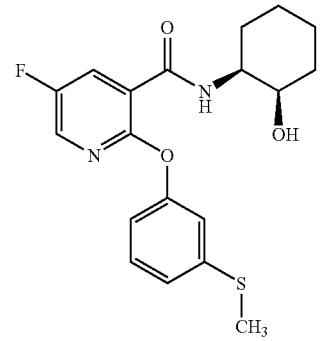

cis-2-Amino-cyclohexane-1-ol (85 mg, 0.56 mmol) and triethylamine (225 µl, 1.61 mmol) were dissolved in dimethylformamide (225 µl) and a solution of 5-fluoro-2-(3-methylsulfanyl-phenoxy)-nicotinic acid (150 mg, 0.54 mmol), 1-(3-dimethylaminopropyl)-3-ethylcarbodiimide hydrochloride (113 mg, 0.59 mmol) and 1-hydroxybenzotriazole (80 mg, 0.59 mmol) in dimethylformamide (5 ml) was added. The reaction was stirred under nitrogen at room temperature for 64 h and the solvent was removed under reduced pressure. The residue was partitioned between 0.5N HCl (10 ml) and ethyl acetate (10 ml) and the aqueous phase was extracted with ethyl acetate (2×10 ml). The combined organic phases were washed with brine (10 ml), dried over MgSO$_4$ and the solvent was removed under reduced pressure. The residue was purified by flash column chromatography on silica gel eluting with pentane:ethyl acetate (70:30, by volume). The product was triturated with pentane (3 ml) to give 5-fluoro-N-[cis-2-hydroxy-cyclohexyl]-2-(3-methylsulfanyl-phenoxy)-nicotinamide (118 mg) as a white solid.

mp 99–101° C. $^1$H NMR (400 MHz, CDCl$_3$): δ=8.22–8.36 (2H, dd+d), 8.03–8.07 (1H, d), 7.28–7.36 (1H, t), 7.09–7.13 (1H, d), 7.03–7.05 (1H, d), 6.87–6.96 (1H, dd), 4.16–4.24 (1H, m), 3.97–4.03 (1H, brs), 2.45 (3H, s), 1.91 (1H, s), 1.59–1.83 (6H, 2×m), 1.38–1.49 (2H, m) ppm. LRMS (electrospray): m/z [M+H]$^+$ 377, [M+Na]$^+$ 399, [M−H]$^+$ 375. Anal. Found C, 60.54; H, 5.63; N, 7.34. C$_{19}$H$_{21}$FN$_2$O$_5$S requires C, 60.62; H, 5.62; N, 7.44%.

EXAMPLE 32

5-Fluoro-N-(1S,2R-2-hydroxy-cyclohexyl)-2-(3-methylsulfanyl-phenoxy)-nicotinamide

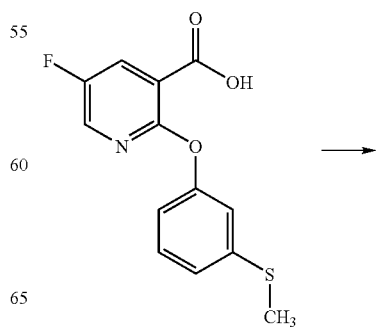

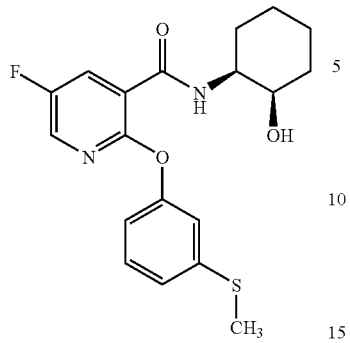

1-(3-Dimethylaminopropyl)-3-ethylcarbodiimide hydrochloride (240 mg, 1.25 mmol) was added to a solution of 5-fluoro-2-(3-methylsulfanyl-phenoxy)-nicotinic acid (175 mg, 0.627 mmol), (1R,2S)-2-amino-cyclohexan-1-ol hydrochloride (100 mg, 0.627 mmol), 1-hydroxybenzotriazole (95 mg, 0.704 mmol) and triethylamine (350 µl, 2.51 mmol) in dimethylformamide (5 ml) under nitrogen at room temperature. The reaction was stirred for 18 h and partitioned between diethylether (60 ml) and water (60 ml). The organic phase was removed and washed with water (30 ml), brine (30 ml), dried over MgSO$_4$ and the solvent was removed under reduced pressure. The residue was purified by flash column chromatography on silica gel eluting with a solvent gradient of ethyl acetate:cyclohexane (10:90 changing to 80:20, by volume) to give 5-fluoro-N-(1S,2R-2-hydroxyacetyl-cyclohexyl)-2-(3-methylsulfanyl-phenoxy)-nicotinamide (40 mg) as an oil.

$^1$H NMR (400 MHz, CDCl$_3$): δ=8.25–8.39 (2H, d+dd), 8.03–8.05 (1H, d), 7.29–7.38 (1H, t), 7.10–7.18 (1H, d), 7.04 (1H, s), 6.92–6.97 (1H, d), 4.17–4.23 (1H, m), 3.98–4.03 (1H, brs), 2.46 (3H, s), 2.04–2.17 (1H, brs), 1.52–1.80 (6H, 2×m), 1.38–1.50 (2H, m) ppm. LRMS (electrospray): m/z [M+H]$^+$ 377, [M+Na]$^+$ 399, [M–H]$^+$ 375. Anal. Found C, 59.26; H, 5.57; N, 7.16. C$_{19}$H$_{21}$FN$_2$O$_3$S. 0.4 mol H$_2$O requires C, 59.48; H, 5.73; N, 7.30%.

EXAMPLE 33

2-[3-(Ethylsulfanyl)phenoxy]-5-fluoro-N-[(1R,2S)-2-hydroxycyclohexyl]nicotinamide

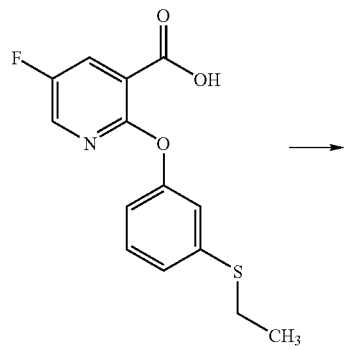

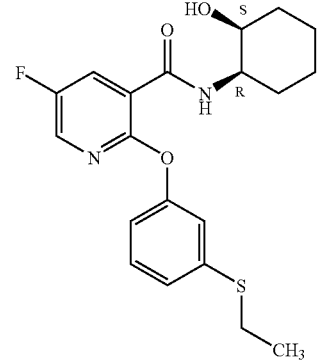

2-[3-(Ethylsulfanyl)phenoxy]-5-fluoronicotinic acid (250 mg, 0.85 mmol) was dissolved in dimethylformamide (5 ml) and triethylamine (475 µl, 3.41 mmol) was added followed by (1S,2R)-2-aminocyclohexanol hydroformate (144 mg, 0.89 mmol), 1-(3-dimethylaminopropyl)-3-ethylcarbodiimide hydrochloride (180 mg, 0.94 mmol) and 1-hydroxybenzotriazole (127 mg, 0.94 mmol). The reaction was stirred under nitrogen at room temperature for 18 h and the solvent was removed under reduced pressure. The residue was partitioned between water (5 ml) and ethyl acetate (10 ml) and the aqueous phase was extracted with ethyl acetate (3×10 ml). The combined organic extracts were washed with brine (5 ml), dried over MgSO$_4$ and the solvent was removed under reduced pressure. The residue was purified by flash column chromatography using dichloromethane:methanol:0.880 ammonia (98:2:0.2) as eluant to give 2-[3-(ethylsulfanyl)phenoxy]-5-fluoro-N-[(1R,2S)-2-hydroxycyclohexyl] nicotinamide (60 mg) as a colourless oil.

$^1$H NMR (400 MHz, CDCl$_3$): δ=8.27–8.38 (2H, dd+m), 8.03–8.07 (1H, m), 7.32–7.38 (1H, m), 7.18–7.22 (1H, d), 7.12 (1H, s), 6.93–6.99 (1H, d), 4.18–4.25 (1H, brs), 3.99–4.05 (1H, brs), 2.94–3.00 (2H, quart), 1.92–1.95 (1H, brs), 1.64–1.80 (4H, 2×m), 1.52–1.64 (2H, m, partially masked by solvent), 1.38–1.51 (2H, m), 1.32–1.37 (3H, t) ppm. LRMS (thermospray): m/z [M+H]$^+$ 391. Anal. Found C, 59.41; H, 5.79; N, 6.95. C$_{20}$H$_{23}$FN$_2$O$_3$S.0.5 mol H$_2$O requires C, 59.65; H, 6.02; N, 6.94%.

EXAMPLE 34

2-[3-(Ethylsulfanyl)phenoxy]-5-fluoro-N-[(1S,2R)-2-hydroxycyclohexyl]nicotinamide

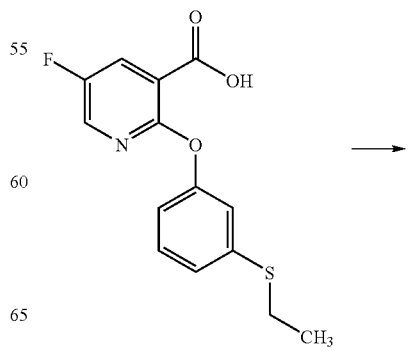

-continued

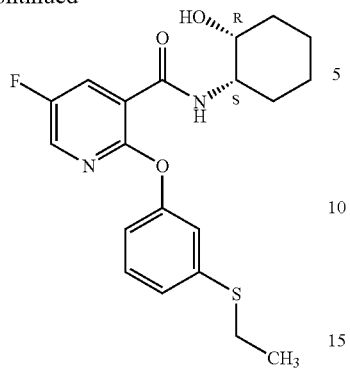

-continued

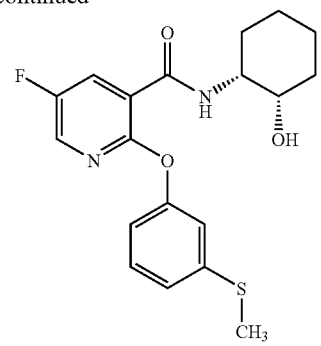

2-[3-(Ethylsulfanyl)phenoxy]-5-fluoronicotinic acid (250 mg, 0.85 mmol) was dissolved in dimethylformamide (5 ml) and triethylamine (475 µl, 3.41 mmol) was added followed by (1R,2S)-2-aminocyclohexanol hydroformate (144 mg, 0.89 mmol), 1-(3-dimethylaminopropyl)-3-ethylcarbodiimide hydrochloride (180 mg, 0.94 mmol) and 1-hydroxybenzotriazole (127 mg, 0.94 mmol). The reaction was stirred under nitrogen at room temperature for 18 h and the solvent was removed under reduced pressure. The residue was partitioned between water (5 ml) and ethyl acetate (10 ml) and the aqueous phase was extracted with ethyl acetate (3×10 ml). The combined organic extracts were washed with brine (5 ml), dried over MgSO$_4$ and the solvent was removed under reduced pressure. The residue was purified by flash column chromatography using dichloromethane:methanol:0.880 ammonia (98:2:0.2) as eluant to give 2-[3-(ethylsulfanyl)phenoxy]-5-fluoro-N-[(1S,2R)-2-hydroxycyclohexyl]nicotinamide (57 mg) as a colourless oil.

$^1$H NMR (400 MHz, CDCl$_3$): δ=8.27–8.38 (2H, dd+m), 8.03–8.07 (1H, m), 7.32–7.38 (1H, m), 7.18–7.22 (1H, d), 7.12 (1H, s), 6.93–6.99 (1H, d), 4.18–4.25 (1H, brs), 3.99–4.05 (1H, brs), 2.94–3.00 (2H, quart), 1.92–1.95 (1H, brs), 1.64–1.80 (4H, 2×m), 1.52–1.64 (2H, m, partially masked by solvent), 1.38–1.51 (2H, m), 1.32–1.37 (3H, t) ppm. LRMS (electrospray): m/z [M+Na]$^+$ 413, [2M+Na]$^+$ 803.

EXAMPLE 35

5-Fluoro-N-(1R,2 S-2-hydroxy-acetyl-cyclohexyl)-2-(3-methylsulfanyl-phenoxy)-nicotinamide 1-(3-Dimethylaminopropyl)-3-ethylcarbodiimide hydrochloride (240 mg, 1.25 mmol) was added to a solution of 5-fluoro-2-(3-methylsulfanyl-phenoxy)-nicotinic acid (175 mg, 0.627 mmol), (1S,2R)-2-amino-cyclohexan-1-ol hydrochloride (100 mg, 0.627 mmol), 1-hydroxybenzotriazole (95 mg, 0.704 mmol) and triethylamine (350 µl, 2.51 mmol) in dimethylformamide (5 ml) under nitrogen at room temperature. The reaction was stirred for 18 h and partitioned between diethylether (60 ml) and water (60 ml). The organic phase was removed and washed with water (30 ml), brine (30 ml), dried over MgSO$_4$ and the solvent was removed under reduced pressure. The residue was purified by flash column chromatography on silica gel eluting with a solvent gradient of ethyl acetate:cyclohexane (10:90 changing to 80:20, by volume) to give 5-fluoro-N-(1R,2S-2-hydroxyacetyl-cyclohexyl)-2-(3-methylsulfanyl-phenoxy)-nicotinamide (40 mg) as an oil.

$^1$H NMR (400 MHz, CD$_3$OD): δ=8.18–8.22 (1H, dd), 8.08–8.11 (1H, d), 7.31–7.37 (1H, t), 7.13–7.18 (1H, d), 7.12 (1H, s), 6.92–6.98 (1H, d), 4.00–4.08 (1H, m), 3.92–3.98 (1H, brs), 2.47 (3H, s), 1.58–1.80 (6H, 2×m), 1.35–1.48 (2H, m) ppm. LRMS (electrospray): m/z [2M+Na]$^+$ 775, [M−H]$^+$ 375. Anal. Found C, 59.40; H, 5.62; N, 7.22. C$_{19}$H$_{21}$FN$_2$O$_3$S. 0.4 mol H$_2$O requires C, 59.48; H, 5.73; N, 7.30%.

EXAMPLE 36

5-Fluoro-N-[(1S,2S)-2-hydroxy-cyclohexyl]-2-(3-methylsulfanyl-phenoxy)-nicotinamide and
5-Fluoro-N-[(1R,2R)-2-hydroxy-cyclohexyl]-2-(3-methylsulfanyl-phenoxy)-nicotinamide

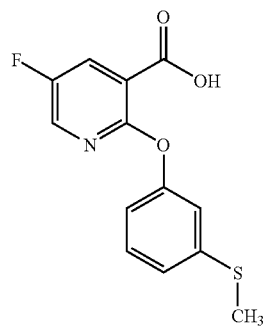 

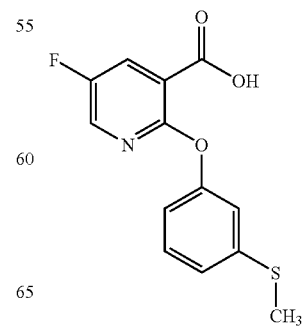 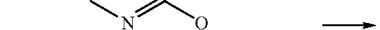

-continued

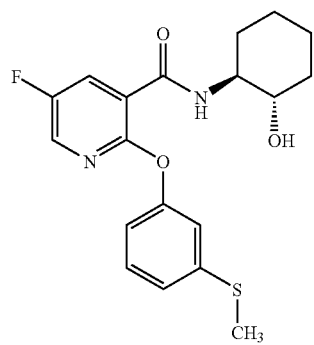

+

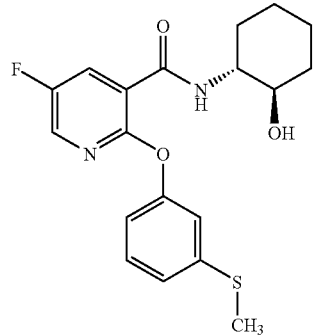

trans-2-Amino-cyclohexane-1-ol (85 mg, 0.56 mmol) and triethylamine (225 µl, 1.61 mmol) were dissolved in dimethylformamide (225 µl) and a solution of 5-fluoro-2-(3-methylsulfanyl-phenoxy)-nicotinic acid (150 mg, 0.54 mmol), 1-(3-dimethylaminopropyl)-3-ethylcarbodiimide hydrochloride (113 mg, 0.59 mmol) and 1-hydroxybenzotriazole (80 mg, 0.59 mmol) in dimethylformamide (5 ml) was added. The reaction was stirred under nitrogen at room temperature for 64 h and the solvent was removed under reduced pressure. The residue was partitioned between 0.5N HCl (10 ml) and ethyl acetate (10 ml) and the aqueous phase was extracted with ethyl acetate (2×10 ml). The combined organic phases were washed with brine (10 ml), dried over MgSO$_4$ and the solvent was removed under reduced pressure. The residue was purified by flash column chromatography on silica gel eluting with pentane:ethyl acetate (70:30, by volume). The product was triturated with pentane (3 ml) to give a mixture of 5-fluoro-N-[(1S,2S)-2-hydroxy-cyclohexyl]-2-(3-methylsulfanyl-phenoxy)-nicotinamide and 5-fluoro-N-[(1R,2R)-2-hydroxy-cyclohexyl]-2-(3-methylsulfanyl-phenoxy)-nicotinamide (104 mg) as a white solid.

mp 89–92° C. $^1$H NMR (400 MHz, CDCl$_3$): δ=8.34–8.39 (1H, dd), 8.02–8.06 (1H, d), 7.88–7.98 (1H, d), 7.32–7.38 (1H, t), 7.13–7.21 (1H, d), 7.02 (1H, s), 6.87–6.92 (1H, m), 3.82–3.92 (1H, m), 3.39–3.49 (1H, m), 3.21 (1H, s), 2.46 (3H, s), 2.02–2.18 (2H, d), 1.66–1.80 (2H, t), 1.20–1.46 (4H, m) ppm. LRMS (electrospray): m/z [M+H]$^+$ 377, [M+Na]$^+$ 399, [M–H]$^+$ 375. Anal. Found C, 59.91; H, 5.60; N, 7.35. C$_{19}$H$_{21}$FN$_2$O$_5$S. 0.2 mol H$_2$O requires C, 60.05; H, 5.68; N, 7.37%.

EXAMPLE 37

5-Fluoro-N-(2-hydroxy-2-methylcyclohexyl)-2-[3-(methylsulfanyl)phenoxy]nicotinamide (Racemic, Single Diastereoisomer, Unknown Rel Stereochemistry)

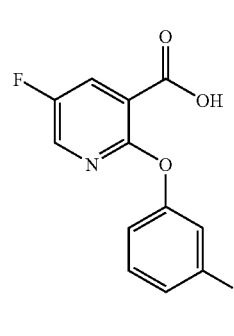

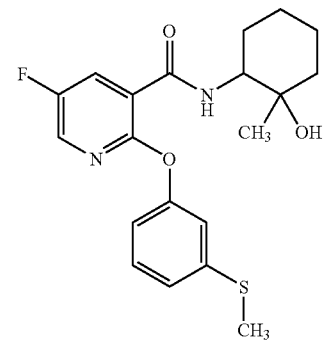

2-[3-(Methylsulfanyl)phenoxy]-5-fluoronicotinic acid (100 mg, 0.358 mmol) was dissolved in dimethylformamide (5 ml) and triethylamine (250 µl, 3.41 mmol) was added followed by 2-amino-1-methylcyclohexanol hydrochloride (65 mg, 0.39 mmol), 1-(3-dimethylaminopropyl)-3-ethylcarbodiimide hydrochloride (205 mg, 1.07 mmol) and 1-hydroxybenzotriazole (53 mg, 0.39 mmol). The reaction was stirred under nitrogen at room temperature for 18 h and the solvent was removed under reduced pressure. The residue was partitioned between 10% aq. citric acid solution and diethyl ether. The organic was washed with sat. sodium bicarbonate solution, water and brine, dried over MgSO$_4$ and the solvent was removed under reduced pressure. The residue was purified by flash column chromatography using ethyl acetate:cyclohexane (5:95 to 50:50) as eluant to give 5-fluoro-N-(2-hydroxy-2-methylcyclohexyl)-2-[3-(methylsulfanyl)phenoxy]nicotinamide (133 mg) as a white solid.

$^1$H NMR (400 MHz, CDCl$_3$): δ=8.25–8.35(1H, dd), 8.17–8.23 (1H, m), 8.02–8.08 (1H, d), 7.28–7.36 (1H, t), 7.06–7.15 (1H, d), 7.04 (1H, s), 6.88–6.95 (1H, dd), 3.85–3.98 (1H, m), 2.45 (3H, s), 1.80–1.94 (1H, m), 1.64–1.78 (2H, m), 1.30–1.58 (5H, m), 1.22 (3H, s) ppm. LRMS (thermospray): m/z [M+H]$^+$ 391. Anal. Found C, 61.22; H, 5.92; N, 7.11. C$_{20}$H$_{23}$FN$_2$O$_3$S. 0.1 mol H2O requires C, 61.24; H, 5.96; N, 7.14%.

EXAMPLE 38

5-Fluoro-N-(2-hydroxy-2-methylcyclohexyl)-2-[3-(methylsulfanyl)phenoxy]nicotinamide (Racemic, Single Diastereoisomer, Unknown Rel Stereochemistry)

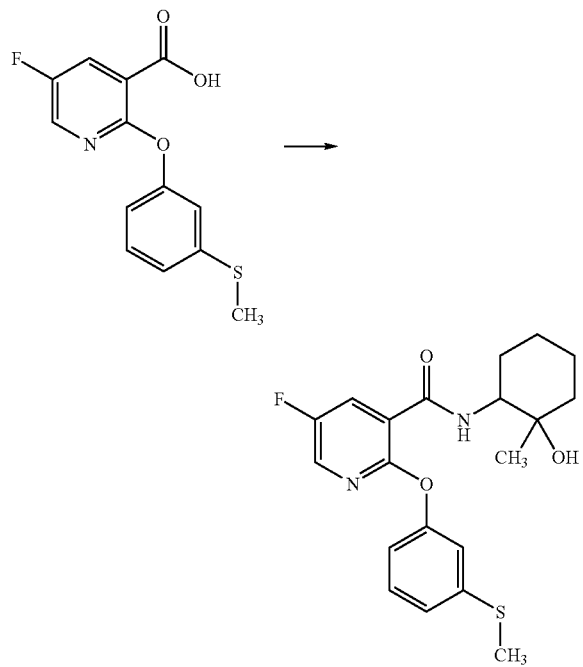

2-[3-(Methylsulfanyl)phenoxy]-5-fluoronicotinic acid (100 mg, 0.358 mmol) was dissolved in dimethylformamide (5 ml) and triethylamine (250 µl, 3.41 mmol) was added followed by 2-amino-1-methylcyclohexanol hydrochloride (65 mg, 0.39 mmol), 1-(3-dimethylaminopropyl)-3-ethylcarbodiimide hydrochloride (205 mg, 1.07 mmol) and 1-hydroxybenzotriazole (53 mg, 0.39 mmol). The reaction was stirred under nitrogen at room temperature for 18 h and the solvent was removed under reduced pressure. The residue was partitioned between 10% aq. citric acid solution and diethyl ether. The organic was washed with sat. sodium bicarbonate solution, water and brine, dried over $MgSO_4$ and the solvent was removed under reduced pressure. The residue was purified by flash column chromatography using ethyl acetate:cyclohexane (5:95 to 50:50) as eluant to give 5-fluoro-N-(2-hydroxy-2-methylcyclohexyl)-2-[3-(methylsulfanyl)phenoxy]nicotinamide (140 mg) as a gum.

$^1$H NMR (400 MHz, CDCl3): δ=8.32–8.36 (1H, dd), 8.04–8.08 (1H, m), 7.88–7.96 (1H, m), 7.30–7.38 (1H, t), 7.10–7.16 (1H, d), 7.00 (1H, s), 6.84–6.90 (1H, dd), 4.00–4.12 (1H, m), 2.45 (3H, s), 1.45–1.96 (5H, m), 1.24–1.48 (3H, m), 1.16 (3H, s) ppm. LRMS (thermospray): m/z [M+H]$^+$ 391. Anal. Found C, 60.67; H, 5.88; N, 6.98. $C_{20}H_{23}FN_2O_3S$. 0.1 mol H2O requires C, 60.60; H, 6.02; N, 7.17%.

EXAMPLE 39

5-Fluoro-N-((1R,3S)-3-hydroxycyclohexyl)-2-[3-(methylsulfanyl)phenoxy]nicotinamide

EXAMPLE 40

5-Fluoro-N-((1S,3R)-3-hydroxy-cyclohexyl)-2-(3-methylsulfanyl-phenoxy)-nicotinamide

EXAMPLE 41

5-Fluoro-N-(trans-3-hydroxy-cyclohexyl)-2-(3-methylsulfanyl-phenoxy)-nicotinamide

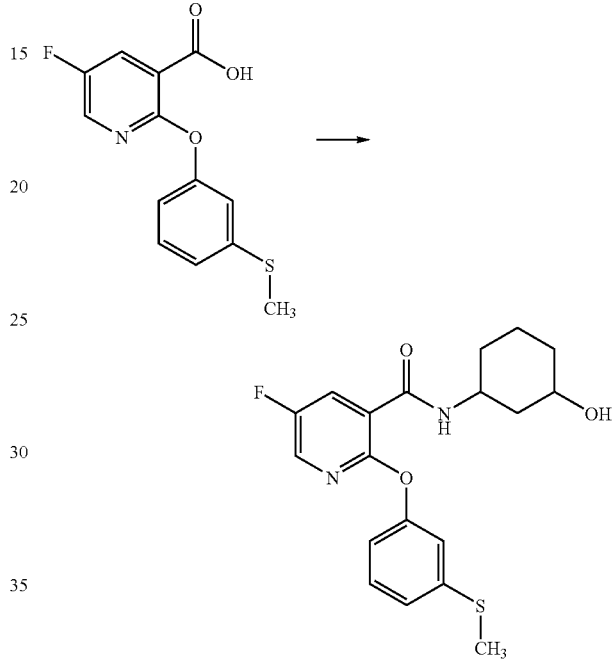

A mixture of 1-aminocycloxexan-3-ol (cis:trans 10:1) (280 mg, 2.43 mmol) was combined with triethylamine (675 µl, 4.86 mmol) in dimethylformamide (20 ml) under nitrogen at room temperature and 5-fluoro-2-(3-methylsulfanyl-phenoxy)-nicotinic acid (680 mg, 2.43 mmol), 1-(3-dimethylaminopropyl)-3-ethylcarbodiimide hydrochloride (513 mg, 2.67 mmol) and 1-hydroxybenzotriazole (362 mg, 2.67 mmol) were added and reaction was stirred at room temperature for 24 h. The reaction mixture was concentrated under reduced pressure, and the residue was partitioned between ethyl acetate (30 ml) and 1M HCl (30 ml). The organic phase was removed, washed with 10% sodium bicarbonate solution (20 ml), brine (20 ml), dried over $Na_2SO_4$ and the solvent was removed under reduced pressure. The residue was purified by flash column chromatography on silica gel eluting with dichloromethane:methanol:concentrated aqueous ammonia (95:5:0.5, by volume) which gave two distinct products, the first of which appeared to be a mixture of two isomers, and the second of which was product 3. The first fraction was further purified by preparative HPLC which separated the cis isomers to give products 1 and 2.

HPLC Conditions: Chiralpak AS 250×20 mm column. Mobile Phase-80% n-hexane, 20% 2-propanol, 0.3% trifluoracetic acid, 0.2% diethyl amine.

Product 1:retention time 8.34 minute

Product 2:retention time 11.3 minute

Product 1:
5-Fluoro-N-(1R,3S-3-hydroxy-cyclohexyl)-2-(3-methyl-sulfanyl-phenoxy)-nicotinamide

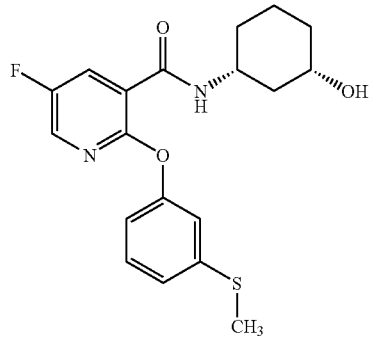

White solid (100 mg) $^1$H NMR (400 MHz, CDCl$_3$): δ=8.38–8.50 (1H, brs), 8.31–8.38 (1H, dd), 8.01–8.06 (1H, d), 7.33–7.38 (1H, t), 7.12–7.18 (1H, d), 7.02 (1H, s), 6.86–6.93 (1H, d), 4.18–4.28 (1H, m), 3.85–3.97 (1H, m), 2.47 (3H, s), 2.08–2.18 (1H, d), 1.77–1.92 (3H, m), 1.38–1.58 (5H, m) ppm. LRMS (electrospray): m/z [M+Na]$^+$ 399, [2M+Na]$^+$ 775, [M–H]$^+$ 357. Absolute structure confirmed by X-ray analysis.

Product 2:

5-Fluoro-N-(1S,3R-3-hydroxy-cyclohexyl)-2-(3-methylsulfanyl-phenoxy)-nicotinamide

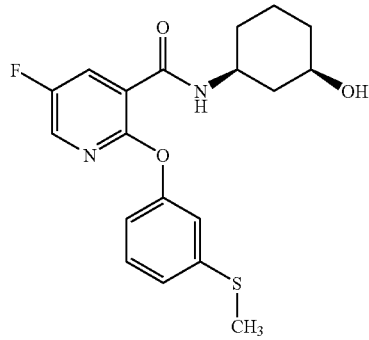

White solid (100 mg) $^1$H NMR (400 MHz, CDCl$_3$): δ=8.38–8.49 (1H, brs), 8.30–8.38 (1H, dd), 8.01–8.03 (1H, d), 7.29–7.38 (1H, t), 7.13–7.18 (1H, d), 7.03 (1H, s), 6.86–6.92 (1H, d), 4.16–4.26 (1H, m), 3.85–3.97 (1H, m), 2.46 (3H, s), 2.10–2.19 (1H, d), 1.78–1.90 (3H, m), 1.32–1.57 (5H, m) ppm. LRMS (electrospray): m/z [M+Na]$^+$ 399, [2M+Na]$^+$ 775, [M–H]$^+$ 357. Absolute structure confirmed by X-ray analysis.

Product 3

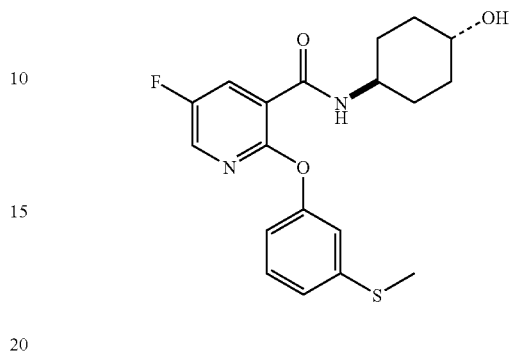

5-Fluoro-N-(trans-3-hydroxy-cyclohexyl)-2-(3-methylsulfanyl-phenoxy)-nicotinamide White solid—racemic mixture (19 mg) $^1$H NMR (400 MHz, CDCl$_3$): δ=8.35–8.39 (1H, dd), 8.03–8.05 (1H, d), 7.78–7.90 (1H, d), 7.32–7.39 (1H, t), 7.14–7.19 (1H, d), 7.02 (1H, s), 6.87–6.93 (1H, d), 4.41–4.51 (1H, m), 3.98–4.05 (1H, m), 2.49 (3H, s), 1.71–1.98 (4H, m), 1.40–1.70 (5H, m+d) ppm. LRMS (electrospray): m/z [M+Na]$^+$ 399, [2M+Na]$^+$ 775, [M–H]$^+$ 357.

EXAMPLE 42

5-Fluoro-N-[(1S,3S)-3-hydroxycyclohexyl]-2-[3-(methylsulfanyl)phenoxy]nicotinamide

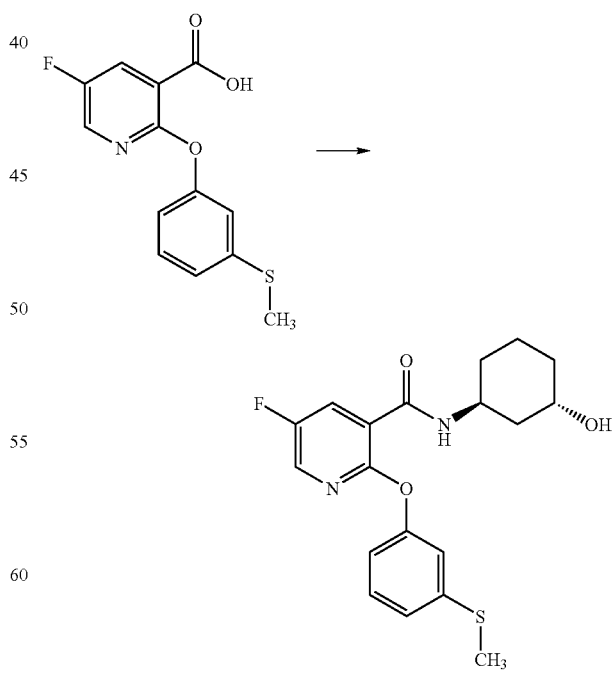

2-[3-(Methylsulfanyl)phenoxy]-5-fluoronicotinic acid (345 mg, 1.26 mmol) was dissolved in dimethylformamide (10 ml) and triethylamine (865 μl, 11.8 mmol) was added followed by (1S,3S)-3-aminocyclohexanol hydroformate (200 mg, 1.24 mmol), 1-(3-dimethylaminopropyl)-3-ethylcarbodiimide hydrochloride (715 mg, 3.73 mmol) and 1-hydroxybenzotriazole (185 mg, 1.37 mmol). The reaction was stirred under nitrogen at room temperature for 18 h and the solvent was removed under reduced pressure. The residue was partitioned between 10% aq. citric acid solution (50 ml) and diethyl ether (50 ml). The organic was washed with sat. sodium bicarbonate solution (50 ml), water (25 ml) and brine (10 ml), dried over $MgSO_4$ and the solvent was removed under reduced pressure. The residue was purified by flash column chromatography using ethyl acetate:cyclohexane (10:90 to 70:30) as eluant to give 5-fluoro-N-[(1S,3S)-3-hydroxycyclohexyl]-2-[3-(methylsulfanyl)phenoxy]nicotinamide (212 mg) as a colourless gum.

$[\alpha]_D$+12.2 (c=1 mg/ml, MeOH) $^1$H NMR (400 MHz, $CDCl_3$): δ=8.34–8.38 (1H, d), 8.06 (1H, s), 7.80–7.90 (1H, m), 7.33–7.39 (1H, t), 7.12–7.18 (1H, m), 7.00–7.05 (1H, m), 6.86–6.72 (1H, dd), 4.40–4.50 (1H, m), 3.98–4.08 (1H, m), 2.48 (3H, s), 1.70–2.00 (4H, m), 1.38–1.68 (13H, s+m) ppm. LRMS (thermospray): [M+H]$^+$ 377 m/z Anal. Found C, 57.71; H, 5.48; N, 6.62. $C_{19}H_{21}FN_2O_3S$. 0.4 mol $H_2O$. $0.2CH_2Cl_2$ requires C, 57.56; H, 5.59; N, 6.99%.

EXAMPLE 43

5-Fluoro-N-[(1R,3R)-3-hydroxycyclohexyl]-2-[3-(methylsulfanyl)phenoxy]nicotinamide

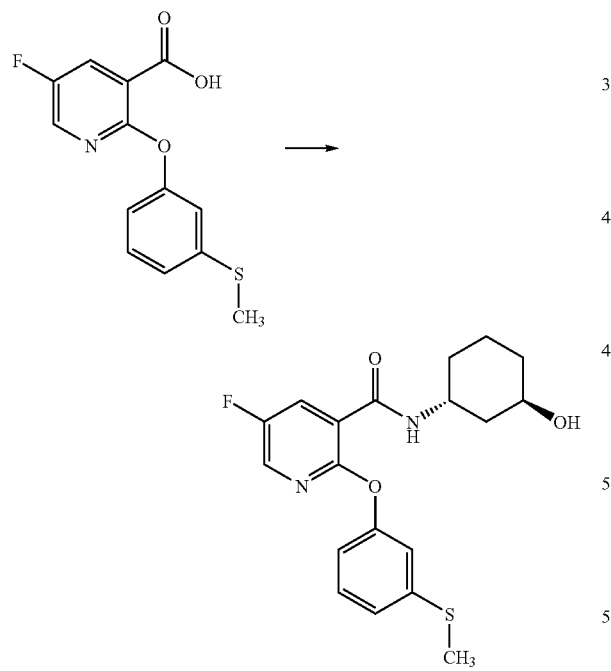

2-[3-(Methylsulfanyl)phenoxy]-5-fluoronicotinic acid (345 mg, 1.26 mmol) was dissolved in dimethylformamide (10 ml) and triethylamine (865 μl, 11.8 mmol) was added followed by (1R,3R)-3-aminocyclohexanol hydroformate (200 mg, 1.24 mmol), 1-(3-dimethylaminopropyl)-3-ethylcarbodiimide hydrochloride (715 mg, 3.73 mmol) and 1-hydroxybenzotriazole (185 mg, 1.37 mmol). The reaction was stirred under nitrogen at room temperature for 18 h and the solvent was removed under reduced pressure. The residue was partitioned between 10% aq. citric acid solution (50 ml) and diethyl ether (50 ml). The organic was washed with sat. sodium bicarbonate solution (50 ml), water (25 ml) and brine (10 ml), dried over $MgSO_4$ and the solvent was removed under reduced pressure. The residue was purified by flash column chromatography using ethyl acetate:cyclohexane (10:90 to 70:30) as eluant to give 5-fluoro-N-[(1R,3R)-3-hydroxycyclohexyl]-2-[3-(methylsulfanyl)phenoxy]nicotinamide (171 mg) as a colourless gum.

$[\alpha]_D$–11.0 (c=1 mg/ml, MeOH) $^1$H NMR (400 MHz, $CDCl_3$): δ=8.34–8.38 (1H, dd), 8.05 (1H, s), 7.78–7.92 (1H, m), 7.34–7.39 (1H, t), 7.12–7.18 (1H, m), 7.00–7.05 (1H, m), 6.86–6.72 (1H, dd), 4.40–4.50 (1H, m), 3.98–4.08 (1H, m), 2.48 (3H, s), 1.40–2.00 (17H, s+m) ppm. LRMS (thermospray): [M+H]$^+$ 377 m/z. Anal. Found C, 56.07; H, 5.19; N, 6.55. $C_{19}H_{21}FN_2O_3S$. 0.6 mol $H_2O$. $0.3CH_2Cl_2$ requires C, 56.16; H, 5.57; N, 6.79%.

EXAMPLE 44

5-Fluoro-N-(cis-4-hydroxycyclohexyl)-2-[3-(methylsulfanyl)phenoxy]nicotinamide

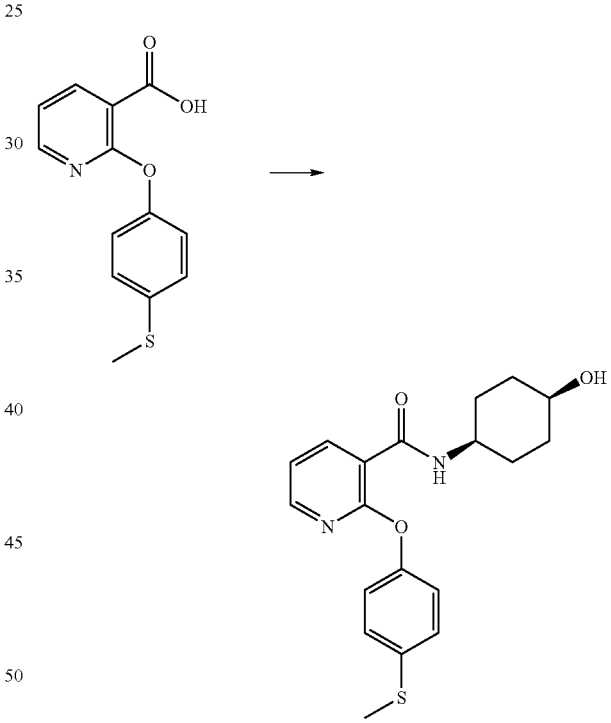

2-(4-Methylsulfanyl-phenoxy)-nicotinic acid (500 mg, 1.91 mmol) was dissolved in dimethylformamide (10 ml) and triethylamine (800 μl, 5.74 mmol) was added, followed by cis-4-amino-cyclohexanol hydrochloride (290 mg, 1.91 mmol), 1-(3-dimethylaminopropyl)-3-ethylcarbodiimide hydrochloride (404 mg, 2.10 mmol) and 1-hydroxybenzotriazole (284 mg, 2.10 mmol). The reaction was stirred under nitrogen at room temperature for 18 h and the solvent was removed under reduced pressure. The residue was partitioned between sat. sodium bicarbonate solution (25 ml) and ethyl acetate (10 ml) and the aqueous phase was extracted with ethyl acetate (3×20 ml). The combined organic extracts were washed with water (10 ml), brine (10 ml), dried over $MgSO_4$ and the solvent was removed under reduced pressure. The residue was purified by flash column chromatography on silica gel eluting with dichloromethane:methanol: concentrated aqueous ammonia (97.5:2.5:0.25, by volume). The resulting oil slowly crystallised to afford the product (620 mg) as a white solid.

$^1$H NMR (400 MHz, CDCl$_3$): δ=8.59–8.61 (1H, d), 8.19–8.21 (1H, d), 7.66–7.73 (1H, d), 7.33–7.36 (2H, d), 7.13–7.16 (1H, dd), 7.09–7.11 (2H, d), 3.97–4.06 (1H, m), 3.61–3.70 (1H, m), 2.51 (3H, s), 2.13–2.16 (2H, d), 1.98–2.02 (2H, d), 1.29–1.52 (4H, m) ppm. LRMS (thermospray): m/z [M+H]$^+$ 359. Anal. Found C, 63.58; H, 6.15; N, 7.80. C$_{19}$H$_{22}$N$_2$O$_3$S. requires C, 63.66; H, 6.19; N, 7.81%.

EXAMPLE 45

5-Fluoro-N-(trans-4-hydroxy-cyclohexyl)-2-(4-methylsulfanyl-phenoxy)-nicotinamide

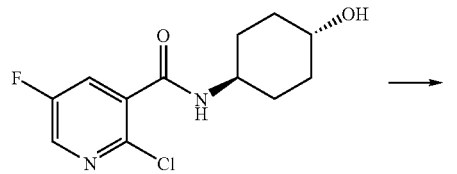

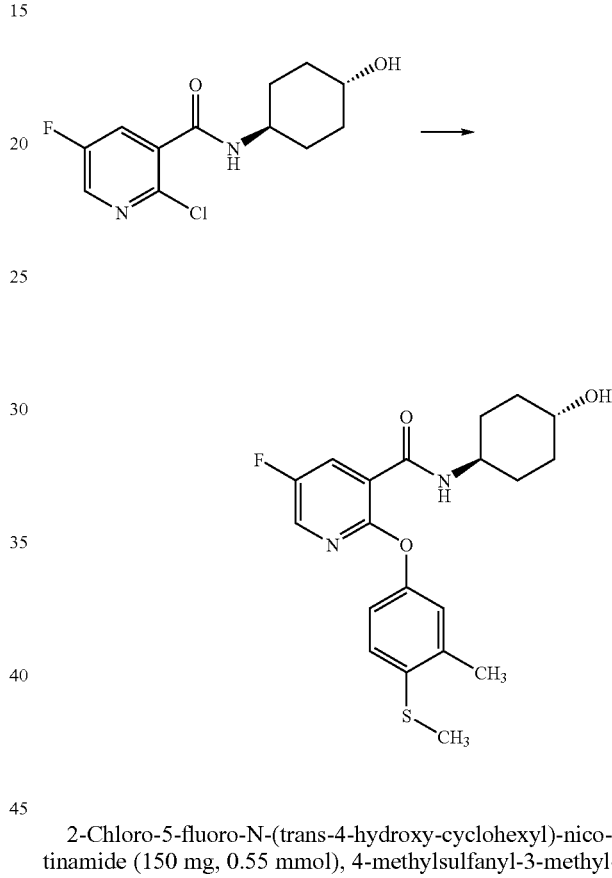

2-Chloro-5-fluoro-N-(trans-4-hydroxy-cyclohexyl)-nicotinamide (150 mg, 0.55 mmol), 4-methylsulfanyl-phenol (77 mg, 0.55 mmol) and caesium carbonate (358 mg, 1.10 mmol) were suspended in DMF (2 ml) and the reaction was heated to 55° C. and stirred at this temperature under nitrogen for 18 h. The reaction was quenched with sat. ammonium chloride solution (1.5 ml) and water (1.5 ml) and the organic phase was collected by passing the mixture through a chemelute cartridge, washing with ethyl acetate. The solvent was removed on a Genevac™ and the residue was purified by flash column chromatography on silica gel eluting with a solvent gradient of dichloromethane:methanol (100:0 changing to 96:4, by volume) to give 5-fluoro-N-(trans-4-hydroxy-cyclohexyl)-2-(4-methylsulfanyl-phenoxy)-nicotinamide (81 mg) as an off-white foam.

$^1$H NMR (400 MHz, CD$_3$OD): δ=8.04–8.06 (1H, d), 7.97–8.01 (1H, dd), 7.31–7.35 (2H, d), 7.04–7.08 (2H, d), 3.79–3.88 (1H, m), 3.32–3.39 (1H, m), 2.44 (3H, s), 1.91–2.05 (4H, 2×m), 1.34–1.45 (4H, m) ppm. LRMS (electrospray): m/z [M+Na]$^+$ 399, [M−H]$^+$ 375. Anal. Found C, 60.49; H, 5.62; N, 7.39. C$_{19}$H$_{21}$FN$_2$O$_3$S. 0.05 mol H$_2$O requires C, 60.48; H, 5.64; N, 7.42%.

EXAMPLE 46

5-Fluoro-N-(trans-4-hydroxy-cyclohexyl)-2-(4-methylsulfanyl-3-methyl-phenoxy)-nicotinamide 2-Chloro-5-fluoro-N-(trans-4-hydroxy-cyclohexyl)-nicotinamide (150 mg, 0.55 mmol), 4-methylsulfanyl-3-methyl-phenol (85 mg, 0.55 mmol) and caesium carbonate (358 mg, 1.10 mmol) were suspended in DMF (2 ml) and the reaction was heated to 55° C. and stirred at this temperature under nitrogen for 18 h. The reaction was quenched with sat. ammonium chloride solution (1.5 ml) and water (1.5 ml) and the organic phase was collected by passing the mixture through a chemelute™ cartridge, washing with ethyl acetate. The solvent was removed on a Genevac™ and the residue was purified by flash column chromatography on silica gel eluting with a solvent gradient of dichloromethane:methanol (100:0 changing to 96:4, by volume) to give 5-fluoro-N-(trans-4-hydroxy-cyclohexyl)-2-(4-methylsulfanyl-3-methyl-phenoxy)-nicotinamide (118 mg) as an off-white foam.

$^1$H NMR (400 MHz, CD$_3$OD): δ=8.04–8.06 (1H, d), 7.97–8.01 (1H, dd), 7.24–7.28 (1H, d), 6.93–6.99 (2H, s+d), 3.80–3.88 (1H, m), 3.30–3.38 (1H, m), 2.43 (3H, s), 2.33 (3H, s), 1.92–2.04 (4H, 2×m), 1.33–1.43 (4H, m) ppm. LRMS (electrospray): m/z [M+Na]$^+$ 413, [M−H]$^+$ 389. Anal. Found C, 60.88; H, 5.98; N, 7.17. C$_{20}$H$_{23}$FN$_2$O$_3$S. 0.2 mol H$_2$O requires C, 60.96; H, 5.99; N, 7.11%.

EXAMPLE 47

5-Fluoro-N-(trans-4-hydroxy-cyclohexyl)-2-(3-methoxy-4-(methylsulfanyl)phenoxy)-nicotinamide

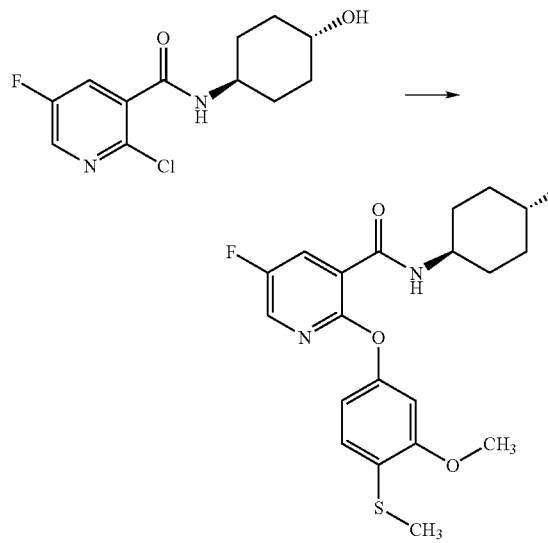

2-Chloro-5-fluoro-N-(trans-4-hydroxy-cyclohexyl)-nicotinamide (150 mg, 0.55 mmol), 4-methylsulfanyl-3-methoxy-phenol (94 mg, 0.55 mmol) and caesium carbonate (358 mg, 1.10 mmol) were suspended in DMF (2 ml) and the reaction was heated to 55° C. and stirred at this temperature under nitrogen for 18 h. The reaction was quenched with sat. ammonium chloride solution (1.5 ml) and water (1.5 ml) and the organic phase was collected by passing the mixture through a Chemelute™ cartridge, washing with ethyl acetate. The solvent was removed on a Genevac™ and the residue was purified by flash column chromatography on silica gel eluting with a solvent gradient of dichloromethane:methanol (100:0 changing to 96:4, by volume) to give 5-fluoro-N-(trans-4-hydroxy-cyclohexyl)-2-(4-methylsulfanyl-3-methoxy-phenoxy)-nicotinamide (99 mg) as an off-white foam.

$^1$H NMR (400 MHz, CD$_3$OD): δ=8.05–8.07 (1H, d), 7.97–8.01 (1H, dd), 7.19–7.23 (1H, d), 6.89 (1H, s), 6.68–6.73 (1H, d), 3.80–3.90 (4H, s+m), 3.51–3.60 (1H, m), 2.38 (3H, s), 1.91–2.06 (4H, 2×m), 1.33–1.42 (4H, m) ppm. LRMS (electrospray): m/z [M+Na]$^+$ 429, [M–H]$^+$ 405. Anal. Found C, 58.84; H, 5.69; N, 8.68. C$_{20}$H$_{23}$FN$_2$O$_4$S. 0.1 mol H$_2$O requires C, 58.84; H, 5.73; N, 6.86%.

EXAMPLE 48

2-[4-Chloro-3-(methylsulfanyl)phenoxy]-5-fluoro-N-(trans-4-hydroxycyclohexyl)nicotinamide

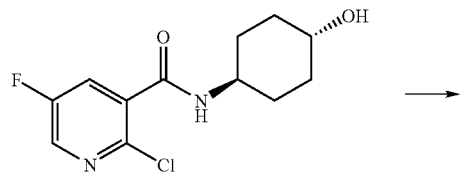

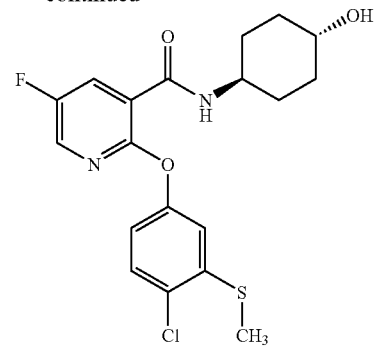

2-Chloro-5-fluoro-N-(trans-4-hydroxycyclohexyl)nicotinamide (150 mg, 0.55 mmol) was added to a solution of 4-chloro-3-(methylsulfanyl)phenol (96 mg, 0.55 mmol), caesium carbonate (358 mg, 1.1 mmol) in N,N-dimethylformamide (2 ml). The reaction was stirred under nitrogen at 55° C. for 18 h, cooled, and quenched with 1:1 water:sat. ammonium chloride solution and passed through a chemelute™ cartridge. The solvent. The residue was purified by flash column chromatography using dichloromethane:methanol (100:0 to 96:4) as eluant to afford 2-[4-chloro-3-(methylsulfanyl)phenoxy]-5-fluoro-N-(trans-4-hydroxycyclohexyl)nicotinamide as an amorphous glass (37 mg).

$^1$H NMR (400 MHz, MeOD): δ=8.1–8.05 (1H, m), 7.95 (1H, dd), 7.85 (1H, d), 7.07 (1H, d), 6.88 (1H, dd), 3.9–3.8 (1H, m), 3.6–3.5 (1H, m), 2.45 (3H, s), 2.05–1.9 (4H, m), 1.45–1.3 (4H, m) ppm.

EXAMPLE 49

5-Fluoro-N-(trans-4-hydroxy-cyclohexyl)-2-(3-methylsulfanyl-phenoxy)-nicoinamide

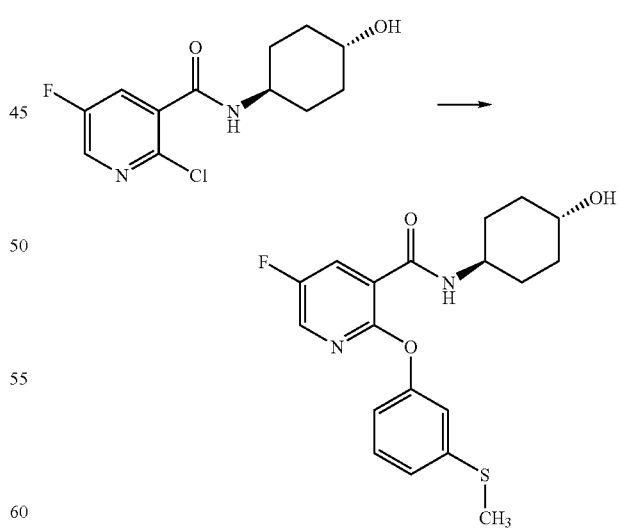

2-Chloro-5-fluoro-N-(trans-4-hydroxy-cyclohexyl)-nicotinamide (150 mg, 0.55 mmol), 3-methylsulfanyl-phenol (77 mg, 0.55 mmol) and caesium carbonate (358 mg, 1.10 mmol) were suspended in DMF (2 ml) and the reaction was heated to 55° C. and stirred at this temperature under nitrogen for 18 h. The reaction was quenched with sat. ammonium chloride solution (1.5 ml) and water (1.5 ml) and the organic phase was collected by passing the mixture through a chemelute cartridge, washing with ethyl acetate. The solvent was removed on a Genevac™ and the residue was purified by flash column chromatography on silica gel eluting with a solvent gradient of dichloromethane:methanol (100:0 changing to 96:4, by volume) to give 5-fluoro-N-(trans-4-hydroxy-cyclohexyl)-2-(3-methylsulfanyl-phenoxy)-nicotinamide (50 mg) as pale green solid.

$^1$H NMR (400 MHz, CD$_3$OD): δ=8.04–8.06 (1H, d), 7.97–8.00 (1H, dd), 7.25–7.32 (1H, t), 7.09–7.14 (1H, d), 7.06 (1H, s), 6.83–6.89 (1H, d), 3.79–3.89 (1H, m), 3.52–3.61 (1H, m), 2.46 (3H, s), 1.89–2.08 (4H, 2×m), 1.34–1.47 (4H, m) ppm. LRMS (electrospray): m/z [M–H]$^-$ 376. Anal. Found C, 59.76; H, 5.62; N, 7.29. C$_{19}$H$_{21}$FN$_2$O$_3$S. 0.3 mol H$_2$O requires C, 59.76; H, 5.70; N, 7.34%.

EXAMPLE 50

5-Fluoro-N-(trans-4-hydroxy-cyclohexyl)-2-(3-methylsulfanyl-4-methyl-phenoxy)-nicotinamide

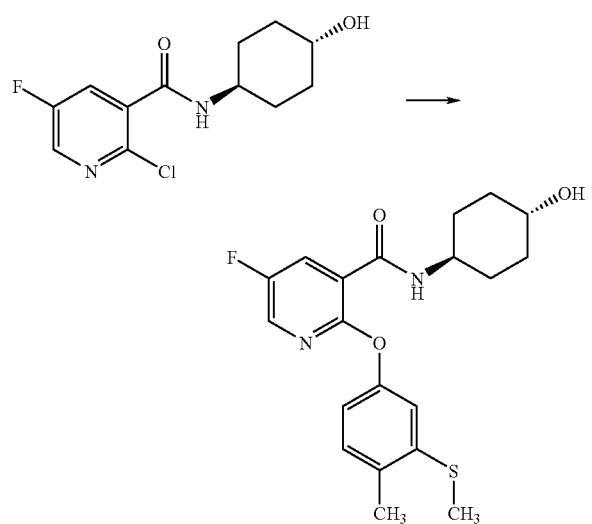

2-Chloro-5-fluoro-N-(trans-4-hydroxycyclohexyl)nicotinamide (300 mg, 0.1.10 mmol) was added to a solution of 4-methyl-3-(methylsulfanyl)phenol (187 mg, 1.21 mmol), caesium carbonate (502 mg, 1.54 mmol) and copper(I) iodide (21 mg, 0.11 mmol) in a 4:1 mixture of toluene:N-methylpyrrolidinone (4 ml). The reaction was stirred under nitrogen at 110° C. for 2 h, cooled, diluted with ethyl acetate and filtered through Arbocel. The filtrate was washed with water, dried over MgSO$_4$, filtered and the filtrate was removed under reduced pressure. The residue was purified by flash column chromatography using dichloromethane:methanol:0.880 ammonia (99.5:1.5:0.05 to 95:5:0.5) as eluant to afford the crude product which was further purified by preparative HPLC to give 5-fluoro-N-(4-hydroxycyclohexyl)-2-[3-(methylsulfanyl)phenoxy]nicotinamide as an amorphous glass (55 mg).

$^1$H NMR (400 MHz, CDCl$_3$): δ=8.30–8.8.36 (1H, dd), 8.00–8.06 (1H, d), 7.70–7.80 (1H, m), 7.16–7.20 (1H, d), 6.88–6.92 (1H, d), 6.74–6.80 (1H, dd), 3.93–4.05 (1H, m), 3.60–3.70 (1H, m), 2.44 (1H, s), 2.35 (3H, s), 2.08–2.20 (2H, m), 1.95–2.06 (2H, m), 1.20–1.55 (4H, m) ppm. LRMS (thermospray): m/z [M+Na]$^+$ 413. HRMS [M+Na]$^+$ 413.1309.

EXAMPLE 51

5-Fluoro-N-(cis-4-hydroxy-cyclohexyl)-2-(3-methylsulfanyl-phenoxy)-nicotinamide

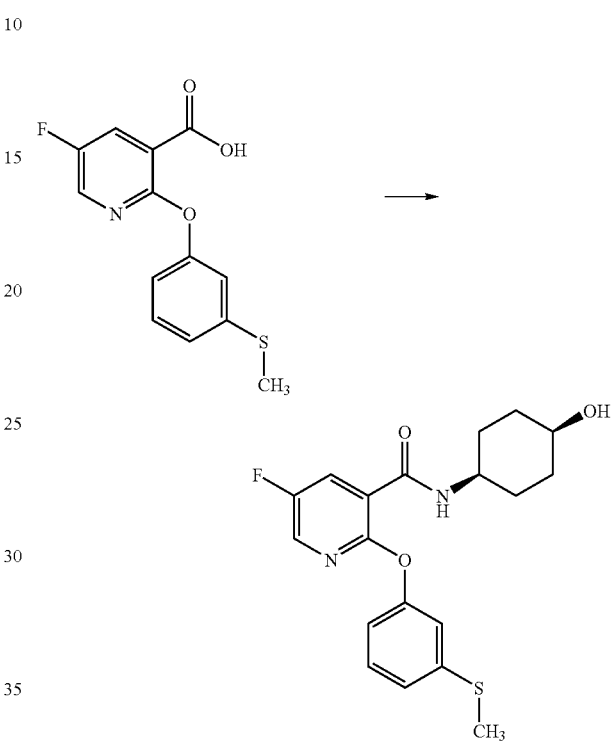

5-Fluoro-2-(3-methylsulfanyl-phenoxy)-nicotinic acid (100 mg, 0.358 mmol) was dissolved in dimethylformamide (2 ml) and triethylamine (150 mg, 1.07 mmol) was added followed by cis-4-aminocyclohexanol hydrochloride (54 mg, 0.358 mmol), 1-(3-dimethylaminopropyl)-3-ethylcarbodiimide hydrochloride (76 mg, 0.394 mmol) and 1-hydroxybenzotriazole (53 mg, 0.394 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (2×10 ml). The combined organic extracts were washed with water (2×3 ml), brine (3 ml), dried over MgSO$_4$ and the solvent was removed under reduced pressure. The residue was purified by flash column chromatography on silica gel eluting with dichloromethane:methanol:concentrated aqueous ammonia (98:2:0.2, by volume) to give 5-fluoro-N-(cis-4-hydroxy-cyclohexyl)-2-(3-methylsulfanyl-phenoxy)-nicotinamide (110 mg) as a white foam.

$^1$H NMR (400 MHz, CDCl$_3$): δ=8.33–8.38 (1H, dd), 8.03–8.06 (1H, d), 7.68–7.73 (1H, d), 7.33–7.39 (1H, t), 7.15–7.18 (1H, d), 7.10 (1H, s), 6.86–6.92 (1H, d), 3.92–4.04 (1H, m), 3.60–3.70 (1H, m), 2.47 (3H, s), 2.09–2.18 (2H, d), 2.04 (2H, d), 1.25–1.54 (4H, m) ppm. LRMS (thermospray): m/z [M+H]$^+$ 377, [M+Na]$^+$ 399. Anal. Found C, 59.95; H, 5.67; N, 7.39. C$_{19}$H$_{21}$FN$_2$O$_5$S. 0.25 mol H$_2$O requires C, 59.90; H, 5.69; N, 7.35%.

EXAMPLE 52

N-(cis-4-Hydroxy-cyclohexyl)-2-(4-methylsulfanyl-phenoxy)-nicotinamide

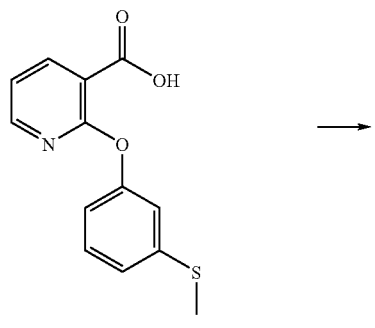

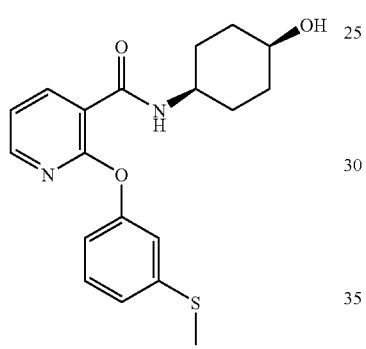

2-(4-Methylsulfanyl-phenoxy)-nicotinic acid (500 mg, 1.91 mmol) was dissolved in dimethylformamide (10 ml) and triethylamine (800 μl, 5.74 mmol) was added followed by cis-4-aminocyclohexanol hydrochloride (290 mg, 1.91 mmol), 1-(3-dimethylaminopropyl)-3-ethylcarbodiimide hydrochloride (404 mg, 2.10 mmol) and 1-hydroxybenzotriazole (284 mg, 2.10 mmol). The reaction was stirred under nitrogen at room temperature for 18 h and the solvent was removed under reduced pressure. The residue was partitioned between sat. sodium bicarbonate solution (25 ml) and ethyl acetate (20 ml) and the aqueous phase was extracted with ethyl acetate (2×20 ml). The combined organic extracts were washed with water (10 ml), brine (10 ml), dried over MgSO$_4$ and the solvent was removed under reduced pressure. The residue was purified by flash column chromatography on silica gel eluting with a solvent gradient of dichloromethane:methanol:concentrated aqueous ammonia (97.5:2.5:0.25 changing to 97:3:0.3, by volume) to give N-(cis-4-hydroxy-cyclohexyl)-2-(4-methylsulfanyl-phenoxy)-nicotinamide (620 mg) as a white solid.

$^1$H NMR (400 MHz, CDCl$_3$): δ=8.58–8.62 (1H, d), 8.18–8.21 (1H, d), 7.64–7.71 (1H, d), 7.32–7.36 (2H, d), 7.12–7.16 (1H, dd), 7.08–7.12 (2H, d), 3.95–4.05 (1H, m), 3.60–3.69 (1H, m), 2.48 (3H, s), 2.10–2.18 (2H, d), 1.95–2.03 (2H, d), 1.29–1.53 (4H, 2×m) ppm. LRMS (thermospray): m/z [M+H]$^+$ 359. Anal. Found C, 63.56; H, 6.14; N, 7.80. C$_{19}$H$_{22}$N$_2$O$_5$S. requires C, 63.66; H, 6.19; N, 7.81%.

EXAMPLE 53

5-Fluoro-N-(1-hydroxymethyl-cyclopentyl)-2-(4-methylsulfanyl-phenoxy)-nicotinamide

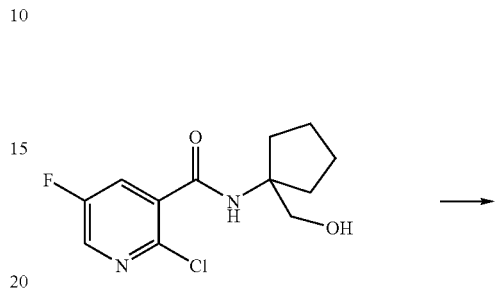

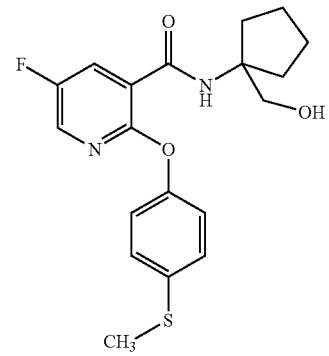

2-Chloro-5-fluoro-N-(1-hydroxymethyl-1-cyclopentyl)-nicotinamide (100 mg, 0.367 mmol), 4-methylsulfanyl phenol (51 mg, 0.367 mmol) and caesium carbonate (131 mg, 0.403 mmol) were suspended in DMF (1.5 ml) and the reaction was heated to 50° C. and stirred at this temperature under nitrogen for 16 h. The reaction mixture was cooled and partitioned between ethyl acetate (25 ml) and water (25 ml). The organic phase was removed and washed with brine (25 ml) followed by water (25 ml). The organic layer was dried over MgSO$_4$ and the solvent was removed under reduced pressure. The residue was purified by flash column chromatography on silica gel eluting with a solvent gradient of dichloromethane:methanol (99:1 changing to 95:5, by volume) to give 5-Fluoro-N-(1-hydroxymethyl-cyclopentyl)-2-(4-methylsulfanyl-phenoxy)-nicotinamide (27 mg) as an off-white solid.

$^1$H NMR (400 MHz, CDCl$_3$): δ=8.25–8.32 (1H, dd), 8.17 (1H, brs), 8.02–8.05 (1H, d), 7.30–7.36 (2H, d), 7.04–7.08 (2H, d), 4.33–4.39 (1H, brs), 3.72–3.79 (2H, d), 2.48 (3H, s), 1.82–1.96 (4H, m), 1.65–1.81 (4H, m) ppm. LRMS (electrospray): m/z [M+Na]$^+$ 399, [M–H]$^+$ 375.

EXAMPLE 54

5-Fluoro-N-(1-hydroxymethyl-cyclohexyl)-2-(3-methylsulfanyl-phenoxy)-nicotinamide

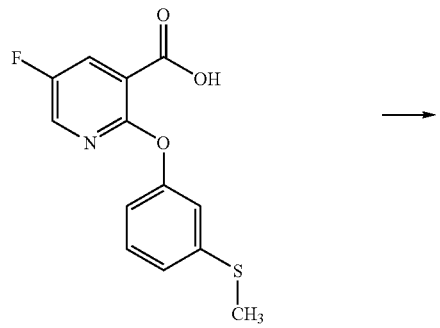

A solution of (1-aminocyclohexyl)-methanol (R. J. W. Cremlyn et al J. Chem. Soc Perkins I, 1972, 1727) (130 mg, 0.78 mmol) and triethylamine (300 µl) in dimethylformamide (5 ml) was added to a solution of 5-fluoro-2-(3-methylsulfanyl-phenoxy)-nicotinic acid (218 mg, 0.78 mmol), 1-(3-dimethylaminopropyl)-3-ethylcarbodiimide hydrochloride (165 mg, 0.86 mmol) and 1-hydroxybenzotriazole (116 mg, 0.86 mmol) in dimethylformamide (4 ml) and the reaction was stirred under nitrogen at room temperature for 64 h. The reaction mixture was concentrated under reduced pressure, and the residue was partitioned between ethyl acetate (25 ml) and water (25 ml). The organic phase was removed and washed with sat. sodium bicarbonate solution (25 ml) followed by 1M citric acid (25 ml) and brine (25 ml). The organic layer was dried over MgSO$_4$ and the solvent was removed under reduced pressure. The residue was purified by flash column chromatography on silica gel eluting with a solvent gradient of ethyl acetate:pentane (20:80 changing to 30:70 then 50:50, by volume) to give 5-fluoro-N-(1-hydroxymethyl-cyclohexyl)-2-(3-methylsulfanyl-phenoxy)-nicotinamide (191 mg) as a colourless oil.

$^1$H NMR (400 MHz, CDCl$_3$): δ=8.31–8.38 (1H, d), 8.02–8.18 (2H, brs), 7.28–7.39 (1H, t), 7.12–7.19 (1H, d), 7.03 (1H, s), 6.85–6.92 (1H, d), 4.60–4.69 (1H, t), 3.71–3.83 (2H, d), 2.47 (3H, s), 1.93–2.07 (2H, d), 1.21–1.69 (8H, m, partially masked by solvent) ppm. LRMS (electrospray): m/z [M+Na]$^+$ 413, [M–H]$^+$ 389.

EXAMPLE 55

5-Fluoro-N-[cis-2-(hydroxymethyl)cyclohexyl]-2-[3-(methylsulfanyl)phenoxy]nicotinamide

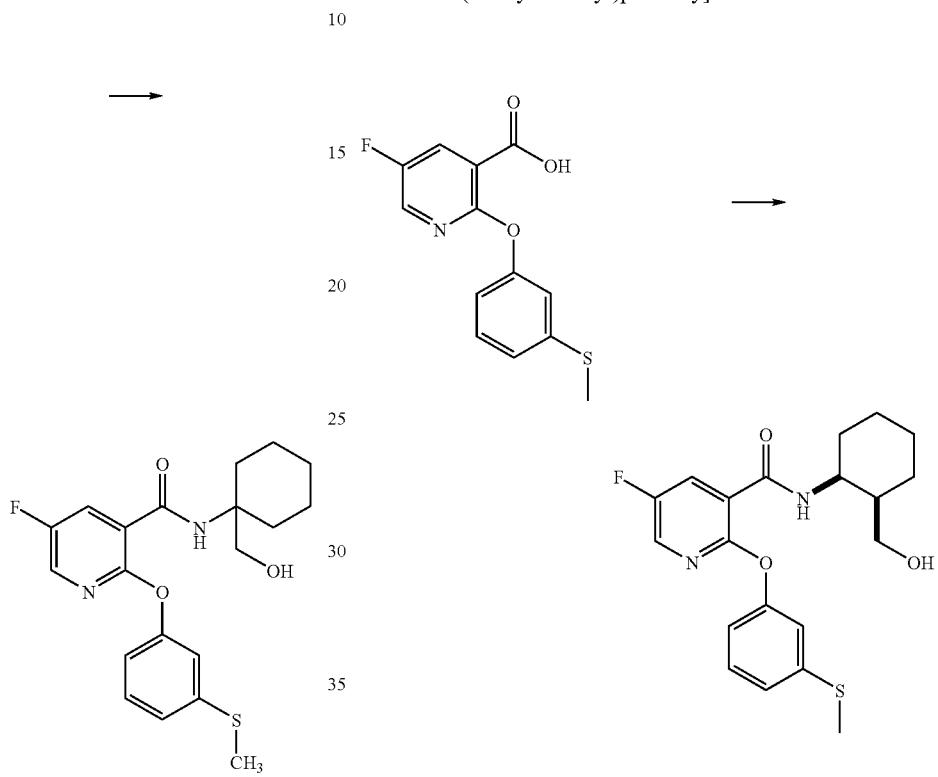

5-Fluoro-2-(3-methylsulfanyl-phenoxy)-nicotinic acid (200 mg, 0.716 mmol) was dissolved in dimethylformamide (3 ml) and triethylamine (300 µl, 2.14 mmol) was added followed by cis-2-hydroxymethyl-1-cyclohexylamine hydrochloride (125 mg, 0.755 mmol), 1-(3-dimethylaminopropyl)-3-ethylcarbodiimide hydrochloride (151 mg, 0.788 mmol) and 1-hydroxybenzotriazole(106 mg, 0.785 mmol). The reaction was stirred at room temperature for 18 h and the solvent was removed under reduced pressure. The residue was partitioned between water (30 ml) and ethyl acetate (30 ml). The organic phase dried over Na$_2$SO$_4$, the solvent removed under reduced pressure, and the residue purified by column chromatography on silica gel using dichloromethane:methanol (95:5) as eluent to afford an oil which crystallized from n-pentane to give the title compound as a white solid (136 mg).

$^1$H NMR (400 MHz, CDCl$_3$): δ=8.35–8.25 (2H, m), 8.05 (1H, d), 7.33 (1H, t), 7.13 (1H, d), 7.00 (1H, s), 6.86 (1H, dd), 4.6–4.5 (1H, m), 4.2–4.15 (1H, m), 3.4–3.3 (1H, m), 3.2–3.15 (1H, m), 2.46 (3H, s), 1.9–1.8 (2H, m), 1.7–1.6 (3H, m), 1.4–1.1 (3H, m), 0.95–0.82 (1H, m) ppm. LRMS (electrospray): m/z [M+H]$^+$ 391, [M+Na]$^+$ 413, [M–H]$^+$ 389. Anal. Found C, 61.44; H, 5.93; N, 7.22. C$_{20}$H$_{23}$FN$_2$O$_3$S. requires C, 61.52; H, 5.94; N, 7.18%.

EXAMPLE 56

5-Fluoro-N-[trans-2-hydroxymethyl-cyclohexyl]-2-(3-methylsulfanyl-phenoxy)-nicotinamide

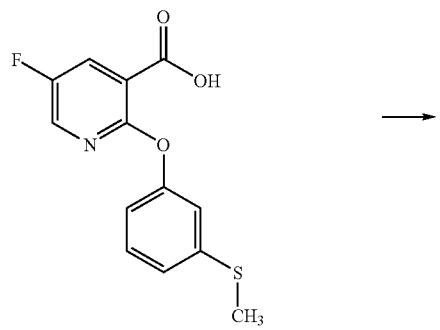

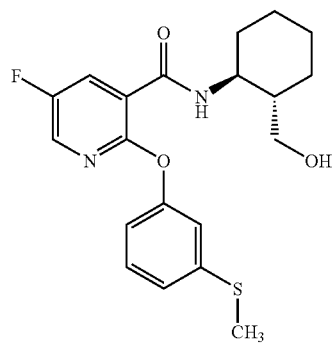

A solution of trans-2-hydroxymethyl-1-cyclohexylamine hydrochloride (130 mg, 0.78 mmol) and triethylamine (300 μl) in dimethylformamide (5 ml) was added to a solution of 5-fluoro-2-(3-methylsulfanyl-phenoxy)-nicotinic acid (218 mg, 0.78 mmol), 1-(3-dimethylaminopropyl)-3-ethylcarbodiimide hydrochloride (165 mg, 0.86 mmol) and 1-hydroxybenzotriazole (116 mg, 0.86 mmol) in dimethylformamide (4 ml) and the reaction was stirred under nitrogen at room temperature for 48 h. The reaction mixture was concentrated under reduced pressure, and the residue was partitioned between ethyl acetate (25 ml) and water (25 ml). The organic phase was removed and washed with sat. sodium bicarbonate solution (25 ml) followed by 1M citric acid (25 ml) and brine (25 ml). The organic layer was dried over MgSO$_4$ and the solvent was removed by reduced pressure. The residue was purified by flash column chromatography on silica gel eluting with a solvent gradient of ethyl acetate:pentane (20:80 changing to 30:70 then 50:50, by volume) to give 5-fluoro-N-[trans-2-hydroxymethyl-cyclohexyl)-2-(3-methylsulfanyl-phenoxy)-nicotinamide (216 mg) as a colourless oil.

mp 128–129° C. $^1$H NMR (400 MHz, CDCl$_3$): δ=8.33–8.39 (1H, dd), 8.03–8.07 (1H, d), 7.75–7.82 (1H, d), 7.32–7.39 (1H, t), 7.25–7.29 (1H, d), 7.03 (1H, s), 6.86–6.90 (1H, d), 3.91–4.02 (1H, m), 3.65–3.72 (1H, m), 3.58–3.63 (1H, m), 3.34–3.42 (1H, t), 2.48 (3H, s), 2.02–2.09 (1H, d), 1.58–1.82 (4H, 2×m), 1.18–1.47 (4H, m) ppm. LRMS (electrospray): m/z [M+H]$^+$ 391, [M+Na]$^+$ 413, [M–H]$^+$ 389. Anal. Found C, 61.20; H, 5.96; N, 7.01. C$_{20}$H$_{23}$FN$_2$O$_3$S. requires C, 61.52; H, 5.94; N, 7.17%.

EXAMPLE 57

EXAMPLE 58

5-Fluoro-N-[2-(hydroxymethyl)cyclohexyl]-2-[3-(methylsulfanyl)phenoxy]nicotinamide

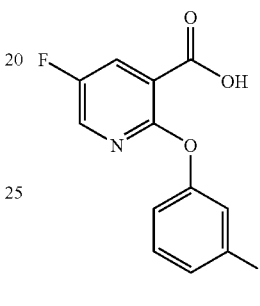

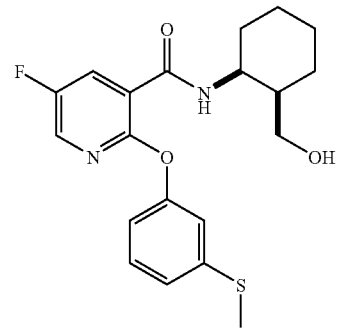

both cis isomers

5-Fluoro-2-(3-methylsulfanyl-phenoxy)-nicotinic acid (1.0 g, 3.58 mmol) was dissolved in dimethylformamide (20 ml) and triethylamine (1.5 ml, 10.7 mmol) was added, followed by cis-2-hydroxymethyl-1-cyclohexylamine hydrochloride (593 mg, 3.58 mmol), 1-(3-dimethylaminopropyl)-3-ethylcarbodiimide hydrochloride (755 mg, 3.94 mmol) and 1-hydroxybenzotriazole (532 mg, 3.94 mmol). The reaction was stirred under nitrogen at room temperature for 18 h and the solvent was removed under reduced pressure. The residue was partitioned between sat. sodium bicarbonate solution (40 ml) and ethyl acetate (30 ml) and the aqueous phase was extracted with ethyl acetate (3×30 ml). The combined organic extracts were washed with water (2×20 ml), brine (20 ml), dried over MgSO$_4$ and the solvent was removed under reduced pressure. The residue was purified by flash column chromatography on silica gel eluting with ethyl acetate:pentane (20:80 increasing to 50:50, by volume). The resulting white solid (1.26 g) was purified by preparative HPLC resulting in two products.

Chiral HPLC Conditions: Column:Chiralce™ OD 250× 20 mm Mobile phase: 90% hexane, 10% iso-propyl alcohol containing 0.3% trifluoroacetic acid and 0.2% diethylamine. Flow rate: 10 ml/min Run Time: 35 ml/min Product 1:

RT=13.47 min, 100% ee

The solvent was removed under reduced pressure, the residue partitioned between sat. sodium bicarbonate solution (30 ml) and ethyl acetate (50 ml) and the aqueous phase was extracted with ethyl acetate (2×50 ml). The combined organic extracts were washed with water (10 ml), brine (10 ml), dried over MgSO$_4$ and the solvent was removed under reduced pressure. The residue was purified by flash column chromatography on silica gel eluting with ethyl acetate:pentane (30:70 increasing to 50:50, by volume). The resulting oil slowly crystallised to give the product (542 mg) as a white solid.

$^1$H NMR (400 MHz, CDCl$_3$): δ=8.32–8.37 (2H, d×2), 8.08 (1H, d), 7.34–7.38 (1H, t), 7.16–7.18 (1H, d), 7.03 (1H, d), 6.89–6.91 (1H, dd), 4.56–4.65 (1H, m), 4.17–4.25 (1H, bs), 3.36–3.47 (1H, m), 3.19–3.25 (1H, t), 2.51 (3H, s), 1.85–1.94 (2H, m), 1.68–1.78 (3H, m), 1.17–1.46 (3H, m), 0.87–1.00 (1H, q) ppm. LRMS (thermospray): m/z [M+H]$^+$ 391. [α$_D$]$^{25}$+38.2° (1 mg/ml, MeOH) Anal. Found C, 61.54; H, 5.85; N, 7.21. C$_{20}$H$_{23}$FN$_2$O$_3$S. requires C, 61.52; H, 5.94; N, 7.17%.

Product 2:

RT=16.97 min, 97.2% ee

The solvent was removed under reduced pressure, the residue partitioned between sat. sodium bicarbonate solution (30 ml) and ethyl acetate (50 ml) and the aqueous phase was extracted with ethyl acetate (2×50 ml). The combined organic extracts were washed with water (10 ml), brine (10 ml), dried over MgSO$_4$ and the solvent was removed under reduced pressure. The residue was purified by flash column chromatography on silica gel eluting with ethyl acetate:pentane (30:70 increasing to 50:50, by volume). The resulting oil slowly crystallised to give the product (542 mg) as a white solid.

$^1$H NMR (400 MHz, CDCl$_3$): δ=8.32–8.37 (2H, d×2), 8.08 (1H, d), 7.34–7.38 (1H, t), 7.16–7.18 (1H, d), 7.03 (1H, d), 6.89–6.91 (1H, dd), 4.56–4.65 (1H, m), 4.17–4.25 (1H, bs), 3.36–3.47 (1H, m), 3.19–3.25 (1H, t), 2.51 (3H, s), 1.85–1.94 (2H, m), 1.68–1.78 (3H, m), 1.17–1.46 (3H, m), 0.87–1.00 (1H, q) ppm. LRMS (thermospray): m/z [M+H]$^+$ 391. [α$_D$]$^{25}$−43.0° (1 mg/ml, MeOH) Anal. Found C, 61.46; H, 5.85; N, 7.18. C$_{20}$H$_{23}$FN$_2$O$_3$S. requires C, 61.52; H, 5.94; N, 7.17%.

EXAMPLE 59

5-Fluoro-N-(trans-4-hydroxymethyl-cyclohexyl)-2-(3-methylsulfanyl-phenoxy)-nicotinamide

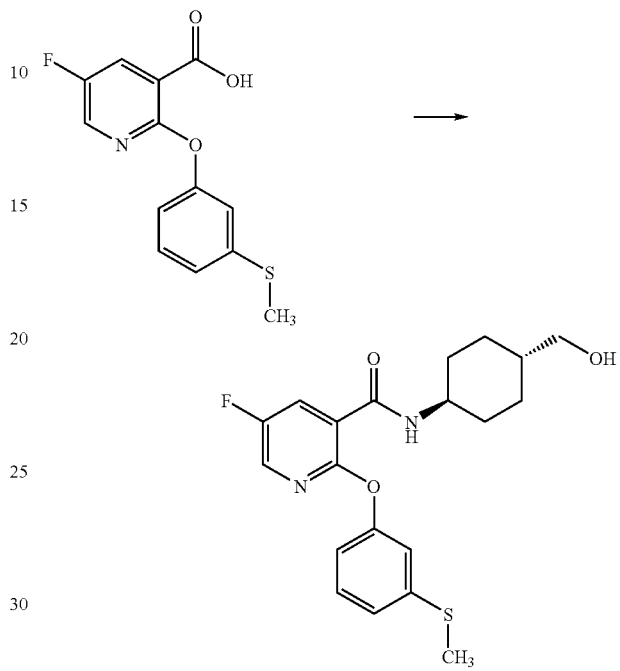

(trans-4-Amino-cyclohexyl)-methanol (73 mg, 0.56 mmol) and triethylamine (225 μl, 1.61 mmol) were dissolved in dimethylformamide (225 μl) and a solution of 5-fluoro-2-(3-methylsulfanyl-phenoxy)-nicotinic acid (150 mg, 0.54 mmol), 1-(3-dimethylaminopropyl)-3-ethylcarbodiimide hydrochloride (113 mg, 0.59 mmol) and 1-hydroxybenzotriazole (80 mg, 0.59 mmol) in dimethylformamide (5 ml) was added. The reaction was stirred under nitrogen at room temperature for 64 h and the solvent was removed under reduced pressure. The residue was partitioned between 0.5N HCl (10 ml) and ethyl acetate (10 ml) and the aqueous phase was extracted with ethyl acetate (2×10 ml). The combined organic phases were washed with brine (10 ml), dried over MgSO$_4$ and the solvent was removed under reduced pressure. The residue was purified by flash column chromatography on silica gel eluting with dichloromethane:methanol:concentrated aqueous ammonia (97.5:2.5:0.25, by volume). The product was triturated with ethyl acetate (3 ml) to give 5-Fluoro-N-(trans-4-hydroxymethyl-cyclohexyl)-2-(3-methylsulfanyl-phenoxy)-nicotinamide (60 mg) as a white solid.

$^1$H NMR (400 MHz, CDCl$_3$): δ=8.32–8.38 (1H, dd), 8.02–8.05 (1H, d), 7.64–7.72 (1H, d), 7.32–7.38 (1H, t), 7.15–7.19 (1H, d), 7.02 (1H, s), 6.87–6.91 (1H, m), 3.98–4.00 (1H, m), 3.45–3.51 (2H, m) 2.47 (3H, s), 2.12–2.19 (2H, d), 1.82–1.90 (2H, d), 1.42–1.57 (1H, m, partially masked by solvent), 1.09–1.30 (5H, m) ppm. LRMS (electrospray): m/z [M+H]$^+$ 391, [M+Na]$^+$ 413, [M−H]$^+$ 389. Anal. Found C, 60.28; H, 5.88; N, 7.00. C$_{20}$H$_{23}$FN$_2$O$_5$S. 0.4 mol H$_2$O requires C, 60.41; H, 6.03; N, 7.04%.

EXAMPLE 60

5-Fluoro-N-(cis-4-hydroxymethyl-cyclohexyl)-2-(3-methylsulfanyl-phenoxy)-nicotinamide

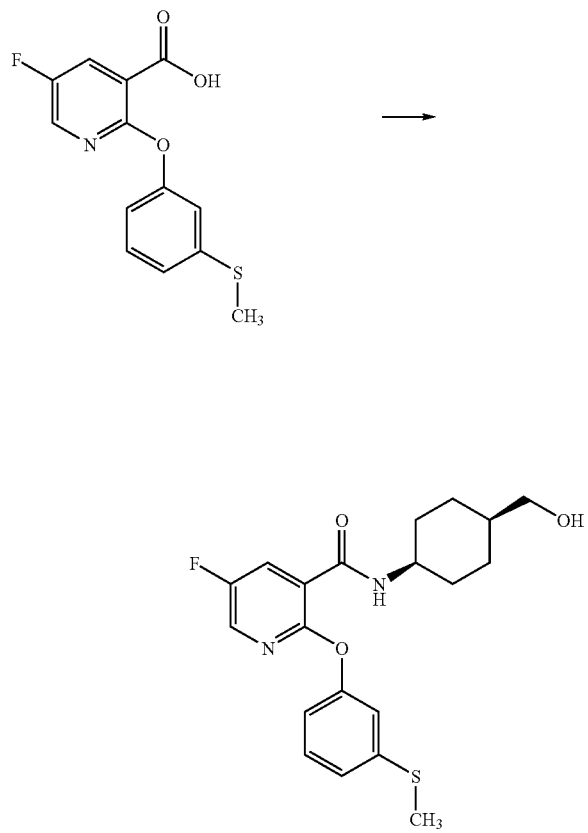

(cis-4-Amino-cyclohexyl)-methanol (73 mg, 0.56 mmol) and triethylamine (225 μl, 1.61 mmol) were dissolved in dimethylformamide (225 μl) and a solution of 5-fluoro-2-(3-methylsulfanyl-phenoxy)-nicotinic acid (150 mg, 0.54 mmol), 1-(3-dimethylaminopropyl)-3-ethylcarbodiimide hydrochloride (113 mg, 0.59 mmol) and 1-hydroxybenzotriazole (80 mg, 0.59 mmol) in dimethylformamide (5 ml) was added. The reaction was stirred under nitrogen at room temperature for 64 h and the solvent was removed under reduced pressure. The residue was partitioned between 0.5N HCl (10 ml) and ethyl acetate (10 ml) and the aqueous phase was extracted with ethyl acetate (2×10 ml). The combined organic phases were washed with brine (10 ml), dried over MgSO$_4$ and the solvent was removed under reduced pressure. The residue was purified by flash column chromatography on silica gel eluting with dichloromethane:methanol:concentrated aqueous ammonia (98.7:1.3:0.13, by volume). The product was triturated with ethyl acetate (3 ml) to give 5-fluoro-N-(cis-4-hydroxymethyl-cyclohexyl)-2-(3-methylsulfanyl-phenoxy)-nicotinamide (111 mg) as a white solid.

mp 123–126° C. $^1$H NMR (400 MHz, CDCl$_3$): δ=8.31–8.39 (1H, m), 8.08–8.20 (1H, m), 8.03–8.10 (1H, d), 7.28–7.38 (1H, t), 7.13–7.18 (1H, d), 7.02 (1H, s), 6.85–6.91 (1H, d), 4.30–4.40 (1H, m), 3.33–3.41 (2H, m) 2.48 (3H, s), 1.81–1.90 (2H, m), 1.50–1.73 (5H, m, partially masked by solvent), 1.11–1.23 (3H, m) ppm. LRMS (electrospray): m/z [M+H]$^+$ 391, [M+Na]$^+$ 413, [M−H]$^+$ 389. Anal. Found C, 61.14; H, 5.95; N, 7.12. C$_{20}$H$_{23}$FN$_2$O$_5$S. 0.1 mol H$_2$O requires C, 61.24; H, 5.96; N, 7.14%.

EXAMPLE 61

5-Fluoro-N-[cis-4-(1-hydroxy-1-methylethyl)cyclohexyl]-2-[3-(methylsulfanyl)phenoxy]nicotinamide

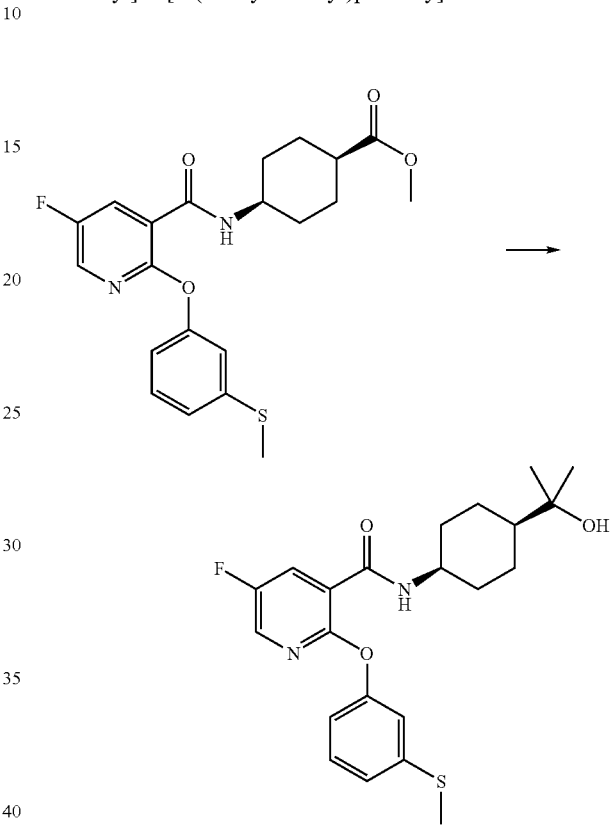

N-(cis-4-methylcarboxylate-cyclohexyl)-5-fluoro-2-(3-methylsulfanyl-phenoxy)-nicotinamide (500 mg, 1.19 mmol) was dissolved in tetrahydrofuran (10 ml) and cooled to −78° C. under nitrogen. Methyl magnesium chloride (3M/tetrahydrofuran, 1.6 ml, 4.78 mmol) was added dropwise and the reaction stirred for 5 mins at −78° C., then allowed to warm to room temperature under nitrogen over 18 h. The reaction was quenched with sat. ammonium chloride solution (10 ml), diluted with water (10 ml) and extracted with ethyl acetate (3×15 ml). The combined organic extracts were washed with brine (10 ml), dried over MgSO$_4$ and the solvent was removed under reduced pressure. The residue was purified by flash column chromatography on silica gel eluting with ethyl acetate:pentane (20:80 increasing to 30:70, then 40:60, by volume). The resulting oil was triturated with diethylether (2 ml) and pentane (2 ml) to give the product (77 mg) as a white solid.

$^1$H NMR (400 MHz, CDCl$_3$): δ=8.35–8.37 (1H, dd), 8.26–8.31 (1H, d), 8.04–8.05 (1H, d), 7.31–7.35 (1H, t), 7.13–7.15 (1H, d), 7.02–7.03 (1H, s), 6.88–6.90 (1H, d), 4.39–4.44 (1H, m), 2.49 (3H, s), 1.99–2.02 (2H, d), 1.74–1.77 (2H, d), 1.56–1.66 (2H, t), 1.32–1.39 (1H, t), 1.08–1.20 (2H, q), 1.03 (6H, s) ppm. LRMS (thermospray): m/z [M+H]$^+$ 419. Anal. Found C, 63.18; H, 6.50; N, 6.69. C$_{22}$H$_{27}$FN$_2$O$_3$S. requires C, 63.14; H, 6.50; N, 6.69%.

EXAMPLE 62

2-(3-Ethylsulfanyl-phenoxy)-5-fluoro-N-(1-hydroxy-cyclohexylmethyl)-nicotinamide

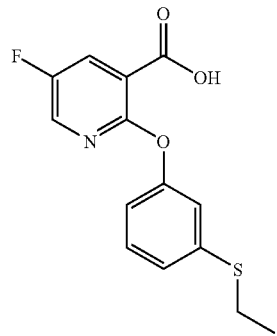

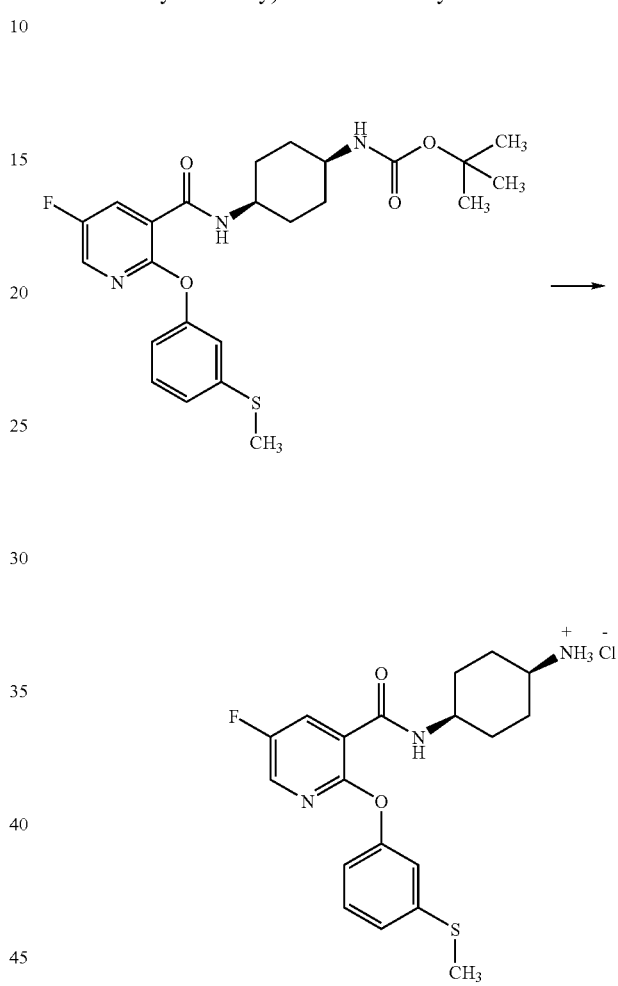

2-(3-Ethylsulfanyl-phenoxy)-5-fluoro-nicotinic acid (150 mg, 0.51 mmol) was added to a solution of 1-aminomethyl-cyclohexanol (93 mg, 0.56 mmol) and triethylamine (0.21 ml, 1.5 mmol) in dimethylformamide (3 ml) under nitrogen at room temperature. 1-(3-Dimethylaminopropyl)-3-ethyl-carbodiimide hydrochloride (108 mg, 0.56 mmol) followed by 1-hydroxybenzotriazole (76 mg, 0.56 mmol) were then added and the reaction was stirred at room temperature for 20 h. The mixture was concentrated under reduced pressure, partitioned between ethyl acetate (20 ml) and water (20 ml) and the organic phase was removed, dried over $MgSO_4$ and concentrated under reduced pressure. The residue was purified by flash column chromatography on a silica gel eluting with a solvent gradient of dichloromethane:methanol (99:1 changing to 98:2, by volume) to give 2-(3-ethylsulfanyl-phenoxy)-5-fluoro-N-(1-hydroxy-cyclohexylmethyl)-nicotinamide (86 mg) as an off-white solid.

$^1$H NMR (400 MHz, $CDCl_3$): δ=8.34–8.38 (1H, dd), 8.20–8.28 (1H, brs), 8.04–8.06 (1H, d), 7.32–7.37 (1H, t), 7.18–7.22 (1H, d), 7.09–7.10 (1H, d), 6.94–6.98 (1H, dd), 3.51–3.56 (2H, d), 2.92–2.99 (2H, quart), 2.01 (1H, s), 1.45–1.62 (10H, m, partially masked by solvent), 1.26–1.37 (3H, t) ppm. LRMS (electrospray): m/z $[M+Na]^+$ 427, $[M-H]^-$ 403.

EXAMPLE 63

N-(cis-4-Amino-cyclohexyl)-5-fluoro-2-(3-methyl-sulfanyl-Phenoxy)-nicotinamide Hydrochloride 4M HCl in dioxan (40 ml) was added to (cis-4-{[5-fluoro-}-2-(3-methylsulfanyl-phenoxy)-pyridine-3-carbonyl]-amino}-cyclohexyl)-carbamic acid tert-butyl ester (3.69 g, 7.76 mmol) and the mixture was stirred for 1 h. The solvent was removed under reduced pressure to give N-(cis-4-Amino-cyclohexyl)-5-fluoro-2-(3-methylsulfanyl-phenoxy)-nicotinamide hydrochloride (3.20 g) as a white solid.

$^1$H NMR (400 MHz, $CD_3OD$): δ=8.06–8.13 (2H, 2 ×m), 7.32–7.37 (1H, t), 7.13–7.18 (1H, d), 7.07–7.10 (1H, m), 6.92–6.96 (1H, m), 4.10–4.16 (1H, m), 3.20–3.30 (1H, m, partially masked by solvent), 2.45 (3H, s), 1.78–1.98 (6H, 2×m), 1.61–1.72 (2H, m) ppm. LRMS (thermospray): m/z $[M+H]^+$ 376. Anal. Found C, 55.19; H, 5.62; N, 10.11. $C_{19}H_{22}FN_3O_2S$. 1 molHCl requires C, 55.19; H, 5.62; N, 10.20%.

EXAMPLE 64

N-(cis-4-Acetylamino-cyclohexyl)-5-fluoro-2-(3-methylsulfanyl-phenoxy)-nicotinamide

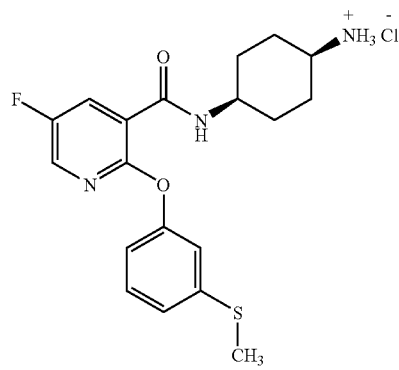

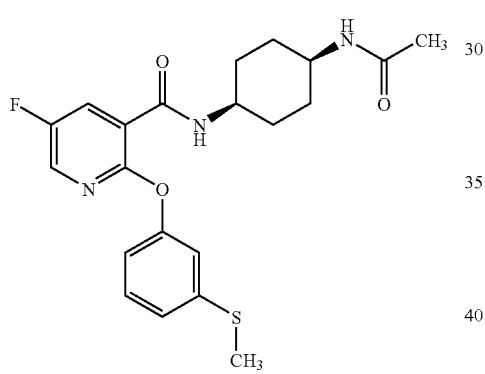

N-(cis-4-Amino-cyclohexyl)-5-fluoro-2-(3-methylsulfanyl-phenoxy)-nicotinamide hydrochloride (150 mg, 0.364 mmol) was suspended in dichloromethane (2 ml) under nitrogen at room temperature and triethylamine (153 μl, 1.09 mmol) was added followed by acetyl chloride (29 μl, 0.4 mmol). The reaction was stirred at room temperature for 1.5 h and the mixture was quenched with sat. sodium bicarbonate solution (3 ml). The organic phase was separated and the aqueous phase was washed with dichloromethane (2×5 ml). The combined organic extracts were dried over MgSO$_4$ and the solvent was removed under reduced pressure. The residue was purified by flash column chromatography on silica gel eluting with dichloromethane:methanol:concentrated aqueous ammonia (95:5:0.5, by volume) and the product was triturated with diethylether (2×3 ml) to give N-(cis-4-Acetylamino-cyclohexyl)-5-fluoro-2-(3-methylsulfanyl-phenoxy)-nicotinamide (50 mg) as a white solid.

$^1$H NMR (400 MHz, CDCl$_3$): δ=8.32–8.37 (1H, dd), 8.06–8.08 (1H, d), 7.96–8.01 (1H, d), 7.35–7.40 (1H, t), 7.15–7.19 (1H, d), 7.03–7.05 (1H, m), 6.87–6.90 (1H, m), 5.14–5.21 (1H, m), 4.17–4.23 (1H, brs), 3.86–3.93 (1H, m), 2.49 (3H, s), 1.93 (3H, s), 1.70–1.86 (6H, m), 1.32–1.41 (2H, m) ppm. LRMS (thermospray): m/z [M+H]$^+$ 418. Anal. Found C, 59.10; H, 5.66; N, 9.84. C$_{21}$H$_{24}$FN$_3$O$_3$S. 0.15 molHCl requires C, 59.04; H, 5.69; N, 9.77%.

EXAMPLE 65

N-(cis-4-{[5-Fluoro-2-(3-methylsulfanyl-phenoxy)-pyridine-3-carbonyl]-amino}-cyclohexyl)-carbamic Acid Methyl Ester

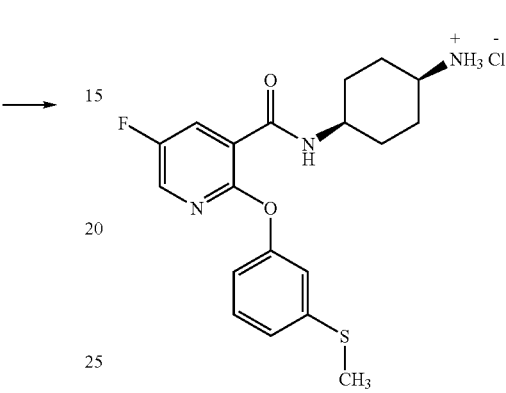

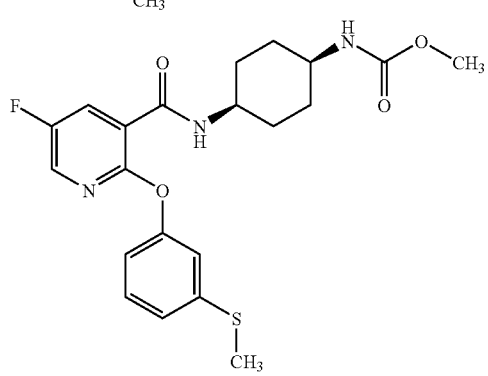

N-(cis-4-Amino-cyclohexyl)-5-fluoro-2-(3-methylsulfanyl-phenoxy)-nicotinamide hydrochloride (150 mg, 0.364 mmol) was suspended in dichloromethane (2 ml) under nitrogen at room temperature and triethylamine (153 μl, 1.09 mmol) was added followed by methylchloroformate (31 μl, 0.4 mmol). The reaction was stirred at room temperature for 1.5 h and the mixture was quenched with sat. sodium bicarbonate solution (3 ml). The organic phase was separated and the aqueous phase was washed with dichloromethane (2×3 ml). The combined organic extracts were dried over MgSO$_4$ and the solvent was removed under reduced pressure. The residue was purified by flash column chromatography on silica gel eluting with dichloromethane:methanol (98:2, by volume) and the product was triturated with diethylether (3 ml) to give (cis-4-{[5-Fluoro-2-(3-methylsulfanyl-phenoxy)-pyridine-3-carbonyl]-amino}-cyclohexyl)-carbamic acid methyl ester (64 mg) as a white solid.

$^1$H NMR (400 MHz, CDCl$_3$): δ=8.33–8.38 (1H, dd), 8.04–8.06 (1H, d), 7.92–7.97 (1H, d), 7.35–7.40 (1H, t), 7.15–7.19 (1H, d), 7.02 (1H, s), 6.84–6.90 (1H, d), 4.47–4.56 (1H, m), 4.13–4.22 (1H, m), 3.63 (4H, s+brs), 2.45 (3H, s), 1.77–1.87 (4H, m), 1.65–1.75 (2H, m), 1.40–1.51 (2H, m) ppm. LRMS (thermospray): m/z [M+H]$^+$ 434. Anal. Found C, 57.97; H, 5.58; N, 9.59. C$_{21}$H$_{24}$FN$_3$O$_4$S requires C, 58.18; H, 5.58; N, 9.69%.

EXAMPLE 66

N-(cis-4-{[5-Fluoro-2-(3-methylsulfanyl-phenoxy)-pyridine-3-carbonyl]-amino}-cyclohexyl)-carbamic Acid Ethyl Ester

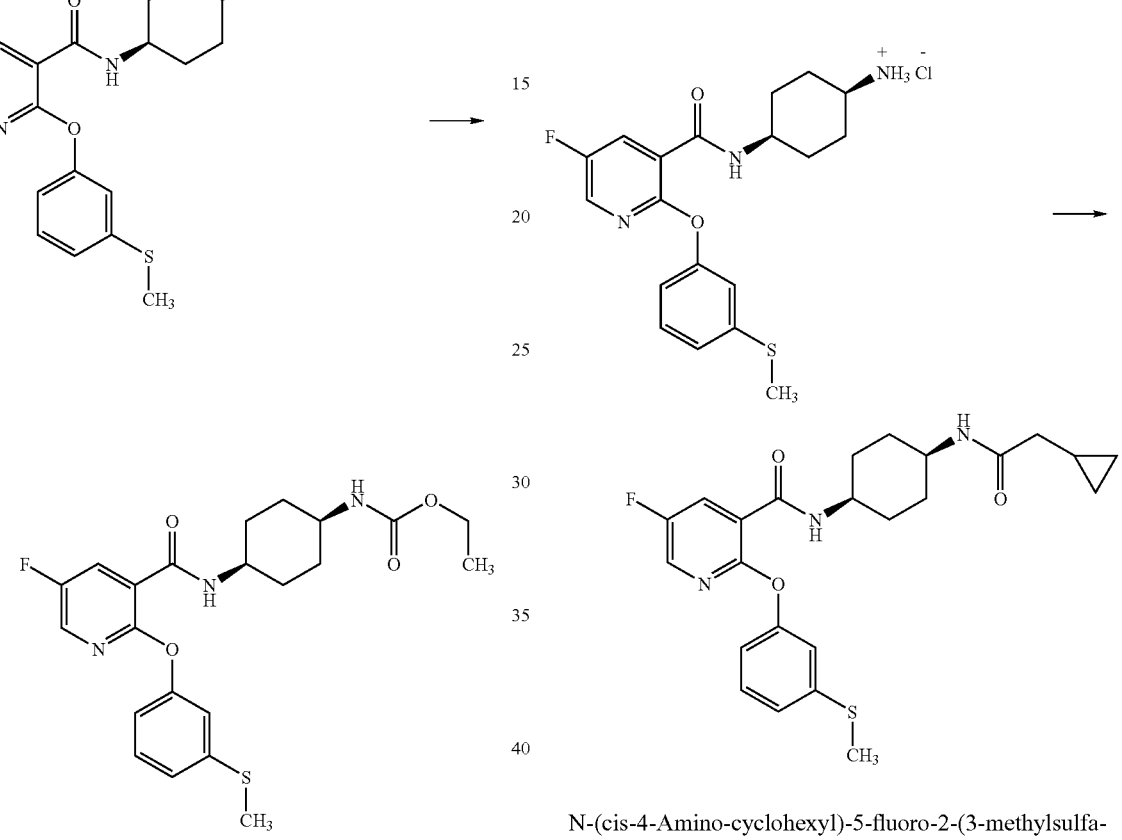

N-(cis-4-Amino-cyclohexyl)-5-fluoro-2-(3-methylsulfanyl-phenoxy)-nicotinamide hydrochloride (150 mg, 0.364 mmol) was suspended in dichloromethane (2 ml) under nitrogen at room temperature and triethylamine (153 µl, 1.09 mmol) was added followed by ethylchloroformate (39 µl, 0.4 mmol). The reaction was stirred at room temperature for 1.5 h and the mixture was quenched with sat. sodium bicarbonate solution (3 ml). The organic phase was separated and the aqueous phase was washed with dichloromethane (2×3 ml). The combined organic extracts were dried over MgSO₄ and the solvent was removed under reduced pressure. The residue was purified by flash column chromatography on silica gel eluting with dichloromethane:methanol (98:2, by volume) and the product was triturated with diethylether (3 ml) to give (cis-4-{[5-Fluoro-2-(3-methylsulfanyl-phenoxy)-pyridine-3-carbonyl]-amino}-cyclohexyl)-carbamic acid ethyl ester (64 mg) as a white solid.

$^1$H NMR (400 MHz, CDCl$_3$): δ=8.32–8.38 (1H, m), 8.04–8.06 (1H, d), 7.92–7.98 (1H, d), 7.33–7.39 (1H, t), 7.15–7.19 (1H, d), 7.02 (1H, s), 6.86–6.91 (1H, d), 4.45–4.55 (1H, brs), 4.13–4.21 (1H, m), 4.07–4.13 (2H, quart), 3.61–3.68 (1H, m), 2.49 (3H, s), 1.78–1.87 (4H, m), 1.64–1.76 (2H, m), 1.44–1.52 (2H, m), 1.20–1.26 (3H, t) ppm. LRMS (thermospray): m/z [M+H]⁺ 448. Anal. Found C, 59.00; H, 5.86; N, 9.30. C$_{22}$H$_{26}$FN$_3$O$_4$S requires C, 59.04; H, 5.86; N, 9.30%.

EXAMPLE 67

N-[cis-4-(2-Cyclopropyl-acetylamino)-cyclohexyl]-5-fluoro-2-(3-methylsulfanyl-phenoxy)-nicotinamide N-(cis-4-Amino-cyclohexyl)-5-fluoro-2-(3-methylsulfanyl-phenoxy)-nicotinamide hydrochloride (150 mg, 0.364 mmol) was dissolved in dimethylformamide (3 ml), and triethylamine (153 µl, 1.1 mmol) was added followed by cyclopropylacetic acid (40 mg, 0.40 mmol), 1-(3-dimethylaminopropyl)-3-ethylcarbodiimide hydrochloride (77 mg, 0.40 mmol) and 1-hydroxybenzotriazole (54 mg, 0.40 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over MgSO₄ and the solvent was removed under reduced pressure. The residue was triturated with diethylether (5 ml) to give N-[cis-4-(2-Cyclopropyl-acetylamino)-5-fluoro-2-(3-methylsulfanyl-phenoxy)-nicotinamide (120 mg) as a white solid.

$^1$H NMR (400 MHz, CDCl$_3$): δ=8.34–8.38 (1H, dd), 8.05–8.07 (1H, d), 7.98–8.04 (1H, d), 7.34–7.39 (1H, t), 7.13–7.17 (1H, d), 7.03 (1H, s), 6.87–6.91 (1H, dd), 5.58–5.64 (1H, m), 4.19–4.25 (1H, brs), 3.89–3.96 (1H, m), 2.46 (3H, s), 2.07–2.11 (2H, d), 1.72–1.90 (6H, 2×m), 1.37–1.46 (2H, m), 0.80–0.90 (1H, m), 0.50–0.56 (2H, m), 0.10–0.15 (2H, m) ppm. LRMS (thermospray): m/z [M+H]⁺

458. Anal. Found C, 62.65; H, 6.13; N, 9.14. $C_{24}H_{28}FN_3O_3S$. 1 mol $H_2O$ requires C, 62.75; H, 6.19; N, 9.15%.

EXAMPLE 68

5-Fluoro-2-(3-methylsulfanyl-phenoxy)-N-{cis-4-[(tetrahydro-furan-3-carbonyl)-amino]-cyclohexyl}-nicotinamide

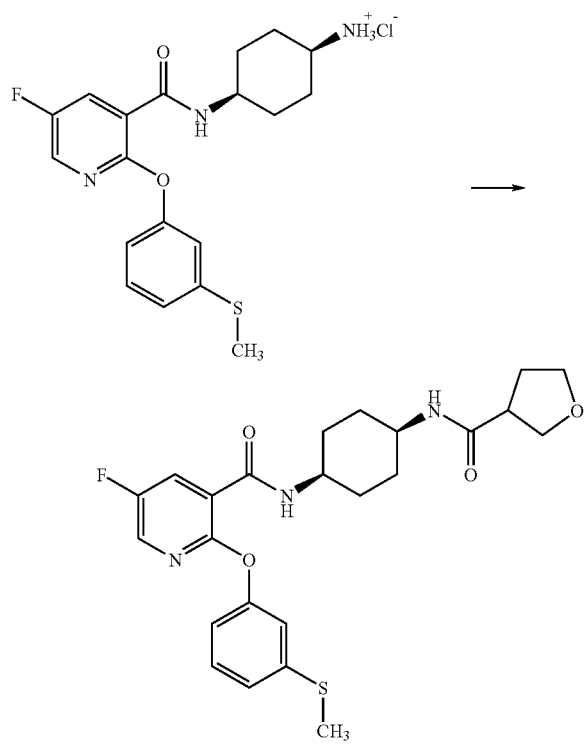

N-(cis-4-Amino-cyclohexyl)-5-fluoro-2-(3-methylsulfanyl-phenoxy)-nicotinamide hydrochloride (150 mg, 0.364 mmol) was dissolved in dimethylformamide (3 ml) and triethylamine (153 μl, 1.1 mmol) was added followed by 3-tetrahydrofuran-carbocylic acid (47 mg, 0.40 mmol), 1-(3-dimethylaminopropyl)-3-ethylcarbodiimide hydrochloride (77 mg, 0.40 mmol) and 1-hydroxybenzotriazole (54 mg, 0.40 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over $MgSO_4$ and the solvent was removed under reduced pressure. The residue was triturated with diethylether (5 ml) to give 5-fluoro-2-(3-methylsulfanyl-phenoxy)-N-{cis-4-[(tetrahydro-furan-3-carbonyl)-amino]-cyclohexyl}-nicotinamide (140 mg) as a white solid.

$^1$H NMR (400 MHz, $CDCl_3$): δ=8.33–8.38 (1H, dd), 8.07–8.10 (1H, d), 7.96–8.03 (1H, d), 7.35–7.41 (1H, t), 7.13–7.19 (1H, d), 7.03–7.07 (1H, m), 6.89–6.94 (1H, m), 5.35–5.41 (1H, m), 4.18–4.25 (1H, m), 3.76–3.93 (5H, m), 2.76–2.84 (1H, quin), 2.50 (3H, s), 2.08–2.15 (2H, quart), 1.73–1.87 (6H, 2×m), 1.32–1.44 (2H, m) ppm. LRMS (thermospray): m/z $[M+H]^+$ 474. Anal. Found C, 60.39; H, 5.98; N, 8.71. $C_{24}H_{28}FN_3O_4S$. 0.2 mol $H_2O$ requires C, 60.41; H, 6.00; N, 8.81%.

EXAMPLE 69

5-Fluoro-N-[cis-4-(2-methoxy-acetylamino)-cyclohexyl]-2-(3-methylsulfanyl-phenoxy)-nicotinamide

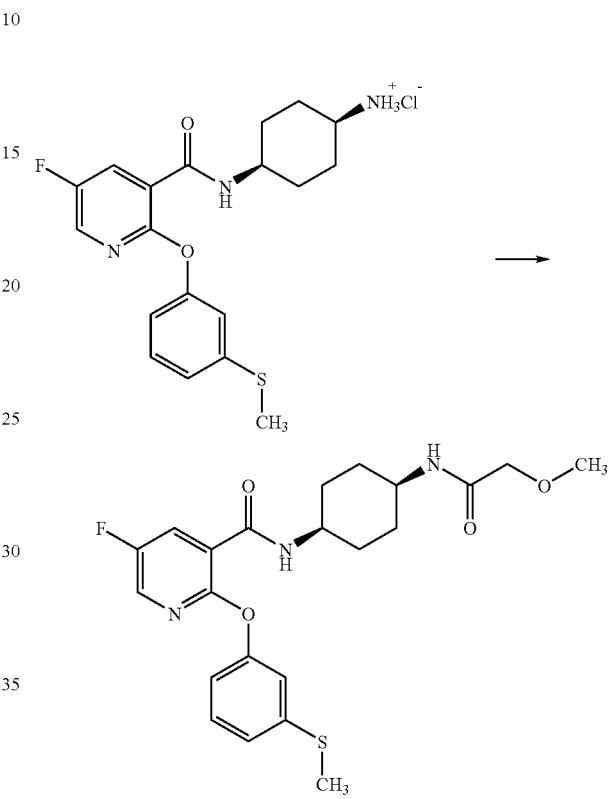

N-(cis-4-Amino-cyclohexyl)-5-fluoro-2-(3-methylsulfanyl-phenoxy)-nicotinamide hydrochloride (150 mg, 0.364 mmol) was dissolved in dimethylformamide (3 ml) and triethylamine (153 μl, 1.1 mmol) was added followed by methoxyacetic acid (31 μl, 0.40 mmol), 1-(3-dimethylaminopropyl)-3-ethylcarbodiimide hydrochloride (77 mg, 0.40 mmol) and 1-hydroxybenzotriazole (54 mg, 0.40 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over $MgSO_4$ and the solvent was removed under reduced pressure. The residue was purified by flash column chromatography on silica gel eluting with dichloromethane:methanol (95:5, by volume) and the product was triturated with diethylether (5 ml) to give 5-Fluoro-N-[cis-4-(2-methoxy-acetylamino)-cyclohexyl]-2-(3-methylsulfanyl-phenoxy)-nicotinamide (112 mg) as a white solid.

$^1$H NMR (400 MHz, $CDCl_3$): δ=8.32–8.38 (1H, dd), 8.05–8.07 (1H, d), 7.96–8.02 (1H, d), 7.35–7.40 (1H, t), 7.15–7.19 (1H, d), 7.04 (1H, s), 6.88–6.93 (1H, dd), 6.31–6.37 (1H, m), 4.17–4.26 (1H, m), 3.88–3.99 (1H, m), 3.83 (2H, s), 3.38 (3H, s), 2.47 (3H, s), 1.80–1.90 (4H, m), 1.72–1.80 (2H, m), 1.44–1.53 (2H, m) ppm. LRMS (thermospray): m/z [M+H]⁺ 448.

Anal. Found C, 58.94; H, 5.86; N, 9.37. $C_{22}H_{26}FN_3O_4S$ requires C, 59.04; H, 5.86; N, 9.39%.

EXAMPLE 70

5-Fluoro-N-[cis-4-(2-hydroxy-acetylamino)-cyclohexyl]-2-(3-methylsulfanyl-phenoxy)-nicotinamide

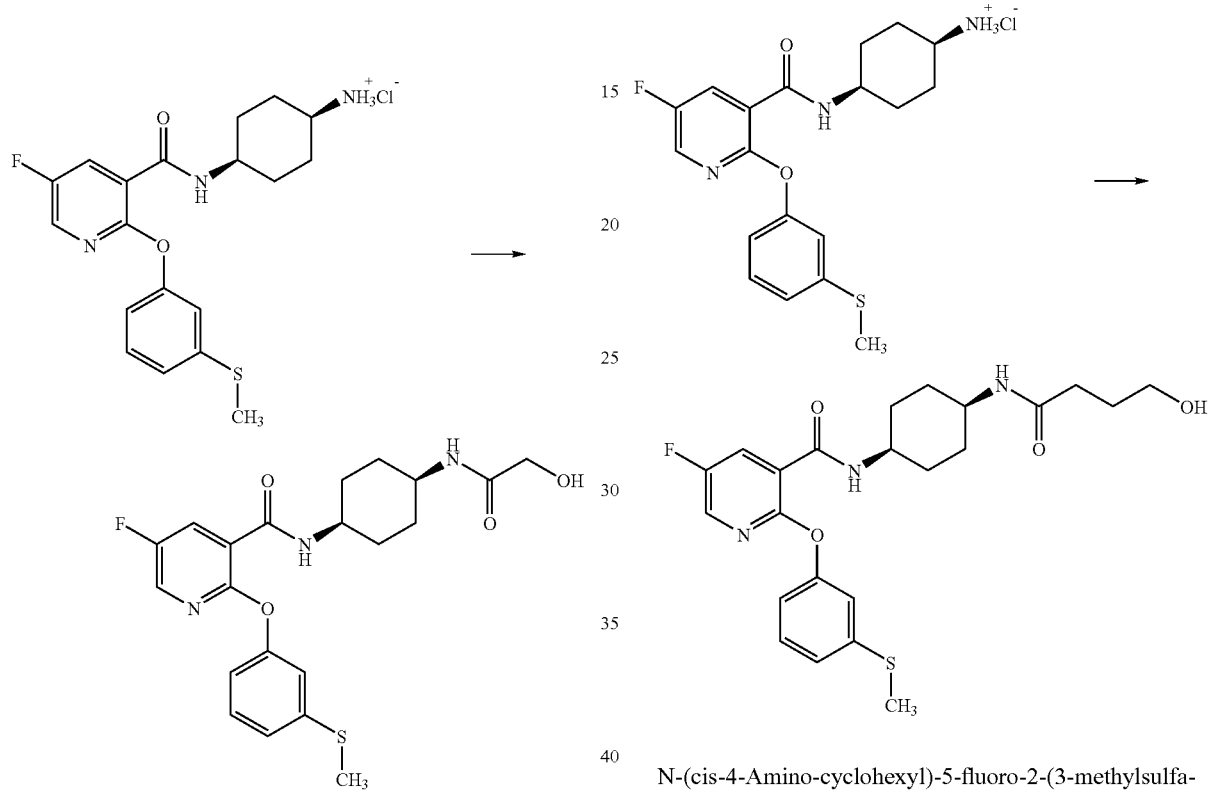

N-(cis-4-Amino-cyclohexyl)-5-fluoro-2-(3-methylsulfanyl-phenoxy)-nicotinamide hydrochloride (150 mg, 0.364 mmol) was dissolved in dimethylformamide (3 ml) and triethylamine (153 μl, 1.1 mmol) was added followed by glycolic acid (31 mg, 0.40 mmol), 1-(3-dimethylaminopropyl)-3-ethylcarbodiimide hydrochloride (77 mg, 0.40 mmol) and 1-hydroxybenzotriazole (54 mg, 0.40 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (2×10 ml). The combined organic extracts were washed with water (2×5 ml), brine (5 ml), dried over MgSO₄ and the solvent was removed under reduced pressure. The residue was triturated with diethylether (5 ml) to give 5-Fluoro-N-[cis-4-(2-hydroxy-acetylamino)-cyclohexyl]-2-(3-methylsulfanyl-phenoxy)-nicotinamide (127 mg) as a white solid.

¹H NMR (400 MHz, CDCl₃): δ=8.34–8.38 (1H, dd), 8.07–8.09 (1H, d), 7.97–8.03 (1H, d), 7.34–7.40 (1H, t), 7.15–7.19 (1H, d), 7.04 (1H, s), 6.87–6.92 (1H, dd), 6.12–6.21 (1H, m), 4.18–4.25 (1H, m), 4.03–4.07 (2H, d), 3.92–3.99 (1H, m), 2.50 (3H, s), 2.38–2.42 (1H, t), 1.72–1.90 (6H, m), 1.40–1.50 (2H, m) ppm. LRMS (thermospray): m/z [M+H]⁺ 434. Anal. Found C, 57.60; H, 5.58; N, 9.53. $C_{21}H_{24}FN_3O_4S$. 0.25H₂O requires C, 57.59; H, 5.64; N, 9.59%.

EXAMPLE 71

5-Fluoro-N-[cis-4-(4-hydroxy-butyrylamino)-cyclohexyl]-2-(3-methylsulfanyl-phenoxy)-nicotinamide

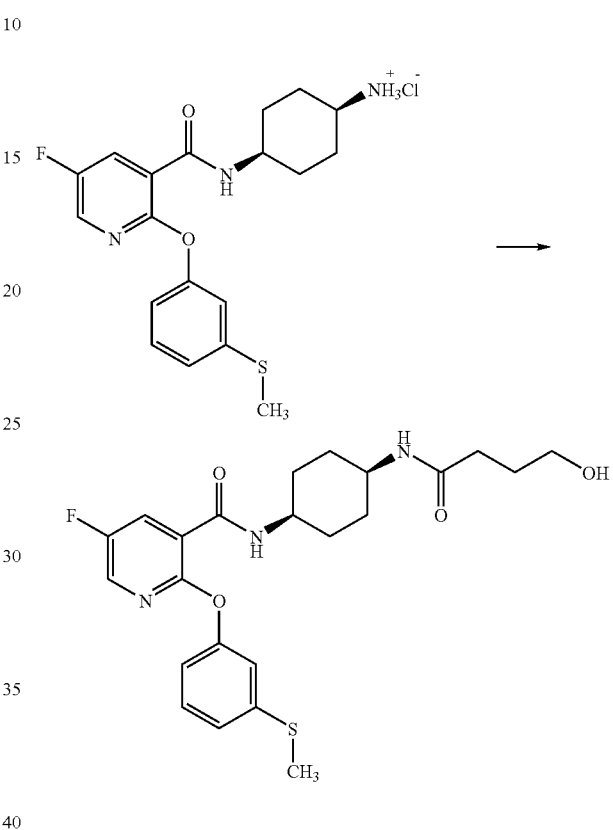

N-(cis-4-Amino-cyclohexyl)-5-fluoro-2-(3-methylsulfanyl-phenoxy)-nicotinamide hydrochloride (150 mg, 0.364 mmol) was dissolved in dimethylformamide (3 ml) and triethylamine (153 μl, 1.1 mmol) was added followed by sodium 4-hydroxybutanoate (51 mg, 0.40 mmol), 1-(3-dimethylaminopropyl)-3-ethylcarbodiimide hydrochloride (77 mg, 0.40 mmol) and 1-hydroxybenzotriazole (54 mg, 0.40 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (2×10 ml). The combined organic extracts were washed with water (2×5 ml), brine (5 ml), dried over MgSO₄ and the solvent was removed under reduced pressure. The residue was purified by flash column chromatography on silica gel eluting with dichloromethane:methanol (95:5, by volume) and the product was triturated with diethylether (5 ml) to give 5-Fluoro-N-[cis-4-(4-hydroxy-butyrylamino)-cyclohexyl]-2-(3-methylsulfanyl-phenoxy)-nicotinamide (75 mg) as a white solid.

¹H NMR (400 MHz, CDCl₃): δ=8.32–8.38 (1H, dd), 8.05–8.07 (1H, d), 7.94–8.01 (1H, d), 7.34–7.40 (1H, t), 7.15–7.19 (1H, d), 7.03 (1H, s), 6.85–6.92 (1H, d), 5.42–5.48 (1H, m), 4.18–4.22 (1H, m), 3.83–3.95 (1H, m), 3.63–3.69 (1H, t), 2.47–2.62 (4H, s+m), 2.27–2.34 (2H, t), 1.72–1.87 (8H, m), 1.35–1.45 (2H, m) ppm. LRMS (thermospray): m/z [M+H]+ 462. Anal. Found C, 58.63; H, 6.24; N, 8.75. $C_{23}H_{28}FN_3O_4S \cdot 0.5H_2O$ requires C, 58.71; H, 6.21; N, 8.93%.

EXAMPLE 72

5-Fluoro-N-[cis-4-(3-hydroxy-2,2-dimethyl-propionylaminolamino)-cyclohexyl]-2-(3-methylsulfanyl-phenoxy)-nicotinamide

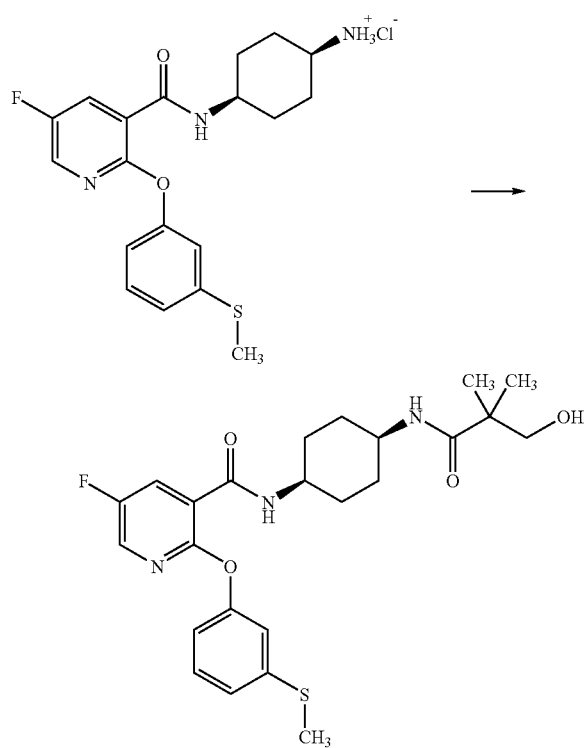

N-(cis-4-Amino-cyclohexyl)-5-fluoro-2-(3-methylsulfanyl-phenoxy)-nicotinamide hydrochloride (150 mg, 0.364 mmol) was dissolved in dimethylformamide (3 ml) and triethylamine (153 µl, 1.1 mmol) was added followed by 2,2-dimethyl-3-hydroxypropionic acid (47 mg, 0.40 mmol), 1-(3-dimethylaminopropyl)-3-ethylcarbodiimide hydrochloride (77 mg, 0.40 mmol) and 1-hydroxybenzotriazole (54 mg, 0.40 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (2×10 ml). The combined organic extracts were washed with water (2×5 ml), brine (5 ml), dried over $MgSO_4$ and the solvent was removed under reduced pressure. The residue was triturated with diethylether (5 ml) to give 5-luoro-N-[cis-4-(3-hydroxy-2,2-dimethyl-propionylamino-lamino)-cyclohexyl]-2-(3-methylsulfanyl-phenoxy)-nicotinamide (90 mg) as a white solid.

$^1$H NMR (400 MHz, $CDCl_3$): δ=8.33–8.37 (1H, dd), 8.04–8.06 (1H, d), 7.99–8.04 (1H, d), 7.36–7.41 (1H, t), 7.14–7.19 (1H, d), 7.04 (1H, s), 6.90–6.94 (1H, d), 5.96–6.04 (1H, m), 4.17–4.25 (1H, m), 3.82–3.90 (1H, m), 3.48–3.52 (2H, m), 2.80–2.86 (1H, m), 2.46 (3H, s), 1.72–1.86 (6H, m), 1.37–1.43 (2H, m), 1.08 (6H, s) ppm.

LRMS (thermospray): m/z [M+H]+ 476. Anal. Found C, 60.33; H, 6.58; N, 8.57. $C_{24}H_{30}FN_3O_4S$ requires C, 60.61; H, 6.36; N, 8.84%.

EXAMPLE 73

N-(cis-4-Butyrylamino-cyclohexyl)-5-fluoro-2-(3-methylsulfanyl-phenoxy-nicotinamide

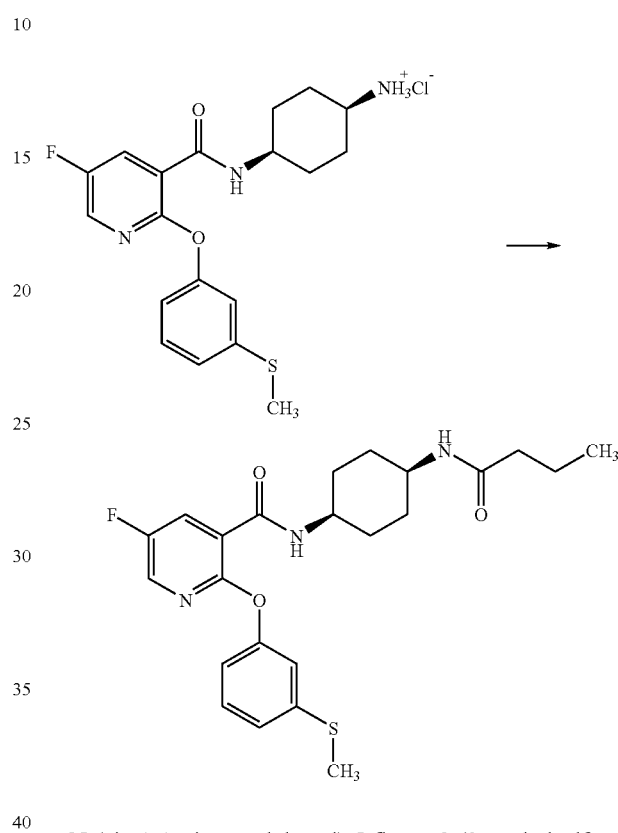

N-(cis-4-Amino-cyclohexyl)-5-fluoro-2-(3-methylsulfanyl-phenoxy)-nicotinamide hydrochloride (100 mg, 0.243 mmol) was dissolved in dimethylformamide (1 ml) and triethylamine (100 µl, 0.729 mmol) was added followed by butyric acid (27 µl, 0.291 mmol), 1-(3-dimethylaminopropyl)-3-ethylcarbodiimide hydrochloride (56 mg, 0.291 mmol) and 1-hydroxybenzotriazole (39 mg, 0.291 mmol). The reaction, was stirred under nitrogen at room temperature for 64 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over $MgSO_4$ and the solvent was removed under reduced pressure. The residue was triturated with diethylether (5 ml) to give N-(cis-4-Butyrylamino-cyclohexyl)-5-fluoro-2-(3-methylsulfanyl-phenoxy)-nicotinamide (89 mg) as a white solid.

$^1$H NMR (400 MHz, $CDCl_3$): δ=8.36–8.40 (1H, dd), 8.07–8.10 (1H, d), 7.97–8.04 (1H, d), 7.37–7.42 (1H, t), 7.15–7.20 (1H, d), 7.04 (1H, s), 6.88–6.92 (1H, d), 5.12–5.19 (1H, d), 4.18–4.24 (1H, brs), 3.85–3.96 (1H, m), 2.51 (3H, s), 2.07–2.12 (2H, t), 1.70–1.89 (6H, m), 1.55–1.68 (2H, m, partially masked by solvent), 1.33–1.43 (2H, m), 0.95–0.98 (3H, t) ppm. LRMS (electrospray): m/z [M+H]+ 446. Anal. Found C, 61.66; H, 6.30; N, 9.36. $C_{23}H_{28}FN_3O_3S$ requires C, 62.00; H, 6.33; N, 9.43%.

EXAMPLE 74

5-Fluoro-N-(cis-4-isobutyrylamino-cyclohexyl)-2-(3-methylsulfanyl-phenoxy)-nicotinamide

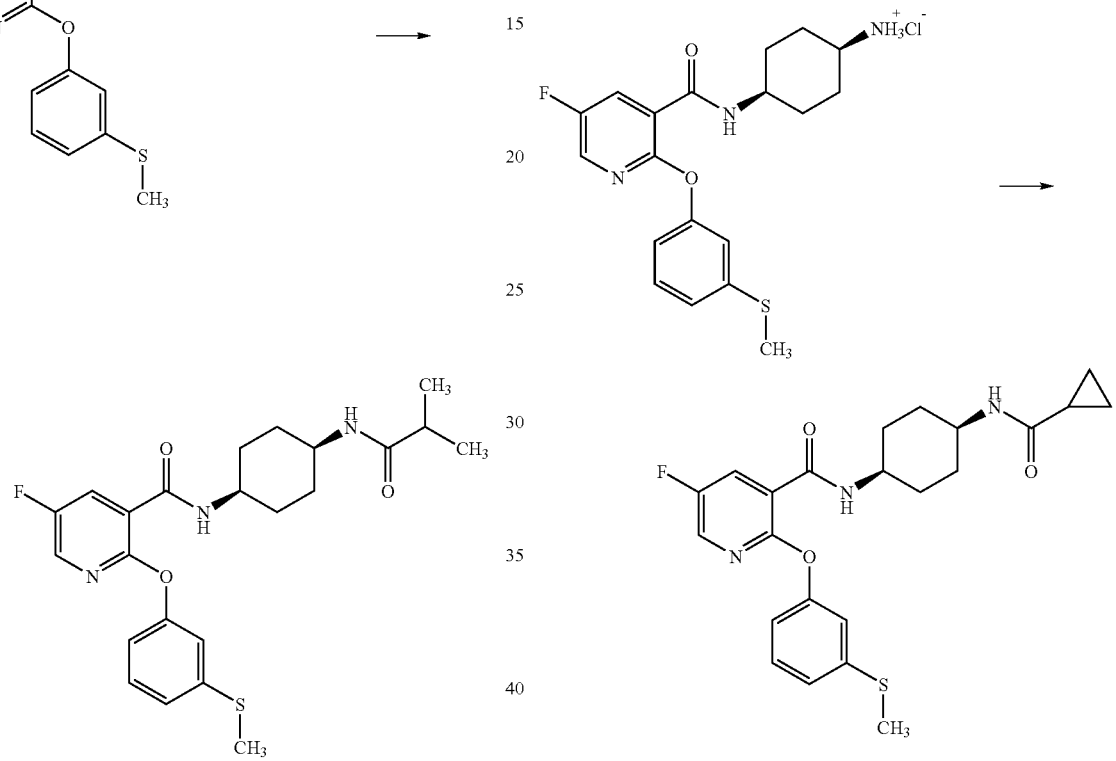

N-(cis-4-Amino-cyclohexyl)-5-fluoro-2-(3-methylsulfanyl-phenoxy)-nicotinamide hydrochloride (100 mg, 0.243 mmol) was dissolved in dimethylformamide (1 ml) and triethylamine (100 μl, 0.729 mmol) was added followed by isobutyric acid (27 μl, 0.291 mmol), 1-(3-dimethylaminopropyl)-3-ethylcarbodiimide hydrochloride (56 mg, 0.291 mmol) and 1-hydroxybenzotriazole (39 mg, 0.291 mmol). The reaction was stirred under nitrogen at room temperature for 64 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over MgSO$_4$ and the solvent was removed under reduced pressure. The residue was triturated with diethylether (5 ml) to give 5-Fluoro-N-(cis-4-isobutyrylamino-cyclohexyl)-2-(3-methylsulfanyl-phenoxy)-nicotinamide (110 mg) as a white solid.

$^1$H NMR (400 MHz, CDCl$_3$): δ=8.35–8.39 (1H, dd), 8.06–8.08 (1H, d), 7.98–8.04 (1H, d), 7.35–7.41 (1H, t), 7.14–7.19 (1H, d), 7.04 (1H, s), 6.89–6.94 (1H, d), 5.12–5.19 (1H, d), 4.19–4.25 (1H, brs), 3.83–3.93 (1H, m), 2.51 (3H, s), 2.21–2.29 (1H, sept), 1.73–1.88 (6H, m), 1.32–1.44 (2H, m), 1.09–1.16 (6H, d) ppm. LRMS (electrospray): m/z [M+H]$^+$ 446. Anal. Found C, 61.73; H, 6.30; N, 9.39. C$_{23}$H$_{28}$FN$_3$O$_3$S requires C, 62.00; H, 6.33; N, 9.43%.

EXAMPLE 75

N-[cis-4-(Cyclopropanecarbonyl-amino)-cyclohexyl]-5-fluoro-2-(3-methylsulfanyl-phenoxy)-nicotinamide N-(cis-4-Amino-cyclohexyl)-5-fluoro-2-(3-methylsulfanyl-phenoxy)-nicotinamide hydrochloride (100 mg, 0.243 mmol) was dissolved in dimethylformamide (1 ml) and triethylamine (100 μl, 0.729 mmol) was added followed by cyclopropanecarboxylic acid (23 μl, 0.291 mmol), 1-(3-dimethylaminopropyl)-3-ethylcarbodiimide hydrochloride (56 mg, 0.291 mmol) and 1-hydroxybenzotriazole (39 mg, 0.291 mmol). The reaction was stirred under nitrogen at room temperature for 64 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over MgSO$_4$ and the solvent was removed under reduced pressure. The residue was triturated with diethylether (5 ml) to give N-[cis-4-(Cyclopropanecarbonyl-amino)-cyclohexyl]-5-fluoro-2-(3-methylsulfanyl-phenoxy)-nicotinamide (106 mg) as a white solid.

$^1$H NMR (400 MHz, CDCl$_3$): δ=8.36–8.41 (1H, dd), 8.07–8.11 (1H, d), 7.97–8.06 (1H, d), 7.36–7.42 (1H, t), 7.15–7.20 (1H, d), 7.08 (1H, s), 6.87–6.96 (1H, d), 5.35–5.46 (1H, d), 4.18–4.23 (1H, brs), 3.87–3.97 (1H, m), 2.47 (3H, s), 1.68–1.87 (6H, m), 1.36–1.48 (2H, m), 1.23–1.31 (1H, m), 0.90–0.98 (2H, m), 0.64–0.77 (2H, m) ppm. LRMS (electrospray): m/z [M+H]$^+$ 444. Anal. Found C, 61.87; H, 5.90; N, 9.44. $C_{23}H_{26}FN_3O_3S$ requires C, 61.91; H, 5.94; N, 9.42%.

EXAMPLE 76

N-[cis-4-(2,2-Dimethylpropionylamino)-cyclohexyl]-5-fluoro-2-(3-methylsulfanyl-phenoxy)-nicotinamide

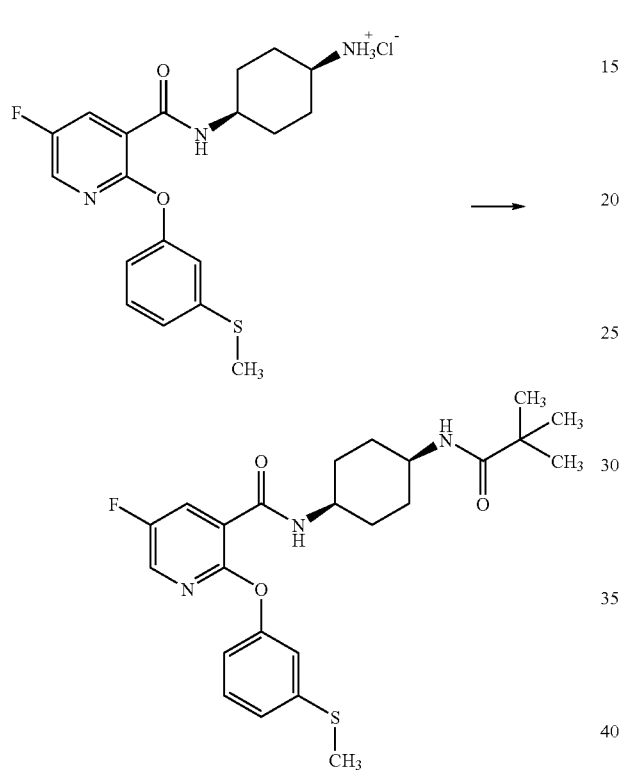

N-(cis-4-Amino-cyclohexyl)-5-fluoro-2-(3-methylsulfanyl-phenoxy)-nicotinamide hydrochloride (100 mg, 0.243 mmol) was dissolved in dimethylformamide (1 ml) and triethylamine (100 μl, 0.729 mmol) was added followed by 2,2-dimethylpropionic acid (34 μl, 0.291 mmol), 1-(3-dimethylaminopropyl)-3-ethylcarbodiimide hydrochloride (56 mg, 0.291 mmol) and 1-hydroxybenzotriazole (39 mg, 0.291 mmol). The reaction was stirred under nitrogen at room temperature for 64 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over MgSO$_4$ and the solvent was removed under reduced pressure. The residue was triturated with diethylether (5 ml) to give N-[cis-4-(2,2-dimethylpropionylamino)-cyclohexyl]-5-fluoro-2-(3-methylsulfanyl-phenoxy)-nicotinamide (112 mg) as a white solid.

$^1$H NMR (400 MHz, CDCl$_3$): δ=8.35–8.39 (1H, dd), 8.03–8.09 (2H, 2×d), 7.36–7.40 (1H, t), 7.15–7.19 (1H, d), 7.03–7.05 (1H, m), 6.88–6.93 (1H, m), 5.27–5.33 (1H, d), 4.19–4.25 (1H, m), 3.79–3.90 (1H, m), 3.79–3.90 (1H, m), 2.48 (3H, s), 1.76–1.87 (6H, m), 1.22–1.40 (2H, m), 1.11 (9H, s) ppm. LRMS (electrospray): m/z [M+H]$^+$ 460. Anal. Found C, 62.22; H, 6.60; N, 8.91. $C_{24}H_{30}FN_3O_3S$. 0.2 mol H$_2$O requires C, 62.24; H, 6.62; N, 9.07%.

EXAMPLE 77

5-Fluoro-2-(3-methylsulfanyl-phenoxy)-N-(cis-4-propionylamino-cyclohexyl)-nicotinamide

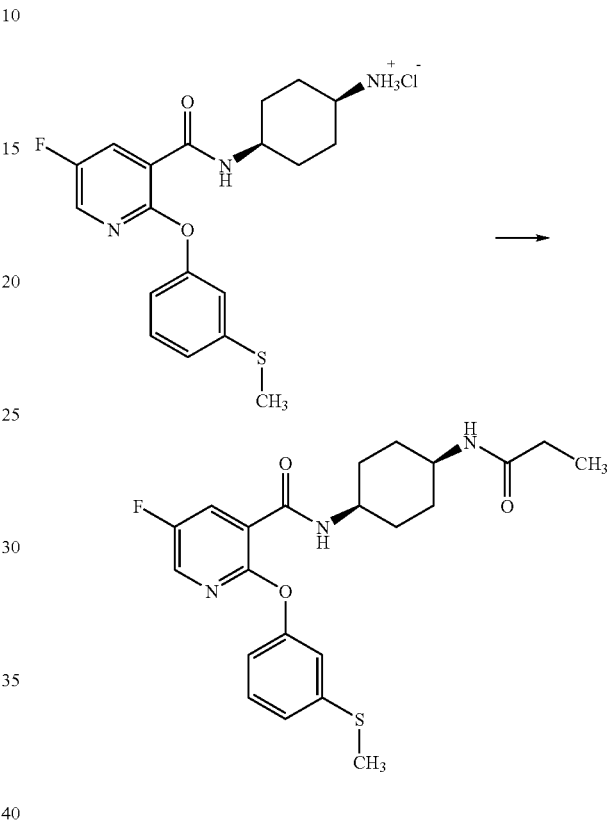

N-(cis-4-Amino-cyclohexyl)-5-fluoro-2-(3-methylsulfanyl-phenoxy)-nicotinamide hydrochloride (100 mg, 0.243 mmol) was dissolved in dimethylformamide (1 ml) and triethylamine (100 μl, 0.729 mmol) was added followed by propionic acid (22 μl, 0.291 mmol), 1-(3-dimethylaminopropyl)-3-ethylcarbodiimide hydrochloride (56 mg, 0.291 mmol) and 1-hydroxybenzotriazole (39 mg, 0.291 mmol). The reaction was stirred under nitrogen at room temperature for 64 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over MgSO$_4$ and the solvent was removed under reduced pressure. The residue was triturated with diethylether (5 ml) to give 5-Fluoro-2-(3-methylsulfanyl-phenoxy)-N-(cis-4-propionylamino-cyclohexyl)-nicotinamide (104 mg) as a white solid.

$^1$H NMR (400 MHz, CDCl$_3$): δ=8.36–8.40 (1H, dd), 8.07–8.10 (1H, d), 7.98–8.05 (1H, d), 7.37–7.41 (1H, t), 7.16–7.20 (1H, d), 7.03 (1H, s), 6.88–6.92 (1H, d), 5.13–5.20 (1H, d), 4.18–4.24 (1H, brs), 3.84–3.95 (1H, m), 2.51 (3H, s), 2.12–2.19 (2H, quart), 1.73 –1.84 (6H, m), 1.32–1.43 (2H, m), 1.09–1.15 (3H, t) ppm. LRMS (electrospray): m/z [M+H]$^+$ 432. Anal. Found C, 60.76; H, 6.07; N, 9.61. $C_{22}H_{26}FN_3O_3S$. 0.2 mol H$_2$O requires C, 60.73; H, 6.12; N, 9.66%.

EXAMPLE 78

5-Fluoro-N-[cis-4-(4-methyl-pentanoylamino)-cyclohexyl]-2-(3-methylsulfanyl-phenoxy)-nicotinamide

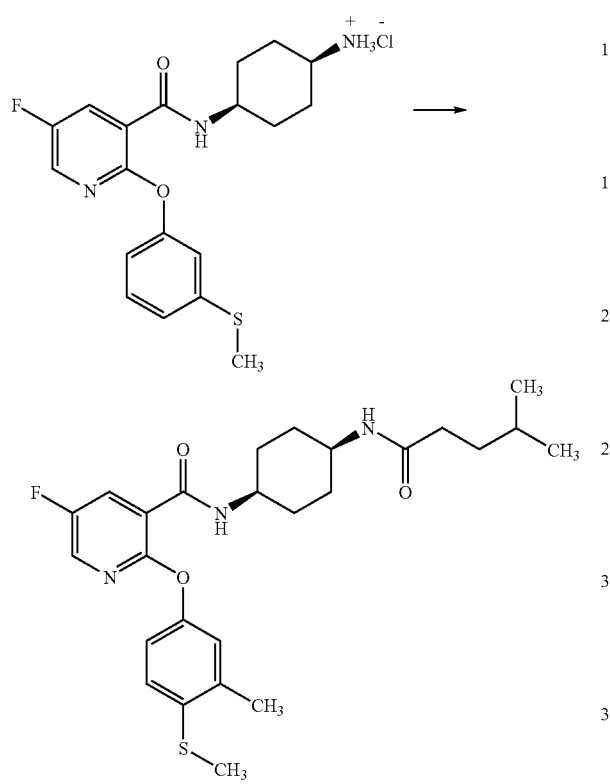

N-(cis-4-Amino-cyclohexyl)-5-fluoro-2-(3-methylsulfanyl-phenoxy)-nicotinamide hydrochloride (100 mg, 0.243 mmol) was dissolved in dimethylformamide (1 ml) and triethylamine (100 µl, 0.729 mmol) was added followed by 4-methylpentanoic acid (37 µl, 0.291 mmol), 1-(3-dimethylaminopropyl)-3-ethylcarbodiimide hydrochloride (56 mg, 0.291 mmol) and 1-hydroxybenzotriazole (39 mg, 0.291 mmol). The reaction was stirred under nitrogen at room temperature for 64 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over MgSO$_4$ and the solvent was removed under reduced pressure. The residue was triturated with diethylether (5 ml) to give 5-Fluoro-N-[cis-4-(4-methyl-pentanoylamino)-cyclohexyl]-2-(3-methylsulfanyl-phenoxy)-nicotinamide (114 mg) as a white solid.

$^1$H NMR (400 MHz, CDCl$_3$): δ=8.36–8.40 (1H, dd), 8.05–8.07 (1H, d), 7.98–8.03 (1H, d), 7.37–7.42 (1H, t), 7.15–7.19 (1H, d), 7.04 (1H, s), 6.88–6.92 (1H, d), 5.12–5.19 (1H, d), 4.18–4.25 (1H, brs), 3.85–3.94 (1H, m), 2.50 (3H, s), 2.09–2.14 (2H, t), 1.70–1.83 (6H, m), 1.44–1.60 (3H, 2×m, partially masked by solvent), 1.32–1.43 (2H, m), 0.87–0.93 (6H, d) ppm. LRMS (electrospray): m/z [M+H]$^+$ 474. Anal. Found C, 63.15; H, 6.78; N, 8.83. C$_{25}$H$_{32}$FN$_3$O$_3$S requires C, 63.40; H, 6.81; N, 8.87%.

EXAMPLE 79

5-Fluoro-N-[cis-4-(3-methyl-butyrylamino)-cyclohexyl]-2-(3-methylsulfanyl-phenoxy)-nicotinamide

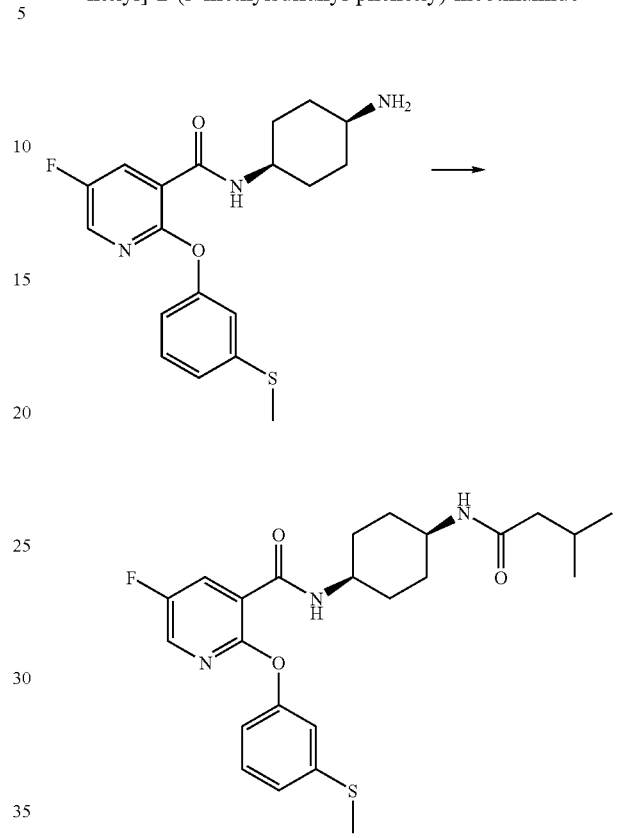

N-(cis-4-Amino-cyclohexyl)-5-fluoro-2-(3-methylsulfanyl-phenoxy)-nicotinamide hydrochloride (100 mg, 0.243 mmol) was dissolved in dimethylformamide (1 ml) and triethylamine (100 µl, 0.729 mmol) was added followed by 3-methylbutyric acid (32 µl, 0.291 mmol), 1-(3-dimethylaminopropyl)-3-ethylcarbodiimide hydrochloride (56 mg, 0.291 mmol) and 1-hydroxybenzotriazole (39 mg, 0.291 mmol). The reaction was stirred under nitrogen at room temperature for 64 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over MgSO$_4$ and the solvent was removed under reduced pressure. The residue was triturated with diethylether (5 ml) to give 5-Fluoro-N-[cis-4-(3-methyl-butyrylamino)-cyclohexyl]-2-(3-methylsulfanyl-phenoxy)-nicotinamide (112 mg) as a white solid.

$^1$H NMR (400 MHz, CDCl$_3$): δ=8.36–8.40 (1H, dd), 8.05–8.07 (1H, d), 7.98–8.03 (1H, d), 7.35–7.41 (1H, t), 7.16–7.20 (1H, d), 7.03–7.04 (1H, m), 6.87–6.93 (1H, m), 5.11–5.18 (1H, d), 4.17–4.25 (1H, brs), 3.86–3.96 (1H, m), 2.51 (3H, s), 2.00–2.09 (1H, m), 1.97–2.00 (2H, d), 1.71–1.85 (6H, m), 1.31–1.43 (2H, m), 0.90–0.95 (6H, d) ppm. LRMS (electrospray): m/z [M+H]$^+$ 460. Anal. Found C, 62.34; H, 6.58; N, 9.07. C$_{24}$H$_{30}$FN$_3$O$_3$S. 0.15 mol H$_2$O requires C, 62.36; H, 6.61; N, 9.09%.

EXAMPLE 80

5-Fluoro-N-{cis-4-[(1-methyl-cyclopropanecarbonyl)-amino]-cyclohexyl}-2-(3-methylsulfanyl-phenoxy)-nicotinamide

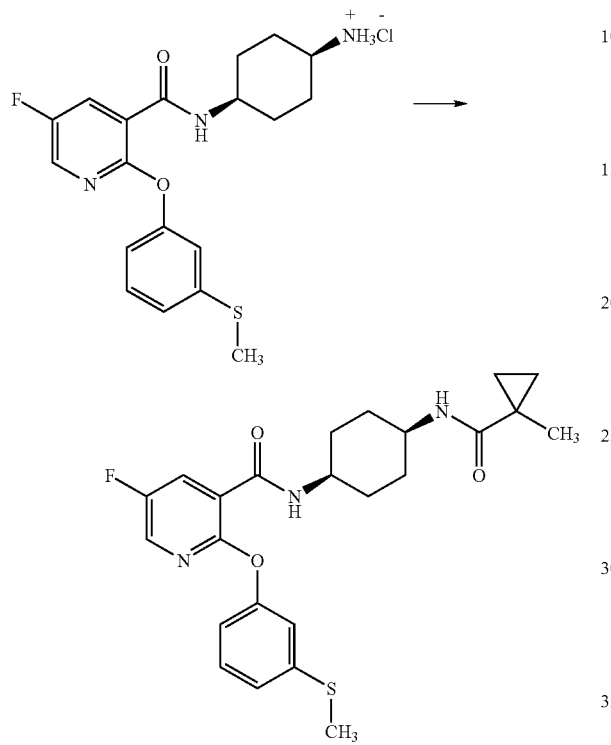

N-(cis-4-Amino-cyclohexyl)-5-fluoro-2-(3-methylsulfanyl-phenoxy)-nicotinamide hydrochloride (100 mg, 0.243 mmol) was dissolved in dimethylformamide (1 ml) and triethylamine (100 μl, 0.729 mmol) was added followed by 1-methylcyclopropanecarboxylic acid (29 mg, 0.291 mmol), 1-(3-dimethylaminopropyl)-3-ethylcarbodiimide hydrochloride (56 mg, 0.291 mmol) and 1-hydroxybenzotriazole (39 mg, 0.291 mmol). The reaction was stirred under nitrogen at room temperature for 64 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over MgSO$_4$ and the solvent was removed under reduced pressure. The residue was triturated with diethylether (5 ml) to give 5-Fluoro-N-{cis-4-[(1-methyl-cyclopropanecarbonyl)-amino]-cyclohexyl}-2-(3-methylsulfanyl-phenoxy)-nicotinamide (109 mg) as a white solid.

$^1$H NMR (400 MHz, CDCl$_3$): δ=8.36–8.40 (1H, dd), 8.02–8.09 (2H, m), 7.36–7.41 (1H, t), 7.13–7.19 (1H, d), 7.04 (1H, s), 6.90–6.95 (1H, d), 5.41–5.50 (1H, d), 4.19–4.26 (1H, m), 3.82–3.91 (1H, m), 2.49 (3H, s), 1.76–1.90 (6H, m), 1.30–1.45 (2H, m), 1.22 (3H, s), 1.14–1.18 (2H, m), 0.50–0.58 (2H, m) ppm. LRMS (electrospray): m/z [M+H]$^+$ 458. Anal. Found C, 62.76; H, 6.16; N, 9.06. C$_{24}$H$_{28}$FN$_3$O$_3$S requires C, 63.00; H, 6.17; N, 9.18%.

EXAMPLE 81

N-[cis-4-(Cyclopentanecarbonyl-amino)-cyclohexyl]-5-fluoro-2-(3-methylsulfanyl-phenoxy)-nicotinamide

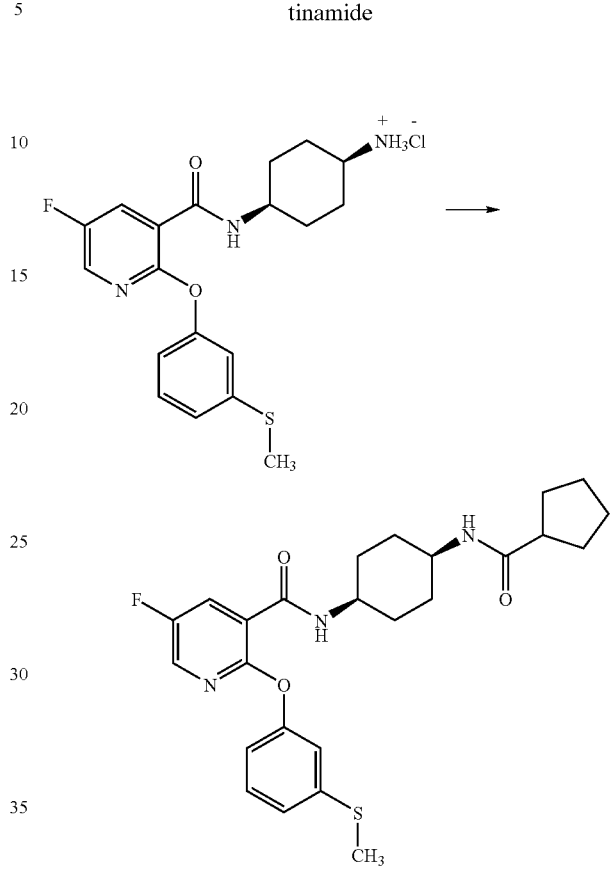

N-(cis-4-Amino-cyclohexyl)-5-fluoro-2-(3-methylsulfanyl-phenoxy)-nicotinamide hydrochloride (100 mg, 0.243 mmol) was dissolved in dimethylformamide (1 ml) and triethylamine (100 μl, 0.729 mmol) was added followed by cyclopentanecarboxylic acid (32 μl, 0.291 mmol), 1-(3-dimethylaminopropyl)-3-ethylcarbodiimide hydrochloride (56 mg, 0.291 mmol) and 1-hydroxybenzotriazole (39 mg, 0.291 mmol). The reaction was stirred under nitrogen at room temperature for 64 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over MgSO$_4$ and the solvent was removed under reduced pressure. The residue was triturated with diethylether (5 ml) to give N-[cis-4-(cyclopentanecarbonyl-amino)-cyclohexyl]-5-fluoro-2-(3-methylsulfanyl-phenoxy)-nicotinamide (113 mg) as a white solid.

$^1$H NMR (400 MHz, CDCl$_3$): δ=8.36–8.40 (1H, dd), 8.07–8.09 (1H, d), 7.97–8.04 (1H, d), 7.37–7.41 (1H, t), 7.17–7.20 (1H, d), 7.05 (1H, s), 6.89–6.94 (1H, d), 5.12–5.19 (1H, d), 4.18–4.25 (1H, brs), 3.84–3.92 (1H, m), 2.51 (3H, s), 2.39–2.48 (1H, m), 1.65–1.84 (12H, 2×m), 1.48–1.60 (2H, m, partially masked by solvent), 1.33–1.42 (2H, m) ppm. LRMS (electrospray): m/z [M+H]$^+$ 472. Anal. Found C, 63.44; H, 6.45; N, 8.82. C$_{25}$H$_{30}$FN$_3$O$_3$S requires C, 63.67; H, 6.41; N, 8.91%.

EXAMPLE 82

N-[cis-4-(Cyclobutanecarbonyl-amino)-cyclohexyl]-5-fluoro-2-(3-methylsulfanyl-phenoxy)-nicotinamide

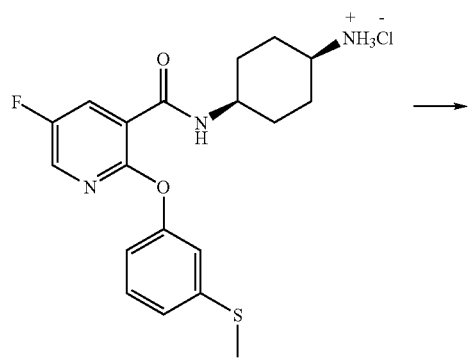

N-(cis-4-Amino-cyclohexyl)-5-fluoro-2-(3-methylsulfanyl-phenoxy)-nicotinamide hydrochloride (100 mg, 0.243 mmol) was dissolved in dimethylformamide (1 ml) and triethylamine (100 μl, 0.729 mmol) was added followed by cyclobutanecarboxylic acid (28 μl, 0.291 mmol), 1-(3-dimethylaminopropyl)-3-ethylcarbodiimide hydrochloride (56 mg, 0.291 mmol) and 1-hydroxybenzotriazole (39 mg, 0.291 mmol). The reaction was stirred under nitrogen at room temperature for 64 h and the solvent was removed under reduced pressure. The residue was partitioned between sat. sodium bicarbonate solution (5 ml) and ethyl acetate (10 ml) and the aqueous phase was extracted with ethyl acetate (3×10 ml). The combined organic extracts were washed with water (2×5 ml), brine (5 ml), dried over $MgSO_4$ and the solvent was removed under reduced pressure. The residue was triturated with diethylether (5 ml) to give N-[cis-4-(cyclobutanecarbonyl-amino)-cyclohexyl]-5-fluoro-2-(3-methylsulfanyl-phenoxy)-nicotinamide (101 mg) as a white solid.

$^1$H NMR (400 MHz, $CDCl_3$): δ=8.35–8.39 (1H, dd), 8.06–8.08 (1H, d), 7.96–8.02 (1H, d), 7.37–7.41 (1H, t), 7.16–7.20 (1H, d), 7.04 (1H, s), 6.88–6.94 (1H, d), 5.00–5.10 (1H, d), 4.17–4.26 (1H, brs), 3.83–3.95 (1H, m), 2.84–2.96 (1H, quin), 2.51 (3H, s), 2.03–2.28 (4H, 2×m), 1.68–1.98 (8H, 2×m), 1.32–1.42 (2H, m) ppm. LRMS (electrospray): m/z [M+H]$^+$ 458. Anal. Found C, 62.80; H, 6.16; N, 9.13. $C_{24}H_{28}FN_3O_3S$ requires C, 63.00; H, 6.17; N, 9.18%.

EXAMPLE 83

2-(3-Ethylsulfanyl-phenoxy)-5-fluoro-N-[cis-4-(2-methoxy-acetylamino)-cyclohexyl]-nicotinamide

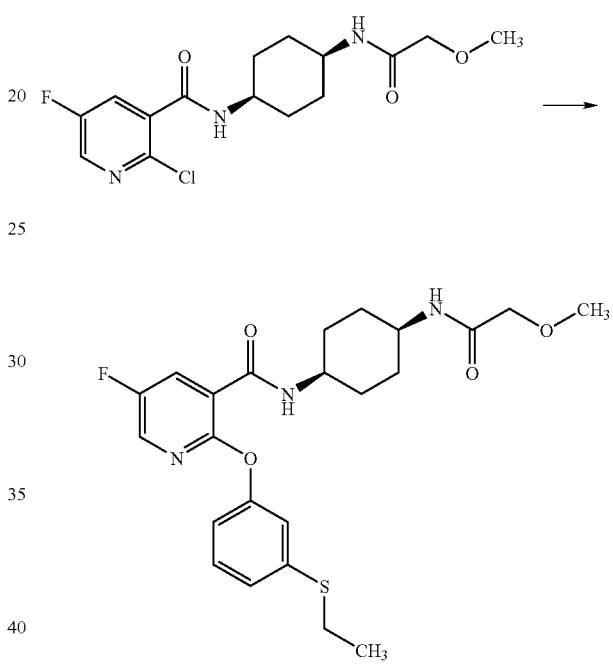

2-Chloro-5-fluoro-N-[cis-4-(2-methoxy-acetylamino)-cyclohexyl]-nicotinamide (110 mg, 0.32 mmol), 3-ethylsulfanyl-phenol (54 mg, 0.35 mmol) and caesium carbonate (156 mg, 0.48 mmol) were suspended in dimethylformamide (2 ml) and the reaction was heated to 55° C. and stirred at this temperature under nitrogen for 18 h. The reaction was quenched with sat. ammonium chloride solution (1 ml) and water (1 ml) and the organic phase was collected by passing the mixture through a chemelute cartridge, washing with ethyl acetate (20 ml). The solvent was removed under reduced pressure and the residue was triturated with diethylether (5 ml) to give 2-(3-ethylsulfanyl-phenoxy)-5-fluoro-N-[cis-4-(2-methoxy-acetylamino)-cyclohexyl]-nicotinamide (57 mg) as an off-white solid.

$^1$H NMR (400 MHz, $CDCl_3$): δ=8.35–8.39 (1H, dd), 8.04–8.06 (1H, d), 7.94–8.07 (1H, d), 7.34–7.39 (1H, t), 7.20–7.24 (1H, d), 7.08–7.10 (1H, d), 6.93–6.97 (1H, dd), 6.30–6.38 (1H, d), 4.17–4.25 (1H, m), 3.89–3.99 (1H, m), 3.82 (2H, s), 3.38 (3H, s), 2.93–3.00 (2H, quart), 1.73–1.87 (6H, 2×m), 1.43–1.55 (2H, m, partially masked by solvent), 1.33–1.38 (3H, t) ppm. LRMS (electrospray): m/z [M+Na]$^+$ 484, [M−H]$^+$ 460.

EXAMPLE 84

2-(3-Ethylsulfanyl-phenoxy)-5-fluoro-N-[cis-4-(3-hydroxy-2,2-dimethyl-propionylamino)-cyclohexyl]-nicotinamide

EXAMPLE 85

2-(3-Ethylsulfanyl-phenoxy)-5-fluoro-N-[trans-4-(3-hydroxy-2,2-dimethyl-propionylamino)-cyclohexyl]-nicotinamide

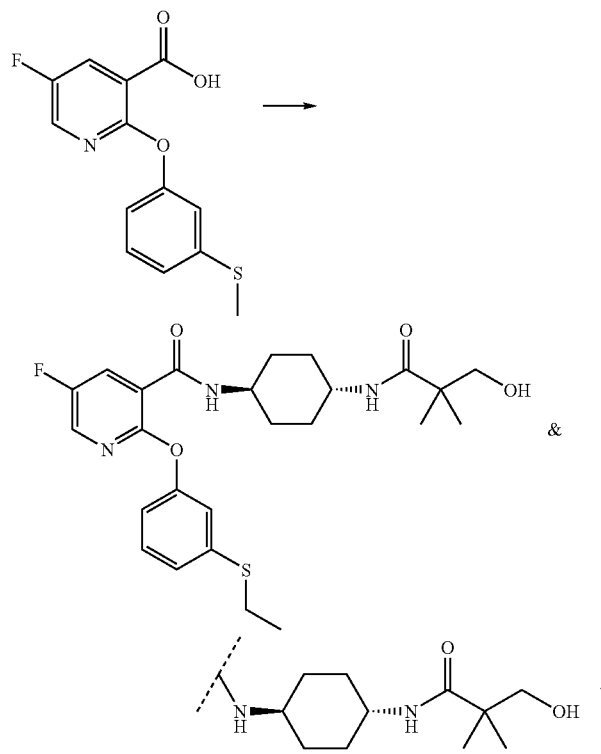

2-(3-Ethylsulfanyl-phenoxy)-5-fluoro-nicotinic acid (150 mg, 0.51 mmol) was added to a solution of N-(4-amino-cyclohexyl)-3-hydroxy-2,2-dimethyl-propionamide hydrochloride (80:20 cis:trans, 135 mg, 0.54 mmol) and triethylamine (0.21 ml, 1.5 mmol) in dimethylformamide (3 ml) under nitrogen at room temperature. 1-(3-Dimethylamino-propyl)-3-ethylcarbodiimide hydrochloride (108 mg, 0.56 mmol) followed by 1-hydroxybenzotriazole (76 mg, 0.56 mmol) were then added and the reaction was stirred at room temperature for 20 h. The mixture was concentrated under reduced pressure, partitioned between ethyl acetate (20 ml) and water (20 ml) and the organic phase was removed, dried over $MgSO_4$ and concentrated under reduced pressure. The residue was purified by flash column chromatography on a silica gel eluting with a solvent gradient of dichloromethane:methanol (95:5) and the product was purified by preparative HPLC to give two products.

Product 1: 2-(3-ethylsulfanyl-phenoxy)-5-fluoro-N-[cis-4-(3-hydroxy-2,2-dimethyl-propionylamino)-cyclohexyl]-nicotinamide (46 mg), off-white foam $^1$H NMR (400 MHz, $CDCl_3$): δ=8.33–8.38 (1H, dd), 8.03–8.05 (1H, d), 7.97–8.03 (1H, d), 7.35–7.40 (1H, t), 7.19–7.23 (1H, d), 7.08–7.09 (1H, d), 6.94–6.98 (1H, dd), 6.07–6.17 (1H, d), 4.17–4.24 (1H, brs), 3.80–3.91 (1H, m), 3.49 (2H, s), 2.95–3.00 (2H, quart), 1.71–1.86 (6H, m), 1.31–1.45 (5H, m+t), 1.29–1.32 (1H, d), 1.10 (6H, s) ppm. LRMS (electrospray): m/z $[M+Na]^+$ 512, $[M-H]^+$ 488. Anal. Found C, 60.83; H, 6.52; N, 8.41. $C_{25}H_{32}FN_3O_4S$. 0.25 mol $H_2O$ requires C, 60.77; H, 6.63; N, 8.50%.

Product 2: 2-(3-ethylsulfanyl-phenoxy)-5-fluoro-N-[trans-4-(3-hydroxy-2,2-dimethyl-propionylamino)-cyclohexyl]-nicotinamide (10 mg), off-white foam $^1$H NMR (400 MHz, $CDCl_3$): δ=8.31–8.36 (1H, dd), 8.02–8.04 (1H, d), 7.69–7.75 (1H, d), 7.34–7.39 (1H, t), 7.19–7.23 (1H, d), 7.04–7.05 (1H, d), 6.91–6.96 (1H, dd), 5.87–5.95 (1H, d), 3.93–4.01 (1H, m), 3.72–3.82 (1H, m), 3.52 (2H, s), 2.92–3.01 (3H, m), 2.12–2.19 (2H, d), 1.99–2.06 (2H, d), 1.23–1.42 (7H, m+t), 1.14 (6H, s) ppm. LRMS (electrospray): m/z $[M+Na]^+$ 512, $[M-H]^+$ 488.

EXAMPLE 86

5-Fluoro-2-(3-methylsulfanyl-phenoxy)-N-[cis-4-(2-oxo-pyrrolidin-1-yl)-cyclohexyl]-nicotinamide

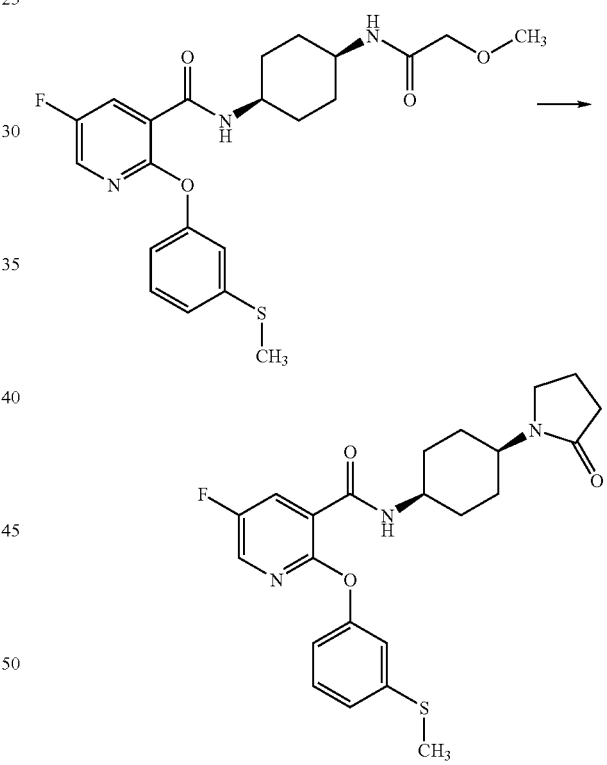

N-[4-(4-Chloro-butyrlyamino)-cyclohexyl]-5-fluoro-2-(3-methylsulfanyl-phenoxy)-nicotinamide (244 mg, 0.486 mmol) was dissolved in N-methylpyrrolidine (5 ml) under nitrogen at room temperature and sodium hydride (60% dispersion in mineral oil, 49 mg, 1.21 mmol) was added. The reaction was stirred at room temperature for 18 h and quenched with water (10 ml) then extracted with ethyl acetate (5×10 ml). The combined organic extracts were washed with water (3×5 ml), brine (5 ml), dried over $MgSO_4$ and the solvent was removed under reduced pressure. The residue was purified by flash column chromatography on silica gel eluting with dichloromethane:methanol (95:5, by volume) and the product was triturated with diethylether (2 ml) to give 5-Fluoro-2-(3-methylsulfanyl-phenoxy)-N-[cis-4-(2-oxo-pyrrolidin-1-yl)-cyclohexyl]-nicotinamide (55 mg) as a white solid.

$^1$H NMR (400 MHz, CDCl$_3$): δ=8.35–8.39 (1H, dd), 8.20–8.26 (1H, d), 8.04–8.06 (1H, d), 7.32–7.38 (1H, t), 7.13–7.18 (1H, d), 7.04 (1H, s), 6.88–6.92 (1H, d), 4.35–4.41 (1H, m), 3.94–4.03 (1H, m), 2.80–2.87 (2H, t), 2.48 (3H, s), 2.25–2.31 (2H, t), 1.96–2.03 (2H, d), 1.66–1.85 (4H, m), 1.57–1.66 (2H, d), 1.39–1.50 (2H, m) ppm. LRMS (electrospray): m/z [M+H]$^+$ 444, [M+Na]$^+$ 466. Anal. Found C, 62.13; H, 5.90; N, 9.46. C$_{23}$H$_{26}$FN$_3$O$_3$S requires C, 62.28; H, 5.91; N, 9.47%.

EXAMPLE 87 cis-N-{4-[(5-Chloropentanoyl)amino]cyclohexyl}-5-fluoro-2-[3-(methylsulfanyl)phenoxy]nicotinamide

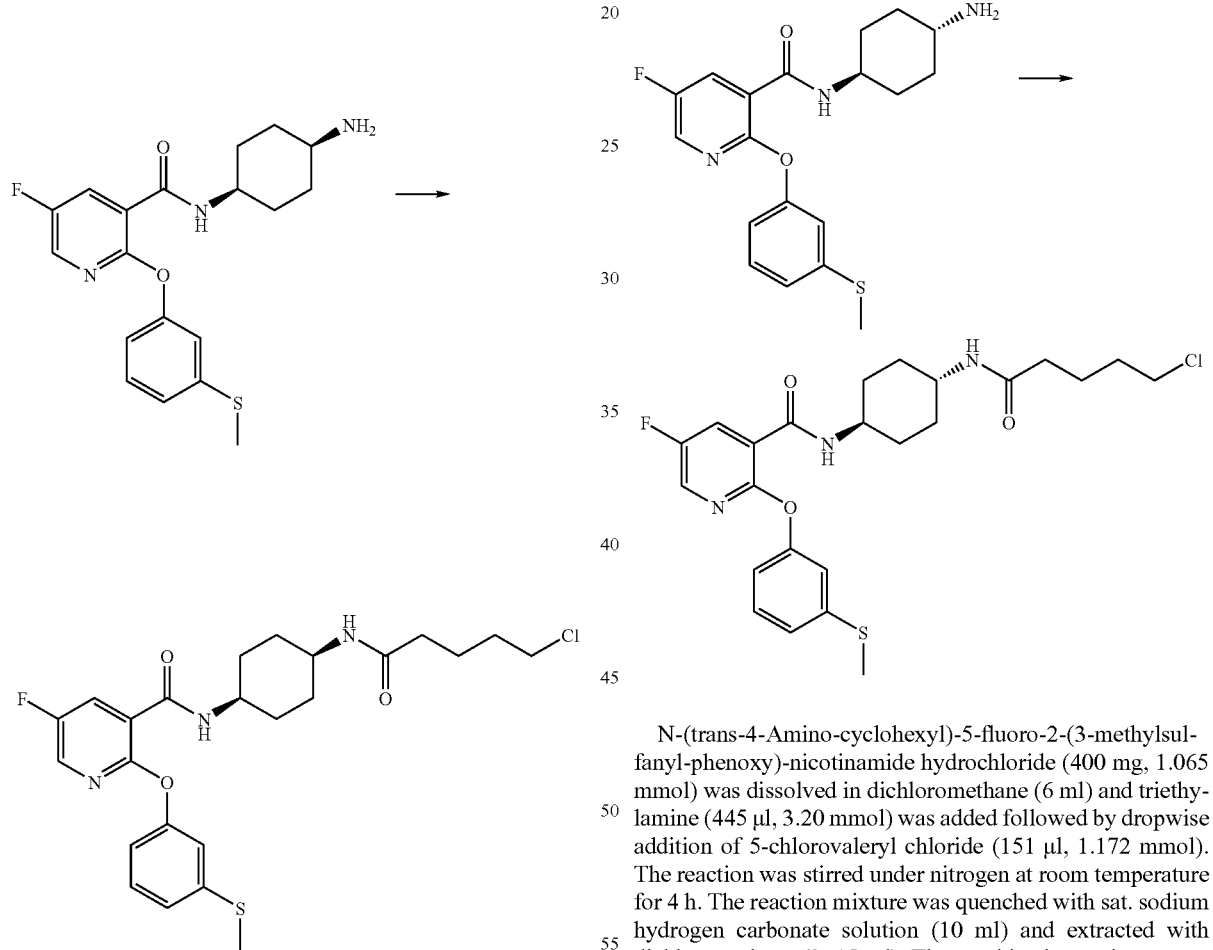

N-(cis-4-Amino-cyclohexyl)-5-fluoro-2-(3-methylsulfanyl-phenoxy)-nicotinamide hydrochloride (200 mg, 0.486 mmol) was dissolved in dichloromethane (3 ml) and triethylamine (203 μl, 1.46 mmol) was added followed by dropwise addition of 5-chlorovaleryl chloride (69 μl, 0.535 mmol). The reaction was stirred under nitrogen at room temperature for 2 h. The reaction mixture was quenched with sat. sodium hydrogen carbonate solution (5 ml) and extracted with dichloromethane (3×10 ml). The combined organic extracts were dried over MgSO$_4$ and the solvent was removed under reduced pressure to give the title compound (259 mg) as a white solid.

$^1$H NMR (400 MHz, CDCl$_3$): δ=8.34–8.37 (1H, dd), 8.08–8.09 (1H, d), 7.96–8.01 (1H, d), 7.36–7.40 (1H, t), 7.16–7.18 (1H, d), 7.05 (1H, s), 6.89–6.91 (1H, dd), 5.12–5.17 (1H, d), 4.18–4.27 (1H, m), 3.85–3.95 (1H, m), 3.52–3.55 (2H, t), 2.51 (3H, s), 2.14–2.17 (2H, t), 1.72–1.89 (10H, m), 1.32–1.45 (2H, m) ppm. LRMS (thermospray): m/z [M+Na]$^+$ 516.

EXAMPLE 88 trans-N-{4-[(5-Chloropentanoyl)amino]cyclohexyl}-5-fluoro-2-[3-(methylsulfanyl)phenoxy]nicotinamide

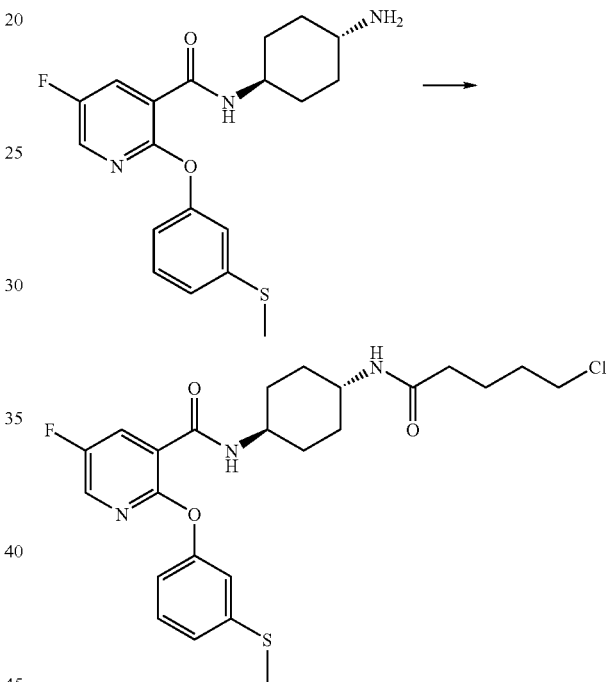

N-(trans-4-Amino-cyclohexyl)-5-fluoro-2-(3-methylsulfanyl-phenoxy)-nicotinamide hydrochloride (400 mg, 1.065 mmol) was dissolved in dichloromethane (6 ml) and triethylamine (445 μl, 3.20 mmol) was added followed by dropwise addition of 5-chlorovaleryl chloride (151 μl, 1.172 mmol). The reaction was stirred under nitrogen at room temperature for 4 h. The reaction mixture was quenched with sat. sodium hydrogen carbonate solution (10 ml) and extracted with dichloromethane (3×15 ml). The combined organic extracts were dried over MgSO$_4$ and the solvent was removed under reduced pressure. The residue was purified by column chromatography, eluting with 95:5 dichloromethane/methanol, clean fractions were combined and the solvent was removed under reduced pressure to obtain the title compound (220 mg) as a white solid.

$^1$H NMR (400 MHz, CDCl$_3$): δ=8.36 (1H, dd), 8.04 (1H, m), 7.74 (1H, d), 7.36 (1H, m), 7.16 (1H, dd), 7.02 (1H, m), 6.90 (1H, dd), 5.30 (1H, d), 3.98 (1H, m), 3.78 (1H, m), 2.56 (2H, m), 2.48 (3H, s), 2.16 (4H, m), 2.02 (2H, bd), 1.80 (4H, m), 1.34 (4H, m) ppm.

EXAMPLE 89

5-Fluoro-2-[3-(methylsulfanyl)phenoxy]-N-[trans-4-(2-oxo-1-piperidinyl)cyclohexyl]nicotinamide

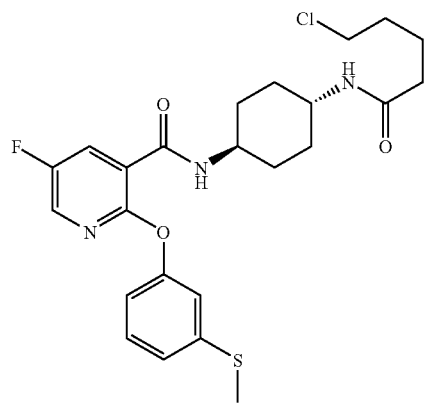

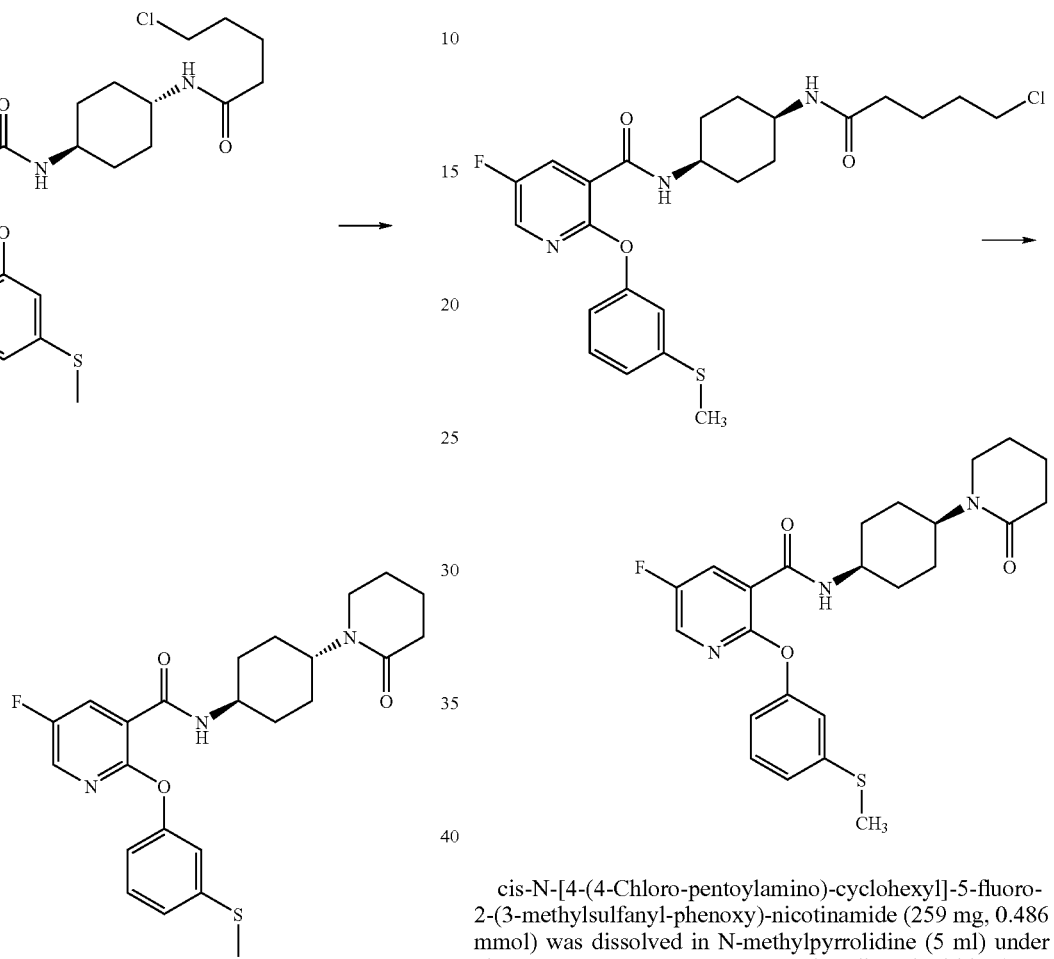

trans-N-{4-[(5-Chloropentanoyl)amino]cyclohexyl}-5-fluoro-2-[3-(methylsulfanyl)phenoxy]nicotinamide (220 mg, 0.405 mmol) was dissolved in dimethylformamide (5 ml) sodium hydride 60% dispersion in oil (41 mg, 1.01 mmol) was added. The reaction was stirred under nitrogen at room temperature for 18 h and the solvent was removed under reduced pressure. The residue was partitioned between sat. sodium hydrogen carbonate solution (10 ml) and dichloromethane (15 ml) and the aqueous phase was extracted with dichloromethane (3×15 ml). The combined organic extracts were washed with water (2×10 ml), brine (10 ml), dried over MgSO$_4$ and the solvent was removed under reduced pressure. The residue was triturated with diethylether (5 ml) to give the title compound (78 mg) as a white solid.

$^1$H NMR (400 MHz, CDCl$_3$): δ=7.46 (1H, m), 7.28 (1H, m), 7.20 (3H, m), 7.02 (1H, bd), 4.60 (1H, m), 4.20 (1H, m), 3.28 (2H, t), 2.44 (3H, s), 2.32 (2H, t), 2.10 (2H, bd), 1.76 (8H, m), 1.38 (2H, m) ppm. LRMS (thermospray): m/z [M+H]$^+$ 458. Anal. Found C, 62.61; H, 6.78; N, 8.23. C$_{24}$H$_{28}$FN$_3$O$_3$S. 0.65 mol EtOAc.0.25 mol H$_2$O requires C, 62.61; H, 6.91; N, 8.24%.

EXAMPLE 90

5-Fluoro-2-(3-methylsulfanyl-phenoxy)-N-[cis-4-(2-oxo-piperidin-1-yl)-cyclohexyl]-nicotinamide cis-N-[4-(4-Chloro-pentoylamino)-cyclohexyl]-5-fluoro-2-(3-methylsulfanyl-phenoxy)-nicotinamide (259 mg, 0.486 mmol) was dissolved in N-methylpyrrolidine (5 ml) under nitrogen at room temperature and sodium hydride (60% dispersion in mineral oil, 49 mg, 1.21 mmol) was added. The reaction was stirred at room temperature for 18 h and quenched with water (10 ml) then extracted with ethyl acetate (5×10 ml). The combined organic extracts were washed with water (3×5 ml), brine (5 ml), dried over MgSO$_4$ and the solvent was removed under reduced pressure. The residue was purified by flash column chromatography on silica gel eluting with dichloromethane:methanol (97:3, by volume) and the product was triturated with diethylether (2 ml) to give 5-Fluoro-2-(3-methylsulfanyl-phenoxy)-N-[cis-4-(2-oxo-piperidin-1-yl)-cyclohexyl]-nicotinamide (69 mg) as a white solid.

$^1$H NMR (400 MHZ, CDCl$_3$): δ=8.34–8.40 (1H, dd), 8.21–8.28 (1H, d), 8.03–8.09 (1H, d), 7.32–7.38 (1H, t), 7.13–7.19 (1H, d), 7.04 (1H, s), 6.89–6.95 (1H, d), 4.50–4.61 (1H, m), 4.37–4.42 (1H, m), 2.67–2.75 (2H, t), 2.47 (3H, s), 2.28–2.37 (2H, t), 1.95–2.05 (2H, d), 1.70–1.82 (2H, t), 1.60–1.70 (2H, m), 1.42–1.60 (6H, m, partially masked by solvent) ppm. LRMS (electrospray): m/z [M+H]$^+$ 458, [M+Na]$^+$ 480, [M–H]$^+$ 456. Anal. Found C, 62.77; H, 6.11; N, 9.06. C$_{24}$H$_{28}$FN$_3$O$_3$S. 0.1 mol H$_2$O requires C, 62.75; H, 6.19; N, 9.15%.

EXAMPLE 91

N-{cis-4-[(Cyclopropylacetyl)amino]cyclohexyl}-2-[3-(methylsulfanyl)phenoxy]nicotinamide

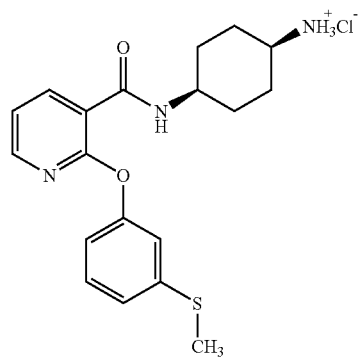

N-(cis-4-Aminocyclohexyl)-2-[3-(methylsulfanyl)phenoxy]nicotinamide hydrochloride (100 mg, 0.25 mmol) was dissolved in dimethylformamide (1.7 ml) and triethylamine (106 μl, 0.76 mmol) was added followed by cyclopropylacetic acid (28 mg, 0.25 mmol), 1-(3-dimethylaminopropyl)-3-ethylcarbodiimide hydrochloride (97 mg, 0.51 mmol) and 1-hydroxybenzotriazole (38 mg, 0.28 mmol). The reaction was stirred under nitrogen at room temperature for 18 h and the solvent was removed under reduced pressure. The residue was suspended in saturated aqueous sodium bicarbonate solution (5 ml) and extracted with ethyl acetate (3×10 ml). The organic phase was washed with brine (5 ml), dried over $MgSO_4$ and the solvent was removed under reduced pressure. The residue was triturated with diethyl ether to give N-{cis-4-[(cyclopropylacetyl)amino]cyclohexyl}-2-[3-(methylsulfanyl)phenoxy]nicotinamide (99 mg) as a white solid.

$^1$H NMR (400 MHz, CDCl3): δ=8.56–8.62 (1H, m), 8.10–8.16 (1H, m), 7.88–8.00 (1H, m), 7.29–7.39 (1H, t), 7.10–7.20 (2H, m), 7.06 (1H, s), 6.86–6.94 (1H, m), 5.55–5.56 (1H, m), 4.18–4.30 (1H, m), 3.84–3.96 (1H, m), 2.46 (3H, s), 2.02–2.10 (2H, m), 1.68 –1.92 (6H, m), 1.33–1.46 (2H, m), 1.78–1.90 (1H, m), 0.44–0.56 (2H, m), 0.08–0.20 (2H, m) ppm. LRMS (thermospray): m/z [M+H]$^+$ 440. Anal. Found C, 65.03; H, 6.66; N, 9.69. $C_{24}H_{29}N_3O_3S$ 0.12 mol H2O requires C, 65.26; H, 6.67; N, 9.51%.

EXAMPLE 92

5-Fluoro-N-{cis-4-[(3-hydroxy-2,2-dimethylpropanoyl)amino]cyclohexyl}-2-[3-(methylsulfanyl)phenoxy]nicotinamide

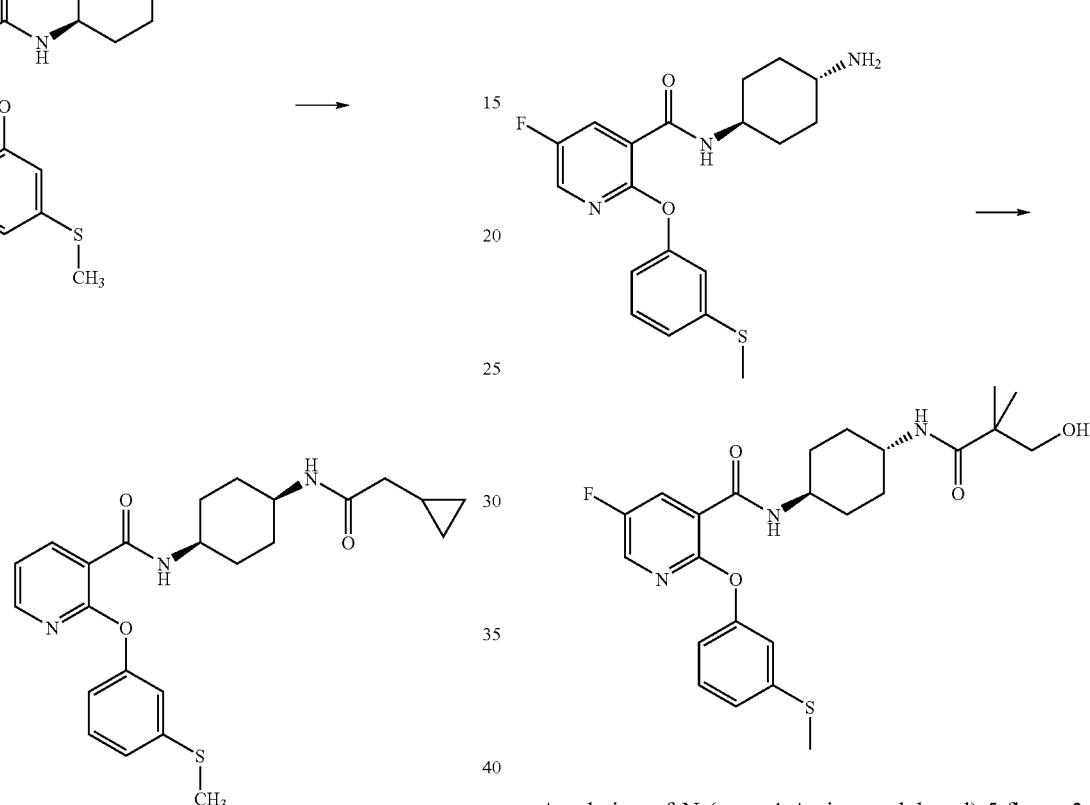

A solution of N-(trans-4-Amino-cyclohexyl)-5-fluoro-2-(3-methylsulfanyl-phenoxy)-nicotinamide hydrochloride (250 mg, 0.666 mmol) in dimethylformamide (5 ml) and triethylamine (278 μl, 2.0 mmol) was treated with 2,2-dimethyl-3-hydroxy propanoic acid (86 mg, 0.73 mmol), 1-(3-dimethylaminopropyl)-3-ethylcarbodiimide hydrochloride (99 mg, 0.73 mmol) and 1-hydroxybenzotriazole (114 mg, 0.73 mmol). The reaction mixture was stirred under nitrogen at room temperature for 36 h and the solvent was removed under reduced pressure. The residue was partitioned between sat. sodium hydrogen carbonate solution (10 ml) and ethyl acetate (15 ml) and the aqueous phase was extracted with ethyl acetate (3×15 ml). The combined organic extracts were washed with water (2×10 ml), brine (10 ml), dried over $MgSO_4$ and the solvent was removed under reduced pressure. Trituration of the residue with diethylether (5 ml) gave the title compound (270 mg) as a white solid.

$^1$H NMR (400 MHz, CDCl$_3$): δ=8.32 (1H, m), 8.04 (1H, m), 7.72 (1H, d), 7.36 (1H, t), 7.18 (1H, d), 7.00 (1H, t), 6.88 (1H, dd), 5.86 (1H, bd), 3.98 (1H, m), 3.78 (1H, m), 2.50 (3H, s), 2.10 (2H, m), 2.08 (4H, dd), 1.36 (4H, m), 1.18 (6H, s) ppm. LRMS (thermospray): m/z [M+H]$^+$ 476. Anal. Found C, 60.08; H, 6.43; N, 8.66. $C_{24}H_{30}FN_3O_4S$. 0.25 mol $H_2O$ requires C, 60.04; H, 6.40; N, 8.75%.

EXAMPLE 93

N-{Trans-4-[({5-fluoro-2-[3-(methylsulfanyl)phenoxy]-3-pyridinyl}carbonyl)amino]cyclohexyl}-2-pyridinecarboxamide

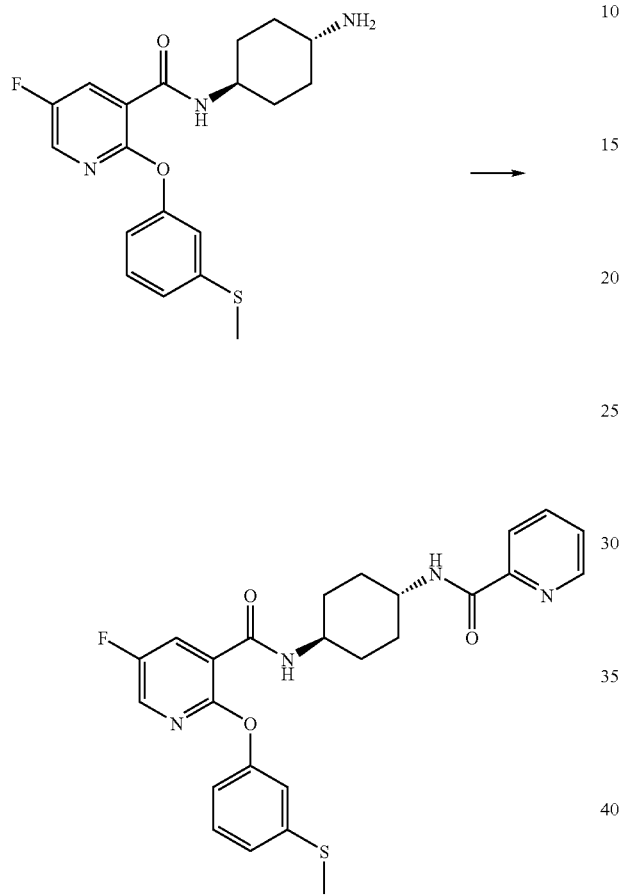

A solution of N-(trans-4-amino-cyclohexyl)-5-fluoro-2-(3-methylsulfanyl-phenoxy)-nicotinamide hydrochloride (250 mg, 0.666 mmol) in dimethylformamide (5 ml) and triethylamine (278 µl, 2.0 mmol) was treated with 2-pyridine carboxylic acid (90 mg, 0.73 mmol), 1-(3-dimethylaminopropyl)-3-ethylcarbodiimide hydrochloride (141 mg, 0.73 mmol) and 1-hydroxybenzotriazole (99 mg, 0.73 mmol). The reaction was stirred under nitrogen at room temperature for 18 h and the solvent was removed under reduced pressure. The residue was partitioned between sat. sodium hydrogen carbonate solution (10 ml) and ethyl acetate (15 ml) and the aqueous phase was extracted with ethyl acetate (3×15 ml). The combined organic extracts were washed with water (2×10 ml), brine (10 ml), dried over MgSO$_4$ and the solvent was removed under reduced pressure to give the title compound (175 mg) as a white solid.

$^1$H NMR (400 MHz, CDCl$_3$): δ=8.58 (1H, d), 8.32 (1H, m), 8.24 (2H, m), 8.02 (1H, m), 7.96 (1H, dd), 7.74 (1H, m), 7.50 (1H, m), 7.36 (1H, m), 7.16 (1H, d), 7.00 (1H, m), 6.86 (1H, dd), 4.04 (2H, m), 2.52 (3H, s), 2.20 (4H, m), 1.58 (4H, m) ppm. LRMS (thermospray): m/z [M+H]$^+$ 481. Anal. Found C, 62.13; H, 5.30; N, 11.32. C$_{25}$H$_{25}$FN$_4$O$_3$S. 0.15 mol H$_2$O requires C, 62.14; H, 5.28; N, 11.59%.

EXAMPLE 94

N-[cis-4-(Acetylamino)cyclohexyl]-2-[3-(methylsulfonyl)phenoxy]nicotinamide

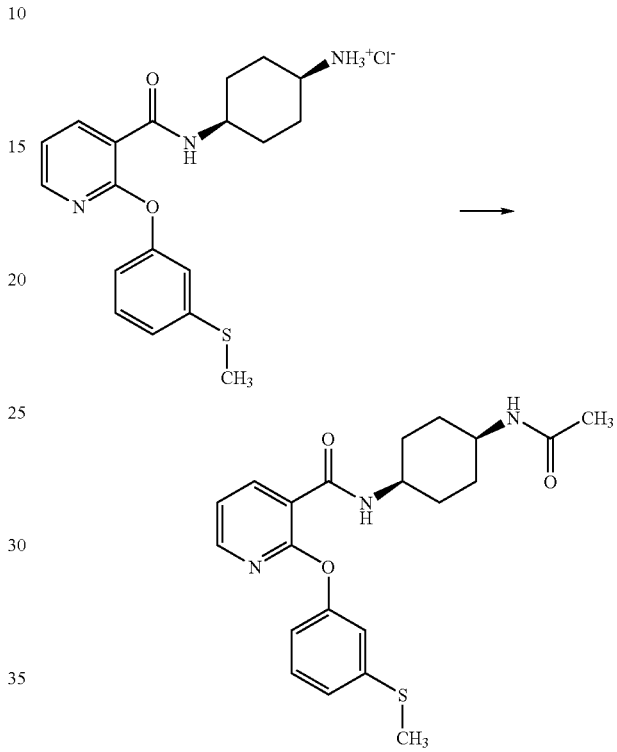

N-(cis-4-Aminocyclohexyl)-2-[3-(methylsulfanyl)phenoxy]nicotinamide hydrochloride (100 mg, 0.25 mmol) was dissolved in dimethylformamide (1.7 ml) and triethylamine (142 µl, 1.0 mmol) was added followed by acetic acid (16 mg, 0.25 mmol), 1-(3-dimethylaminopropyl)-3-ethylcarbodiimide hydrochloride (97 mg, 0.51 mmol) and 1-hydroxybenzotriazole (38 mg, 0.28 mmol). The reaction was stirred under nitrogen at room temperature for 18 h and the solvent was removed under reduced pressure. The residue was partitioned between water (25 ml) and a mixture of diethyl ether (25 ml) and ethyl acetate (50 ml). The organic phase was washed with brine (5 ml), dried over MgSO$_4$ and the solvent was removed under reduced pressure. The residue was purified by flash column chromatography using dichloromethane:methanol:0.880 ammonia (95:5:0.5) as eluant to give a white solid which was triurated with diethyl ether to give N-[cis-4-(acetylamino)cyclohexyl]-2-[3-(methylsulfanyl)phenoxy]nicotinamide (47 mg) as a white solid.

1H NMR (400 MHz, CDCl3): δ=8.55–8.62 (1H, d), 8.10–8.18 (1H, d), 8.06–8.18 (1H, m), 7.33–7.40 (1H, t), 7.10–7.22 (1H, m), 7.06 (1H, s), 6.88–6.95 (1H, m), 5.08–5.20 (1H, m), 4.15–4.26 (1H, m), 3.82–3.93 (1H, m), 2.50 (3H, s), 1.91 (3H, s), 1.66–1.68 (4H, m), 1.28–1.45 (4H, m) ppm. LRMS (thermospray): m/z [M+Na]$^+$ 422. Anal. Found C, 62.93; H, 6.30; N, 10.50. C$_{21}$H$_{25}$N$_3$O$_3$S requires C, 63.13; H, 6.31; N, 10.52%.

EXAMPLE 95 cis-4-[({5-Fluoro-2-[3-(methylsulfanyl)phenoxy]-3-pyridinyl}carbonyl)amino]cyclohexanecarboxylic acid

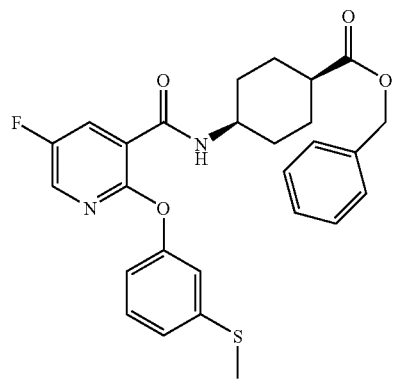

N-(cis-4-Benzylcarboxylate-cyclohexyl)-5-fluoro-2-(3-methylsulfanyl-phenoxy)-nicotinamide (290 mg, 0.586 mmol) was dissolved in a solution of formic acid:methanol (4.4:95.6, by volume; 5 ml) and dimethylformamide (2 ml). This was added to palladium black (300 mg) in a solution of formic acid:methanol (4.4:95.6, by volume; 20 ml) and the reaction stirred under nitrogen at room temperature for 18 hrs. The reaction was filtered through Arbocel, washed with methanol (5×20 ml) and the solvent removed under reduced pressure. The residue was partitioned between sodium hydroxide solution (1M, 5 ml) and diethylether (5 ml) and the aqueous phase was extracted with diethylether (2×5 ml). The aqueous layer was cooled in an iced-water bath and acidified to pH1 with concentrated hydrochloric acid (1 ml). The resulting white suspension was extracted with diethylether (5×10 ml). These combined organic extracts were washed with water (2 ml), brine (5 ml), dried over MgSO$_4$ and the solvent was removed under reduced pressure to afford the product (170 mg) as a white solid.

$^1$H NMR (400 MHz, CDCl$_3$): δ=8.33–8.36 (1H, dd), 8.05–8.06 (1H, d), 7.99–7.97 (1H, d), 7.31–7.35 (1H, t), 7.13–7.15 (1H, d), 7.03 (1H, s), 6.89–6.91 (1H, d), 4.18–4.25 (1H, m), 2.53–2.60 (1H, m), 2.48 (3H, s), 1.69–1.97 (8H, m) ppm. LRMS (thermospray): m/z [M+H]$^+$ 405.2. Anal. Found C, 59.45; H, 5.38; N, 6.85. C$_{20}$H$_{21}$FN$_2$O$_4$S. requires C, 59.39; H, 5.23; N, 6.93%.

EXAMPLE 96

N-[cis-4-(2-Fluoro-benzylcarbamoyl)-cyclohexyl]-2-(4-methylsulfanyl-phenoxy)-nicotinamide

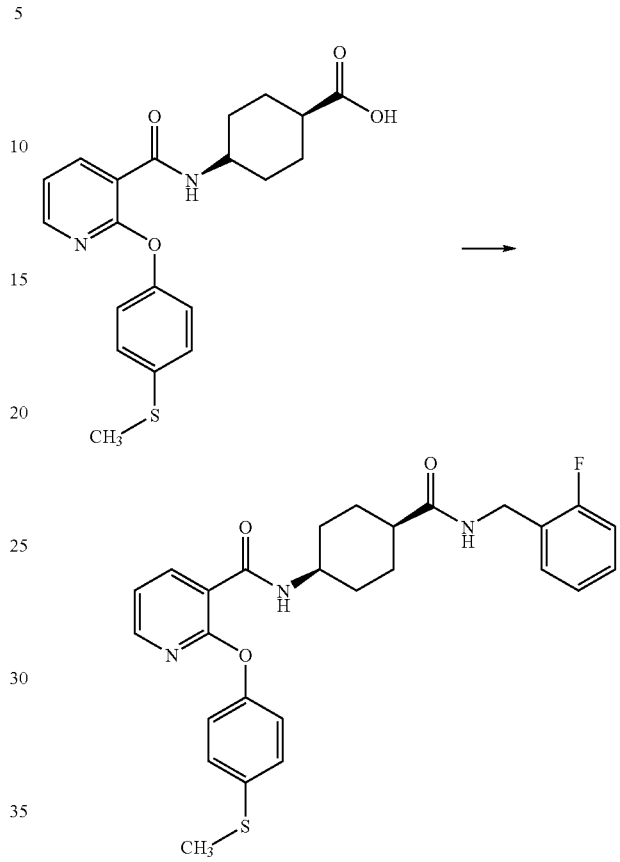

4-{cis-[2-(4-Methylsulfanyl-phenoxy)-pyridine-3-carbonyl]-amino}-cyclohexanecarboxylic acid (350 mg, 0.91 mmol) was dissolved in dimethylformamide (5 ml) and triethylamine (380 µl, 2.72 mmol) was added followed by 2-fluorobenzylamine (103 µl, 0.91 mmol), 1-(3-dimethylaminopropyl)-3-ethylcarbodiimide hydrochloride (191 mg, 1.0 mmol) and 1-hydroxybenzotriazole (135 mg, 1.0 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (4×10 ml). The combined organic extracts were washed with brine (10 ml), dried over MgSO$_4$ and the solvent was removed under reduced pressure. The residue was purified by flash column chromatography on silica gel eluting with dichloromethane:methanol:concentrated aqueous ammonia (98:2:0.2, by volume) to give N-[cis-4-(2-Fluoro-benzylcarbamoyl)-cyclohexyl]-2-(4-methylsulfanyl-phenoxy)-nicotinamide (65 mg) as an off-white solid.

$^1$H NMR (400 MHz, CDCl$_3$): δ=8.57–8.61 (1H, m), 8.19–8.22 (1H, m), 8.00–8.08 (1H, m), 7.31–7.36 (2H, d), 7.17–7.29 (2H, m, partially masked by solvent), 7.12–7.17 (3H, m), 6.98–7.09 (2H, 2xt), 5.68–5.75 (1H, m), 4.42–4.46 (2H, d), 4.23–4.32 (1H, m), 2.48 (3H, s), 2.21–2.28 (1H, m), 1.83–1.92 (2H, m), 1.68–1.80 (6H, m) ppm. LRMS (thermospray): m/z [M+H]$^+$ 494. Anal. Found C, 66.05; H, 5.78; N, 8.80. C$_{27}$H$_{28}$FN$_3$O$_5$S requires C, 65.70; H, 5.72; N, 8.51%.

EXAMPLE 97

2-(4-Methylsulfanyl-phenoxy)-N-{cis-4-[(pyridine-2-ylmethyl)-carbamoyl]-cyclohexyl}-nicotinamide

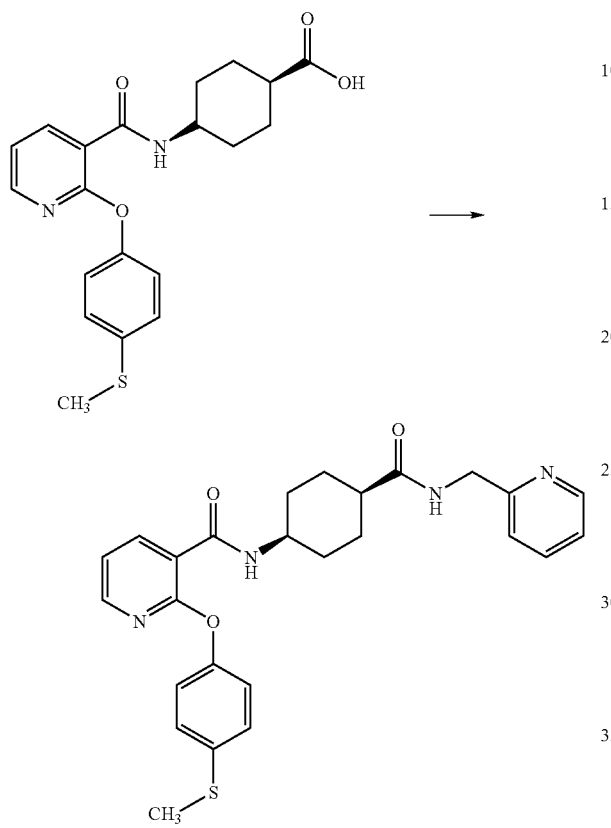

4-{cis-[2-(4-Methylsulfanyl-phenoxy)-pyridine-3-carbonyl]-amino}-cyclohexanecarboxylic acid (350 mg, 0.91 mmol) was dissolved in dimethylformamide (5 ml) and triethylamine (380 μl, 2.72 mmol) was added followed by 2-aminomethylpyridine (94 μl, 0.91 mmol), 1-(3-dimethylaminopropyl)-3-ethylcarbodiimide hydrochloride (191 mg, 1.0 mmol) and 1-hydroxybenzotriazole (135 mg, 1.0 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (4×10 ml). The combined organic extracts were washed with water (5 ml), brine (5 ml), dried over MgSO$_4$ and the solvent was removed under reduced pressure. The residue was purified by flash column chromatography on silica gel eluting with a solvent gradient of dichloromethane:methanol:concentrated aqueous ammonia (98.5:1.5:0.25 changing to 97.5:2.5:0.25 then 97:3:0.3, by volume) to give 2-(4-methylsulfanyl-phenoxy)-N-{cis-4-[(pyridine-2-ylmethyl)-carbamoyl]-cyclohexyl}-nicotinamide (305 mg) as a white solid.

$^1$H NMR (400 MHz, CDCl$_3$): δ=8.56–8.61 (1H, dd), 8.48–8.52 (1H, d), 8.08–8.11 (1H, d), 8.04–8.13 (1H, m), 7.60–7.66 (1H, m), 7.11–7.28 (7H, m, partially masked by solvent), 6.76–6.82 (1H, m), 4.47–4.52 (2H, m), 4.25–4.35 (1H, m), 2.45 (3H, s), 2.31–2.39 (1H, m), 1.87–1.98 (2H, m), 1.70–1.86 (6H, m) ppm. LRMS (thermospray): m/z [M+H]$^+$ 477. Anal. Found C, 65.70; H, 5.93; N, 11.87. C$_{26}$H$_{28}$N$_4$O$_3$S requires C, 65.52; H, 5.92; N, 11.76%.

EXAMPLE 98

5-Fluoro-N-[cis-4-(2-fluoro-benzylcarbamoyl)-cyclohexyl]-2-(3-methylsulfanyl-phenoxy)-nicotinamide

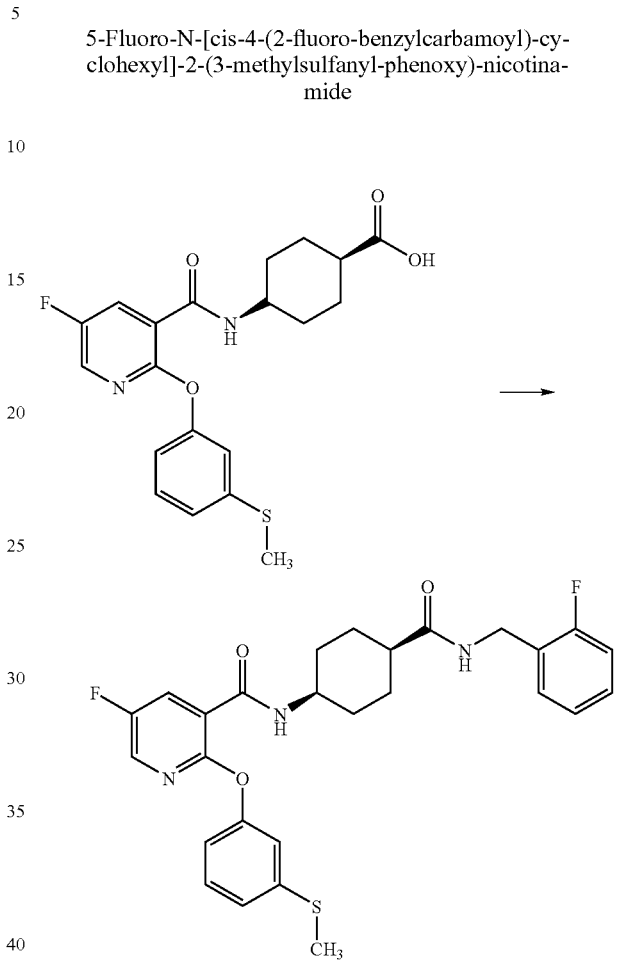

5-Fluoro-4-{cis-[2-(4-Methylsulfanyl-phenoxy)-pyridine-3-carbonyl]-amino}-cyclohexanecarboxylic acid (170 mg, 0.42 mmol) was dissolved in dimethylformamide (3 ml) and triethylamine (176 μl, 1.26 mmol) was added followed by 2-fluorobenzylamine (48 μl, 0.42 mmol), 1-(3-dimethylaminopropyl)-3-ethylcarbodiimide hydrochloride (89 mg, 0.46 mmol) and 1-hydroxybenzotriazole (63 mg, 0.46 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (2×10 ml). The combined organic extracts were washed with water (2×5 ml), brine (5 ml), dried over MgSO$_4$ and the solvent was removed under reduced pressure. The residue was purified by flash column chromatography on silica gel eluting with dichloromethane:methanol:concentrated aqueous ammonia (99:1:0.1 changing to 98:2:0.2, by volume) to give 5-Fluoro-N-[cis-4-(2-fluoro-benzylcarbamoyl)-cyclohexyl]-2-(3-methylsulfanyl-phenoxy)-nicotinamide (65 mg) as a white foam.

$^1$H NMR (400 MHz, CDCl$_3$): δ=8.32–8.36 (1H, dd), 8.01–8.06 (2H, 2×d), 7.30–7.36 (1H, t), 7.20–7.30 (2H, m), 7.10–7.15 (1H, d), 6.98–7.08 (3H, s+m), 6.90–6.95 (1H, d), 5.71–5.78 (1H, m), 4.42–4.48 (2H, d), 4.20–4.28 (1H, m), 2.48 (3H, s), 2.21–2.30 (1H, m), 1.83–1.92 (2H, m), 1.67–1.80 (6H, m) ppm. LRMS (thermospray): m/z [M+H]+ 512, [M+H]+ 529. Anal. Found C, 63.32; H, 5.28; N, 8.24. $C_{27}H_{27}F_2N_3O_5S$ requires C, 63.39; H, 5.32; N, 8.21%.

EXAMPLE 99

N-(cis-4-Carbamoyl-cyclohexyl]-5-fluoro-2-(3-methylsulfanyl-phenoxy)-nicotinamide

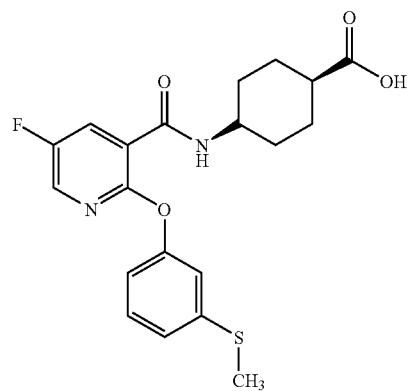

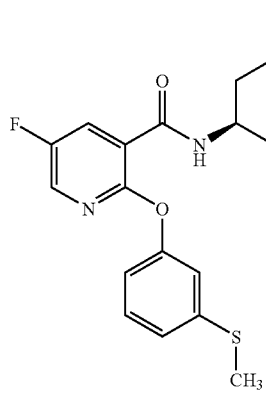

5-Fluoro-4-{cis-[2-(4-Methylsulfanyl-phenoxy)-pyridine-3-carbonyl]-amino}-cyclohexanecarboxylic acid (105 mg, 0.26 mmol) was dissolved in dimethylformamide (2 ml) and triethylamine (109 μl, 0.78 mmol) was added followed ammonium carbonate (125 mg, 1.3 mmol), 1-(3-dimethylaminopropyl)-3-ethylcarbodiimide hydrochloride (55 mg, 0.29 mmol) and 1-hydroxybenzotriazole (39 mg, 0.29 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (2×10 ml). The combined organic extracts were washed with water (2×5 ml), brine (5 ml), dried over $MgSO_4$ and the solvent was removed under reduced pressure. The residue was purified by flash column chromatography on silica gel eluting with dichloromethane:methanol:concentrated aqueous ammonia (98:2:0.2, by volume) to give N-(cis-4-carbamoyl-cyclohexyl]-5-fluoro-2-(3-methylsulfanyl-phenoxy)-nicotinamide (55 mg) as a white solid.

$^1$H NMR (400 MHz, $CDCl_3$): δ=8.30–8.38 (1H, d), 8.00–8.10 (2H, brs), 7.32–7.37 (1H, t), 7.11–7.18 (1H, d), 7.05 (1H, s), 6.90–6.95 (1H, d), 5.15–5.40 (2H, 2×brs), 4.21–4.28 (1H, brs), 2.48 (3H, s), 2.28–2.37 (1H, brs), 1.68–1.95 (8H, 2×m) ppm. LRMS (thermospray): m/z [M+H]+ 404. Anal. Found C, 59.77; H, 5.58; N, 10.35. $C_{20}H_{22}FN_3O_5S$ requires C, 59.54; H, 5.50; N, 10.41%.

EXAMPLE 100

5-Fluoro-N-{cis-4-[(pyridine-2-ylmethyl)-carbamoyl]-cyclohexyl}-2-(3-Methylsulfanyl-phenoxy)-nicotinamide

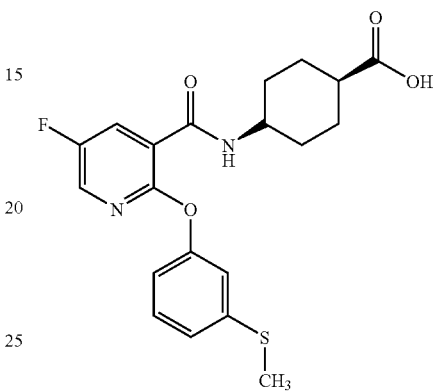

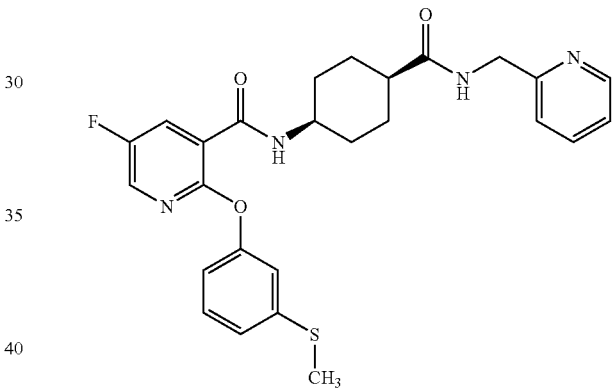

5-Fluoro-4-{cis-[2-(4-Methylsulfanyl-phenoxy)-pyridine-3-carbonyl]-amino}-cyclohexanecarboxylic acid (170 mg, 0.42 mmol) was dissolved in dimethylformamide (3 ml) and triethylamine (176 μl, 1.26 mmol) was added followed by 2-aminomethylpyridine (43 μl, 0.42 mmol), 1-(3-dimethylaminopropyl)-3-ethylcarbodiimide hydrochloride (89 mg, 0.46 mmol) and 1-hydroxybenzotriazole (63 mg, 0.46 mmol). The reaction was stirred under nitrogen at room temperature for 18 h and the solvent was removed under reduced pressure. The residue was partitioned between sat. sodium bicarbonate solution (5 ml) and ethyl acetate (10 ml) and the aqueous phase was extracted with ethyl acetate (2×10 ml). The combined organic extracts were washed with water (2×5 ml), brine (5 ml), dried over $MgSO_4$ and the solvent was removed under reduced pressure. The residue was purified by flash column chromatography on silica gel eluting with a solvent gradient of dichloromethane:methanol:concentrated aqueous ammonia (98.5:1.5:0.15 changing to 97.5:2.5:0.25, by volume) to give 5-fluoro-N-{cis-4-[(pyridine-2-ylmethyl)-carbamoyl]-cyclohexyl}-2-(3-Methylsulfanyl-phenoxy)-nicotinamide (97 mg) as a white solid.

$^1$H NMR (400 MHz, $CDCl_3$): δ=8.43–8.47 (1H, d), 8.28–8.33 (1H, dd), 7.97–8.05 (1H, m), 7.58–7.63. (1H, t), 7.10–7.27 (3H, 2×m, partially masked by solvent), 7.02–7.09 (1H, d), 7.01 (1H, s), 6.84–6.90 (1H, d), 6.76 (1H, brs), 4.46–4.51 (2H, d), 4.18–4.26 (1H, brs), 2.42 (3H, s), 2.30–2.39 (1H, m), 1.82–1.90 (2H, m), 1.68–1.82 (6H, m) ppm. LRMS (thermospray): m/z [M+H]+ 495. Anal. Found C, 63.51; H, 5.48; N, 11.46. $C_{26}H_{27}FN_4O_5S$ requires C, 63.14; H, 5.50; N, 11.13%.

EXAMPLE 101

5-Fluoro-N-[(1S,2R)-2-hydroxycyclohexyl]-2-[3-(methylsulfonyl)phenoxy]nicotinamide

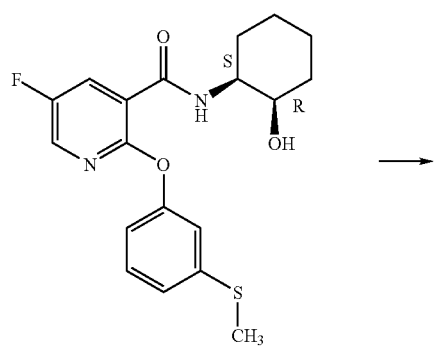

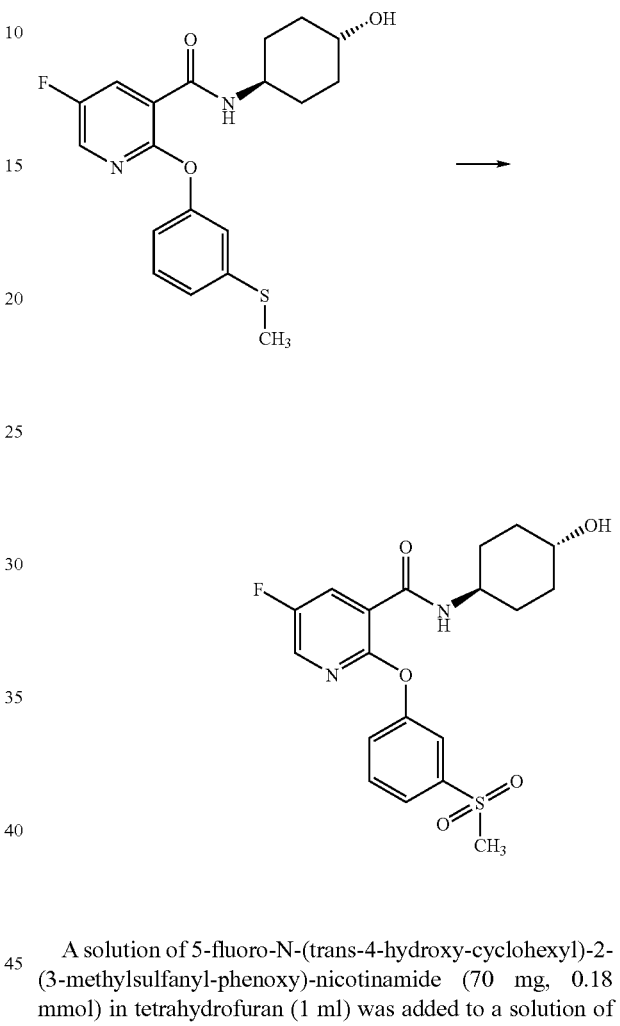

Oxone™ (245 mg, 0.40 mmol) was added to a solution of 5-fluoro-N-[(1S,2R)-2-hydroxycyclohexyl]-2-[3-(methylsulfanyl)phenoxy]nicotinamide (50 mg, 0.13 mmol) in a mixture of isopropanol (2 ml), tetrahydrofurann (1 ml) and water (1 ml) at 0° C. The mixture was warmed to ambient temperature and stirred for 18 h then partitioned between water (2 ml) and dichloromethane (10 ml) using a Chemelute™ cartridge. The organic phase was evaporated and the residue purified by flash column chromatography using dichloromethane:methanol (98:2) as eluant to give 5-fluoro-N-[(1S,2R)-2-hydroxycyclohexyl]-2-[3-(methylsulfonyl)phenoxy]nicotinamide (39 mg) as a colourless glass.

$^1$H NMR (400 MHz, CDCl$_3$): δ=8.25–8.37 (1H, m), 8.05–8.12 (1H, d), 8.00 (1H, s), 7.70–7.85 (1H, m), 7.56–7.64 (1H, m), 7.44–7.48 (1H, m), 4.08–4.17 (1H, m), 3.85–4.03 (1H, m), 3.06 (3H, s), 1.82–2.10 (1H, br s), 1.34–1.80 (8H, m) ppm. LRMS (electrospray): m/z [M+H]+ 409.

EXAMPLE 102

5-Fluoro-N-(trans-4-hydroxy-cyclohexyl)-2-(3-methylsulfonyl-phenoxy)-nicotinamide A solution of 5-fluoro-N-(trans-4-hydroxy-cyclohexyl)-2-(3-methylsulfanyl-phenoxy)-nicotinamide (70 mg, 0.18 mmol) in tetrahydrofuran (1 ml) was added to a solution of oxone™ (229 mg, 0.37 mmol) in water (1 ml) and isopropylalcohol (4 ml) under nitrogen at room temperature and the reaction was stirred for 3 h. The reaction mixture was passed through a chemelute cartridge, washing with tetrahydrofuran, and the eluent was concentrated under reduced pressure. The residue was purified by flash column chromatography on silica gel eluting with dichloromethane:methanol:concentrated aqueous ammonia (98:2:0.2 changing to 96:4:0.4, by volume) to give 5-fluoro-N-(trans-4-hydroxy-cyclohexyl)-2-(3-methylsulfonyl-phenoxy)-nicotinamide (50 mg) as a yellow solid.

$^1$H NMR (400 MHz, CDCl$_3$): δ=8.35–8.39 (1H, dd), 7.98–8.00 (1H, d), 7.82–7.85 (1H, d), 7.76 (1H, s), 7.62–7.67 (1H, t), 7.40–7.50 (2H, 2×d), 3.96–4.03 (1H, m), 3.60 –3.70 (1H, m), 3.09 (3H, s), 2.10–2.18 (2H, d), 1.97–2.03 (2H, d), 1.27–1.50 (4H, m) ppm. LRMS (electrospray): m/z [M+Na]+ 431, [M–H]+ 407. Anal. Found C, 55.03; H, 5.19; N, 6.65. $C_{19}H_{21}FN_2O_5S$. 0.35 mol $H_2O$ requires C, 55.02; H, 5.27; N, 6.75%.

EXAMPLE 103

5-Fluoro-N-{cis-4-[(pyridine-2-ylmethyl)-carbamoyl]-cyclohexyl}-2-(3-methylsulfoxide-phenoxy)-nicotinamide

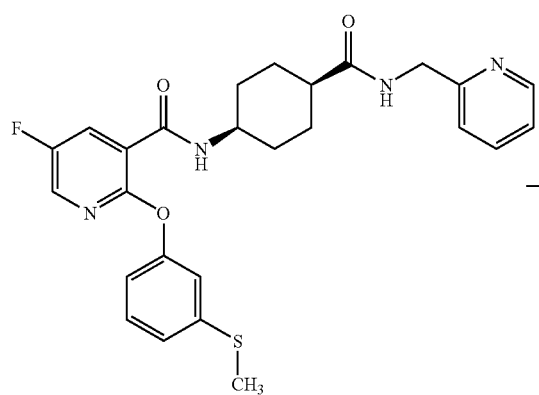

EXAMPLE 104

2-[3-(Methylsulfonyl)phenoxy]-N-(cis-4-{[(2-pyridinylmethyl)amino]carbonyl}cyclohexyl)nicotinamide

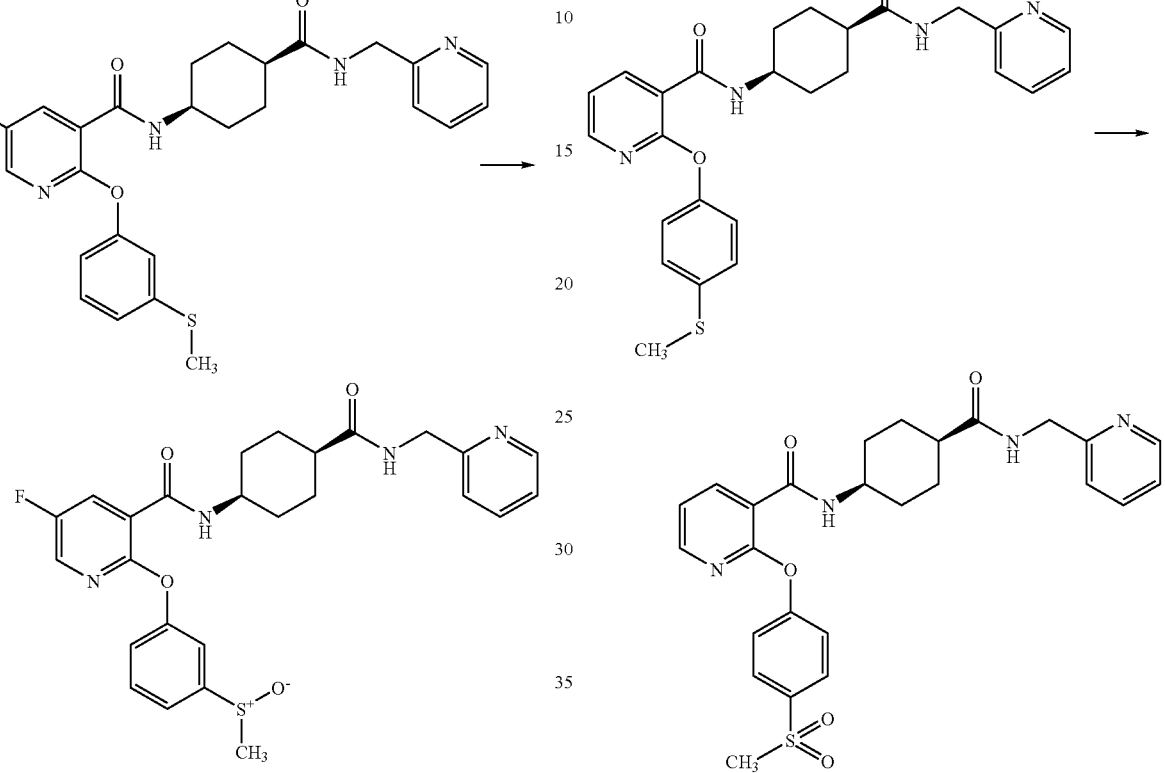

5-Fluoro-N-{cis-4-[(pyridine-2-ylmethyl)-carbamoyl]-cyclohexyl}-2-(3-methylsulfanyl-phenoxy)-nicotinamide (100 mg, 0.202 mmol) was dissolved in a solvent mixture of isopropyl alcohol (4 ml), tetrahydrofuran (1 ml) and water (0.5 ml) and oxone™ (87 mg, 0.142 mmol) was added. The reaction was stirred under nitrogen at room temperature for 3 h. The reaction mixture was diluted with water (2 ml), basified to pH 11 with concentrated aqueous ammonia and extracted with dichloromethane (3×10 ml). The combined organic extracts were dried over MgSO$_4$ and the solvent was removed under reduced pressure. The residue was purified by flash column chromatography on silica gel eluting with a solvent gradient of dichloromethane:methanol:concentrated aqueous ammonia (97.5:2.5:0.5 changing to 95:5:0.5, by volume) to give 5-fluoro-N-{cis-4-[(pyridine-2-ylmethyl)-carbamoyl]-cyclohexyl}-2-(3-methylsulfoxide-phenoxy)-nicotinamide (56 mg) as a white foam.

$^1$H NMR (400 MHz, CDCl$_3$): δ=8.45–8.52 (1H, d), 8.29–8.34 (1H, dd), 7.92–8.10 (2H, m), 7.57–7.65 (1H, t), 7.43–7.56 (3H, m), 7.24–7.34 (1H, d), 7.16–7.24 (2H, m, partially masked by solvent), 6.74–6.82 (1H, brs), 4.42–4.56 (2H, d), 4.21–4.34 (1H, brs), 2.76 (3H, s), 2.28–2.38 (1H, m), 1.80–1.94 (2H, m), 1.63–1.80 (6H, m) ppm. LRMS (thermospray): m/z [M+H]$^+$ 511, [M+NH$_4$]$^+$ 529. Anal. Found C, 59.16; H, 5.52; N, 10.57. C$_{26}$H$_{27}$FN$_4$O$_4$S. 1 mol H$_2$O requires C, 59.08; H, 5.53; N, 10.60%.

2-(4-Methylsulfanyl-phenoxy)-N-{cis-4-[(pyridine-2-ylmethyl)-carbamoyl]-cyclohexyl}-nicotinamide (88 mg, 0.19 mmol) was dissolved in a solvent mixture of isopropyl alcohol (4 ml), tetrahydrofuran (1 ml) and water (0.5 ml) and oxone™ (116 mg, 0.1 mmol) was added. The reaction was stirred under nitrogen at room temperature for 1.5 h. A further aliquot of oxone™ was added and the reaction was advanced for a further 1 h. The reaction mixture was diluted with water (2 ml), basified to pH 11 with concentrated aqueous ammonia and extracted with dichloromethane (3×10 ml). The combined organic extracts were dried over MgSO$_4$ and the solvent was removed under reduced pressure. The residue was purified by flash column chromatography on silica gel eluting with dichloromethane:methanol:concentrated aqueous ammonia (97:3:0.3, by volume) to give 2-(1-dioxo-4-methylsulfanyl-phenoxy)-N-{cis-4-[(pyridine-2-ylmethyl)-carbamoyl]-cyclohexyl}-nicotinamide (77 mg) as a white foam.

$^1$H NMR (400 MHz, CDCl$_3$): δ=8.58–8.63 (1H, d), 8.48–8.57 (1H, m), 8.19–8.25 (1H, m), 7.91–8.03 (2H, d), 7.76–7.87 (1H, d), 7.62–7.71 (1H, t), 7.37–7.49 (2H, d), 7.17–7.30 (3H, m, partially masked by solvent), 4.43–4.57 (2H, d), 4.27–4.38 (1H, m), 3.07 (3H, s), 2.29–2.32 (1H, m), 1.83–1.98 (2H, m), 1.66–1.98 (6H, m) ppm. LRMS (thermospray): m/z [M+H]$^+$ 509. Anal. Found C, 59.83; H, 5.55; N, 10.77. C$_{26}$H$_{28}$N$_4$O$_5$S. 0.75 mol H$_2$O requires C, 59.81; H, 5.70; N, 10.73%.

EXAMPLE 105

5-Fluoro-N-{cis-4-[(pyridine-2-ylmethyl)-carbamoyl]-cyclohexyl}-2-(3-methylsulfonyl-phenoxy)-nicotinamide

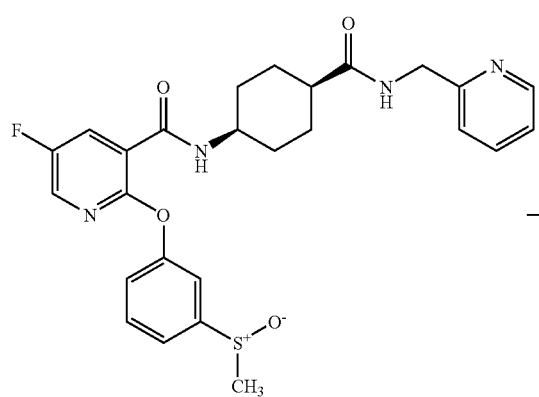

EXAMPLE 106

2-(4-Methylsulfoxide-phenoxy)-N-{cis-4-[(pyridine-2-ylmethyl)-carbamoyl]-cyclohexyl}-nicotinamide

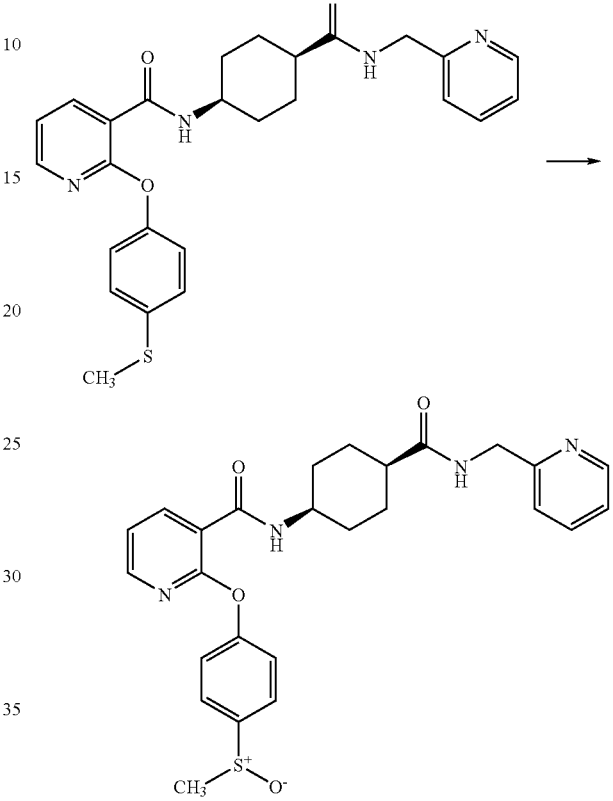

5-Fluoro-N-{cis-4-[(pyridine-2-ylmethyl)-carbamoyl]-cyclohexyl}-2-(3-methylsulfanyl-phenoxy)-nicotinamide (100 mg, 0.202 mmol) was dissolved in a solvent mixture of isopropyl alcohol (4 ml), tetrahydrofuran (1 ml) and water (0.5 ml) and oxone™ (249 mg, 0.404 mmol) was added. The reaction was stirred under nitrogen at room temperature for 3 h. The reaction mixture was diluted with water (2 ml), basified to pH 11 with concentrated aqueous ammonia and extracted with dichloromethane (4×10 ml). The combined organic extracts were dried over $MgSO_4$ and the solvent was removed under reduced pressure. The residue was purified by flash column chromatography on silica gel eluting with dichloromethane:methanol:concentrated aqueous ammonia (97.5:2.5:0.5, by volume) to give 5-fluoro-N-{cis-4-[(pyridine-2-ylmethyl)-carbamoyl]-cyclohexyl}-2-(3-methylsulfonyl-phenoxy)-nicotinamide (75 mg) as a white foam.

$^1$H NMR (400 MHz, $CDCl_3$): δ=8.47–8.52 (1H, d), 8.32–8.38 (1H, dd), 8.03 (1H, s), 7.92–7.98 (1H, d), 7.76–7.86 (2H, m), 7.57–7.67 (2H, m), 7.48–7.56 (1H, d), 7.14–7.22 (2H, m), 6.77 (1H, brs), 4.44–4.52 (2H, d), 4.26–4.34 (1H, brs), 3.11 (3H, s), 2.30–2.41 (1H, m), 1.86–1.96 (2H, m), 1.69–1.85 (6H, m) ppm. LRMS (thermospray): m/z [M+H]$^+$ 527. Anal. Found C, 59.06; H, 5.14; N, 10.57. $C_{26}H_{27}FN_4O_5S$ requires C, 59.30; H, 5.14; N, 10.64%.

2-(4-Methylsulfanyl-phenoxy)-N-{cis-4-[(pyridine-2-ylmethyl)-carbamoyl]-cyclohexyl}-nicotinamide (95 mg, 0.20 mmol) was dissolved in a solvent mixture of isopropyl alcohol (4 ml), tetrahydrofuran (1 ml) and water (0.5 ml) and oxone™ (61 mg, 0.1 mmol) was added. The reaction was stirred under nitrogen at room temperature, for 1.5 h. A further aliquot of oxone™ was added and the reaction was advanced for a further 1 h. The reaction mixture was diluted with water (2 ml), basified to pH 11 with concentrated aqueous ammonia and extracted with dichloromethane (5×5 ml). The combined organic extracts were dried over $MgSO_4$ and the solvent was removed under reduced pressure. The residue was purified by flash column chromatography on silica gel eluting with dichloromethane:methanol:concentrated aqueous ammonia (95:5:0.5, by volume) to give 2-(1-Oxo-4-methylsulfanyl-phenoxy)-N-{cis-4-[(pyridine-2-ylmethyl)-carbamoyl]-cyclohexyl}-nicotinamide (60 mg) as a white foam.

$^1$H NMR (400 MHz, $CDCl_3$): δ=8.58–8.62 (1H, d), 8.47–8.54 (1H, m), 8.18–8.24 (1H, m), 7.88–7.96 (1H, d), 7.60–7.72 (3H, m), 7.35–7.43 (2H, d), 7.14–7.26 (3H, m), 6.77–6.87 (1H, m), 4.48–4.55 (2H, d), 4.26–4.37 (1H, m), 2.77 (3H, s), 2.32–2.41 (1H, m), 1.85–1.96 (2H, m), 1.69–1.85 (6H, m) ppm. LRMS (thermospray): m/z [M+H]$^+$ 493. Anal. Found C, 61.46; H, 5.83; N, 10.98. $C_{26}H_{28}N_4O_4S$. 0.85 mol $H_2O$ requires C, 61.48; H, 5.89; N, 11.03%.

EXAMPLE 107

N-[cis-4-(2-Cyclopropyl-acetylamino)-cyclohexyl]-5-fluoro-2-(3-methylsulfoxyl-phenoxy)-nicotinamide

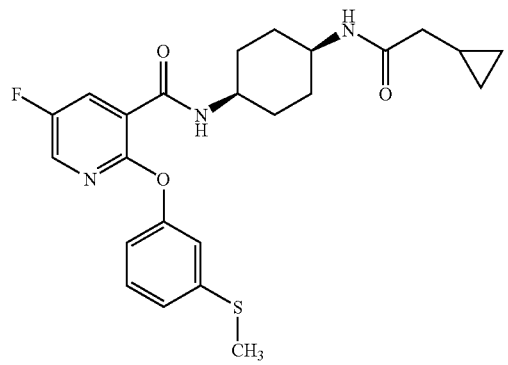

N-[cis-4-(2-Cyclopropyl-acetylamino)-cyclohexyl]-5-fluoro-2-(3-methylsulfanyl-phenoxy)-nicotinamide (125 mg, 0.273 mmol) was dissolved in a solvent mixture of isopropyl alcohol (4 ml), tetrahydrofuran (1 ml) and water (0.5 ml) and oxone™ (118 mg, 0.191 mmol) was added. The reaction was stirred under nitrogen at room temperature for 2 h. The reaction mixture was diluted with water (2 ml) and extracted with dichloromethane (3×10 ml). The combined organic extracts were dried over $MgSO_4$ and the solvent was removed under reduced pressure. The residue was purified by flash column chromatography on silica gel eluting with dichloromethane:methanol:concentrated aqueous ammonia (97.5:2.5:0.5, by volume) to give N-[cis-4-(2-Cyclopropyl-acetylamino)-cyclohexyl]-5-fluoro-2-(3-methylsulfoxyl-phenoxy)-nicotinamide (104 mg) as a white solid.

$^1$H NMR (400 MHz, $CDCl_3$): δ=8.37–8.41 (1H, dd), 8.05–8.07 (1H, d), 7.94–8.01 (1H, d), 7.66 (1H, s), 7.56–7.62 (1H, t), 7.40–7.44 (1H, dd), 7.37–7.40 (1H, d), 6.13–6.22 (1H, d), 4.23–4.31 (1H, m), 3.85–3.96 (1H, m), 2.79 (3H, s), 2.11–2.16 (2H, d), 1.72–1.92 (6H, 2×m), 1.43–1.53 (1H, m, partially masked by solvent), 1.29–1.42 (1H, m), 0.93–1.01 (1H, m), 0.49–0.55 (2H, m), 0.12–0.20 (2H, m) ppm. LRMS (thermospray): m/z [M+H]$^+$ 496. Anal. Found C, 60.63; H, 6.01; N, 8.76. $C_{24}H_{28}FN_3O_4S$ requires C, 60.87; H, 5.96; N, 8.87%.

EXAMPLE 108

N-[cis-4-(2-Cyclopropyl-acetylamino)-cyclohexyl]-5-fluoro-2-(3-methylsulfonyl-phenoxy)-nicotinamide

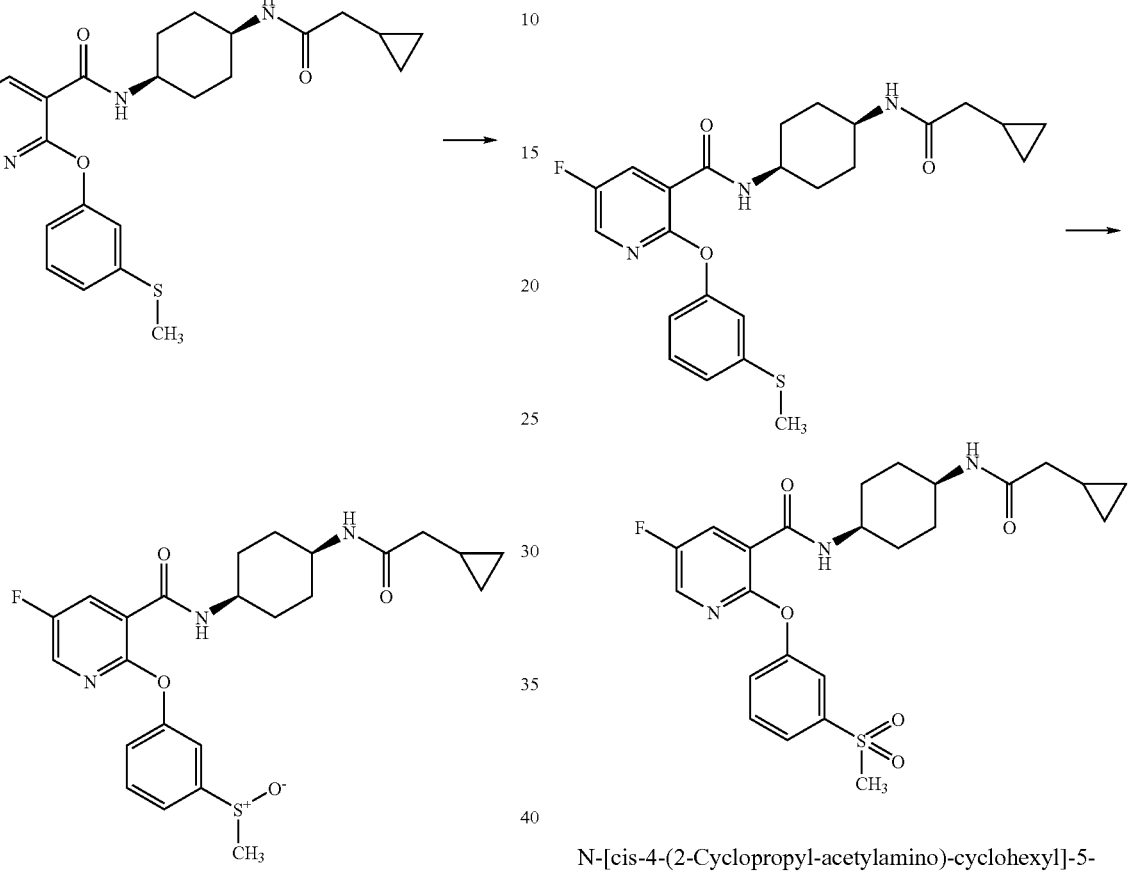

N-[cis-4-(2-Cyclopropyl-acetylamino)-cyclohexyl]-5-fluoro-2-(3-methylsulfanyl-phenoxy)-nicotinamide (125 mg, 0.273 mmol) was dissolved in a solvent mixture of isopropyl alcohol (4 ml), tetrahydrofuran (1 ml) and water (0.5 ml) and oxone™ (336 mg, 0.546 mmol) was added. The reaction was stirred under nitrogen at room temperature for 18 h. The reaction mixture was diluted with water (2 ml) and extracted with dichloromethane (3×5 ml). The combined organic extracts were dried over $MgSO_4$ and the solvent was removed under reduced pressure. The residue was purified by flash column chromatography on silica gel eluting with dichloromethane:methanol:concentrated aqueous ammonia (97.5:2.5:0.5, by volume) to give N-[cis-4-(2-Cyclopropyl-acetylamino)-cyclohexyl]-5-fluoro-2-(3-methylsulfonyl-phenoxy)-nicotinamide (120 mg) as a white solid.

$^1$H NMR (400 MHz, $CDCl_3$): δ=8.38–8.41 (1H, dd), 8.04–8.06 (1H, d), 7.80–7.89 (2H, 2×d), 7.77 (1H, s), 7.67–7.71 (1H, t), 7.51–7.56 (1H, d), 5.80–5.86 (1H, d), 4.21–4.28 (1H, brs), 3.88–3.99 (1H, m), 3.12 (3H, s), 2.11–2.16 (2H, d), 1.81–1.91 (4H, m), 1.73–1.80 (2H, m), 1.38–1.48 (2H, m), 0.90–1.00 (1H, m), 0.51–0.56 (2H, m), 0.15–0.20 (2H, m) ppm. LRMS (thermospray): m/z [M+H]$^+$ 490, [M+Na]$^+$ 512. Anal. Found C, 58.38; H, 5.80; N, 8.42. $C_{24}H_{28}FN_3O_5S$. 0.25 mol $H_2O$ requires C, 58.35; H, 5.81; N, 8.50%.

EXAMPLE 109

5-Fluoro-2-(3-methylsulfoxyl-phenoxy)-N-{cis-4-[(pyridine-2-carbonyl)-amino]-cyclohexyl}-nicotinamide

EXAMPLE 110

5-Fluoro-2-(3-methylsulfonyl-phenoxy)-N-{cis-4-[(pyridine-2-carbonyl)-amino]-cyclohexyl}-nicotinamide

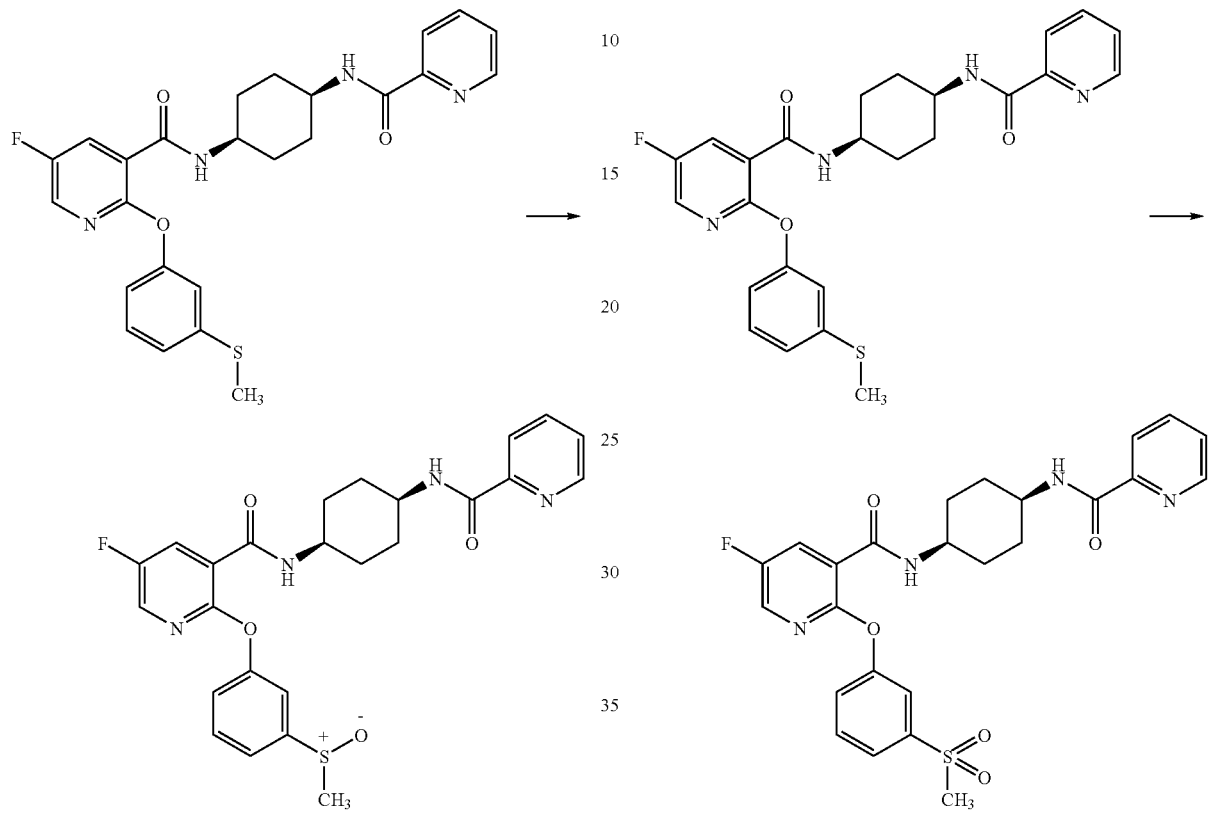

5-Fluoro-2-(3-methylsulfanyl-phenoxy)-N-{cis-4-[(pyridine-2-carbonyl)-amino]-cyclohexyl}-nicotinamide (156 mg, 0.325 mmol) was dissolved in a solvent mixture of isopropyl alcohol (4 ml), tetrahydrofuran (1 ml) and water (0.5 ml) and oxone™ (140 mg, 0.227 mmol) was added. The reaction was stirred under nitrogen at room temperature for 2 h. The reaction mixture was diluted with water (2 ml) and extracted with dichloromethane (3×10 ml). The combined organic extracts were dried over $MgSO_4$ and the solvent was removed under reduced pressure. The residue was purified by flash column chromatography on silica gel eluting with dichloromethane:methanol:concentrated aqueous ammonia (98:2:0.2, by volume) and the product was triturated with diethylether (5 ml) to give 5-fluoro-2-(3-methylsulfoxyl-phenoxy)-N-{cis-4-[(pyridine-2-carbonyl)-amino]-cyclohexyl}-nicotinamide (102 mg) as a white solid.

$^1$H NMR (400 MHz, $CDCl_3$): δ=8.51–8.56 (1H, d), 8.36–8.40 (1H, dd), 8.16–8.21 (1H, d), 8.03–8.06 (1H, d), 7.96–8.02 (1H, d), 7.80–7.90 (2H, m), 7.60–7.65 (1H, t), 7.55–7.58 (1H, m), 7.48–7.52 (1H, d), 7.39–7.43 (1H, m), 7.29–7.35 (1H, m), 4.20–4.30 (1H, m), 4.07–4.17 (1H, m), 2.76 (3H, s), 1.87–1.98 (4H, m), 1.76–1.87 (2H, m), 1.63–1.75 (2H, m) ppm. LRMS (electrospray): m/z [M+H]$^+$ 497. Anal. Found C, 60.02; H, 5.08; N, 11.11. $C_{25}H_{25}FN_4O_4S$. 0.2 mol $H_2O$ requires C, 60.04; H, 5.12; N, 11.20%.

5-Fluoro-2-(3-methylsulfanyl-phenoxy)-N-{cis-4-[(pyridine-2-carbonyl)-amino]-cyclohexyl}-nicotinamide (135 mg, 0.281 mmol) was dissolved in a solvent mixture of isopropyl alcohol (4 ml), tetrahydrofuran (1 ml) and water (0.5 ml) and oxone™ (345 mg, 0.562 mmol) was added. The reaction was stirred under nitrogen at room temperature for 24 h. The reaction mixture was diluted with water (5 ml) and extracted with dichloromethane (3×10 ml). The combined organic extracts were dried over $MgSO_4$ and the solvent was removed under reduced pressure. The residue was purified by flash column chromatography on silica gel eluting with a solvent gradient of dichloromethane:methanol:concentrated aqueous ammonia (99:1:0.1 changing to 98:2:0.2, by volume) and the product was triturated with dichloromethane/diethylether (5 ml) to give 5-fluoro-2-(3-methylsulfonyl-phenoxy)-N-{cis-4-[(pyridine-2-carbonyl)-amino]-cyclohexyl}-nicotinamide (83 mg) as a white solid.

$^1$H NMR (400 MHz, $CDCl_3$): δ=8.51–8.55 (1H, d), 8.37–8.41 (1H, dd), 8.15–8.20 (1H, d), 8.00–8.05 (2H, 2×d), 7.74–7.88 (4H, m), 7.66–7.71 (1H, t), 7.46–7.50 (1H, m), 7.39–7.45 (1H, m), 7.39–7.45 (1H, m), 4.20–4.28 (1H, m), 4.09–4.18 (1H, m), 3.06 (3H, s), 1.88–1.99 (4H, m), 1.77–1.86 (2H, m), 1.65–1.77 (2H, m) ppm. LRMS (electrospray): m/z [M+H]$^+$ 513. Anal. Found C, 58.26; H, 4.92; N, 10.78. $C_{25}H_{25}FN_4O_5S$. 0.15 mol $H_2O$ requires C, 58.28; H, 4.95; N, 10.87%.

EXAMPLE 111

5-Fluoro-N-[cis-4-(2-methoxy-acetylamino)-cyclohexyl]-2-(3-methylsulfoxyl-phenoxy)-nicotinamide

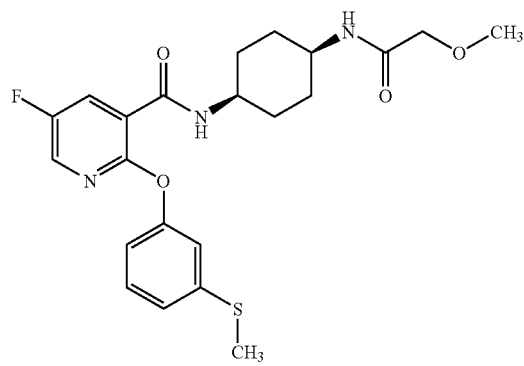

5-Fluoro-N-[cis-4-(2-methoxy-acetylamino)-cyclohexyl]-2-(3-methylsulfanyl-phenoxy)-nicotinamide (150 mg, 0.335 mmol) was dissolved in a solvent mixture of isopropyl alcohol (4 ml), tetrahydrofuran (1 ml) and water (0.5 ml) and oxone™ (144 mg, 0.235 mmol) was added. The reaction was stirred under nitrogen at room temperature for 2 h. The reaction mixture was diluted with water (5 ml) and extracted with dichloromethane (3×10 ml). The combined organic extracts were dried over MgSO$_4$ and the solvent was removed under reduced pressure. The residue was purified by flash column chromatography on silica gel eluting with dichloromethane:methanol:concentrated aqueous ammonia (97.5:2.5:0.25, by volume) and the product was triturated with diethylether (5 ml) to give 5-Fluoro-N-[cis-4-(2-methoxy-acetylamino)-cyclohexyl]-2-(3-methylsulfoxyl-phenoxy)-nicotinamide (122 mg) as a white solid.

$^1$H NMR (400 MHz, CDCl$_3$): δ=8.36–8.40 (1H, dd), 8.04–8.06 (1H, d), 7.81–7.87 (1H, d), 7.57–7.64 (2H, m), 7.44–7.49 (1H, d), 7.30–7.34 (1H, dd), 6.38–6.46 (1H, d), 4.16–4.24 (1H, m), 3.92–4.00 (1H, m), 3.83 (2H, s), 3.39 (3H, s), 2.78 (3H, s), 1.81–1.90 (4H, m), 1.71–1.80 (2H, m), 1.46–1.59 (2H, m, partially masked by solvent) ppm. LRMS (electrospray): m/z [M+Na]$^+$ 486, [M−H]$^+$ 462. Anal. Found C, 56.84; H, 5.70; N, 8.88. C$_{22}$H$_{26}$FN$_3$O$_5$S requires C, 57.01; H, 5.65; N, 9.07%.

EXAMPLE 112

5-Fluoro-N-[cis-4-(2-methoxy-acetylamino)-cyclohexyl]-2-(3-methylsulfonyl-phenoxy)-nicotinamide

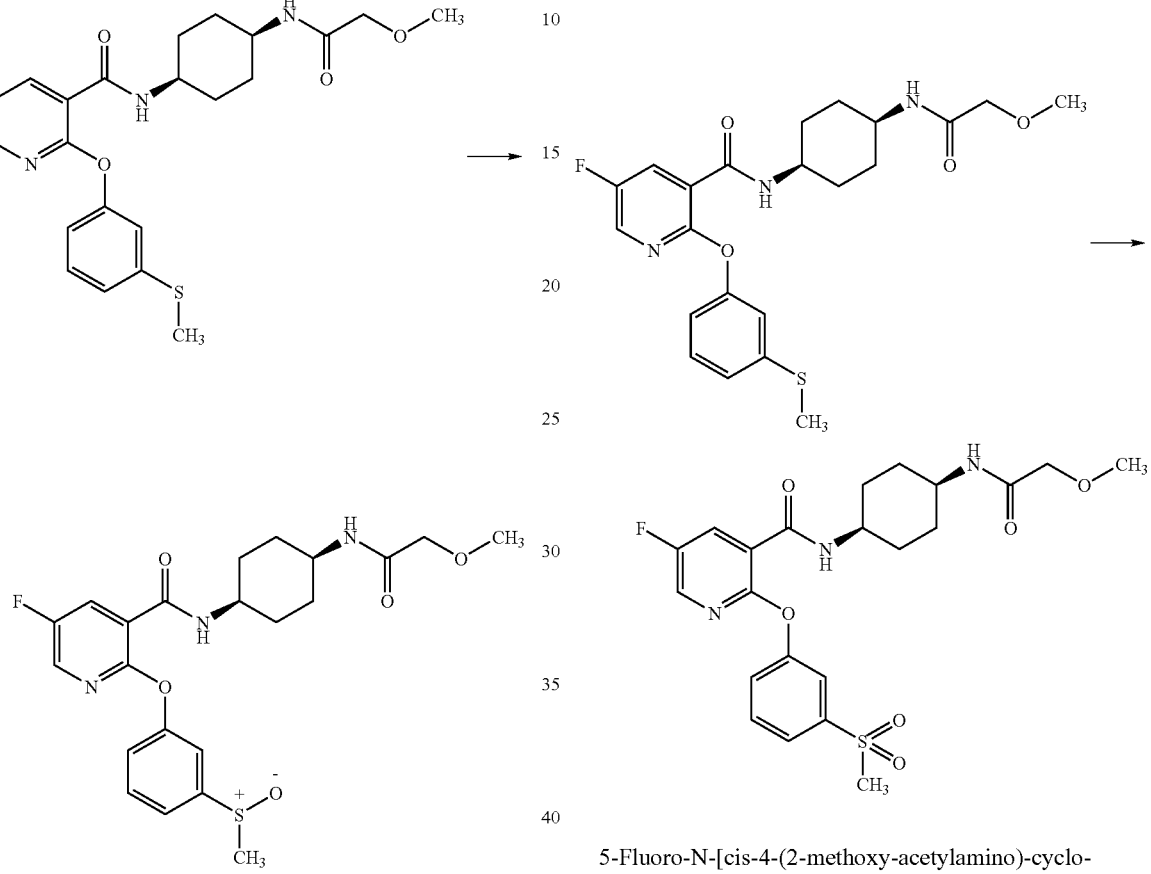

5-Fluoro-N-[cis-4-(2-methoxy-acetylamino)-cyclohexyl]-2-(3-methylsulfanyl-phenoxy)-nicotinamide (130 mg, 0.29 mmol) was dissolved in a solvent mixture of isopropyl alcohol (4 ml), tetrahydrofuran (1 ml) and water (0.5 ml) and oxone™ (360 mg, 0.58 mmol) was added. The reaction was stirred under nitrogen at room temperature for 2 h. The reaction mixture was diluted with water (5 ml) and extracted with dichloromethane (3×10 ml). The combined organic extracts were dried over MgSO$_4$ and the solvent was removed under reduced pressure. The residue was purified by flash column chromatography on silica gel eluting with dichloromethane:methanol:concentrated aqueous ammonia (97.5:2.5:0.25, by volume) and the product was triturated with diethylether (5 ml) to give 5-Fluoro-N-[cis-4-(2-methoxy-acetylamino)-cyclohexyl]-2-(3-methylsulfonyl-phenoxy)-nicotinamide (128 mg) as a white solid.

$^1$H NMR (400 MHz, CDCl$_3$): δ=8.36–8.40 (1H, dd), 8.03–8.06 (1H, d), 7.85–7.90 (1H, d), 7.78 (1H, s), 7.72–7.76 (1H, m), 7.67–7.71 (1H, t), 7.46–7.50 (1H, d), 6.37–6.45 (1H, d), 4.18–4.23 (1H, m), 3.92–4.00 (1H, m), 3.84 (2H, s), 3.39 (3H, s), 3.11(3H, s), 1.80–1.92 (4H, m), 1.70–1.80 (2H, m), 1.49–1.60 (2H, m, partially masked by solvent) ppm. LRMS (electrospray): m/z [M+Na]$^+$ 502, [M−H]$^+$ 478. Anal. Found C, 54.72; H, 5.62; N, 8.36. C$_{22}$H$_{26}$FN$_3$O$_6$S requires C, 54.75; H, 5.44; N, 8.69%.

EXAMPLE 113

5-Fluoro-N-[Cis-4-(hydroxymethyl)cyclohexyl]-2-[3-(methylsulfinyl)phenoxy]nicotinamide

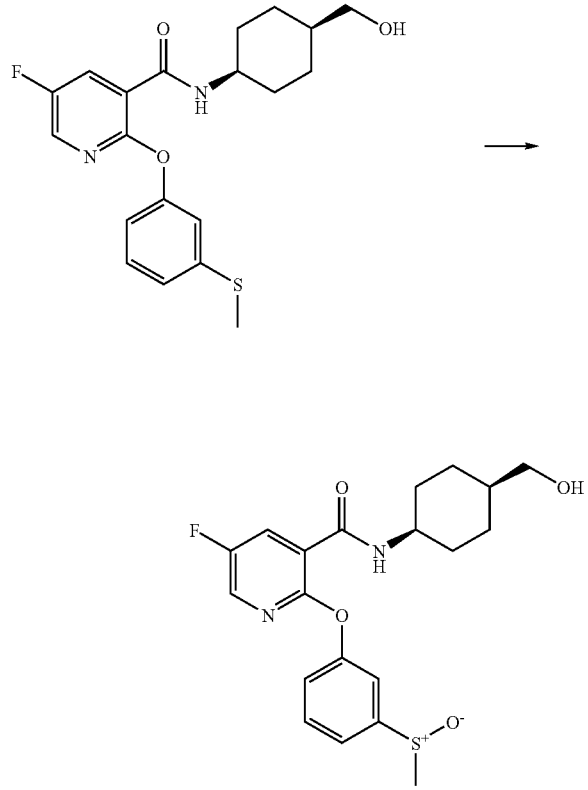

N-(cis-4-Hydroxymethyl-cyclohexyl)-5-fluoro-2-(3-methylsulfanyl-phenoxy)-nicotinamide (120 mg, 0.307 mmol) was dissolved in a solvent mixture of isopropyl alcohol (4 ml), tetrahydrofuran (1 ml) and water (0.5 ml) and oxone™ (132 mg, 0.215 mmol) was added. The reaction was stirred at room temperature for 2 h. The reaction mixture was diluted with water (5 ml) and extracted with dichloromethane (3×10 ml). The combined organic extracts were dried over $MgSO_4$ and the solvent was removed under reduced pressure. The residue was purified by flash column chromatography on silica gel eluting with dichloromethane: methanol (98:2 increasing to 97:3, by volume). The resulting foam was triturated with diethylether (5 ml) to give the product (108 mg) as a white solid.

$^1$H NMR (400 MHz, $CDCl_3$): δ=8.36–8.39 (1H, dd), 8.11–8.16 (1H, d), 8.05–8.06 (1H, d), 7.70 (1H, s), 7.55–7.59 (1H, t), 7.39–7.41 (1H, d), 7.35–7.38 (1H, dd), 4.38–4.43 (1H, m), 3.39–3.48 (2H, s), 2.80 (3H, s), 1.85–1.97 (2H, m), 1.63–1.74 (5H, m), 1.25–1.39 (2H, m) ppm. LRMS (thermospray): m/z $[M+H]^+$ 407. Anal. Found C, 59.09; H, 5.72; N, 6.76. $C_{20}H_{23}FN_2O_4S$ requires C, 59.10; H, 5.70; N, 6.89%.

EXAMPLE 114

5-Fluoro-N-[cis-4-(hydroxymethyl)cyclohexyl]-2-[3-(methylsulfonyl)phenoxy]nicotinamide

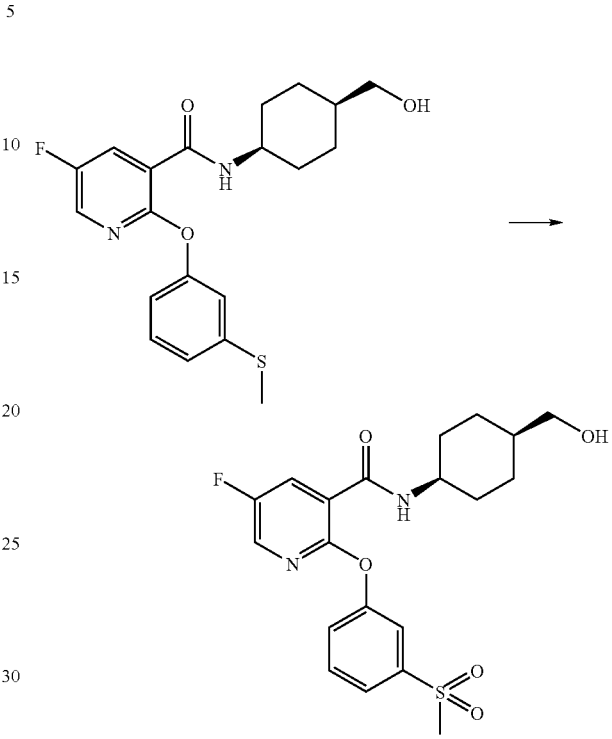

N-(cis-4-Hydroxymethyl-cyclohexyl)-5-fluoro-2-(3-methylsulfanyl-phenoxy)-nicotinamide (110 mg, 0.282 mmol) was dissolved in a solvent mixture of isopropyl alcohol (4 ml), tetrahydrofuran (1 ml) and water (0.5 ml) and oxone™ (347 mg, 0.563 mmol) was added. The reaction was stirred at room temperature for 6 h. The reaction mixture was diluted with water (10 ml) and extracted with dichloromethane (3×10 ml). The combined organic extracts were dried over $MgSO_4$ and the solvent was removed under reduced pressure. The residue was triturated with diethylether (5 ml) to give the product (122 mg) as a white solid.

$^1$H NMR (400 MHz, $CDCl_3$): δ=8.36–8.40 (1H, dd), 8.04 (1H, d), 7.97–8.02 (1H, d), 7.84–7.86 (1H, d), 7.82 (1H, s), 7.64–7.68 (1H, t), 7.48–7.50 (1H, d), 4.36–4.41 (1H, m), 3.41–3.47 (2H, d), 3.13 (3H, s), 1.85–1.92 (2H, m), 1.64–1.75 (5H, m), 1.25–1.36 (2H, m) ppm. LRMS (thermospray): m/z $[M+H]^+$ 423. Anal. Found C, 56.76; H, 5.56; N, 6.49. $C_{20}H_{23}FN_2O_5S$ requires C, 56.86; H, 5.49; N, 6.63%.

In Vitro Activity of the Nicotinamide Derivatives

The PDE4 inhibitory activity of the nicotinamide derivatives of the formula (1) is determined by the ability of compounds to inhibit the hydrolysis of cAMP to AMP by PDE4 (see also reference 1). Tritium labelled cAMP is incubated with PDE4. Following incubation, the radiolabelled AMP produced is able to bind yttrium silicate SPA beads. These SPA beads subsequently produce light that can be quantified by scintillation counting. The addition of a PDE4 inhibitor prevents the formation of AMP from cAMP and counts are diminished. The $IC_{50}$ of a PDE4 inhibitor can be defined as the concentration of a compound that leads to a 50% reduction in counts compared to the PDE4 only (no inhibitor) control wells.

The anti-inflammatory properties of the nicotinamide derivatives of the formula (1) are demonstrated by their ability to inhibit TNFα release from human peripheral blood mononuclear cells (see also reference 2). Venous blood is collected from healthy volunteers and the mononuclear cells purified by centrifugation through Histopaque (Ficoll) cushions. TNFα production from these cells is stimulated by addition of lipopolysaccharide. After 18 hours incubation in the presence of LPS, the cell supernatant is removed and the concentration of TNFα in the supernatant determined by ELISA. Addition of PDE4 inhibitors reduces the amount of TNFα produced. An $IC_{50}$ is determined which is equal to the concentration of compound that gives 50% inhibition of TNFα production as compared to the LPS stimulated control wells.

All the examples were tested in the assay described above and found to have an $IC_{50}$ (TNFα screen) of less than 300 nM. And for most of the tested compounds, they were found to have an $IC_{50}$ (TNFα screen) of even less than 100 nM.

For illustrative purposes, the following table indicates the exact $IC_{50}$ (TNFα screen) of some representative examples of the present invention:

| Example N° | $IC_{50}$ (nM) | Example N° | IC50 (nM) |
|---|---|---|---|
| 18 | 0.6 | 11 | 0.05 |
| 10 | 0.05 | 1 | 0.4 |
| 3 | 0.37 | 4 | 0.15 |
| 22 | 0.07 | 6 | 0.9 |
| 5 | 0.15 | | |

REFERENCES

1. Thompson J W, Teraski W L, Epstein P M, Strada S J., "Assay of nucleotidephosphodiesterase and resolution of multiple molecular forms of the isoenzyme", *Advances in cyclic nucleotides research*, edited by Brooker G, Greengard P, Robinson G A. Raven Press, New York 1979, 10, p. 69–92.
2. Yoshimura T, Kurita C, Nagao T, Usami E, Nakao T, Watanabe S, Kobayashi J, Yamazaki F, Tanaka H, Nagai H., "Effects of cAMP-phosphodiesterase isozyme inhibitor on cytokine production by lipopolysaccharide-stimulated human peripheral blood mononuclear cells", *Gen. Pharmacol.*, 1997, 29(4), p. 63.

What is claimed is:
1. A compound of formula (I):

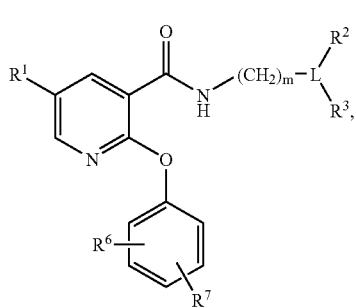

or a pharmaceutically acceptable salt or solvate thereof, wherein:
 $R^1$ is hydrogen, methyl or halo;
 $R^7$ is attached to the 3- or 4-position of the phenyl ring and is $S(O)_p R^8$;
 $R^8$ is $(C_1-C_4)$alkyl optionally substituted by $(C_3-C_6)$cycloalkyl;
 p is 0, 1 or 2;
 $R^6$ is hydrogen, halo, $(C_1-C_3)$alkyl or $(C_1-C_3)$alkoxy;
 m is 0 or 1;
 L is a $(C_3-C_8)$carbocyclic non-aromatic ring;
 $R^2$ is hydrogen; hydroxy; $(C_1-C_3)$alkoxy; $(C_1-C_3)$alkyl optionally substituted by hydroxy or $(C_1-C_3)$alkoxy; $CO_2R^9$; $NR^{10}R^{11}$ or $CONR^{10}R^{11}$;
 $R^3$ is hydrogen or $(C_1-C_3)$alkyl;
 $R^9$ is hydrogen or $(C_1-C_3)$alkyl; and
 $R^{10}$ and $R^{11}$ are taken separately and are each independently hydrogen, or are:
  (a) $(C_1-C_6)$alkyl optionally substituted by phenyl or a 5- or 6-membered heterocyclic ring incorporating one to three heteroatoms independently selected from N, O and S; said phenyl being optionally substituted independently by one to three hydroxy, halo, $(C_1-C_3)$alkyl or $(C_1-C_3)$alkoxy; said heterocyclic ring being optionally substituted independently by one to three hydroxy, halo, $(C_1-C_3)$alkyl, $(C_1-C_3)$alkoxy or oxo;
  (b) $(C_3-C_8)$cycloalkyl;
  (c) $CO((C_1-C_6)$alkyl) optionally substituted by hydroxy, halo, $(C_3-C_8)$cycloalkyl, $(C_1-C_3)$alkoxy, phenyl or a 5- or 6-membered heterocyclic ring incorporating one to three heteroatoms independently selected from N, O and S; said phenyl being optionally substituted independently by one to three hydroxy, halo, $(C_1-C_3)$alkyl or $(C_1-C_3)$alkoxy; said heterocyclic ring being optionally substituted independently by one to three hydroxy, halo, $(C_1-C_3)$alkyl, $(C_1-C_3)$alkoxy or oxo;
  (d) $CO(R^{12})$, wherein $R^{12}$ is $(C_3-C_8)$cycloalkyl optionally substituted by $(C_1-C_3)$alkyl
 or $R^{12}$ is phenyl or a 5- or 6-membered heterocyclic ring incorporating one to three heteroatoms independently selected from N, O and S; said phenyl being optionally substituted by one to three hydroxy, halo, $(C_1-C_3)$alkyl or $(C_1-C_3)$alkoxy; said heterocyclic ring being optionally substituted independently by one to three hydroxy, halo, $(C_1-C_3)$alkyl, $(C_1-C_3)$alkoxy or oxo; or
  (e) $CO_2(C_1-C_3)$alkyl); or
 $R^{10}$ and $R^{11}$ are taken together with the nitrogen atom to which they are attached to form a 5- or 6-membered lactam.

2. A compound of formula (Ia):

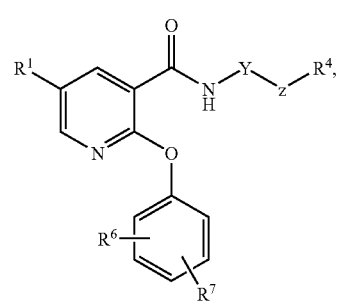

or a pharmaceutically acceptable salt or solvate thereof, wherein:

R¹ is hydrogen, halo or methyl;

R⁷ is attached to the 3- or 4- position of the phenyl ring and is (C₁–C₄)alkylthio;

R⁶ is hydrogen, halo, (C₁–C₃)alkyl or (C₁–C₃)alkoxy;

Y is a radical of partial formula

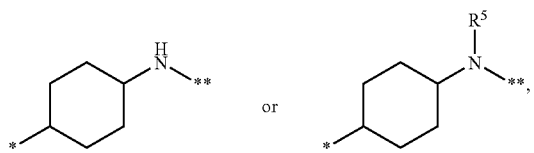

where the symbol "*" indicates the point of attachment of each partial formula to the —NH— of formula (Ia) and "**" indicates the point of attachment of each partial formula to the Z of formula (Ia);

R⁵ is (C₁–C₄)alkyl or phenyl(C₁–C₄)alkyl, said phenyl being optionally substituted by halo, (C₁–C₃)alkyl, (C₁–C₃)alkoxy or hydroxy;

Z is —C(═O)—; and

R⁴ is (a) (C₃–C₈)cycloalkyl optionally substituted by (C₁–C₃)alkyl;

(b) phenyl or a 5- or 6-membered heterocyclic ring incorporating one to three heteroatoms independently selected from N, O and S; said phenyl and said heterocyclic ring each being optionally substituted independently by one to three hydroxy, halo, (C₁–C₃)alkyl or (C₁–C₃)alkoxy; or (C₁–C₆)alkyl optionally substituted with hydroxy, phenyl or a 5- or 6-membered heterocyclic ring incorporating one to three heteroatoms independently selected from N, O and S; said phenyl and said heterocyclic ring each being optionally substituted independently by one to three hydroxy, halo, (C₁–C₃)alkyl or (C₁–C₃)alkoxy.

3. A compound of claim 2, or a pharmaceutically acceptable salt or solvate thereof, wherein Y is

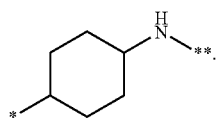

4. A compound of claim 2, or a pharmaceutically acceptable salt or solvate thereof, wherein R⁷ is (C₁–C₄)alkylthio substituted at the 3-position of the phenyl ring.

5. A compound of claim 2, or a pharmaceutically acceptable salt or solvate thereof, wherein R⁴ is benzyl, phenyl or a 5- or 6-membered heterocyclic ring incorporating one to three heteroatoms independently selected from N, O and S; and said benzyl, phenyl and heterocyclic ring are each optionally substituted independently by one to three hydroxy, halo, (C₁–C₃)alkyl and (C₁–C₃)alkoxy.

6. A compound of claim 2 of formula (Ib),

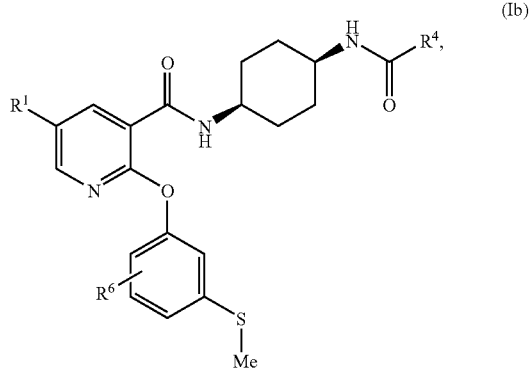

or a pharmaceutically acceptable salt or solvate thereof, wherein:

R¹ is hydrogen, halo or methyl;

R⁴ is benzyl, phenyl or a 5- or 6-membered heterocyclic ring incorporating one to three heteroatoms independently selected from N, O and S; said benzyl, phenyl and heterocyclic ring each being optionally substituted independently by one to three hydroxy, halo, (C₁–C₃) alkyl or (C₁–C₃)alkoxy; and R⁶ is substituted at the 4- or 5-position and is hydrogen, fluoro, chloro or (C₁–C₃)alkyl.

7. A compound of claim 6, or a pharmaceutically acceptable salt or solvate thereof, wherein R⁴ is benzyl, phenyl, pyridyl, pyrimidinyl, pyrazinyl, imidazolyl, pyrazolyl, pyridazinyl ortriazolyl; said benzyl, phenyl, pyridyl, pyrimidinyl, pyrazinyl, imidazolyl, pyrazolyl, pyridazinyl and triazolyl, each being optionally substituted independently by one to three hydroxy, halo, (C₁–C₃)alkyl or (C₁–C₃)alkoxy.

8. A compound of claim 7 wherein R¹ is fluoro.

9. Syn-5-fluoro-N-[4-(2-hydroxy-5-methyl-benzoylamino)-cyclohexyl]-2-(3-methylsulfanyl-phenoxy)-nicotinamide;

Syn-5-fluoro-N-[4-(2-hydroxy-3-methyl-benzoylamino)-cyclohexyl]-2-(3-methylsulfanyl-phenoxy)-nicotinamide;

Syn-5-fluoro-2-(3-methylsulfanyl-phenoxy)-N-{4-[(2,3-dimethyl-1/-/-pyrazole-5-carbonyl)-amino]-cyclohexyl}-nicotinamide;

Syn-5-fluoro-N-{4-[(4-methyl-1/-/-imidazole-2-carbonyl)-amino]-cyclohexyl}-2-(3-methylsulfanyl-phenoxy)-nicotinamide;

Syn-5-fluoro-N-[4-(5-chloro-2-hydroxy-benzoylamino)-cyclohexyl]-2-(3-methylsulfanyl-phenoxy)-nicotinamide;

Syn-5-fluoro-N-[4-(3,5-dimethyl-4-hydroxy-benzoylamino)-cyclohexyl]-2-(3-methylsulfanyl-phenoxy)-nicotinamide;

Syn-5-fluoro-N-[4-(4-hydroxy-3-methyl-benzoylamino)-cyclohexyl]-2-(3-methylsulfanyl-phenoxy)-nicotinamide;

Syn-5-fluoro-N-[4-(3-chloro-4-hydroxy-benzoylamino)-cyclohexyl]-2-(3-methylsulfanyl-phenoxy)-nicotinamide;

Syn-5-fluoro-N-{4-[2-(2-hydroxy-phenyl)-acetylamino]-cyclohexyl}-2-(3-methylsulfanyl-phenoxy)-nicotinamide;

Syn-5-fluoro-N-[4-(2-hydroxy-4-methyl-benzoylamino)-cyclohexyl]-2-(3-methylsulfanyl-phenoxy)-nicotinamide;

Syn-5-fluoro-N-[4-(2-hydroxy-benzoylamino)-cyclohexyl]-2-(3-methylsulfanyl-phenoxy)-nicotinamide;

Syn-5-fluoro-N-[4-(2-hydroxy-4-methoxy-benzoylamino)-cyclohexyl]-2-(3-methylsulfanyl-phenoxy)-nicotinamide;

Syn-N-[4-(2-hydroxy-4-methyl-benzoylamino)-cyclohexyl]-2-(3-methylsulfanyl-phenoxy)-nicotinamide;

Syn-N-[4-(2-hydroxy-4-methoxy-benzoylamino)-cyclohexyl]-2-(3-methylsulfanyl-phenoxy)-nicotinamide;

Syn-5-fluoro-2-(3-methylsulfanyl-phenoxy)-N-{4-[(pyridine-2-carbonyl)-amino]-cyclohexyl}-nicotinamide;

Syn-5-fluoro-2-(3-methylsulfanyl-phenoxy)-N-{4-[(pyrimidine-5-carbonyl)-amino]-cyclohexyl}-nicotinamide;

Syn-5-fluoro-2-(3-methylsulfanyl-phenoxy)-N-{4-[(pyrazine-2-carbonyl)-amino]-cyclohexyl}-nicotinamide;

Syn-5-fluoro-N-{4-[(1H-imidazole-5-carbonyl)-amino]-cyclohexyl}-2-(3-methylsulfanyl-phenoxy)-nicotinamide;

Syn-5-fluoro-N-{4-[(1H-pyrazole-4-carbonyl)-amino]-cyclohexyl}-2-(3-methylsulfanyl-phenoxy)-nicotinamide;

Syn-2-(3-methylsulfanyl-phenoxy)-N-{4-[(pyridine-2-carbonyl)-amino]-cyclohexyl}-nicotinamide;

Syn-N-[4-(2-hydroxy-benzoylamino)-cyclohexyl]-2-(3-methylsulfanyl-phenoxy)-nicotinamide;

Syn-5-fluoro-N-[4-(4-hydroxy-2-methoxy-benzoylamino)-cyclohexyl]-2-(3-methylsulfanyl-phenoxy)-nicotinamide;

Syn-5-fluoro-2-(4-fluoro-3-methylsulfanyl-phenoxy)-N-[4-(2-hydroxy-4-methyl-benzoylamino)-cyclohexyl]-nicotinamide;

Syn-N-[4-(3,5-dihydroxy-benzoylamino)-cyclohexyl]-5-fluoro-2-(3-methylsulfanyl-phenoxy)-nicotinamide;

Syn-N-[4-(3,5-dimethoxy-benzoylamino)-cyclohexyl]-5-fluoro-2-(3-methylsulfanyl-phenoxy)-nicotinamide;

Syn-5-fluoro-N-[4-(3-hydroxy-5-methoxy-benzoylamino)-cyclohexyl]-2-(3-methylsulfanyl-phenoxy)-nicotinamide; or Syn-N-{4-[(1,5-dimethyl-1H-pyrazole-3-carbonyl)-amino]-cyclohexyl}-2-(3-methylsulfanyl-phenoxy)-nicotinamide; or a pharmaceutically acceptable salt or solvate thereof.

10. Syn-5-fluoro-N-{4-[(1H-imidazole-5-carbonyl)-amino]-cyclohexyl}-2-(3-methylsulfanyl-phenoxy)-nicotinamide;

Syn-5-fluoro-N-[4-(2-hydroxy-4-methyl-benzoylamino)-cyclohexyl]-2-(3-methylsulfanyl-phenoxy)-nicotinamide;

Syn-5-fluoro-N-[4-(2-hydroxy-benzoylamino)-cyclohexyl]-2-(3-methylsulfanyl-phenoxy)-nicotinamide;

Syn-5-fluoro-N-[4-(2-hydroxy-5-methyl-benzoylamino)-cyclohexyl]-2-(3-methylsulfanyl-phenoxy)-nicotinamide;

Syn-5-fluoro-2-(3-methylsulfanyl-phenoxy)-N-{4-[(2,3-dimethyl-1H-pyrazole-5-carbonyl)-amino]-cyclohexyl}-nicotinamide;

Syn-5-fluoro-N-{4-[(4-methyl-1H-imidazole-2-carbonyl)-amino]-cyclohexyl}-2-(3-methylsulfanyl-phenoxy)-nicotinamide;

Syn-5-fluoro-N-[4-(4-hydroxy-2-methoxy-benzoylamino)-cyclohexyl]-2-(3-methylsulfanyl-phenoxy)-nicotinamide; or Syn-5-fluoro-N-[4-(5-chloro-2-hydroxy-benzoylamino)-cyclohexyl]-2-(3-methylsulfanyl-phenoxy)-nicotinamide; or a pharmaceutically acceptable salts and solvates thereof.

11. A pharmaceutical composition comprising a compound of claim 1 or 2 or a pharmaceutically acceptable salt of a compound of claim 1 or 2, and a pharmaceutically acceptable excipient, diluent or carrier.

12. A method of treating a disease, disorder or condition in a mammal comprising administering to said mammal in need of such treatment a therapeutically effective amount of a compound of claim 1 or 2, a pharmaceutically acceptable salt thereof or administering a pharmaceutical composition comprising a compound of claim 1 or 2 or a pharmaceutically acceptable salt of a compound of claim 1 or 2 and a pharmaceutically acceptable carrier, diluent or excipient, wherein the disease disorder or condition is selected from;

atopic asthma, non-atopic asthma, allergic asthma, atopic bronchial IgEmediated asthma, bronchial asthma, essential asthma, true asthma, intrinsic asthma caused by pathophysiologic disturbances, extrinsic asthma caused by environmental factors, essential asthma of unknown or inapparent cause, nonatopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma and wheezy infant syndrome, chronic or acute bronchoconstriction, chronic bronchitis, small airways obstruction, and emphysema, chronic eosinophilic pneumonia, chronic obstructive pulmonary disease (COPD), COPD that includes chronic bronchitis, pulmonary emphysema or dyspnea associated therewith, COPD that is characterized by irreversible, progressive airways obstruction, adult respiratory distress syndrome (ARDS) and exacerbation of airways hyper-reactivity consequent to other drug therapy, aluminosis or bauxite workers' disease, anthracosis or miners' asthma, asbestosis or steam-fitters' asthma, challcosis or flint disease, ptilosis caused by inhaling the dust from ostrich feathers, siderosis caused by the inhalation of iron particles, silicosis or grinders' disease, byssinosis or cotton-dust asthma and talc pneumoconiosis;

acute bronchitis, acute laryngotracheal-bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis, cylindric bronchiectasis, sacculated bronchiectasis, fusiform bronchiectasis, capillary bronchiectasis, cystic bronchiectasis, dry bronchiectasis and follicular bronchiectasis, and seasonal allergic rhinitism, perennial allergic rhinitis, purulent or nonpurulent sinusitis, acute or chronic sinusitis and ethmold frontal, maxillary or sphenoid sinusitis.

13. A method of claim 12 wherein the disease, disorder or condition is chronic obstructive pulmonary disease, asthma, or chronic bronchitis.

* * * * *